US011964010B2

United States Patent
Graham et al.

(10) Patent No.: US 11,964,010 B2
(45) Date of Patent: *Apr. 23, 2024

(54) PREFUSION CORONAVIRUS SPIKE PROTEINS AND THEIR USE

(71) Applicants: The United States of America, as represented by the Secretary, Department of Health and Human Services, Bethesda, MD (US); The Scripps Research Institute, La Jolla, CA (US); Trustees of Dartmouth College, Hanover, NH (US)

(72) Inventors: Barney Graham, Rockville, MD (US); Jason Mclellan, Austin, TX (US); Andrew Ward, La Jolla, CA (US); Robert Kirchdoerfer, La Jolla, CA (US); Christopher Cottrell, La Jolla, CA (US); Michael Gordon Joyce, Washington, DC (US); Masaru Kanekiyo, Chevy Chase, MD (US); Nianshuang Wang, Austin, TX (US); Jesper Pallesen, La Jolla, CA (US); Hadi Yassine, Doha (QA); Hannah Turner, La Jolla, CA (US); Kizzmekia Corbett, Wheaton, MD (US)

(73) Assignees: The United States of America, as represented by the Secretary, Department of Health and Human Services, Bethesda, MD (US); The Scripps Research Institute, La Jolla, CA (US); Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/194,834

(22) Filed: Mar. 8, 2021

(65) Prior Publication Data
US 2021/0275664 A1    Sep. 9, 2021

Related U.S. Application Data

(63) Continuation of application No. 16/344,774, filed as application No. PCT/US2017/058370 on Oct. 25, 2017, now Pat. No. 10,960,070.
(Continued)

(51) Int. Cl.
A61K 39/215    (2006.01)
A61P 31/14    (2006.01)
(Continued)

(52) U.S. Cl.
CPC ............ *A61K 39/215* (2013.01); *A61P 31/14* (2018.01); *C07K 14/005* (2013.01); *C12N 7/00* (2013.01);
(Continued)

(58) Field of Classification Search
None
See application file for complete search history.

(56) References Cited

U.S. PATENT DOCUMENTS

2018/0346521 A1    12/2018    Langedijk

FOREIGN PATENT DOCUMENTS

WO    WO 2016/037154    3/2016
WO    WO-2017070626 A2 *    4/2017    ............. A61K 39/12

OTHER PUBLICATIONS

Chan et al., "Functional Characterization of Heptad Repeat 1 and 2 Mutants of the Spike Protein of Severe Acute Respiratory Syndrome Coronavirus," *J Virol.* 80.7: 3225-3237, Apr. 2006.
(Continued)

*Primary Examiner* — M Franco G Salvoza
(74) *Attorney, Agent, or Firm* — Klarquist Sparkman, LLP

(57) ABSTRACT

Coronavirus S ectodomain trimers stabilized in a prefusion conformation, nucleic acid molecules and vectors encoding these proteins, and methods of their use and production are disclosed. In several embodiments, the coronavirus S ectodomain trimers and/or nucleic acid molecules can be used to generate an immune response to coronavirus in a subject. In additional embodiments, the therapeutically
(Continued)

effective amount of the coronavirus S ectodomain trimers and/or nucleic acid molecules can be administered to a subject in a method of treating or preventing coronavirus infection.

15 Claims, 23 Drawing Sheets
(3 of 23 Drawing Sheet(s) Filed in Color)
Specification includes a Sequence Listing.

Related U.S. Application Data

(60) Provisional application No. 62/412,703, filed on Oct. 25, 2016.

(51) Int. Cl.
*C07K 14/005* (2006.01)
*C12N 7/00* (2006.01)

(52) U.S. Cl.
CPC .............. *C12N 2770/20022* (2013.01); *C12N 2770/20034* (2013.01); *C12N 2770/20071* (2013.01)

(56) References Cited

OTHER PUBLICATIONS

Escriou et al., "Protection from SARS coronavirus conferred by live measles vaccine expressing the spike glycoprotein." *Virology* 452: 32-41, 2014.

International Search Report and Written Opinion of International Patent Application No. PCT/US2017/058370, European Searching Authority, dated Jan. 24, 2018 (17 pages).
Kirchdoerfer et al., "Pre-fusion structure of a human coronavirus spike protein," *Nature* 531.7592: 118, 2016.
Lucchese et al., "How a single amino acid change may alter the immunological information of a peptide," *Front Biosci (Elite Ed)* 4: 1843-1852, 2012.
Ma et al., "Searching for an ideal vaccine candidate among different MERS coronavirus receptor-binding fragments—the importance of immunofocusing in subunit vaccine design," *Vaccine* 32.46: 6170-6176, 2014.
Menachery et al., "SARS-like WIV1-CoV poised for human emergence," *Proc Natl Acad Sci.* 113.17: 3048-3053, 2016.
Pallesen et al., "Immunogenicity and structures of a rationally designed prefusion MERS-CoV spike antigen," *Proc Natl Acad Sci.* 114.35: E7348-E7357, 2017.
Qian et al., "Identification of the receptor-binding domain of the spike glycoprotein of human betacoronavirus HKU1," *J Virol.* 89.17: 8816-8827, 2015.
Qiao et al., "Specific single or double proline substitutions in the "spring-loaded" coiled-coil region of the influenza hemagglutinin impair or abolish membrane fusion activity", *J Cell Biol.* 141.6: 1335-1347, Jun. 1998.
Sanders et al., "Stabilization of the soluble, cleaved, trimeric form of the envelope glycoprotein complex of human immunodeficiency virus type 1," *J Virol.* 76.17: 8875-8889, 2002.
Wang et al., "Evaluation of candidate vaccine approaches for MERS-CoV," *Nature Comm.* 6: 7712, 2015.
Woo et al., "Characterization and complete genome sequence of a novel coronavirus, coronavirus HKU1, from patients with pneumonia," *J Virol.* 79.2: 884-895, 2005.

* cited by examiner

FIG. 1A FIG. 1B
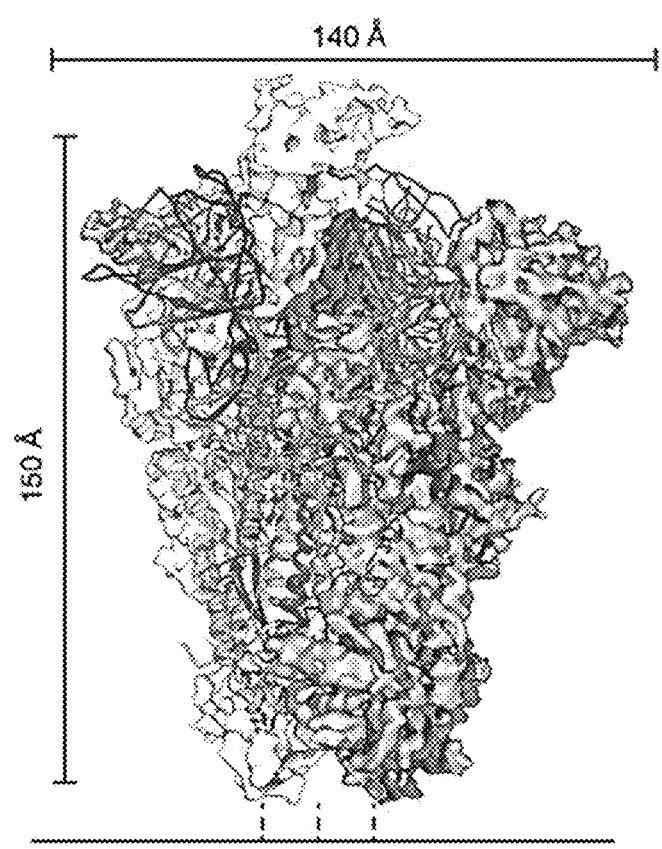
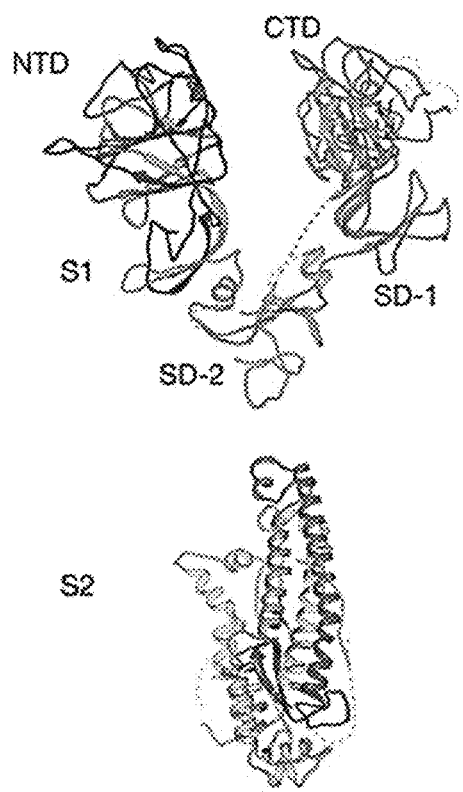
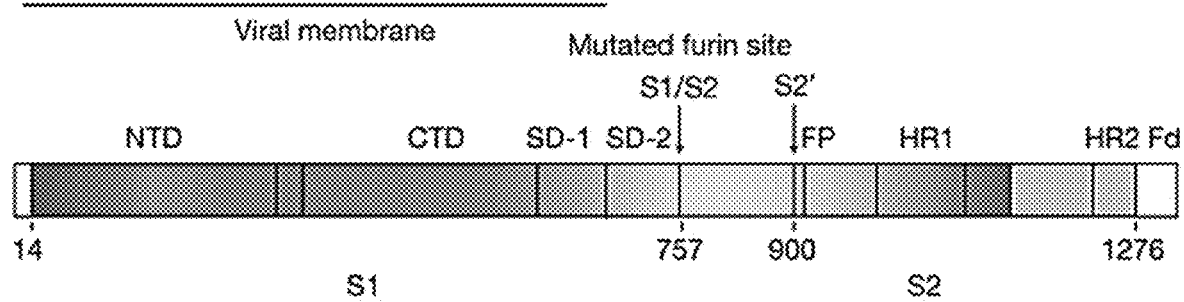
FIG. 1C

FIG. 2A  FIG. 2B
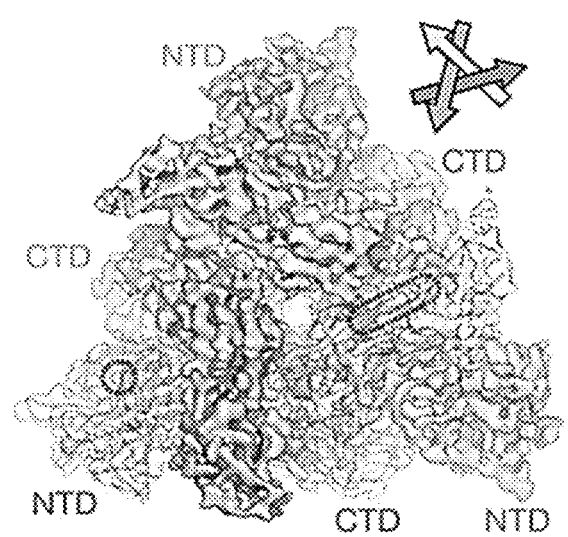
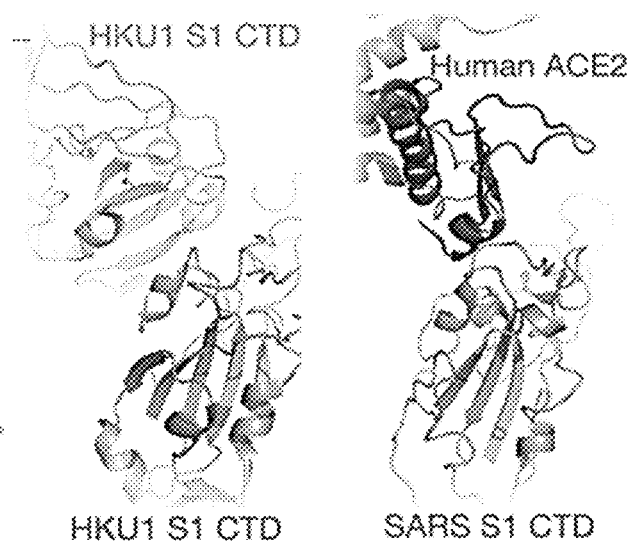
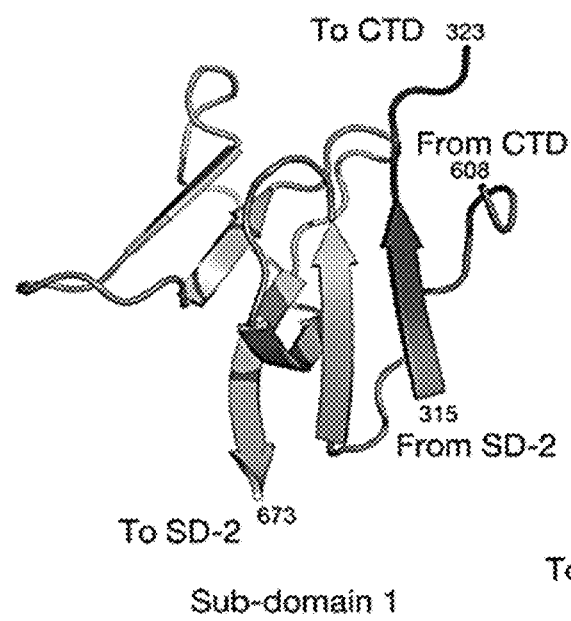
Sub-domain 1
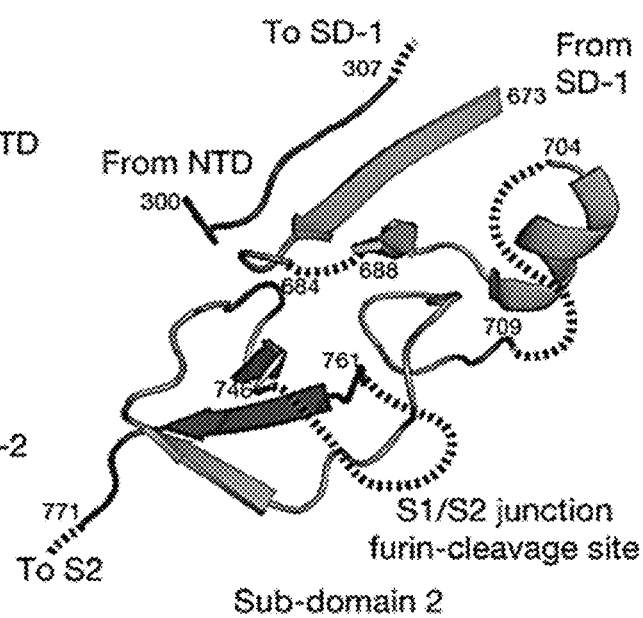
Sub-domain 2
FIG. 2C  FIG. 2D

FIG. 3A
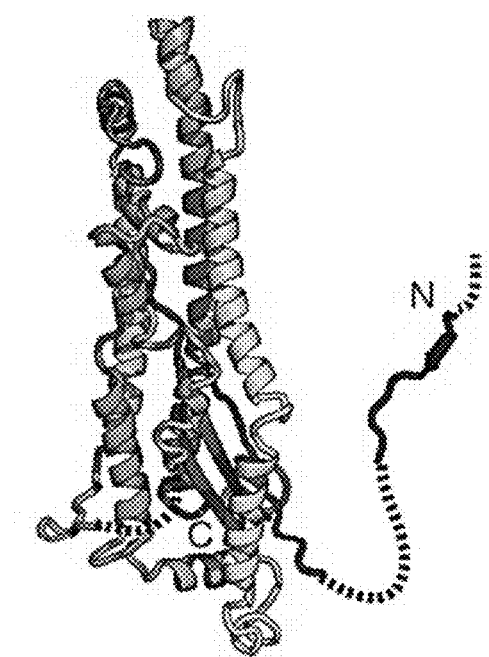
FIG. 3C
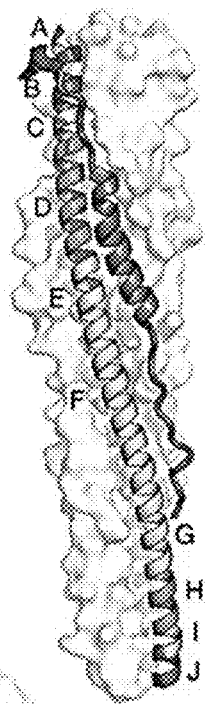
SARS post-fusion S, six-helix bundle
HKU1 pre-fusion S
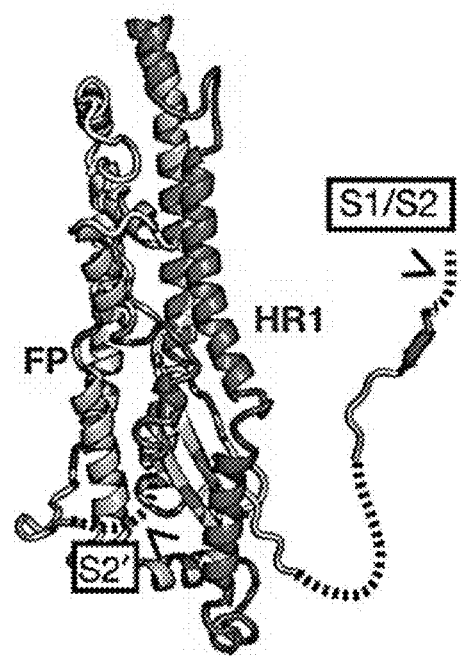
FIG. 3B
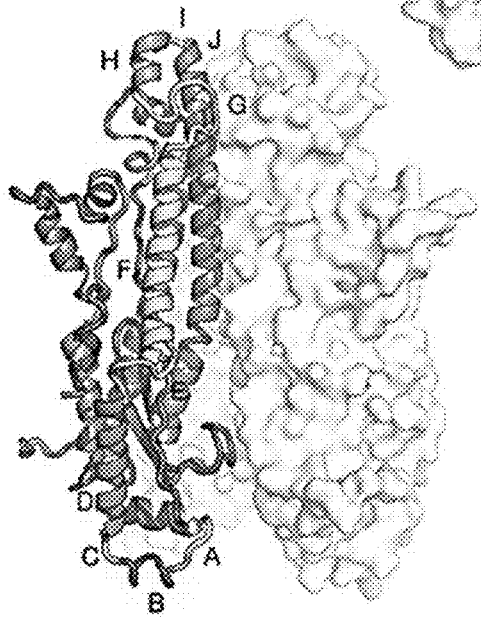

Immunogenicity of MERS S-2P in mice

Autologous Neutralization

Reciprocal $IC_{90}$ Titer vs. Immunogen Dose (μg)

- S-2P
- S WT
- S1

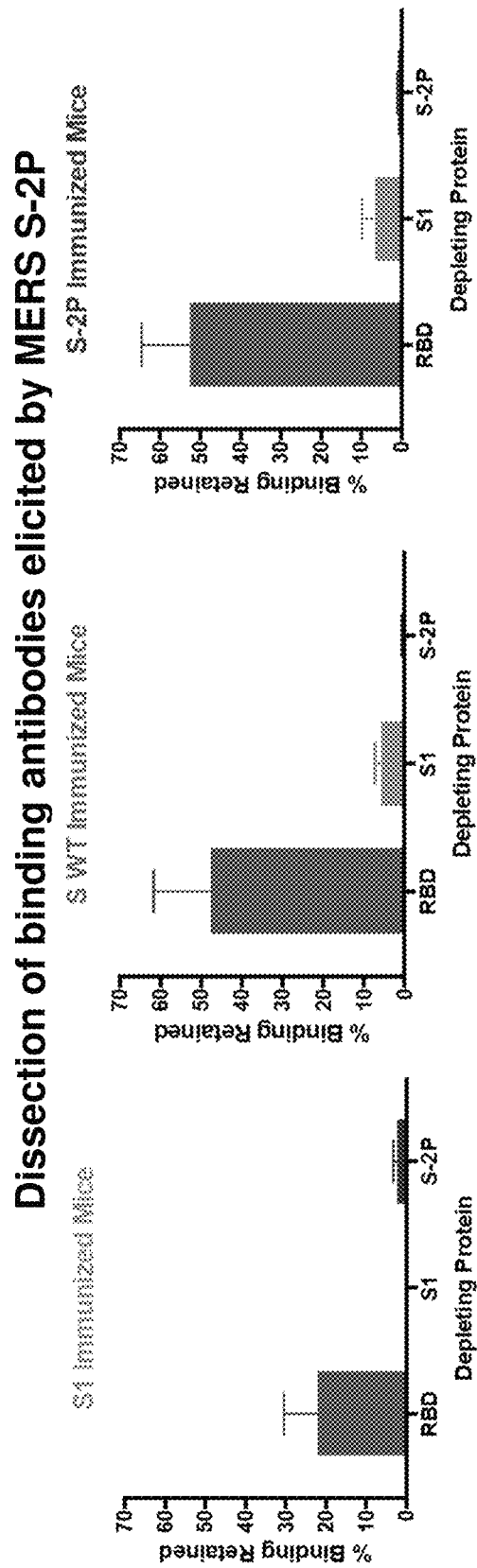

FIG. 6B

Dissection of neutralizing antibodies elicited by MERS S-2P

SARS-S WT        SARS-S-2P

FIG. 12
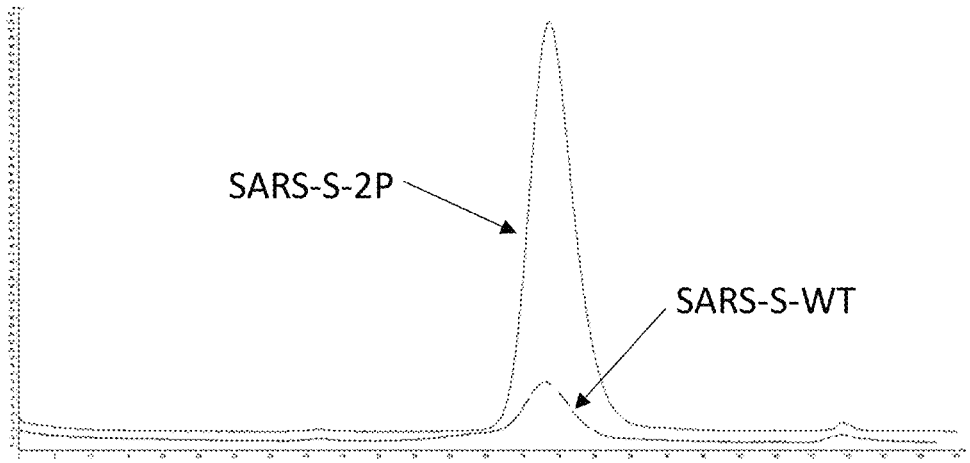
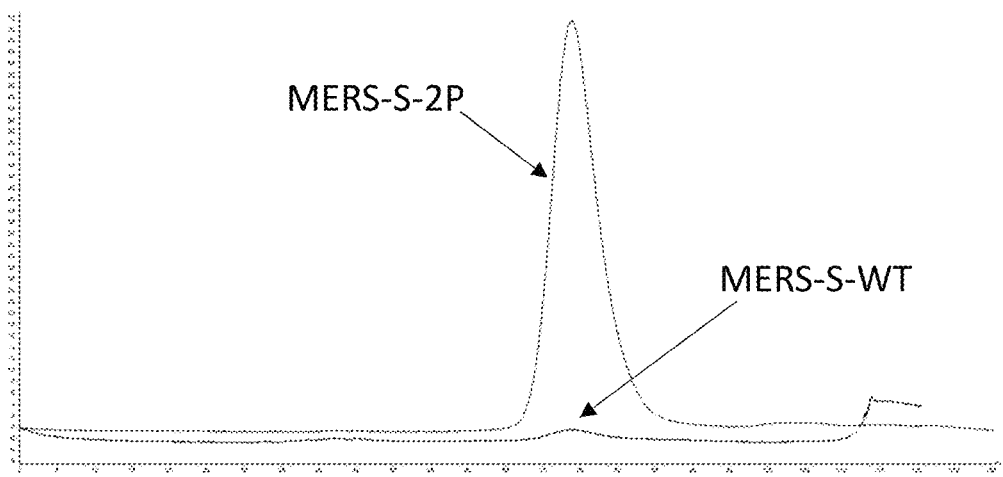
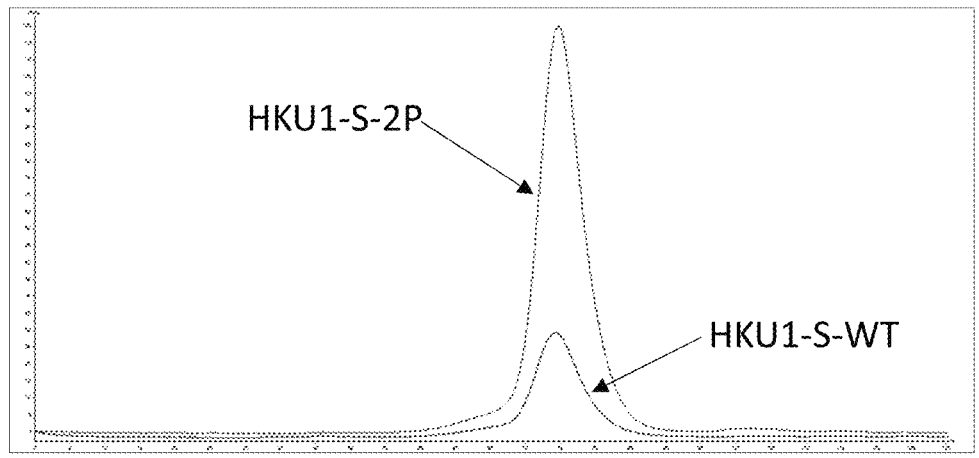

HKU1 S 2P  MERS S 2P  SARS S 2P FIG. 14D
OC43 S-2P
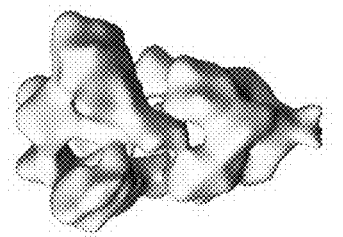
WIV1 S-2P
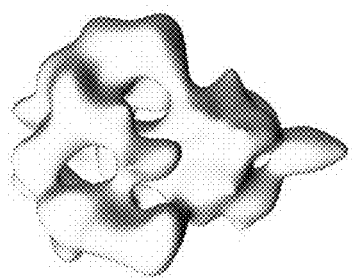
PEDV S-2P
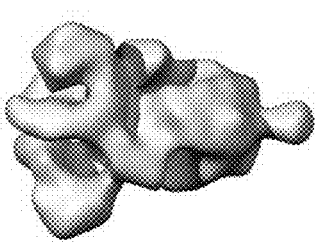
229E S-2P
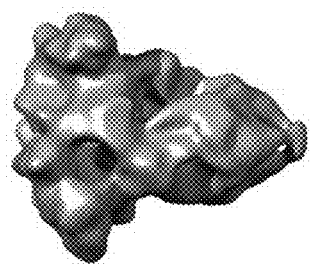

FIG. 15
Immunogenicity of SARS S-2P in mice
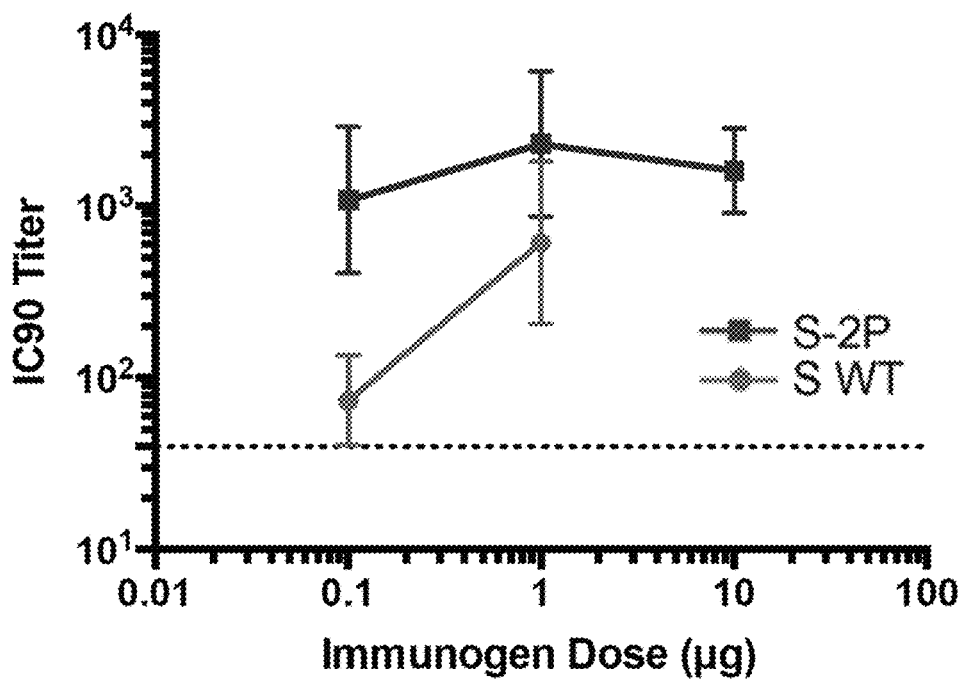
HKU1 S-2P vs. HKU1 S-WT
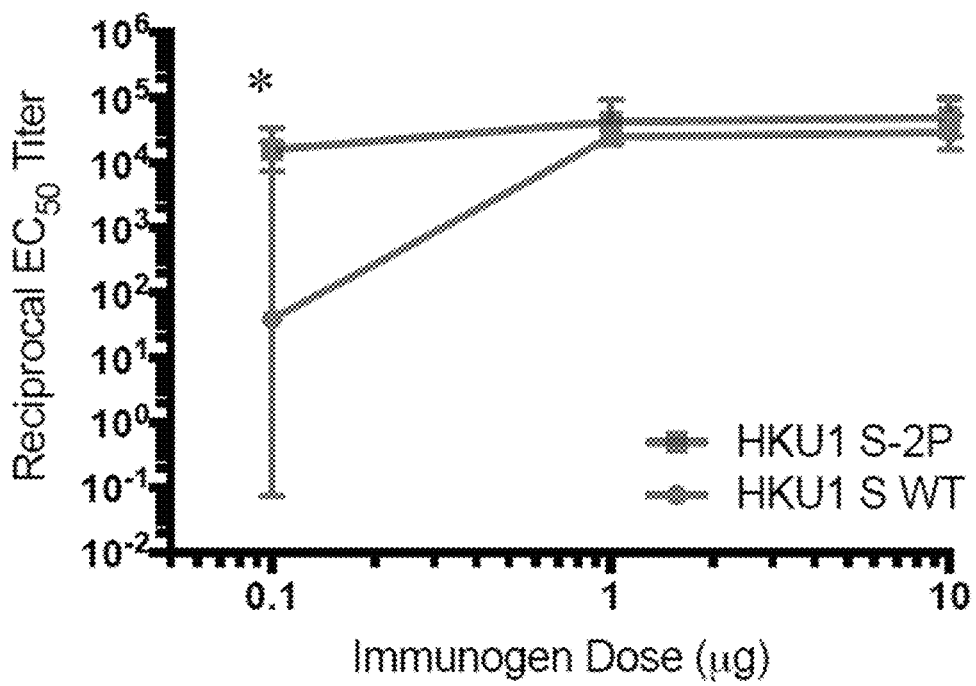

SEQUENCE LISTING

<160> NUMBER OF SEQ ID NOS: 43

<210> SEQ ID NO 1
<211> LENGTH: 1353
<212> TYPE: PRT
<213> ORGANISM: middle east respiratory syndrome coronavirus

<400> SEQUENCE: 1

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205
```

```
Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Phe Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620
```

```
Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
        645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
            725                 730                 735

Ala Leu Pro Asp Thr Pro Ser Thr Leu Thr Pro Arg Ser Val Arg Ser
                740                 745                 750

Val Pro Gly Glu Met Arg Leu Ala Ser Ile Ala Phe Asn His Pro Ile
            755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
                835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
            885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
            965                 970                 975

Phe Tyr Arg Leu Asn Gly Val Gly Ile Thr Gln Gln Val Leu Ser Glu
        980                 985                 990

Asn Gln Lys Leu Ile Ala Asn Lys Phe Asn Gln Ala Leu Gly Ala Met
        995                 1000                1005

Gln Thr Gly Phe Thr Thr Thr Asn Glu Ala Phe His Lys Val Gln
    1010                1015                1020

Asp Ala Val Asn Asn Asn Ala Gln Ala Leu Ser Lys Leu Ala Ser
    1025                1030                1035

Glu Leu Ser Asn Thr Phe Gly Ala Ile Ser Ala Ser Ile Gly Asp
```

```
               1040                1045                1050

Ile Ile Gln Arg Leu Asp Val Leu Glu Gln Asp Ala Gln Ile Asp
       1055                1060                1065

Arg Leu Ile Asn Gly Arg Leu Thr Thr Leu Asn Ala Phe Val Ala
       1070                1075                1080

Gln Gln Leu Val Arg Ser Glu Ser Ala Ala Leu Ser Ala Gln Leu
       1085                1090                1095

Ala Lys Asp Lys Val Asn Glu Cys Val Lys Ala Gln Ser Lys Arg
       1100                1105                1110

Ser Gly Phe Cys Gly Gln Gly Thr His Ile Val Ser Phe Val Val
       1115                1120                1125

Asn Ala Pro Asn Gly Leu Tyr Phe Met His Val Gly Tyr Tyr Pro
       1130                1135                1140

Ser Asn His Ile Glu Val Val Ser Ala Tyr Gly Leu Cys Asp Ala
       1145                1150                1155

Ala Asn Pro Thr Asn Cys Ile Ala Pro Val Asn Gly Tyr Phe Ile
       1160                1165                1170

Lys Thr Asn Asn Thr Arg Ile Val Asp Glu Trp Ser Tyr Thr Gly
       1175                1180                1185

Ser Ser Phe Tyr Ala Pro Glu Pro Ile Thr Ser Leu Asn Thr Lys
       1190                1195                1200

Tyr Val Ala Pro Gln Val Thr Tyr Gln Asn Ile Ser Thr Asn Leu
       1205                1210                1215

Pro Pro Pro Leu Leu Gly Asn Ser Thr Gly Ile Asp Phe Gln Asp
       1220                1225                1230

Glu Leu Asp Glu Phe Phe Lys Asn Val Ser Thr Ser Ile Pro Asn
       1235                1240                1245

Phe Gly Ser Leu Thr Gln Ile Asn Thr Thr Leu Leu Asp Leu Thr
       1250                1255                1260

Tyr Glu Met Leu Ser Leu Gln Gln Val Val Lys Ala Leu Asn Glu
       1265                1270                1275

Ser Tyr Ile Asp Leu Lys Glu Leu Gly Asn Tyr Thr Tyr Tyr Asn
       1280                1285                1290

Lys Trp Pro Trp Tyr Ile Trp Leu Gly Phe Ile Ala Gly Leu Val
       1295                1300                1305

Ala Leu Ala Leu Cys Val Phe Phe Ile Leu Cys Cys Thr Gly Cys
       1310                1315                1320

Gly Thr Asn Cys Met Gly Lys Leu Lys Cys Asn Arg Cys Cys Asp
       1325                1330                1335

Arg Tyr Glu Glu Tyr Asp Leu Glu Pro His Lys Val His Val His
       1340                1345                1350

<210> SEQ ID NO 2
<211> LENGTH: 1291
<212> TYPE: PRT
<213> ORGANISM: Artificial Sequence
<220> FEATURE:
<223> OTHER INFORMATION: recombinant coronavirus spike protein

<400> SEQUENCE: 2

Met Ile His Ser Val Phe Leu Leu Met Phe Leu Leu Thr Pro Thr Glu
  1               5                  10                  15

Ser Tyr Val Asp Val Gly Pro Asp Ser Val Lys Ser Ala Cys Ile Glu
                 20                  25                  30

Val Asp Ile Gln Gln Thr Phe Phe Asp Lys Thr Trp Pro Arg Pro Ile
```

```
                35                  40                  45
Asp Val Ser Lys Ala Asp Gly Ile Ile Tyr Pro Gln Gly Arg Thr Tyr
 50                  55                  60

Ser Asn Ile Thr Ile Thr Tyr Gln Gly Leu Phe Pro Tyr Gln Gly Asp
 65                  70                  75                  80

His Gly Asp Met Tyr Val Tyr Ser Ala Gly His Ala Thr Gly Thr Thr
                 85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
            115                 120                 125

Thr Val Ile Ile Ser Pro Ser Thr Ser Ala Thr Ile Arg Lys Ile Tyr
130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
            195                 200                 205

Thr Pro Ala Thr Asp Cys Ser Asp Gly Asn Tyr Asn Arg Asn Ala Ser
210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
            275                 280                 285

Thr Ile Lys Tyr Tyr Ser Ile Ile Pro His Ser Ile Arg Ser Ile Gln
290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
            355                 360                 365

Lys Pro Ser Gly Ser Val Val Glu Gln Ala Glu Gly Val Glu Cys Asp
            370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
            435                 440                 445

Pro Leu Ser Met Lys Ser Asp Leu Ser Val Ser Ser Ala Gly Pro Ile
450                 455                 460
```

```
Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Phe Leu Ser Asp Asp Arg Thr
                500                 505                 510

Glu Val Pro Gln Leu Val Asn Ala Asn Gln Tyr Ser Pro Cys Val Ser
                515                 520                 525

Ile Val Pro Ser Thr Val Trp Glu Asp Gly Asp Tyr Tyr Arg Lys Gln
                530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
                595                 600                 605

Tyr Gly Val Ser Gly Arg Gly Val Phe Gln Asn Cys Thr Ala Val Gly
                610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
                675                 680                 685

Tyr Ser Arg Ser Thr Arg Ser Met Leu Lys Arg Arg Asp Ser Thr Tyr
                690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
                740                 745                 750

Val Pro Gly Glu Met Arg Leu Ala Ser Ile Ala Phe Asn His Pro Ile
                755                 760                 765

Gln Val Asp Gln Leu Asn Ser Ser Tyr Phe Lys Leu Ser Ile Pro Thr
                770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
                820                 825                 830

Gln Ala Leu His Gly Ala Asn Leu Arg Gln Asp Asp Ser Val Arg Asn
                835                 840                 845

Leu Phe Ala Ser Val Lys Ser Ser Gln Ser Ser Pro Ile Ile Pro Gly
                850                 855                 860

Phe Gly Gly Asp Phe Asn Leu Thr Leu Leu Glu Pro Val Ser Ile Ser
865                 870                 875                 880
```

```
Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
            915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys Phe Asn Gln Ala Leu Gly Ala Met
        995                 1000                1005

Gln Thr Gly Phe Thr Thr Asn Glu Ala Phe His Lys Val Gln
    1010                1015                1020

Asp Ala Val Asn Asn Ala Gln Ala Leu Ser Lys Leu Ala Ser
    1025                1030                1035

Glu Leu Ser Asn Thr Phe Gly Ala Ile Ser Ala Ser Ile Gly Asp
    1040                1045                1050

Ile Ile Gln Arg Leu Asp Pro Pro Glu Gln Asp Ala Gln Ile Asp
    1055                1060                1065

Arg Leu Ile Asn Gly Arg Leu Thr Thr Leu Asn Ala Phe Val Ala
    1070                1075                1080

Gln Gln Leu Val Arg Ser Glu Ser Ala Ala Leu Ser Ala Gln Leu
    1085                1090                1095

Ala Lys Asp Lys Val Asn Glu Cys Val Lys Ala Gln Ser Lys Arg
    1100                1105                1110

Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro Gln Val Thr Tyr Gln Asn Ile Ser Thr Asn Leu
    1205                1210                1215

Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr Tyr
```

-continued 1280            1285            1290

<210> SEQ ID NO 3
<211> LENGTH: 1291
<212> TYPE: PRT
<213> ORGANISM: Artificial Sequence
<220> FEATURE:
<223> OTHER INFORMATION: recombinant coronavirus spike protein

<400> SEQUENCE: 3

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala

|     |     |     | 355 |     |     |     | 360 |     |     |     | 365 |     |
| --- | --- | --- | --- | --- | --- | --- | --- | --- | --- | --- | --- | --- |
| Lys | Pro | Ser | Gly | Ser | Val | Val | Glu | Gln | Ala | Glu | Gly | Val | Glu | Cys | Asp |
|     |     |     | 370 |     |     |     | 375 |     |     |     | 380 |     |

Phe Ser Pro Leu Leu Ser Gly Thr Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
                420                 425                 430

Ile Ala Ser Asn Cys Tyr Ser Ser Leu Ile Leu Asp Tyr Phe Ser Tyr
                435                 440                 445

Pro Leu Ser Met Lys Ser Asp Leu Ser Val Ser Ser Ala Gly Pro Ile
                450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Phe Leu Ser Asp Asp Arg Thr
                500                 505                 510

Glu Val Pro Gln Leu Val Asn Ala Asn Gln Tyr Ser Pro Cys Val Ser
                515                 520                 525

Ile Val Pro Ser Thr Val Trp Glu Asp Gly Asp Tyr Tyr Arg Lys Gln
                530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
                595                 600                 605

Tyr Gly Val Ser Gly Arg Gly Val Phe Gln Asn Cys Thr Ala Val Gly
                610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
                675                 680                 685

Tyr Ser Arg Ser Thr Arg Ser Met Leu Lys Arg Arg Asp Ser Thr Tyr
                690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Ala Ser Val Gly Ser
                740                 745                 750

Val Pro Gly Glu Met Arg Leu Ala Ser Ile Ala Phe Asn His Pro Ile
                755                 760                 765

Gln Val Asp Gln Leu Asn Ser Ser Tyr Phe Lys Leu Ser Ile Pro Thr
                770                 775                 780

-continued

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
            805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
            835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
            915                 920                 925

Val Ala Gly Tyr Lys Val Leu Pro Pro Leu Met Asp Val Asn Met Glu
            930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys Phe Asn Gln Ala Leu Gly Ala Met
            995                 1000                1005

Gln Thr Gly Phe Thr Thr Thr Asn Glu Ala Phe His Lys Val Gln
    1010            1015                1020

Asp Ala Val Asn Asn Asn Ala Gln Ala Leu Ser Lys Leu Ala Ser
    1025            1030                1035

Glu Leu Ser Asn Thr Phe Gly Ala Ile Ser Ala Ser Ile Gly Asp
    1040            1045                1050

Ile Ile Gln Arg Leu Asp Pro Pro Glu Gln Asp Ala Gln Ile Asp
    1055            1060                1065

Arg Leu Ile Asn Gly Arg Leu Thr Thr Leu Asn Ala Phe Val Ala
    1070            1075                1080

Gln Gln Leu Val Arg Ser Glu Ser Ala Ala Leu Ser Ala Gln Leu
    1085            1090                1095

Ala Lys Asp Lys Val Asn Glu Cys Val Lys Ala Gln Ser Lys Arg
    1100            1105                1110

Ser Gly Phe Cys Gly Gln Gly Thr His Ile Val Ser Phe Val Val
    1115            1120                1125

Asn Ala Pro Asn Gly Leu Tyr Phe Met His Val Gly Tyr Tyr Pro
    1130            1135                1140

Ser Asn His Ile Glu Val Val Ser Ala Tyr Gly Leu Cys Asp Ala
    1145            1150                1155

Ala Asn Pro Thr Asn Cys Ile Ala Pro Val Asn Gly Tyr Phe Ile
    1160            1165                1170

Lys Thr Asn Asn Thr Arg Ile Val Asp Glu Trp Ser Tyr Thr Gly
    1175            1180                1185

```
Ser  Ser  Phe  Tyr  Ala  Pro  Glu  Pro  Ile  Thr  Ser  Leu  Asn  Thr  Lys
     1190               1195                    1200

Tyr  Val  Ala  Pro  Gln  Val  Thr  Tyr  Gln  Asn  Ile  Ser  Thr  Asn  Leu
1205                     1210                    1215

Pro  Pro  Pro  Leu  Leu  Gly  Asn  Ser  Thr  Gly  Ile  Asp  Phe  Gln  Asp
1220                     1225                    1230

Glu  Leu  Asp  Glu  Phe  Phe  Lys  Asn  Val  Ser  Thr  Ser  Ile  Pro  Asn
     1235                    1240                    1245

Phe  Gly  Ser  Leu  Thr  Gln  Ile  Asn  Thr  Thr  Leu  Leu  Asp  Leu  Thr
     1250                    1255                    1260

Tyr  Glu  Met  Leu  Ser  Leu  Gln  Val  Val  Lys  Ala  Leu  Asn  Glu
1265                     1270                    1275

Ser  Tyr  Ile  Asp  Leu  Lys  Glu  Leu  Gly  Asn  Tyr  Thr  Tyr
1280                     1285                    1290

<210> SEQ ID NO 4
<211> LENGTH: 1291
<212> TYPE: PRT
<213> ORGANISM: Artificial Sequence
<220> FEATURE:
<223> OTHER INFORMATION: recombinant coronavirus spike protein

<400> SEQUENCE: 4

Met  Ile  His  Ser  Val  Phe  Leu  Leu  Met  Phe  Leu  Leu  Thr  Pro  Thr  Glu
1                     5                        10                      15

Ser  Tyr  Val  Asp  Val  Gly  Pro  Asp  Ser  Val  Lys  Ser  Ala  Cys  Ile  Glu
               20                        25                      30

Val  Asp  Ile  Gln  Gln  Thr  Phe  Phe  Asp  Lys  Thr  Trp  Pro  Arg  Pro  Ile
          35                        40                      45

Asp  Val  Ser  Lys  Ala  Asp  Gly  Ile  Ile  Tyr  Pro  Gln  Gly  Arg  Thr  Tyr
     50                        55                      60

Ser  Asn  Ile  Thr  Ile  Thr  Tyr  Gln  Gly  Leu  Phe  Pro  Tyr  Gln  Gly  Asp
65                        70                      75                      80

His  Gly  Asp  Met  Tyr  Val  Tyr  Ser  Ala  Gly  His  Ala  Thr  Gly  Thr  Thr
                    85                        90                      95

Pro  Gln  Lys  Leu  Phe  Val  Ala  Asn  Tyr  Ser  Gln  Asp  Val  Lys  Gln  Phe
               100                       105                     110

Ala  Asn  Gly  Phe  Val  Val  Arg  Ile  Gly  Ala  Ala  Ala  Asn  Ser  Thr  Gly
          115                       120                     125

Thr  Val  Ile  Ile  Ser  Pro  Ser  Thr  Ser  Ala  Thr  Ile  Arg  Lys  Ile  Tyr
     130                       135                     140

Pro  Ala  Phe  Met  Leu  Gly  Ser  Ser  Val  Gly  Asn  Phe  Ser  Asp  Gly  Lys
145                       150                     155                     160

Met  Gly  Arg  Phe  Phe  Asn  His  Thr  Leu  Val  Leu  Leu  Pro  Asp  Gly  Cys
                    165                       170                     175

Gly  Thr  Leu  Leu  Arg  Ala  Phe  Tyr  Cys  Ile  Leu  Glu  Pro  Arg  Ser  Gly
               180                       185                     190

Asn  His  Cys  Pro  Ala  Gly  Asn  Ser  Tyr  Thr  Ser  Phe  Ala  Thr  Tyr  His
          195                       200                     205

Thr  Pro  Ala  Thr  Asp  Cys  Ser  Asp  Gly  Asn  Tyr  Asn  Arg  Asn  Ala  Ser
     210                       215                     220

Leu  Asn  Ser  Phe  Lys  Glu  Tyr  Phe  Asn  Leu  Arg  Asn  Cys  Thr  Phe  Met
225                       230                     235                     240

Tyr  Thr  Tyr  Asn  Ile  Thr  Glu  Asp  Glu  Ile  Leu  Glu  Trp  Phe  Gly  Ile
                    245                       250                     255
```

-continued

```
Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
            275                 280                 285

Thr Ile Lys Tyr Tyr Ser Ile Ile Pro His Ser Ile Arg Ser Ile Gln
            290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
            325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
            355                 360                 365

Lys Pro Ser Gly Ser Val Val Glu Gln Ala Glu Gly Val Glu Cys Asp
            370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
            405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
            435                 440                 445

Pro Leu Ser Met Lys Ser Asp Leu Ser Val Ser Ser Ala Gly Pro Ile
            450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
            485                 490                 495

Tyr Ser Tyr Ile Asn Lys Cys Ser Arg Phe Leu Ser Asp Asp Arg Thr
            500                 505                 510

Glu Val Pro Gln Leu Val Asn Ala Asn Gln Tyr Ser Pro Cys Val Ser
            515                 520                 525

Ile Val Pro Ser Thr Val Trp Glu Asp Gly Asp Tyr Tyr Arg Lys Gln
            530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
            565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
            610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
            645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
```

```
              675                 680                 685
Tyr Ser Arg Ser Thr Arg Ser Met Leu Lys Arg Arg Asp Ser Thr Tyr
    690                 695                 700
Gly Pro Leu Gln Thr Pro Val Gly Cys Val Leu Gly Leu Val Asn Ser
705                 710                 715                 720
Ser Leu Phe Val Glu Asp Cys Lys Leu Pro Leu Gly Gln Ser Leu Cys
                725                 730                 735
Ala Leu Pro Asp Thr Pro Ser Thr Leu Thr Pro Ala Ser Val Gly Ser
                740                 745                 750
Val Pro Gly Glu Met Arg Leu Ala Ser Ile Ala Phe Asn His Pro Ile
                755                 760                 765
Gln Val Asp Gln Leu Asn Ser Ser Tyr Phe Lys Leu Ser Ile Pro Thr
770                 775                 780
Asn Phe Ser Phe Gly Val Thr Gln Glu Tyr Ile Gln Thr Thr Ile Gln
785                 790                 795                 800
Lys Val Thr Val Asp Cys Lys Gln Tyr Val Cys Asn Gly Phe Gln Lys
                805                 810                 815
Cys Glu Gln Leu Leu Arg Glu Tyr Gly Gln Phe Cys Ser Lys Ile Asn
                820                 825                 830
Gln Ala Leu His Gly Ala Asn Leu Arg Gln Asp Asp Ser Val Arg Asn
                835                 840                 845
Leu Phe Ala Ser Val Lys Ser Ser Gln Ser Ser Pro Ile Ile Pro Gly
850                 855                 860
Phe Gly Gly Asp Phe Asn Leu Thr Leu Leu Glu Pro Val Ser Ile Ser
865                 870                 875                 880
Thr Gly Ser Gly Ser Ala Gly Ser Ala Ile Glu Asp Leu Leu Phe Asp
                885                 890                 895
Lys Val Thr Ile Ala Asp Pro Gly Tyr Met Gln Gly Tyr Asp Asp Cys
                900                 905                 910
Met Gln Gln Gly Pro Ala Ser Ala Arg Asp Leu Ile Cys Ala Gln Tyr
                915                 920                 925
Val Ala Gly Tyr Lys Val Leu Pro Pro Leu Met Asp Val Asn Met Glu
                930                 935                 940
Ala Ala Tyr Thr Ser Ser Leu Leu Gly Ser Ile Ala Gly Val Gly Trp
945                 950                 955                 960
Thr Ala Gly Leu Ser Ser Phe Ala Ala Ile Pro Phe Ala Gln Ser Ile
                965                 970                 975
Phe Tyr Arg Leu Asn Gly Val Gly Ile Thr Gln Gln Val Leu Ser Glu
                980                 985                 990
Asn Gln Lys Leu Ile Ala Asn Lys Phe Asn Gln Ala Leu Gly Ala Met
                995                 1000                1005
Gln Thr Gly Phe Thr Thr Thr Asn Glu Ala Phe His Lys Val Gln
            1010                1015                1020
Asp Ala Val Asn Asn Asn Ala Gln Ala Leu Ser Lys Leu Ala Ser
            1025                1030                1035
Glu Leu Ser Asn Thr Phe Gly Ala Ile Ser Ala Ser Ile Gly Asp
            1040                1045                1050
Ile Ile Gln Arg Leu Asp Pro Pro Glu Gln Asp Ala Gln Ile Asp
            1055                1060                1065
Arg Leu Ile Asn Gly Arg Leu Thr Thr Leu Asn Ala Phe Val Ala
            1070                1075                1080
Gln Gln Leu Val Arg Ser Glu Ser Ala Ala Leu Ser Ala Gln Leu
            1085                1090                1095
```

| | | | | | | | | | | |
|---|---|---|---|---|---|---|---|---|---|---|
|Ala|Lys|Asp|Lys|Val|Asn|Glu|Cys|Val|Lys|Ala|Gln|Ser|Lys|Arg|
| |1100| | | |1105| | | |1110| |

Ala Lys Asp Lys Val Asn Glu Cys Val Lys Ala Gln Ser Lys Arg
        1100                1105                1110

Ser Gly Phe Cys Gly Gln Gly Thr His Ile Val Ser Phe Val Val
        1115                1120                1125

Asn Ala Pro Asn Gly Leu Tyr Phe Met His Val Gly Tyr Tyr Pro
        1130                1135                1140

Ser Asn His Ile Glu Val Val Ser Ala Tyr Gly Leu Cys Asp Ala
        1145                1150                1155

Ala Asn Pro Thr Asn Cys Ile Ala Pro Val Asn Gly Tyr Phe Ile
        1160                1165                1170

Lys Thr Asn Asn Thr Arg Ile Val Asp Glu Trp Ser Tyr Thr Gly
        1175                1180                1185

Ser Ser Phe Tyr Ala Pro Glu Pro Ile Thr Ser Leu Asn Thr Lys
        1190                1195                1200

Tyr Val Ala Pro Gln Val Thr Tyr Gln Asn Ile Ser Thr Asn Leu
        1205                1210                1215

Pro Pro Pro Leu Leu Gly Asn Ser Thr Gly Ile Asp Phe Gln Asp
        1220                1225                1230

Glu Leu Asp Glu Phe Phe Lys Asn Val Ser Thr Ser Ile Pro Asn
        1235                1240                1245

Phe Gly Ser Leu Thr Gln Ile Asn Thr Thr Leu Leu Asp Leu Thr
        1250                1255                1260

Tyr Glu Met Leu Ser Leu Gln Gln Val Val Lys Ala Leu Asn Glu
        1265                1270                1275

Ser Tyr Ile Asp Leu Lys Glu Leu Gly Asn Tyr Thr Tyr
        1280                1285                1290

<210> SEQ ID NO 5
<211> LENGTH: 4062
<212> TYPE: DNA
<213> ORGANISM: middle east respiratory syndrome coronavirus

<400> SEQUENCE: 5

```
atgattcact ccgtgttcct gctgatgttc ctgctgactc ctacagagag ctatgtggat    60
gtgggacctg attccgtcaa gagcgcctgc atcgaagtgg acattcagca gaccttcttt   120
gataagacat ggccaagacc catcgacgtg agcaaagccg atggcatcat ctaccctcag   180
gggaggacct attccaatat cacaattact taccagggcc tgttcccata tcagggagac   240
cacggcgata tgtacgtgta ttctgctggc catgcaacag ggaccacacc tcagaagctg   300
tttgtggcta actacagcca ggacgtcaaa cagttcgcaa atggatttgt ggtccgcatc   360
ggcgccgctg caaactctac cggcacagtg atcatttcac ctagcacttc cgcaaccatc   420
cgaaaaatct acccagcctt catgctggga agctccgtgg caattttag cgacgggaaa   480
atgggacggt tctttaacca cacctggtg ctgctgcctg atggatgcgg cacactgctg   540
agggctttct actgtatcct ggagccacgc agcggaaacc actgccccgc aggaaatagc   600
tacacctcct tgccacata tcatactcca gctaccgact gttccgatgg caactacaat   660
cgaaacgcct ctctgaatag tttcaaggaa tacttcaacc tgcgcaattg cacattcatg   720
tacacttata acatcaccga ggacgaaatt ctggagtggt tcggaatcac tcagaccgca   780
cagggcgtgc acctgttttc tagtcgctac gtcgacctgt atggcgggaa catgttccag   840
tttgccactc tgcccgtgta cgataccatc aagtactatt ccatcattcc tcattcaatc   900
cgcagcattc agtccgatcg aaaggcttgg gccgcttttc acgtgtataa actgcagcca   960
```

```
ctgaccttcc tgctggactt tagcgtcgat ggctacatcc ggagagccat tgactgcggg    1020
tttaatgatc tgtcccagct gcactgttct tacgaaagtt tcgacgtgga gtccggcgtg    1080
tattctgtct caagctttga ggccaagccc tctgggagtg tggtcgagca ggctgaagga    1140
gtggagtgcg atttcagtcc tctgctgtca gggaccccccc ctcaggtgta caacttcaag    1200
cggctggtct ttactaactg taactacaat ctgaccaagc tgctgtcact gttcagcgtg    1260
aatgacttta catgctccca gatcagcccc gcagccattg ctagtaactg ttactcctct    1320
ctgatcctgg actacttctc atatccactg agtatgaaga gcgacctgag cgtgagttca    1380
gccggcccca tcagccagtt caactataaa cagagcttca gcaatcctac atgcctgatt    1440
ctggctactg tgccacataa tctgactacc atcactaagc ccctgaaata ctcctatatt    1500
aacaagtgca gccggttcct gtccgacgat agaaccgaag tgccacagct ggtcaacgcc    1560
aatcagtact ctccctgtgt gagtatcgtc ccttcaaccg tgtgggaaga cggggattac    1620
tatagaaaac agctgagccc cctggaggga ggaggatggc tggtggcatc cggatctaca    1680
gtcgccatga ctgagcagct gcagatgggg ttcggaatca cagtgcagta cggcacagac    1740
actaactctg tctgtcccaa gctggaattc gctaacgata ctaagatcgc aagtcagctg    1800
ggaaactgcg tggagtactc tctgtatggc gtgagtggca gggggtcttc cagaattgt    1860 accgcagtgg gcgtccgaca gcagcggttt gtgtacgacg cctatcagaa tctggtcggc    1920
tactatagcg acgatgggaa ctactattgc ctgagggcct gtgtgagcgt ccctgtgtcc    1980
gtcatctacg ataaggaaac caaaacacac gccacactgt tcgggtccgt ggcttgcgag    2040
catattagct ccacaatgtc tcagtacagt agatcaacta ggtcaatgct gaagaggcgc    2100
gatagcacct atggacctct gcagacacca gtggggtgtg tcctgggact ggtgaactct    2160
agtctgtttg tcgaggactg caagctgccc ctgggccaga gcctgtgcgc cctgcccgac    2220 accccccagca ccctgacccc ccggagcgtg cggagcgtgc ccggcgagat gcggctggcc    2280
agcatcgcct tcaaccaccc catccaggtg gaccagctga acagcagcta cttcaagctg    2340
agcatcccca ccaacttcag cttcggcgtg acccaggagt acatccagac caccatccag    2400
aaggtgaccg tggactgcaa gcagtacgtg tgcaacggct tccagaagtg cgagcagctg    2460
ctgcgggagt acggccagtt ctgcagcaag atcaaccagg ccctgcacgg cgccaacctg    2520
cggcaggacg acagcgtgcg gaacctgttc gccagcgtga gagcagcca gagcagcccc    2580 atcatccccg gcttcggcgg cgacttcaac ctgaccctgc tggagcccgt gagcatcagc    2640
accggcagcc ggagcgcccg gagcgccatc gaggacctgc tgttcgacaa ggtgaccatc    2700 gccgacccccg gctacatgca gggctacgac gactgcatgc agcagggccc cgccagcgcc    2760
cgggacctga tctgcgccca gtacgtggcc ggctacaagg tgctgccccc cctgatggac    2820
gtgaacatgg aggccgccta caccagcagc ctgctgggca gcatcgccgg cgtgggctgg    2880
accgccggcc tgagcagctt cgccgccatc ccttcgccc agagcatctt ctaccggctg    2940
aacggcgtgg gcatcaccca gcaggtgctg agcgagaacc agaagctgat cgccaacaag    3000
ttcaaccagg ccctgggcgc catgcagacc ggcttcacca ccaccaacga ggccttccac    3060
aaggtgcagg acgccgtgaa caacaacgcc caggccctga gcaagctggc cagcgagctg    3120
agcaacacct cggcgccat cagcgccagc atcggcgaca tcatccagcg gctggacgtg    3180
ctggagcagg acgcccagat cgaccggctg atcaacggcc ggctgaccac cctgaacgcc    3240
ttcgtggccc agcagctggt gcggagcgag agcgccgccc tgagcgccca gctggccaag    3300
```

-continued

```
gacaaggtga acgagtgcgt gaaggcccag agcaagcgga gcggcttctg cggccagggc      3360
acccacatcg tgagcttcgt ggtgaacgcc cccaacggcc tgtacttcat gcacgtgggc      3420
tactacccca gcaaccacat cgaggtggtg agcgcctacg cctgtgcga cgccgccaac       3480 cccaccaact gcatcgcccc cgtgaacggc tacttcatca agaccaacaa cacccggatc      3540
gtggacgagt ggagctacac cggcagcagc ttctacgccc ccgagcccat caccagcctg      3600
aacaccaagt acgtggcccc ccaggtgacc taccagaaca tcagcaccaa cctgccccc       3660 cccctgctgg gcaacagcac cggcatcgac ttccaggacg agctggacga gttcttcaag      3720
aacgtgagca ccagcatccc caacttcggc agcctgaccc agatcaacac cacccctgctg    3780 gacctgacct acgagatgct gagcctgcag caggtggtga aggccctgaa cgagagctac      3840
atcgacctga aggagctggg caactacacc tactacaaca gtggccctg gtacatctgg       3900 ctgggcttca tcgccggcct ggtggccctg gccctgtgcg tgttcttcat cctgtgctgc      3960
accggctgcg gcaccaactg catgggcaag ctgaagtgca accggtgctg cgaccggtac      4020
gaggagtacg acctggagcc ccacaaggtg cacgtgcact ga                         4062
```

<210> SEQ ID NO 6
<211> LENGTH: 1255
<212> TYPE: PRT
<213> ORGANISM: severe acute respiratory syndrome coronavirus

<400> SEQUENCE: 6

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240
```

```
Ala Gln Asp Ile Trp Gly Thr Ser Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
            275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
```

-continued

```
                660                 665                 670
Ser Ile Val Ala Tyr Thr Met Ser Leu Gly Ala Asp Ser Ile Ala
                675                 680                 685

Tyr Ser Asn Asn Thr Ile Ala Ile Pro Thr Asn Phe Ser Ile Ser Ile
                690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
                755                 760                 765

Gln Met Tyr Lys Thr Pro Thr Leu Lys Tyr Phe Gly Gly Phe Asn Phe
                770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
                835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
                900                 905                 910

Ile Ser Gln Ile Gln Glu Ser Leu Thr Thr Thr Ser Thr Ala Leu Gly
                915                 920                 925

Lys Leu Gln Asp Val Val Asn Gln Asn Ala Gln Ala Leu Asn Thr Leu
                930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
                980                 985                 990

Gln Leu Ile Arg Ala Ala Glu Ile Arg Ala Ser Ala Asn Leu Ala Ala
                995                 1000                1005

Thr Lys Met Ser Glu Cys Val Leu Gly Gln Ser Lys Arg Val Asp
                1010                1015                1020

Phe Cys Gly Lys Gly Tyr His Leu Met Ser Phe Pro Gln Ala Ala
                1025                1030                1035

Pro His Gly Val Val Phe Leu His Val Thr Tyr Val Pro Ser Gln
                1040                1045                1050

Glu Arg Asn Phe Thr Thr Ala Pro Ala Ile Cys His Glu Gly Lys
                1055                1060                1065

Ala Tyr Phe Pro Arg Glu Gly Val Phe Val Phe Asn Gly Thr Ser
                1070                1075                1080
```

-continued

```
Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255

<210> SEQ ID NO 7
<211> LENGTH: 1190
<212> TYPE: PRT
<213> ORGANISM: Artificial Sequence
<220> FEATURE:
<223> OTHER INFORMATION: recombinant coronavirus spike protein

<400> SEQUENCE: 7

Met Phe Ile Phe Leu Leu Phe Leu Thr Leu Thr Ser Gly Ser Asp Leu
1               5                   10                  15

Asp Arg Cys Thr Thr Phe Asp Val Gln Ala Pro Asn Tyr Thr Gln
                20                  25                  30

His Thr Ser Ser Met Arg Gly Val Tyr Tyr Pro Asp Glu Ile Phe Arg
                35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
                100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175
```

```
Gly Asn Phe Lys His Leu Arg Glu Phe Val Phe Lys Asn Lys Asp Gly
                180                 185                 190

Phe Leu Tyr Val Tyr Lys Gly Tyr Gln Pro Ile Asp Val Val Arg Asp
            195                 200                 205

Leu Pro Ser Gly Phe Asn Thr Leu Lys Pro Ile Phe Lys Leu Pro Leu
        210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
        290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
        370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
        450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
        530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
            580                 585                 590
```

```
Glu Val Ala Val Leu Tyr Gln Asp Val Asn Cys Thr Asp Val Ser Thr
            595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
        690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
            770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
                900                 905                 910

Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
930                 935                 940

Val Lys Gln Leu Ser Ser Asn Phe Gly Ala Ile Ser Ser Val Leu Asn
945                 950                 955                 960

Asp Ile Leu Ser Arg Leu Asp Pro Pro Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
            995                 1000                1005

Thr Lys Met Ser Glu Cys Val Leu Gly Gln Ser Lys Arg Val Asp
```

-continued

```
            1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln
    1190

<210> SEQ ID NO 8
<211> LENGTH: 1351
<212> TYPE: PRT
<213> ORGANISM: human coronavirus HKU1

<400> SEQUENCE: 8

Met Phe Leu Ile Ile Phe Ile Leu Pro Thr Thr Leu Ala Val Ile Gly
1               5                   10                  15

Asp Phe Asn Cys Thr Asn Ser Phe Ile Asn Asp Tyr Asn Lys Thr Ile
                20                  25                  30

Pro Arg Ile Ser Glu Asp Val Val Asp Val Ser Leu Gly Leu Gly Thr
            35                  40                  45

Tyr Tyr Val Leu Asn Arg Val Tyr Leu Asn Thr Thr Leu Leu Phe Thr
        50                  55                  60

Gly Tyr Phe Pro Lys Ser Gly Ala Asn Phe Arg Asp Leu Ala Leu Lys
65                  70                  75                  80

Gly Ser Ile Tyr Leu Ser Thr Leu Trp Tyr Lys Pro Pro Phe Leu Ser
                85                  90                  95

Asp Phe Asn Asn Gly Ile Phe Ser Lys Val Lys Asn Thr Lys Leu Tyr
            100                 105                 110

Val Asn Asn Thr Leu Tyr Ser Glu Phe Ser Thr Ile Val Ile Gly Ser
        115                 120                 125

Val Phe Val Asn Thr Ser Tyr Thr Ile Val Val Gln Pro His Asn Gly
    130                 135                 140

Ile Leu Glu Ile Thr Ala Cys Gln Tyr Thr Met Cys Glu Tyr Pro His
145                 150                 155                 160

Thr Val Cys Lys Ser Lys Gly Ser Ile Arg Asn Glu Ser Trp His Ile
                165                 170                 175
```

```
Asp Ser Ser Glu Pro Leu Cys Leu Phe Lys Lys Asn Phe Thr Tyr Asn
            180                 185                 190

Val Ser Ala Asp Trp Leu Tyr Phe His Phe Tyr Gln Glu Arg Gly Val
        195                 200                 205

Phe Tyr Ala Tyr Tyr Ala Asp Val Gly Met Pro Thr Thr Phe Leu Phe
        210                 215                 220

Ser Leu Tyr Leu Gly Thr Ile Leu Ser His Tyr Tyr Val Met Pro Leu
225                 230                 235                 240

Thr Cys Asn Ala Ile Ser Ser Asn Thr Asp Asn Glu Thr Leu Glu Tyr
                245                 250                 255

Trp Val Thr Pro Leu Ser Arg Arg Gln Tyr Leu Leu Asn Phe Asp Glu
            260                 265                 270

His Gly Val Ile Thr Asn Ala Val Asp Cys Ser Ser Ser Phe Leu Ser
        275                 280                 285

Glu Ile Gln Cys Lys Thr Gln Ser Phe Ala Pro Asn Thr Gly Val Tyr
        290                 295                 300

Asp Leu Ser Gly Phe Thr Val Lys Pro Val Ala Thr Val Tyr Arg Arg
305                 310                 315                 320

Ile Pro Asn Leu Pro Asp Cys Asp Ile Asp Asn Trp Leu Asn Asn Val
                325                 330                 335

Ser Val Pro Ser Pro Leu Asn Trp Glu Arg Arg Ile Phe Ser Asn Cys
            340                 345                 350

Asn Phe Asn Leu Ser Thr Leu Leu Arg Leu Val His Val Asp Ser Phe
        355                 360                 365

Ser Cys Asn Asn Leu Asp Lys Ser Lys Ile Phe Gly Ser Cys Phe Asn
        370                 375                 380

Ser Ile Thr Val Asp Lys Phe Ala Ile Pro Asn Arg Arg Arg Asp Asp
385                 390                 395                 400

Leu Gln Leu Gly Ser Ser Gly Phe Leu Gln Ser Ser Asn Tyr Lys Ile
                405                 410                 415

Asp Ile Ser Ser Ser Ser Cys Gln Leu Tyr Tyr Ser Leu Pro Leu Val
            420                 425                 430

Asn Val Thr Ile Asn Asn Phe Asn Pro Ser Ser Trp Asn Arg Arg Tyr
        435                 440                 445

Gly Phe Gly Ser Phe Asn Leu Ser Ser Tyr Asp Val Val Tyr Ser Asp
        450                 455                 460

His Cys Phe Ser Val Asn Ser Asp Phe Cys Pro Cys Ala Asp Pro Ser
465                 470                 475                 480

Val Val Asn Ser Cys Ala Lys Ser Lys Pro Pro Ser Ala Ile Cys Pro
                485                 490                 495

Ala Gly Thr Lys Tyr Arg His Cys Asp Leu Asp Thr Thr Leu Tyr Val
            500                 505                 510

Lys Asn Trp Cys Arg Cys Ser Cys Leu Pro Asp Pro Ile Ser Thr Tyr
        515                 520                 525

Ser Pro Asn Thr Cys Pro Gln Lys Lys Val Val Val Gly Ile Gly Glu
        530                 535                 540

His Cys Pro Gly Leu Gly Ile Asn Glu Glu Lys Cys Gly Thr Gln Leu
545                 550                 555                 560

Asn His Ser Ser Cys Phe Cys Ser Pro Asp Ala Phe Leu Gly Trp Ser
                565                 570                 575

Phe Asp Ser Cys Ile Ser Asn Asn Arg Cys Asn Ile Phe Ser Asn Phe
            580                 585                 590

Ile Phe Asn Gly Ile Asn Ser Gly Thr Thr Cys Ser Asn Asp Leu Leu
```

-continued

```
              595                 600                 605
Tyr Ser Asn Thr Glu Ile Ser Thr Gly Val Cys Val Asn Tyr Asp Leu
        610                 615                 620

Tyr Gly Ile Thr Gly Gln Gly Ile Phe Lys Glu Val Ser Ala Ala Tyr
625                 630                 635                 640

Tyr Asn Asn Trp Gln Asn Leu Leu Tyr Asp Ser Asn Gly Asn Ile Ile
            645                 650                 655

Gly Phe Lys Asp Phe Leu Thr Asn Lys Thr Tyr Thr Ile Leu Pro Cys
        660                 665                 670

Tyr Ser Gly Arg Val Ser Ala Ala Phe Tyr Gln Asn Ser Ser Ser Pro
        675                 680                 685

Ala Leu Leu Tyr Arg Asn Leu Lys Cys Ser Tyr Val Leu Asn Asn Ile
        690                 695                 700

Ser Phe Ile Ser Gln Pro Phe Tyr Phe Asp Ser Tyr Leu Gly Cys Val
705                 710                 715                 720

Leu Asn Ala Val Asn Leu Thr Ser Tyr Ser Val Ser Ser Cys Asp Leu
            725                 730                 735

Arg Met Gly Ser Gly Phe Cys Ile Asp Tyr Ala Leu Pro Ser Ser Arg
            740                 745                 750

Arg Lys Arg Arg Gly Ile Ser Ser Pro Tyr Arg Phe Val Thr Phe Glu
        755                 760                 765

Pro Phe Asn Val Ser Phe Val Asn Asp Ser Val Glu Thr Val Gly Gly
770                 775                 780

Leu Phe Glu Ile Gln Ile Pro Thr Asn Phe Thr Ile Ala Gly His Glu
785                 790                 795                 800

Glu Phe Ile Gln Thr Ser Ser Pro Lys Val Thr Ile Asp Cys Ser Ala
            805                 810                 815

Phe Val Cys Ser Asn Tyr Ala Ala Cys His Asp Leu Leu Ser Glu Tyr
            820                 825                 830

Gly Thr Phe Cys Asp Asn Ile Asn Ser Ile Leu Asn Glu Val Asn Asp
            835                 840                 845

Leu Leu Asp Ile Thr Gln Leu Gln Val Ala Asn Ala Leu Met Gln Gly
850                 855                 860

Val Thr Leu Ser Ser Asn Leu Asn Thr Asn Leu His Ser Asp Val Asp
865                 870                 875                 880

Asn Ile Asp Phe Lys Ser Leu Leu Gly Cys Leu Gly Ser Gln Cys Gly
            885                 890                 895

Ser Ser Ser Arg Ser Leu Leu Glu Asp Leu Leu Phe Asn Lys Val Lys
            900                 905                 910

Leu Ser Asp Val Gly Phe Val Glu Ala Tyr Asn Asn Cys Thr Gly Gly
        915                 920                 925

Ser Glu Ile Arg Asp Leu Leu Cys Val Gln Ser Phe Asn Gly Ile Lys
        930                 935                 940

Val Leu Pro Pro Ile Leu Ser Glu Thr Gln Ile Ser Gly Tyr Thr Thr
945                 950                 955                 960

Ala Ala Thr Val Ala Ala Met Phe Pro Pro Trp Ser Ala Ala Ala Gly
            965                 970                 975

Val Pro Phe Ser Leu Asn Val Gln Tyr Arg Ile Asn Gly Leu Gly Val
        980                 985                 990

Thr Met Asp Val Leu Asn Lys Asn Gln Lys Leu Ile Ala Asn Ala Phe
        995                 1000                1005

Asn Lys Ala Leu Leu Ser Ile Gln Asn Gly Phe Thr Ala Thr Asn
        1010                1015                1020
```

Ser Ala Leu Ala Lys Ile Gln Ser Val Val Asn Ala Asn Ala Gln
    1025            1030                1035

Ala Leu Asn Ser Leu Leu Gln Gln Leu Phe Asn Lys Phe Gly Ala
    1040            1045                1050

Ile Ser Ser Ser Leu Gln Glu Ile Leu Ser Arg Leu Asp Asn Leu
    1055            1060                1065

Glu Ala Gln Val Gln Ile Asp Arg Leu Ile Asn Gly Arg Leu Thr
    1070            1075                1080

Ala Leu Asn Ala Tyr Val Ser Gln Gln Leu Ser Asp Ile Thr Leu
    1085            1090                1095

Ile Lys Ala Gly Ala Ser Arg Ala Ile Glu Lys Val Asn Glu Cys
    1100            1105                1110

Val Lys Ser Gln Ser Pro Arg Ile Asn Phe Cys Gly Asn Gly Asn
    1115            1120                1125

His Ile Leu Ser Leu Val Gln Asn Ala Pro Tyr Gly Leu Leu Phe
    1130            1135                1140

Ile His Phe Ser Tyr Lys Pro Thr Ser Phe Lys Thr Val Leu Val
    1145            1150                1155

Ser Pro Gly Leu Cys Leu Ser Gly Asp Arg Gly Ile Ala Pro Lys
    1160            1165                1170

Gln Gly Tyr Phe Ile Lys Gln Asn Asp Ser Trp Met Phe Thr Gly
    1175            1180                1185

Ser Ser Tyr Tyr Tyr Pro Glu Pro Ile Ser Asp Lys Asn Val Val
    1190            1195                1200

Phe Met Asn Ser Cys Ser Val Asn Phe Thr Lys Ala Pro Phe Ile
    1205            1210                1215

Tyr Leu Asn Asn Ser Ile Pro Asn Leu Ser Asp Phe Glu Ala Glu
    1220            1225                1230

Leu Ser Leu Trp Phe Lys Asn His Thr Ser Ile Ala Pro Asn Leu
    1235            1240                1245

Thr Phe Asn Ser His Ile Asn Ala Thr Phe Leu Asp Leu Tyr Tyr
    1250            1255                1260

Glu Met Asn Val Ile Gln Glu Ser Ile Lys Ser Leu Asn Ser Ser
    1265            1270                1275

Phe Ile Asn Leu Lys Glu Ile Gly Thr Tyr Glu Met Tyr Val Lys
    1280            1285                1290

Trp Pro Trp Tyr Ile Trp Leu Leu Ile Val Ile Leu Phe Ile Ile
    1295            1300                1305

Phe Leu Met Ile Leu Phe Phe Ile Cys Cys Cys Thr Gly Cys Gly
    1310            1315                1320

Ser Ala Cys Phe Ser Lys Cys His Asn Cys Cys Asp Glu Tyr Gly
    1325            1330                1335

Gly His Asn Asp Phe Val Ile Lys Ala Ser His Asp Asp
    1340            1345                1350

<210> SEQ ID NO 9
<211> LENGTH: 1276
<212> TYPE: PRT
<213> ORGANISM: Artificial Sequence
<220> FEATURE:
<223> OTHER INFORMATION: recombinant coronavirus spike protein

<400> SEQUENCE: 9

Met Phe Leu Ile Ile Phe Ile Leu Pro Thr Thr Leu Ala Val Ile Gly
1               5                   10                  15

-continued

```
Asp Phe Asn Cys Thr Asn Ser Phe Ile Asn Asp Tyr Asn Lys Thr Ile
             20                  25                  30
Pro Arg Ile Ser Glu Asp Val Val Asp Val Ser Leu Gly Leu Gly Thr
         35                  40                  45
Tyr Tyr Val Leu Asn Arg Val Tyr Leu Asn Thr Thr Leu Leu Phe Thr
 50                  55                  60
Gly Tyr Phe Pro Lys Ser Gly Ala Asn Phe Arg Asp Leu Ala Leu Lys
 65                  70                  75                  80
Gly Ser Ile Tyr Leu Ser Thr Leu Trp Tyr Lys Pro Pro Phe Leu Ser
                 85                  90                  95
Asp Phe Asn Asn Gly Ile Phe Ser Lys Val Lys Asn Thr Lys Leu Tyr
             100                 105                 110
Val Asn Asn Thr Leu Tyr Ser Glu Phe Ser Thr Ile Val Ile Gly Ser
         115                 120                 125
Val Phe Val Asn Thr Ser Tyr Thr Ile Val Val Gln Pro His Asn Gly
 130                 135                 140
Ile Leu Glu Ile Thr Ala Cys Gln Tyr Thr Met Cys Glu Tyr Pro His
145                 150                 155                 160
Thr Val Cys Lys Ser Lys Gly Ser Ile Arg Asn Glu Ser Trp His Ile
                 165                 170                 175
Asp Ser Ser Glu Pro Leu Cys Leu Phe Lys Lys Asn Phe Thr Tyr Asn
             180                 185                 190
Val Ser Ala Asp Trp Leu Tyr Phe His Phe Tyr Gln Glu Arg Gly Val
         195                 200                 205
Phe Tyr Ala Tyr Ala Asp Val Gly Met Pro Thr Thr Phe Leu Phe
 210                 215                 220
Ser Leu Tyr Leu Gly Thr Ile Leu Ser His Tyr Tyr Val Met Pro Leu
225                 230                 235                 240
Thr Cys Asn Ala Ile Ser Ser Asn Thr Asp Asn Glu Thr Leu Glu Tyr
                 245                 250                 255
Trp Val Thr Pro Leu Ser Arg Arg Gln Tyr Leu Leu Asn Phe Asp Glu
             260                 265                 270
His Gly Val Ile Thr Asn Ala Val Asp Cys Ser Ser Ser Phe Leu Ser
         275                 280                 285
Glu Ile Gln Cys Lys Thr Gln Ser Phe Ala Pro Asn Thr Gly Val Tyr
 290                 295                 300
Asp Leu Ser Gly Phe Thr Val Lys Pro Val Ala Thr Val Tyr Arg Arg
305                 310                 315                 320
Ile Pro Asn Leu Pro Asp Cys Asp Ile Asp Asn Trp Leu Asn Asn Val
                 325                 330                 335
Ser Val Pro Ser Pro Leu Asn Trp Glu Arg Arg Ile Phe Ser Asn Cys
             340                 345                 350
Asn Phe Asn Leu Ser Thr Leu Leu Arg Leu Val His Val Asp Ser Phe
         355                 360                 365
Ser Cys Asn Asn Leu Asp Lys Ser Lys Ile Phe Gly Ser Cys Phe Asn
 370                 375                 380
Ser Ile Thr Val Asp Lys Phe Ala Ile Pro Asn Arg Arg Arg Asp Asp
385                 390                 395                 400
Leu Gln Leu Gly Ser Ser Gly Phe Leu Gln Ser Ser Asn Tyr Lys Ile
                 405                 410                 415
Asp Ile Ser Ser Ser Ser Cys Gln Leu Tyr Tyr Ser Leu Pro Leu Val
             420                 425                 430
```

```
Asn Val Thr Ile Asn Asn Phe Asn Pro Ser Ser Trp Asn Arg Arg Tyr
            435                 440                 445

Gly Phe Gly Ser Phe Asn Leu Ser Ser Tyr Asp Val Val Tyr Ser Asp
    450                 455                 460

His Cys Phe Ser Val Asn Ser Asp Phe Cys Pro Cys Ala Asp Pro Ser
465                 470                 475                 480

Val Val Asn Ser Cys Ala Lys Ser Lys Pro Pro Ser Ala Ile Cys Pro
                485                 490                 495

Ala Gly Thr Lys Tyr Arg His Cys Asp Leu Asp Thr Thr Leu Tyr Val
            500                 505                 510

Lys Asn Trp Cys Arg Cys Ser Cys Leu Pro Asp Pro Ile Ser Thr Tyr
            515                 520                 525

Ser Pro Asn Thr Cys Pro Gln Lys Lys Val Val Gly Ile Gly Glu
    530                 535                 540

His Cys Pro Gly Leu Gly Ile Asn Glu Glu Lys Cys Gly Thr Gln Leu
545                 550                 555                 560

Asn His Ser Ser Cys Phe Cys Ser Pro Asp Ala Phe Leu Gly Trp Ser
                565                 570                 575

Phe Asp Ser Cys Ile Ser Asn Asn Arg Cys Asn Ile Phe Ser Asn Phe
            580                 585                 590

Ile Phe Asn Gly Ile Asn Ser Gly Thr Thr Cys Ser Asn Asp Leu Leu
    595                 600                 605

Tyr Ser Asn Thr Glu Ile Ser Thr Gly Val Cys Val Asn Tyr Asp Leu
            610                 615                 620

Tyr Gly Ile Thr Gly Gln Gly Ile Phe Lys Glu Val Ser Ala Ala Tyr
625                 630                 635                 640

Tyr Asn Asn Trp Gln Asn Leu Leu Tyr Asp Ser Asn Gly Asn Ile Ile
            645                 650                 655

Gly Phe Lys Asp Phe Leu Thr Asn Lys Thr Tyr Thr Ile Leu Pro Cys
            660                 665                 670

Tyr Ser Gly Arg Val Ser Ala Ala Phe Tyr Gln Asn Ser Ser Ser Pro
    675                 680                 685

Ala Leu Leu Tyr Arg Asn Leu Lys Cys Ser Tyr Val Leu Asn Asn Ile
    690                 695                 700

Ser Phe Ile Ser Gln Pro Phe Tyr Phe Asp Ser Tyr Leu Gly Cys Val
705                 710                 715                 720

Leu Asn Ala Val Asn Leu Thr Ser Tyr Ser Val Ser Ser Cys Asp Leu
                725                 730                 735

Arg Met Gly Ser Gly Phe Cys Ile Asp Tyr Ala Leu Pro Ser Ser Gly
            740                 745                 750

Gly Ser Gly Ser Gly Ile Ser Ser Pro Tyr Arg Phe Val Thr Phe Glu
    755                 760                 765

Pro Phe Asn Val Ser Phe Val Asn Asp Ser Val Glu Thr Val Gly Gly
    770                 775                 780

Leu Phe Glu Ile Gln Ile Pro Thr Asn Phe Thr Ile Ala Gly His Glu
785                 790                 795                 800

Glu Phe Ile Gln Thr Ser Ser Pro Lys Val Thr Ile Asp Cys Ser Ala
            805                 810                 815

Phe Val Cys Ser Asn Tyr Ala Ala Cys His Asp Leu Leu Ser Glu Tyr
            820                 825                 830

Gly Thr Phe Cys Asp Asn Ile Asn Ser Ile Leu Asn Glu Val Asn Asp
            835                 840                 845

Leu Leu Asp Ile Thr Gln Leu Gln Val Ala Asn Ala Leu Met Gln Gly
```

```
                850              855              860
Val Thr Leu Ser Ser Asn Leu Asn Thr Asn Leu His Ser Asp Val Asp
865                  870              875              880

Asn Ile Asp Phe Lys Ser Leu Leu Gly Cys Leu Gly Ser Gln Cys Gly
                885              890              895

Ser Ser Ser Arg Ser Leu Leu Glu Asp Leu Leu Phe Asn Lys Val Lys
            900              905              910

Leu Ser Asp Val Gly Phe Val Glu Ala Tyr Asn Asn Cys Thr Gly Gly
        915              920              925

Ser Glu Ile Arg Asp Leu Leu Cys Val Gln Ser Phe Asn Gly Ile Lys
    930              935              940

Val Leu Pro Pro Ile Leu Ser Glu Thr Gln Ile Ser Gly Tyr Thr Thr
945              950              955              960

Ala Ala Thr Val Ala Ala Met Phe Pro Pro Trp Ser Ala Ala Ala Gly
                965              970              975

Val Pro Phe Ser Leu Asn Val Gln Tyr Arg Ile Asn Gly Leu Gly Val
            980              985              990

Thr Met Asp Val Leu Asn Lys Asn Gln Lys Leu Ile Ala Asn Ala Phe
        995              1000             1005

Asn Lys Ala Leu Leu Ser Ile Gln Asn Gly Phe Thr Ala Thr Asn
    1010             1015             1020

Ser Ala Leu Ala Lys Ile Gln Ser Val Val Asn Ala Asn Ala Gln
    1025             1030             1035

Ala Leu Asn Ser Leu Leu Gln Gln Leu Phe Asn Lys Phe Gly Ala
    1040             1045             1050

Ile Ser Ser Ser Leu Gln Glu Ile Leu Ser Arg Leu Asp Pro Pro
    1055             1060             1065

Glu Ala Gln Val Gln Ile Asp Arg Leu Ile Asn Gly Arg Leu Thr
    1070             1075             1080

Ala Leu Asn Ala Tyr Val Ser Gln Gln Leu Ser Asp Ile Thr Leu
    1085             1090             1095

Ile Lys Ala Gly Ala Ser Arg Ala Ile Glu Lys Val Asn Glu Cys
    1100             1105             1110

Val Lys Ser Gln Ser Pro Arg Ile Asn Phe Cys Gly Asn Gly Asn
    1115             1120             1125

His Ile Leu Ser Leu Val Gln Asn Ala Pro Tyr Gly Leu Leu Phe
    1130             1135             1140

Ile His Phe Ser Tyr Lys Pro Thr Ser Phe Lys Thr Val Leu Val
    1145             1150             1155

Ser Pro Gly Leu Cys Leu Ser Gly Asp Arg Gly Ile Ala Pro Lys
    1160             1165             1170

Gln Gly Tyr Phe Ile Lys Gln Asn Asp Ser Trp Met Phe Thr Gly
    1175             1180             1185

Ser Ser Tyr Tyr Tyr Pro Glu Pro Ile Ser Asp Lys Asn Val Val
    1190             1195             1200

Phe Met Asn Ser Cys Ser Val Asn Phe Thr Lys Ala Pro Phe Ile
    1205             1210             1215

Tyr Leu Asn Asn Ser Ile Pro Asn Leu Ser Asp Phe Glu Ala Glu
    1220             1225             1230

Leu Ser Leu Trp Phe Lys Asn His Thr Ser Ile Ala Pro Asn Leu
    1235             1240             1245

Thr Phe Asn Ser His Ile Asn Ala Thr Phe Leu Asp Leu Tyr Tyr
    1250             1255             1260
```

-continued

```
Glu Met Asn Val Ile Gln Glu Ser Ile Lys Ser Leu Asn
1265                1270                1275
```

<210> SEQ ID NO 10
<211> LENGTH: 1362
<212> TYPE: PRT
<213> ORGANISM: human coronavirus OC43

<400> SEQUENCE: 10

```
Met Phe Leu Ile Leu Leu Ile Ser Leu Pro Thr Ala Phe Ala Val Ile
1               5                   10                  15

Gly Asp Leu Lys Cys Pro Leu Asp Ser Arg Thr Gly Ser Leu Asn Asn
            20                  25                  30

Ile Asp Thr Gly Pro Pro Ser Ile Ser Thr Ala Thr Val Asp Val Thr
        35                  40                  45

Asn Gly Leu Gly Thr Tyr Tyr Val Leu Asp Arg Val Tyr Leu Asn Thr
    50                  55                  60

Thr Leu Phe Leu Asn Gly Tyr Tyr Pro Thr Ser Gly Ser Thr Tyr Arg
65                  70                  75                  80

Asn Met Ala Leu Lys Gly Thr Asp Lys Leu Ser Thr Leu Trp Phe Lys
                85                  90                  95

Pro Pro Phe Leu Ser Asp Phe Ile Asn Gly Ile Phe Ala Lys Val Lys
            100                 105                 110

Asn Thr Lys Val Phe Lys Asp Gly Val Met Tyr Ser Glu Phe Pro Ala
        115                 120                 125

Ile Thr Ile Gly Ser Thr Phe Val Asn Thr Ser Tyr Ser Val Val Val
    130                 135                 140

Gln Pro Arg Thr Ile Asn Ser Thr Gln Asp Gly Val Asn Lys Leu Gln
145                 150                 155                 160

Gly Leu Leu Glu Val Ser Val Cys Gln Tyr Asn Met Cys Glu Tyr Pro
                165                 170                 175

His Thr Ile Cys His Pro Lys Leu Gly Asn His Phe Lys Glu Leu Trp
            180                 185                 190

His Met Asp Thr Gly Val Val Ser Cys Leu Tyr Lys Arg Asn Phe Thr
        195                 200                 205

Tyr Asp Val Asn Ala Thr Tyr Leu Tyr Phe His Phe Tyr Gln Glu Gly
    210                 215                 220

Gly Thr Phe Tyr Ala Tyr Phe Thr Asp Thr Gly Val Val Thr Lys Phe
225                 230                 235                 240

Leu Phe Asn Val Tyr Leu Gly Met Ala Leu Ser His Tyr Tyr Val Met
                245                 250                 255

Pro Leu Thr Cys Ile Ser Arg Arg Asp Ile Gly Phe Thr Leu Glu Tyr
            260                 265                 270

Trp Val Thr Pro Leu Thr Ser Arg Gln Tyr Leu Leu Ala Phe Asn Gln
        275                 280                 285

Asp Gly Ile Ile Phe Asn Ala Val Asp Cys Met Ser Asp Phe Met Ser
    290                 295                 300

Glu Ile Lys Cys Lys Thr Gln Ser Ile Ala Pro Pro Thr Gly Val Tyr
305                 310                 315                 320

Glu Leu Asn Gly Tyr Thr Val Gln Pro Ile Ala Asp Val Tyr Arg Arg
                325                 330                 335

Lys Pro Asp Leu Pro Asn Cys Asn Ile Glu Ala Trp Leu Asn Asp Lys
            340                 345                 350

Ser Val Pro Ser Pro Leu Asn Trp Glu Arg Lys Thr Phe Ser Asn Cys
```

```
                355                 360                 365
Asn Phe Asn Met Ser Ser Leu Met Ser Phe Ile Gln Ala Asp Ser Phe
        370                 375                 380
Thr Cys Asn Asn Ile Asp Ala Ala Lys Ile Tyr Gly Met Cys Phe Ser
385                 390                 395                 400
Ser Ile Thr Ile Asp Lys Phe Ala Ile Pro Asn Gly Arg Lys Val Asp
                405                 410                 415
Leu Gln Leu Gly Asn Leu Gly Tyr Leu Gln Ser Phe Asn Tyr Arg Ile
        420                 425                 430
Asp Thr Thr Ala Thr Ser Cys Gln Leu Tyr Tyr Asn Leu Pro Ala Ala
        435                 440                 445
Asn Val Ser Val Ser Arg Phe Asn Pro Ser Thr Trp Asn Lys Arg Phe
    450                 455                 460
Gly Phe Ile Glu Asn Ser Val Phe Lys Pro Gln Pro Ala Gly Val Leu
465                 470                 475                 480
Thr Asn His Asp Val Val Tyr Ala Gln His Cys Phe Lys Ala Pro Lys
                485                 490                 495
Asn Phe Cys Pro Cys Lys Leu Asn Ser Ser Leu Cys Val Gly Ser Gly
            500                 505                 510
Pro Gly Lys Asn Asn Gly Ile Gly Thr Cys Pro Ala Gly Thr Asn Tyr
        515                 520                 525
Leu Thr Cys His Asn Leu Cys Asn Pro Asp Pro Ile Thr Phe Thr Gly
    530                 535                 540
Pro Tyr Lys Cys Pro Gln Thr Lys Ser Leu Val Gly Ile Gly Glu His
545                 550                 555                 560
Cys Ser Gly Leu Ala Val Lys Ser Asp Tyr Cys Gly Gly Asn Pro Cys
            565                 570                 575
Thr Cys Gln Pro Gln Ala Phe Leu Gly Trp Ser Ala Asp Ser Cys Leu
        580                 585                 590
Gln Gly Asp Lys Cys Asn Ile Phe Ala Asn Leu Ile Leu His Asp Val
        595                 600                 605
Asn Ser Gly Leu Thr Cys Ser Thr Asp Leu Gln Lys Ala Asn Thr Asp
    610                 615                 620
Ile Lys Leu Gly Val Cys Val Asn Tyr Asp Leu Tyr Gly Ile Ser Gly
625                 630                 635                 640
Gln Gly Ile Phe Val Glu Val Asn Ala Thr Tyr Tyr Asn Ser Trp Gln
            645                 650                 655
Asn Leu Leu Tyr Asp Ser Asn Gly Asn Leu Tyr Gly Phe Arg Asp Tyr
        660                 665                 670
Ile Thr Asn Arg Thr Phe Met Ile Arg Ser Cys Tyr Ser Gly Arg Val
        675                 680                 685
Ser Ala Ala Phe His Ala Asn Ser Ser Glu Pro Ala Leu Leu Phe Arg
    690                 695                 700
Asn Ile Lys Cys Asn Tyr Val Phe Asn Asn Ser Leu Ile Arg Gln Leu
705                 710                 715                 720
Gln Pro Ile Asn Tyr Phe Asp Ser Tyr Leu Gly Cys Val Val Asn Ala
            725                 730                 735
Tyr Asn Ser Thr Ala Ile Ser Val Gln Thr Cys Asp Leu Thr Val Gly
        740                 745                 750
Ser Gly Tyr Cys Val Asp Tyr Ser Lys Asn Arg Arg Ser Arg Arg Ala
        755                 760                 765
Ile Thr Thr Gly Tyr Arg Phe Thr Asn Phe Glu Pro Phe Thr Val Asn
    770                 775                 780
```

```
Ser Val Asn Asp Ser Leu Glu Pro Val Gly Gly Leu Tyr Glu Ile Gln
785                 790                 795                 800

Ile Pro Ser Glu Phe Thr Ile Gly Asn Met Glu Glu Phe Ile Gln Thr
            805                 810                 815

Ser Ser Pro Lys Val Thr Ile Asp Cys Ala Ala Phe Val Cys Gly Asp
            820                 825                 830

Tyr Ala Ala Cys Lys Ser Gln Leu Val Glu Tyr Gly Ser Phe Cys Asp
            835                 840                 845

Asn Ile Asn Ala Ile Leu Thr Glu Val Asn Glu Leu Leu Asp Thr Thr
850                 855                 860

Gln Leu Gln Val Ala Asn Ser Leu Met Asn Gly Val Thr Leu Ser Thr
865                 870                 875                 880

Lys Leu Lys Asp Gly Val Asn Phe Asn Val Asp Asp Ile Asn Phe Ser
                885                 890                 895

Ser Val Leu Gly Cys Leu Gly Ser Glu Cys Ser Lys Ala Ser Ser Arg
            900                 905                 910

Ser Ala Ile Glu Asp Leu Leu Phe Asp Lys Val Lys Leu Ser Asp Val
            915                 920                 925

Gly Phe Val Ala Ala Tyr Asn Asn Cys Thr Gly Gly Ala Glu Ile Arg
930                 935                 940

Asp Leu Ile Cys Val Gln Ser Tyr Lys Gly Ile Lys Val Leu Pro Pro
945                 950                 955                 960

Leu Leu Ser Glu Asn Gln Ile Ser Gly Tyr Thr Leu Ala Ala Thr Ser
                965                 970                 975

Ala Ser Leu Phe Pro Pro Trp Thr Ala Ala Gly Val Pro Phe Tyr
            980                 985                 990

Leu Asn Val Gln Tyr Arg Ile Asn Gly Leu Gly Val Thr Met Asp Val
            995                 1000                1005

Leu Ser Gln Asn Gln Lys Leu Ile Ala Asn Ala Phe Asn Asn Ala
    1010                1015                1020

Leu Asp Ala Ile Gln Glu Gly Phe Asp Ala Thr Asn Ser Ala Leu
    1025                1030                1035

Val Lys Ile Gln Ala Val Val Asn Ala Asn Ala Glu Ala Leu Asn
    1040                1045                1050

Asn Leu Leu Gln Gln Leu Ser Asn Arg Phe Gly Ala Ile Ser Ser
    1055                1060                1065

Ser Leu Gln Glu Ile Leu Ser Arg Leu Asp Ala Leu Glu Ala Glu
    1070                1075                1080

Ala Gln Ile Asp Arg Leu Ile Asn Gly Arg Leu Thr Ala Leu Asn
    1085                1090                1095

Ala Tyr Val Ser Gln Gln Leu Ser Asp Ser Thr Leu Val Lys Phe
    1100                1105                1110

Ser Ala Ala Gln Ala Met Glu Lys Val Asn Glu Cys Val Lys Ser
    1115                1120                1125

Gln Ser Ser Arg Ile Asn Phe Cys Gly Asn Gly Asn His Ile Ile
    1130                1135                1140

Ser Leu Val Gln Asn Ala Pro Tyr Gly Leu Tyr Phe Ile His Phe
    1145                1150                1155

Ser Tyr Val Pro Thr Lys Tyr Val Thr Ala Lys Val Ser Pro Gly
    1160                1165                1170

Leu Cys Ile Ala Gly Asp Arg Gly Ile Ala Pro Lys Ser Gly Tyr
    1175                1180                1185
```

```
Phe Val Asn Val Asn Asn Thr Trp Met Tyr Thr Gly Ser Gly Tyr
    1190                1195                1200

Tyr Tyr Pro Glu Pro Ile Thr Glu Asn Asn Val Val Val Met Ser
    1205                1210                1215

Thr Cys Ala Val Asn Tyr Thr Lys Ala Pro Tyr Val Met Leu Asn
    1220                1225                1230

Thr Ser Thr Pro Asn Leu Pro Asp Phe Arg Glu Glu Leu Asp Gln
    1235                1240                1245

Trp Phe Lys Asn Gln Thr Ser Val Ala Pro Asp Leu Ser Leu Asp
    1250                1255                1260

Tyr Ile Asn Val Thr Phe Leu Asp Leu Gln Val Glu Met Asn Arg
    1265                1270                1275

Leu Gln Glu Ala Ile Lys Val Leu Asn Gln Ser Tyr Ile Asn Leu
    1280                1285                1290

Lys Asp Ile Gly Thr Tyr Glu Tyr Tyr Val Lys Trp Pro Trp Tyr
    1295                1300                1305

Val Trp Leu Leu Ile Gly Leu Ala Gly Val Ala Met Leu Val Leu
    1310                1315                1320

Leu Phe Phe Ile Cys Cys Cys Thr Gly Cys Gly Thr Ser Cys Phe
    1325                1330                1335

Lys Lys Cys Gly Gly Cys Cys Asp Asp Tyr Thr Gly Tyr Gln Glu
    1340                1345                1350

Leu Val Ile Lys Thr Ser His Asp Asp
    1355                1360

<210> SEQ ID NO 11
<211> LENGTH: 1287
<212> TYPE: PRT
<213> ORGANISM: Artificial Sequence
<220> FEATURE:
<223> OTHER INFORMATION: recombinant coronavirus spike protein

<400> SEQUENCE: 11

Met Phe Leu Ile Leu Leu Ile Ser Leu Pro Thr Ala Phe Ala Val Ile
1               5                   10                  15

Gly Asp Leu Lys Cys Pro Leu Asp Ser Arg Thr Gly Ser Leu Asn Asn
            20                  25                  30

Ile Asp Thr Gly Pro Pro Ser Ile Ser Thr Ala Thr Val Asp Val Thr
        35                  40                  45

Asn Gly Leu Gly Thr Tyr Tyr Val Leu Asp Arg Val Tyr Leu Asn Thr
    50                  55                  60

Thr Leu Phe Leu Asn Gly Tyr Tyr Pro Thr Ser Gly Ser Thr Tyr Arg
65                  70                  75                  80

Asn Met Ala Leu Lys Gly Thr Asp Lys Leu Ser Thr Leu Trp Phe Lys
                85                  90                  95

Pro Pro Phe Leu Ser Asp Phe Ile Asn Gly Ile Phe Ala Lys Val Lys
            100                 105                 110

Asn Thr Lys Val Phe Lys Asp Gly Val Met Tyr Ser Glu Phe Pro Ala
        115                 120                 125

Ile Thr Ile Gly Ser Thr Phe Val Asn Thr Ser Tyr Ser Val Val Val
    130                 135                 140

Gln Pro Arg Thr Ile Asn Ser Thr Gln Asp Gly Val Asn Lys Leu Gln
145                 150                 155                 160

Gly Leu Leu Glu Val Ser Val Cys Gln Tyr Asn Met Cys Glu Tyr Pro
                165                 170                 175
```

-continued

```
His Thr Ile Cys His Pro Lys Leu Gly Asn His Phe Lys Glu Leu Trp
            180                 185                 190

His Met Asp Thr Gly Val Val Ser Cys Leu Tyr Lys Arg Asn Phe Thr
        195                 200                 205

Tyr Asp Val Asn Ala Thr Tyr Leu Tyr Phe His Phe Tyr Gln Glu Gly
    210                 215                 220

Gly Thr Phe Tyr Ala Tyr Phe Thr Asp Thr Gly Val Val Thr Lys Phe
225                 230                 235                 240

Leu Phe Asn Val Tyr Leu Gly Met Ala Leu Ser His Tyr Tyr Val Met
                245                 250                 255

Pro Leu Thr Cys Ile Ser Arg Arg Asp Ile Gly Phe Thr Leu Glu Tyr
            260                 265                 270

Trp Val Thr Pro Leu Thr Ser Arg Gln Tyr Leu Leu Ala Phe Asn Gln
        275                 280                 285

Asp Gly Ile Ile Phe Asn Ala Val Asp Cys Met Ser Asp Phe Met Ser
    290                 295                 300

Glu Ile Lys Cys Lys Thr Gln Ser Ile Ala Pro Pro Thr Gly Val Tyr
305                 310                 315                 320

Glu Leu Asn Gly Tyr Thr Val Gln Pro Ile Ala Asp Val Tyr Arg Arg
                325                 330                 335

Lys Pro Asp Leu Pro Asn Cys Asn Ile Glu Ala Trp Leu Asn Asp Lys
            340                 345                 350

Ser Val Pro Ser Pro Leu Asn Trp Glu Arg Lys Thr Phe Ser Asn Cys
        355                 360                 365

Asn Phe Asn Met Ser Ser Leu Met Ser Phe Ile Gln Ala Asp Ser Phe
    370                 375                 380

Thr Cys Asn Asn Ile Asp Ala Ala Lys Ile Tyr Gly Met Cys Phe Ser
385                 390                 395                 400

Ser Ile Thr Ile Asp Lys Phe Ala Ile Pro Asn Gly Arg Lys Val Asp
                405                 410                 415

Leu Gln Leu Gly Asn Leu Gly Tyr Leu Gln Ser Phe Asn Tyr Arg Ile
            420                 425                 430

Asp Thr Thr Ala Thr Ser Cys Gln Leu Tyr Tyr Asn Leu Pro Ala Ala
        435                 440                 445

Asn Val Ser Val Ser Arg Phe Asn Pro Ser Thr Trp Asn Lys Arg Phe
    450                 455                 460

Gly Phe Ile Glu Asn Ser Val Phe Lys Pro Gln Pro Ala Gly Val Leu
465                 470                 475                 480

Thr Asn His Asp Val Val Tyr Ala Gln His Cys Phe Lys Ala Pro Lys
                485                 490                 495

Asn Phe Cys Pro Cys Lys Leu Asn Ser Ser Leu Cys Val Gly Ser Gly
            500                 505                 510

Pro Gly Lys Asn Asn Gly Ile Gly Thr Cys Pro Ala Gly Thr Asn Tyr
        515                 520                 525

Leu Thr Cys His Asn Leu Cys Asn Pro Asp Pro Ile Thr Phe Thr Gly
    530                 535                 540

Pro Tyr Lys Cys Pro Gln Thr Lys Ser Leu Val Gly Ile Gly Glu His
545                 550                 555                 560

Cys Ser Gly Leu Ala Val Lys Ser Asp Tyr Cys Gly Gly Asn Pro Cys
                565                 570                 575

Thr Cys Gln Pro Gln Ala Phe Leu Gly Trp Ser Ala Asp Ser Cys Leu
            580                 585                 590

Gln Gly Asp Lys Cys Asn Ile Phe Ala Asn Leu Ile Leu His Asp Val
```

```
            595                 600                 605
Asn Ser Gly Leu Thr Cys Ser Thr Asp Leu Gln Lys Ala Asn Thr Asp
    610                 615                 620

Ile Lys Leu Gly Val Cys Val Asn Tyr Asp Leu Tyr Gly Ile Ser Gly
625                 630                 635                 640

Gln Gly Ile Phe Val Glu Val Asn Ala Thr Tyr Tyr Asn Ser Trp Gln
                645                 650                 655

Asn Leu Leu Tyr Asp Ser Asn Gly Asn Leu Tyr Gly Phe Arg Asp Tyr
            660                 665                 670

Ile Thr Asn Arg Thr Phe Met Ile Arg Ser Cys Tyr Ser Gly Arg Val
        675                 680                 685

Ser Ala Ala Phe His Ala Asn Ser Ser Glu Pro Ala Leu Leu Phe Arg
    690                 695                 700

Asn Ile Lys Cys Asn Tyr Val Phe Asn Asn Ser Leu Ile Arg Gln Leu
705                 710                 715                 720

Gln Pro Ile Asn Tyr Phe Asp Ser Tyr Leu Gly Cys Val Val Asn Ala
                725                 730                 735

Tyr Asn Ser Thr Ala Ile Ser Val Gln Thr Cys Asp Leu Thr Val Gly
            740                 745                 750

Ser Gly Tyr Cys Val Asp Tyr Ser Lys Asn Gly Ser Gly Ser Ala
        755                 760                 765

Ile Thr Thr Gly Tyr Arg Phe Thr Asn Phe Glu Pro Phe Thr Val Asn
770                 775                 780

Ser Val Asn Asp Ser Leu Glu Pro Val Gly Gly Leu Tyr Glu Ile Gln
785                 790                 795                 800

Ile Pro Ser Glu Phe Thr Ile Gly Asn Met Glu Glu Phe Ile Gln Thr
                805                 810                 815

Ser Ser Pro Lys Val Thr Ile Asp Cys Ala Ala Phe Val Cys Gly Asp
            820                 825                 830

Tyr Ala Ala Cys Lys Ser Gln Leu Val Glu Tyr Gly Ser Phe Cys Asp
        835                 840                 845

Asn Ile Asn Ala Ile Leu Thr Glu Val Asn Glu Leu Leu Asp Thr Thr
850                 855                 860

Gln Leu Gln Val Ala Asn Ser Leu Met Asn Gly Val Thr Leu Ser Thr
865                 870                 875                 880

Lys Leu Lys Asp Gly Val Asn Phe Asn Val Asp Asp Ile Asn Phe Ser
                885                 890                 895

Ser Val Leu Gly Cys Leu Gly Ser Glu Cys Ser Lys Ala Ser Ser Arg
            900                 905                 910

Ser Ala Ile Glu Asp Leu Leu Phe Asp Lys Val Lys Leu Ser Asp Val
        915                 920                 925

Gly Phe Val Ala Ala Tyr Asn Asn Cys Thr Gly Gly Ala Glu Ile Arg
    930                 935                 940

Asp Leu Ile Cys Val Gln Ser Tyr Lys Gly Ile Lys Val Leu Pro Pro
945                 950                 955                 960

Leu Leu Ser Glu Asn Gln Ile Ser Gly Tyr Thr Leu Ala Ala Thr Ser
                965                 970                 975

Ala Ser Leu Phe Pro Pro Trp Thr Ala Ala Gly Val Pro Phe Tyr
            980                 985                 990

Leu Asn Val Gln Tyr Arg Ile Asn Gly Leu Gly Val Thr Met Asp Val
        995                1000                1005

Leu Ser Gln Asn Gln Lys Leu Ile Ala Asn Ala Phe Asn Asn Ala
    1010                1015                1020
```

-continued

Leu Asp Ala Ile Gln Glu Gly Phe Asp Ala Thr Asn Ser Ala Leu
    1025            1030                1035

Val Lys Ile Gln Ala Val Val Asn Ala Asn Ala Glu Ala Leu Asn
    1040            1045                1050

Asn Leu Leu Gln Gln Leu Ser Asn Arg Phe Gly Ala Ile Ser Ser
    1055            1060                1065

Ser Leu Gln Glu Ile Leu Ser Arg Leu Asp Pro Pro Glu Ala Glu
    1070            1075                1080

Ala Gln Ile Asp Arg Leu Ile Asn Gly Arg Leu Thr Ala Leu Asn
    1085            1090                1095

Ala Tyr Val Ser Gln Gln Leu Ser Asp Ser Thr Leu Val Lys Phe
    1100            1105                1110

Ser Ala Ala Gln Ala Met Glu Lys Val Asn Glu Cys Val Lys Ser
    1115            1120                1125

Gln Ser Ser Arg Ile Asn Phe Cys Gly Asn Gly Asn His Ile Ile
    1130            1135                1140

Ser Leu Val Gln Asn Ala Pro Tyr Gly Leu Tyr Phe Ile His Phe
    1145            1150                1155

Ser Tyr Val Pro Thr Lys Tyr Val Thr Ala Lys Val Ser Pro Gly
    1160            1165                1170

Leu Cys Ile Ala Gly Asp Arg Gly Ile Ala Pro Lys Ser Gly Tyr
    1175            1180                1185

Phe Val Asn Val Asn Asn Thr Trp Met Tyr Thr Gly Ser Gly Tyr
    1190            1195                1200

Tyr Tyr Pro Glu Pro Ile Thr Glu Asn Asn Val Val Val Met Ser
    1205            1210                1215

Thr Cys Ala Val Asn Tyr Thr Lys Ala Pro Tyr Val Met Leu Asn
    1220            1225                1230

Thr Ser Thr Pro Asn Leu Pro Asp Phe Arg Glu Glu Leu Asp Gln
    1235            1240                1245

Trp Phe Lys Asn Gln Thr Ser Val Ala Pro Asp Leu Ser Leu Asp
    1250            1255                1260

Tyr Ile Asn Val Thr Phe Leu Asp Leu Gln Val Glu Met Asn Arg
    1265            1270                1275

Leu Gln Glu Ala Ile Lys Val Leu Asn
    1280            1285

<210> SEQ ID NO 12
<211> LENGTH: 1274
<212> TYPE: PRT
<213> ORGANISM: Rousettus bat coronavirus HKU9

<400> SEQUENCE: 12

Met Leu Leu Ile Leu Val Leu Gly Val Ser Leu Ala Ala Ser Arg
1               5                   10                  15

Pro Glu Cys Phe Asn Pro Arg Phe Thr Leu Thr Pro Leu Asn His Thr
                20                  25                  30

Leu Asn Tyr Thr Ser Ile Lys Ala Lys Val Ser Asn Val Leu Leu Pro
            35                  40                  45

Asp Pro Tyr Ile Ala Tyr Ser Gly Gln Thr Leu Arg Gln Asn Leu Phe
        50                  55                  60

Met Ala Asp Met Ser Asn Thr Ile Leu Tyr Pro Val Thr Pro Pro Ala
65                  70                  75                  80

Asn Gly Ala Asn Gly Gly Phe Ile Tyr Asn Thr Ser Ile Ile Pro Val

```
                    85                  90                  95
Ser Ala Gly Leu Phe Val Asn Thr Trp Met Tyr Arg Gln Pro Ala Ser
            100                 105                 110

Ser Arg Ala Tyr Cys Gln Glu Pro Phe Gly Val Ala Phe Gly Asp Thr
            115                 120                 125

Phe Glu Asn Asp Arg Ile Ala Ile Leu Ile Met Ala Pro Asp Asn Leu
            130                 135                 140

Gly Ser Trp Ser Ala Val Ala Pro Arg Asn Gln Thr Asn Ile Tyr Leu
145                 150                 155                 160

Leu Val Cys Ser Asn Ala Thr Leu Cys Ile Asn Pro Gly Phe Asn Arg
                165                 170                 175

Trp Gly Pro Ala Gly Ser Phe Ile Ala Pro Asp Ala Leu Val Asp His
            180                 185                 190

Ser Asn Ser Cys Phe Val Asn Asn Thr Phe Ser Val Asn Ile Ser Thr
            195                 200                 205

Ser Arg Ile Ser Leu Ala Phe Leu Phe Lys Asp Gly Asp Leu Leu Ile
            210                 215                 220

Tyr His Ser Gly Trp Leu Pro Thr Ser Asn Phe Glu His Gly Phe Ser
225                 230                 235                 240

Arg Gly Ser His Pro Met Thr Tyr Phe Met Ser Leu Pro Val Gly Gly
                245                 250                 255

Asn Leu Pro Arg Ala Gln Phe Phe Gln Ser Ile Val Arg Ser Asn Ala
            260                 265                 270

Ile Asp Lys Gly Asp Gly Met Cys Thr Asn Phe Asp Val Asn Leu His
            275                 280                 285

Val Ala His Leu Ile Asn Arg Asp Leu Leu Val Ser Tyr Phe Asn Asn
            290                 295                 300

Gly Ser Val Ala Asn Ala Ala Asp Cys Ala Asp Ser Ala Ala Glu Glu
305                 310                 315                 320

Leu Tyr Cys Val Thr Gly Ser Phe Asp Pro Pro Thr Gly Val Tyr Pro
                325                 330                 335

Leu Ser Arg Tyr Arg Ala Gln Val Ala Gly Phe Val Arg Val Thr Gln
            340                 345                 350

Arg Gly Ser Tyr Cys Thr Pro Pro Tyr Ser Val Leu Gln Asp Pro Pro
            355                 360                 365

Gln Pro Val Val Trp Arg Arg Tyr Met Leu Tyr Asp Cys Val Phe Asp
            370                 375                 380

Phe Thr Val Val Asp Ser Leu Pro Thr His Gln Leu Gln Cys Tyr
385                 390                 395                 400

Gly Val Ser Pro Arg Arg Leu Ala Ser Met Cys Tyr Gly Ser Val Thr
            405                 410                 415

Leu Asp Val Met Arg Ile Asn Glu Thr His Leu Asn Asn Leu Phe Asn
            420                 425                 430

Arg Val Pro Asp Thr Phe Ser Leu Tyr Asn Tyr Ala Leu Pro Asp Asn
            435                 440                 445

Phe Tyr Gly Cys Leu His Ala Phe Tyr Leu Asn Ser Thr Ala Pro Tyr
            450                 455                 460

Ala Val Ala Asn Arg Phe Pro Ile Lys Pro Gly Gly Arg Gln Ser Asn
465                 470                 475                 480

Ser Ala Phe Ile Asp Thr Val Ile Asn Ala Ala His Tyr Ser Pro Phe
                485                 490                 495

Ser Tyr Val Tyr Gly Leu Ala Val Ile Thr Leu Lys Pro Ala Ala Gly
            500                 505                 510
```

```
Ser Lys Leu Val Cys Pro Val Ala Asn Asp Thr Val Ile Thr Asp
        515                 520                 525

Arg Cys Val Gln Tyr Asn Leu Tyr Gly Tyr Thr Gly Thr Gly Val Leu
        530                 535                 540

Ser Lys Asn Thr Ser Leu Val Ile Pro Asp Gly Lys Val Phe Thr Ala
545                 550                 555                 560

Ser Ser Thr Gly Thr Ile Ile Gly Val Ser Ile Asn Ser Thr Thr Tyr
                565                 570                 575

Ser Ile Met Pro Cys Val Thr Val Pro Val Ser Val Gly Tyr His Pro
                580                 585                 590

Asn Phe Glu Arg Ala Leu Leu Phe Asn Gly Leu Ser Cys Ser Gln Arg
                595                 600                 605

Ser Arg Ala Val Thr Glu Pro Val Ser Val Leu Trp Ser Ala Ser Ala
        610                 615                 620

Thr Ala Gln Asp Ala Phe Asp Thr Pro Ser Gly Cys Val Val Asn Val
625                 630                 635                 640

Glu Leu Arg Asn Thr Thr Ile Val Asn Thr Cys Ala Met Pro Ile Gly
                645                 650                 655

Asn Ser Leu Cys Phe Ile Asn Gly Ser Ile Ala Thr Ala Asn Ala Asp
                660                 665                 670

Ser Leu Pro Arg Leu Gln Leu Val Asn Tyr Asp Pro Leu Tyr Asp Asn
        675                 680                 685

Ser Thr Ala Thr Pro Met Thr Pro Val Tyr Trp Val Lys Val Pro Thr
        690                 695                 700

Asn Phe Thr Leu Ser Ala Thr Glu Glu Tyr Ile Gln Thr Thr Ala Pro
705                 710                 715                 720

Lys Ile Thr Ile Asp Cys Ala Arg Tyr Leu Cys Gly Asp Ser Ser Arg
                725                 730                 735

Cys Leu Asn Val Leu Leu His Tyr Gly Thr Phe Cys Asn Asp Ile Asn
                740                 745                 750

Lys Ala Leu Ser Arg Val Ser Thr Ile Leu Asp Ser Ala Leu Leu Ser
        755                 760                 765

Leu Val Lys Glu Leu Ser Ile Asn Thr Arg Asp Glu Val Thr Thr Phe
        770                 775                 780

Ser Phe Asp Gly Asp Tyr Asn Phe Thr Gly Leu Met Gly Cys Leu Gly
785                 790                 795                 800

Pro Asn Cys Gly Ala Thr Thr Tyr Arg Ser Ala Phe Ser Asp Leu Leu
                805                 810                 815

Tyr Asp Lys Val Arg Ile Thr Asp Pro Gly Phe Met Gln Ser Tyr Gln
                820                 825                 830

Lys Cys Ile Asp Ser Gln Trp Gly Ser Ile Arg Asp Leu Leu Cys
        835                 840                 845

Thr Gln Thr Tyr Asn Gly Ile Ala Val Leu Pro Pro Ile Val Ser Pro
850                 855                 860

Ala Met Gln Ala Leu Tyr Thr Ser Leu Leu Val Gly Ala Val Ala Ser
865                 870                 875                 880

Ser Gly Tyr Thr Phe Gly Ile Thr Ser Ala Gly Val Ile Pro Phe Ala
                885                 890                 895

Thr Gln Leu Gln Phe Arg Leu Asn Gly Ile Gly Val Thr Thr Gln Val
                900                 905                 910

Leu Val Glu Asn Gln Lys Leu Ile Ala Ser Ser Phe Asn Asn Ala Leu
        915                 920                 925
```

Val Asn Ile Gln Lys Gly Phe Thr Glu Thr Ser Ile Ala Leu Ser Lys
930                 935                 940

Met Gln Asp Val Ile Asn Gln His Ala Ala Gln Leu His Thr Leu Val
945                 950                 955                 960

Val Gln Leu Gly Asn Ser Phe Gly Ala Ile Ser Ser Ile Asn Glu
                965                 970                 975

Ile Phe Ser Arg Leu Glu Gly Leu Ala Ala Asn Ala Glu Val Asp Arg
            980                 985                 990

Leu Ile Asn Gly Arg Met Met Val Leu Asn Thr Tyr Val Thr Gln Leu
        995                 1000                1005

Leu Ile Gln Ala Ser Glu Ala Lys Ala Gln Asn Ala Leu Ala Ala
    1010                1015                1020

Gln Lys Ile Ser Glu Cys Val Lys Ala Gln Ser Leu Arg Asn Asp
    1025                1030                1035

Phe Cys Gly Asn Gly Thr His Val Leu Ser Ile Pro Gln Leu Ala
    1040                1045                1050

Pro Asn Gly Val Leu Phe Ile His Tyr Ala Tyr Thr Pro Thr Glu
    1055                1060                1065

Tyr Ala Phe Val Gln Thr Ser Ala Gly Leu Cys His Asn Gly Thr
    1070                1075                1080

Gly Tyr Ala Pro Arg Gln Gly Met Phe Val Leu Pro Asn Asn Thr
    1085                1090                1095

Asn Met Trp His Phe Thr Thr Met Gln Phe Tyr Asn Pro Val Asn
    1100                1105                1110

Ile Ser Ala Ser Asn Thr Gln Val Leu Thr Ser Cys Ser Val Asn
    1115                1120                1125

Tyr Thr Ser Val Asn Tyr Thr Val Leu Glu Pro Ser Val Pro Gly
    1130                1135                1140

Asp Tyr Asp Phe Gln Lys Glu Phe Asp Lys Phe Tyr Lys Asn Leu
    1145                1150                1155

Ser Thr Ile Phe Asn Asn Thr Phe Asn Pro Asn Asp Phe Asn Phe
    1160                1165                1170

Ser Thr Val Asp Val Thr Ala Gln Ile Lys Ser Leu His Asp Val
    1175                1180                1185

Val Asn Gln Leu Asn Gln Ser Phe Ile Asp Leu Lys Lys Leu Asn
    1190                1195                1200

Val Tyr Glu Lys Thr Ile Lys Trp Pro Trp Tyr Val Trp Leu Ala
    1205                1210                1215

Met Ile Ala Gly Ile Val Gly Leu Val Leu Ala Val Ile Met Leu
    1220                1225                1230

Met Cys Met Thr Asn Cys Cys Ser Cys Phe Lys Gly Met Cys Asp
    1235                1240                1245

Cys Arg Arg Cys Cys Gly Ser Tyr Asp Ser Tyr Asp Asp Val Tyr
    1250                1255                1260

Pro Ala Val Arg Val Asn Lys Lys Arg Thr Val
    1265                1270

<210> SEQ ID NO 13
<211> LENGTH: 1207
<212> TYPE: PRT
<213> ORGANISM: Artificial Sequence
<220> FEATURE:
<223> OTHER INFORMATION: recombinant coronavirus spike protein

<400> SEQUENCE: 13

```
Met Leu Leu Ile Leu Val Leu Gly Val Ser Leu Ala Ala Ala Ser Arg
1               5                   10                  15

Pro Glu Cys Phe Asn Pro Arg Phe Thr Leu Thr Pro Leu Asn His Thr
            20                  25                  30

Leu Asn Tyr Thr Ser Ile Lys Ala Lys Val Ser Asn Val Leu Leu Pro
            35                  40                  45

Asp Pro Tyr Ile Ala Tyr Ser Gly Gln Thr Leu Arg Gln Asn Leu Phe
            50                  55                  60

Met Ala Asp Met Ser Asn Thr Ile Leu Tyr Pro Val Thr Pro Pro Ala
65                  70                  75                  80

Asn Gly Ala Asn Gly Gly Phe Ile Tyr Asn Thr Ser Ile Ile Pro Val
                85                  90                  95

Ser Ala Gly Leu Phe Val Asn Thr Trp Met Tyr Arg Gln Pro Ala Ser
            100                 105                 110

Ser Arg Ala Tyr Cys Gln Glu Pro Phe Gly Val Ala Phe Gly Asp Thr
            115                 120                 125

Phe Glu Asn Asp Arg Ile Ala Ile Leu Ile Met Ala Pro Asp Asn Leu
            130                 135                 140

Gly Ser Trp Ser Ala Val Ala Pro Arg Asn Gln Thr Asn Ile Tyr Leu
145                 150                 155                 160

Leu Val Cys Ser Asn Ala Thr Leu Cys Ile Asn Pro Gly Phe Asn Arg
                165                 170                 175

Trp Gly Pro Ala Gly Ser Phe Ile Ala Pro Asp Ala Leu Val Asp His
            180                 185                 190

Ser Asn Ser Cys Phe Val Asn Asn Thr Phe Ser Val Asn Ile Ser Thr
            195                 200                 205

Ser Arg Ile Ser Leu Ala Phe Leu Phe Lys Asp Gly Asp Leu Leu Ile
            210                 215                 220

Tyr His Ser Gly Trp Leu Pro Thr Ser Asn Phe Glu His Gly Phe Ser
225                 230                 235                 240

Arg Gly Ser His Pro Met Thr Tyr Phe Met Ser Leu Pro Val Gly Gly
                245                 250                 255

Asn Leu Pro Arg Ala Gln Phe Phe Gln Ser Ile Val Arg Ser Asn Ala
            260                 265                 270

Ile Asp Lys Gly Asp Gly Met Cys Thr Asn Phe Asp Val Asn Leu His
            275                 280                 285

Val Ala His Leu Ile Asn Arg Asp Leu Leu Val Ser Tyr Phe Asn Asn
290                 295                 300

Gly Ser Val Ala Asn Ala Ala Asp Cys Ala Asp Ser Ala Ala Glu Glu
305                 310                 315                 320

Leu Tyr Cys Val Thr Gly Ser Phe Asp Pro Thr Gly Val Tyr Pro
            325                 330                 335

Leu Ser Arg Tyr Arg Ala Gln Val Ala Gly Phe Val Arg Val Thr Gln
            340                 345                 350

Arg Gly Ser Tyr Cys Thr Pro Pro Tyr Ser Val Leu Gln Asp Pro Pro
            355                 360                 365

Gln Pro Val Val Trp Arg Arg Tyr Met Leu Tyr Asp Cys Val Phe Asp
            370                 375                 380

Phe Thr Val Val Val Asp Ser Leu Pro Thr His Gln Leu Gln Cys Tyr
385                 390                 395                 400

Gly Val Ser Pro Arg Arg Leu Ala Ser Met Cys Tyr Gly Ser Val Thr
                405                 410                 415

Leu Asp Val Met Arg Ile Asn Glu Thr His Leu Asn Asn Leu Phe Asn
```

-continued

```
                420             425             430
Arg Val Pro Asp Thr Phe Ser Leu Tyr Asn Tyr Ala Leu Pro Asp Asn
            435                 440                 445
Phe Tyr Gly Cys Leu His Ala Phe Tyr Leu Asn Ser Thr Ala Pro Tyr
        450                 455                 460
Ala Val Ala Asn Arg Phe Pro Ile Lys Pro Gly Arg Gln Ser Asn
465                 470                 475                 480
Ser Ala Phe Ile Asp Thr Val Ile Asn Ala Ala His Tyr Ser Pro Phe
                485                 490                 495
Ser Tyr Val Tyr Gly Leu Ala Val Ile Thr Leu Lys Pro Ala Ala Gly
            500                 505                 510
Ser Lys Leu Val Cys Pro Val Ala Asn Asp Thr Val Ile Thr Asp
        515                 520                 525
Arg Cys Val Gln Tyr Asn Leu Tyr Gly Tyr Thr Gly Thr Gly Val Leu
        530                 535                 540
Ser Lys Asn Thr Ser Leu Val Ile Pro Asp Gly Lys Val Phe Thr Ala
545                 550                 555                 560
Ser Ser Thr Gly Thr Ile Ile Gly Val Ser Ile Asn Ser Thr Thr Tyr
                565                 570                 575
Ser Ile Met Pro Cys Val Thr Val Pro Val Ser Val Gly Tyr His Pro
            580                 585                 590
Asn Phe Glu Arg Ala Leu Leu Phe Asn Gly Leu Ser Cys Ser Gln Arg
        595                 600                 605
Ser Arg Ala Val Thr Glu Pro Val Ser Val Leu Trp Ser Ala Ser Ala
        610                 615                 620
Thr Ala Gln Asp Ala Phe Asp Thr Pro Ser Gly Cys Val Val Asn Val
625                 630                 635                 640
Glu Leu Arg Asn Thr Thr Ile Val Asn Thr Cys Ala Met Pro Ile Gly
                645                 650                 655
Asn Ser Leu Cys Phe Ile Asn Gly Ser Ile Ala Thr Ala Asn Ala Asp
            660                 665                 670
Ser Leu Pro Arg Leu Gln Leu Val Asn Tyr Asp Pro Leu Tyr Asp Asn
        675                 680                 685
Ser Thr Ala Thr Pro Met Thr Pro Val Tyr Trp Val Lys Val Pro Thr
        690                 695                 700
Asn Phe Thr Leu Ser Ala Thr Glu Glu Tyr Ile Gln Thr Thr Ala Pro
705                 710                 715                 720
Lys Ile Thr Ile Asp Cys Ala Arg Tyr Leu Cys Gly Asp Ser Ser Arg
                725                 730                 735
Cys Leu Asn Val Leu Leu His Tyr Gly Thr Phe Cys Asn Asp Ile Asn
            740                 745                 750
Lys Ala Leu Ser Arg Val Ser Thr Ile Leu Asp Ser Ala Leu Leu Ser
        755                 760                 765
Leu Val Lys Glu Leu Ser Ile Asn Thr Arg Asp Glu Val Thr Thr Phe
        770                 775                 780
Ser Phe Asp Gly Asp Tyr Asn Phe Thr Gly Leu Met Gly Cys Leu Gly
785                 790                 795                 800
Pro Asn Cys Gly Ala Thr Thr Tyr Arg Ser Ala Phe Ser Asp Leu Leu
                805                 810                 815
Tyr Asp Lys Val Arg Ile Thr Asp Pro Gly Phe Met Gln Ser Tyr Gln
            820                 825                 830
Lys Cys Ile Asp Ser Gln Trp Gly Gly Ser Ile Arg Asp Leu Leu Cys
        835                 840                 845
```

```
Thr Gln Thr Tyr Asn Gly Ile Ala Val Leu Pro Pro Ile Val Ser Pro
    850                 855                 860
Ala Met Gln Ala Leu Tyr Thr Ser Leu Leu Val Gly Ala Val Ala Ser
865                 870                 875                 880
Ser Gly Tyr Thr Phe Gly Ile Thr Ser Ala Gly Val Ile Pro Phe Ala
                885                 890                 895
Thr Gln Leu Gln Phe Arg Leu Asn Gly Ile Gly Val Thr Thr Gln Val
            900                 905                 910
Leu Val Glu Asn Gln Lys Leu Ile Ala Ser Ser Phe Asn Asn Ala Leu
        915                 920                 925
Val Asn Ile Gln Lys Gly Phe Thr Glu Thr Ser Ile Ala Leu Ser Lys
    930                 935                 940
Met Gln Asp Val Ile Asn Gln His Ala Ala Gln Leu His Thr Leu Val
945                 950                 955                 960
Val Gln Leu Gly Asn Ser Phe Gly Ala Ile Ser Ser Ile Asn Glu
                965                 970                 975
Ile Phe Ser Arg Leu Glu Pro Pro Ala Ala Asn Ala Glu Val Asp Arg
            980                 985                 990
Leu Ile Asn Gly Arg Met Met Val Leu Asn Thr Tyr Val Thr Gln Leu
        995                 1000                1005
Leu Ile Gln Ala Ser Glu Ala Lys Ala Gln Asn Ala Leu Ala Ala
    1010                1015                1020
Gln Lys Ile Ser Glu Cys Val Lys Ala Gln Ser Leu Arg Asn Asp
    1025                1030                1035
Phe Cys Gly Asn Gly Thr His Val Leu Ser Ile Pro Gln Leu Ala
    1040                1045                1050
Pro Asn Gly Val Leu Phe Ile His Tyr Ala Tyr Thr Pro Thr Glu
    1055                1060                1065
Tyr Ala Phe Val Gln Thr Ser Ala Gly Leu Cys His Asn Gly Thr
    1070                1075                1080
Gly Tyr Ala Pro Arg Gln Gly Met Phe Val Leu Pro Asn Asn Thr
    1085                1090                1095
Asn Met Trp His Phe Thr Thr Met Gln Phe Tyr Asn Pro Val Asn
    1100                1105                1110
Ile Ser Ala Ser Asn Thr Gln Val Leu Thr Ser Cys Ser Val Asn
    1115                1120                1125
Tyr Thr Ser Val Asn Tyr Thr Val Leu Glu Pro Ser Val Pro Gly
    1130                1135                1140
Asp Tyr Asp Phe Gln Lys Glu Phe Asp Lys Phe Tyr Lys Asn Leu
    1145                1150                1155
Ser Thr Ile Phe Asn Asn Thr Phe Asn Pro Asn Asp Phe Asn Phe
    1160                1165                1170
Ser Thr Val Asp Val Thr Ala Gln Ile Lys Ser Leu His Asp Val
    1175                1180                1185
Val Asn Gln Leu Asn Gln Ser Phe Ile Asp Leu Lys Lys Leu Asn
    1190                1195                1200
Val Tyr Glu Lys
    1205

<210> SEQ ID NO 14
<211> LENGTH: 1256
<212> TYPE: PRT
<213> ORGANISM: Artificial Sequence
<220> FEATURE:
```

<223> OTHER INFORMATION: recombinant coronavirus spike protein

<400> SEQUENCE: 14

```
Met Lys Leu Leu Val Leu Val Phe Ala Thr Leu Val Ser Ser Tyr Thr
1               5                   10                  15

Ile Glu Lys Cys Leu Asp Phe Asp Asp Arg Thr Pro Pro Ala Asn Thr
            20                  25                  30

Gln Phe Leu Ser Ser His Arg Gly Val Tyr Tyr Pro Asp Asp Ile Phe
        35                  40                  45

Arg Ser Asn Val Leu His Leu Val Gln Asp His Phe Leu Pro Phe Asp
    50                  55                  60

Ser Asn Val Thr Arg Phe Ile Thr Phe Gly Leu Asn Phe Asp Asn Pro
65                  70                  75                  80

Ile Ile Pro Phe Lys Asp Gly Ile Tyr Phe Ala Ala Thr Glu Lys Ser
                85                  90                  95

Asn Val Ile Arg Gly Trp Val Phe Gly Ser Thr Met Asn Asn Lys Ser
            100                 105                 110

Gln Ser Val Ile Ile Met Asn Asn Ser Thr Asn Leu Val Ile Arg Ala
        115                 120                 125

Cys Asn Phe Glu Leu Cys Asp Asn Pro Phe Phe Val Val Leu Lys Ser
    130                 135                 140

Asn Asn Thr Gln Ile Pro Ser Tyr Ile Phe Asn Asn Ala Phe Asn Cys
145                 150                 155                 160

Thr Phe Glu Tyr Val Ser Lys Asp Phe Asn Leu Asp Leu Gly Glu Lys
                165                 170                 175

Pro Gly Asn Phe Lys Asp Leu Arg Glu Phe Val Phe Arg Asn Lys Asp
            180                 185                 190

Gly Phe Leu His Val Tyr Ser Gly Tyr Gln Pro Ile Ser Ala Ala Ser
        195                 200                 205

Gly Leu Pro Thr Gly Phe Asn Ala Leu Lys Pro Ile Phe Lys Leu Pro
    210                 215                 220

Leu Gly Ile Asn Ile Thr Asn Phe Arg Thr Leu Leu Thr Ala Phe Pro
225                 230                 235                 240

Pro Arg Pro Asp Tyr Trp Gly Thr Ser Ala Ala Tyr Phe Val Gly
                245                 250                 255

Tyr Leu Lys Pro Thr Thr Phe Met Leu Lys Tyr Asp Glu Asn Gly Thr
            260                 265                 270

Ile Thr Asp Ala Val Asp Cys Ser Gln Asn Pro Leu Ala Glu Leu Lys
        275                 280                 285

Cys Ser Val Lys Ser Phe Glu Ile Asp Lys Gly Ile Tyr Gln Thr Ser
    290                 295                 300

Asn Phe Arg Val Ala Pro Ser Lys Glu Val Val Arg Phe Pro Asn Ile
305                 310                 315                 320

Thr Asn Leu Cys Pro Phe Gly Glu Val Phe Asn Ala Thr Thr Phe Pro
                325                 330                 335

Ser Val Tyr Ala Trp Glu Arg Lys Arg Ile Ser Asn Cys Val Ala Asp
            340                 345                 350

Tyr Ser Val Leu Tyr Asn Ser Thr Ser Phe Ser Thr Phe Lys Cys Tyr
        355                 360                 365

Gly Val Ser Ala Thr Lys Leu Asn Asp Leu Cys Phe Ser Asn Val Tyr
    370                 375                 380

Ala Asp Ser Phe Val Val Lys Gly Asp Asp Val Arg Gln Ile Ala Pro
385                 390                 395                 400
```

-continued

```
Gly Gln Thr Gly Val Ile Ala Asp Tyr Asn Tyr Lys Leu Pro Asp Asp
                405                 410                 415

Phe Thr Gly Cys Val Leu Ala Trp Asn Thr Arg Asn Ile Asp Ala Thr
            420                 425                 430

Gln Thr Gly Asn Tyr Asn Tyr Lys Tyr Arg Ser Leu Arg His Gly Lys
        435                 440                 445

Leu Arg Pro Phe Glu Arg Asp Ile Ser Asn Val Pro Phe Ser Pro Asp
    450                 455                 460

Gly Lys Pro Cys Thr Pro Ala Phe Asn Cys Tyr Trp Pro Leu Asn
465                 470                 475                 480

Asp Tyr Gly Phe Tyr Ile Thr Asn Gly Ile Gly Tyr Gln Pro Tyr Arg
                485                 490                 495

Val Val Val Leu Ser Phe Glu Leu Leu Asn Ala Pro Ala Thr Val Cys
            500                 505                 510

Gly Pro Lys Leu Ser Thr Asp Leu Ile Lys Asn Gln Cys Val Asn Phe
        515                 520                 525

Asn Phe Asn Gly Leu Thr Gly Thr Gly Val Leu Thr Pro Ser Ser Lys
    530                 535                 540

Arg Phe Gln Pro Phe Gln Gln Phe Gly Arg Asp Val Ser Asp Phe Thr
545                 550                 555                 560

Asp Ser Val Arg Asp Pro Lys Thr Ser Glu Ile Leu Asp Ile Ser Pro
                565                 570                 575

Cys Ser Phe Gly Gly Val Ser Val Ile Thr Pro Gly Thr Asn Thr Ser
            580                 585                 590

Ser Glu Val Ala Val Leu Tyr Gln Asp Val Asn Cys Thr Asp Val Pro
        595                 600                 605

Val Ala Ile His Ala Asp Gln Leu Thr Pro Ser Trp Arg Val His Ser
    610                 615                 620

Thr Gly Asn Asn Val Phe Gln Thr Gln Ala Gly Cys Leu Ile Gly Ala
625                 630                 635                 640

Glu His Val Asp Thr Ser Tyr Glu Cys Asp Ile Pro Ile Gly Ala Gly
                645                 650                 655

Ile Cys Ala Ser Tyr His Thr Val Ser Ser Leu Arg Ser Thr Ser Gln
            660                 665                 670

Lys Ser Ile Val Ala Tyr Thr Met Ser Leu Gly Ala Asp Ser Ser Ile
        675                 680                 685

Ala Tyr Ser Asn Asn Thr Ile Ala Ile Pro Thr Asn Phe Ser Ile Ser
    690                 695                 700

Ile Thr Thr Glu Val Met Pro Val Ser Met Ala Lys Thr Ser Val Asp
705                 710                 715                 720

Cys Asn Met Tyr Ile Cys Gly Asp Ser Thr Glu Cys Ala Asn Leu Leu
                725                 730                 735

Leu Gln Tyr Gly Ser Phe Cys Thr Gln Leu Asn Arg Ala Leu Ser Gly
            740                 745                 750

Ile Ala Val Glu Gln Asp Arg Asn Thr Arg Glu Val Phe Ala Gln Val
        755                 760                 765

Lys Gln Met Tyr Lys Thr Pro Thr Leu Lys Asp Phe Gly Gly Phe Asn
    770                 775                 780

Phe Ser Gln Ile Leu Pro Asp Pro Leu Lys Pro Thr Lys Arg Ser Phe
785                 790                 795                 800

Ile Glu Asp Leu Leu Phe Asn Lys Val Thr Leu Ala Asp Ala Gly Phe
                805                 810                 815

Met Lys Gln Tyr Gly Glu Cys Leu Gly Asp Ile Asn Ala Arg Asp Leu
```

```
              820                 825                 830
Ile Cys Ala Gln Lys Phe Asn Gly Leu Thr Val Leu Pro Pro Leu Leu
                835                 840                 845

Thr Asp Asp Met Ile Ala Ala Tyr Thr Ala Ala Leu Val Ser Gly Thr
850                 855                 860

Ala Thr Ala Gly Trp Thr Phe Gly Ala Gly Ala Ala Leu Gln Ile Pro
865                 870                 875                 880

Phe Ala Met Gln Met Ala Tyr Arg Phe Asn Gly Ile Gly Val Thr Gln
                885                 890                 895

Asn Val Leu Tyr Glu Asn Gln Lys Gln Ile Ala Asn Gln Phe Asn Lys
                900                 905                 910

Ala Ile Ser Gln Ile Gln Glu Ser Leu Thr Thr Thr Ser Thr Ala Leu
                915                 920                 925

Gly Lys Leu Gln Asp Val Val Asn Gln Asn Ala Gln Ala Leu Asn Thr
                930                 935                 940

Leu Val Lys Gln Leu Ser Ser Asn Phe Gly Ala Ile Ser Ser Val Leu
945                 950                 955                 960

Asn Asp Ile Leu Ser Arg Leu Asp Lys Val Glu Ala Glu Val Gln Ile
                965                 970                 975

Asp Arg Leu Ile Thr Gly Arg Leu Gln Ser Leu Gln Thr Tyr Val Thr
                980                 985                 990

Gln Gln Leu Ile Arg Ala Ala Glu Ile Arg Ala Ser Ala Asn Leu Ala
                995                1000                1005

Ala Thr Lys Met Ser Glu Cys Val Leu Gly Gln Ser Lys Arg Val
       1010                1015                1020

Asp Phe Cys Gly Lys Gly Tyr His Leu Met Ser Phe Pro Gln Ala
       1025                1030                1035

Ala Pro His Gly Val Val Phe Leu His Val Thr Tyr Val Pro Ser
       1040                1045                1050

Gln Glu Arg Asn Phe Thr Thr Ala Pro Ala Ile Cys His Glu Gly
       1055                1060                1065

Lys Ala Tyr Phe Pro Arg Glu Gly Val Phe Val Phe Asn Gly Thr
       1070                1075                1080

Ser Trp Phe Ile Thr Gln Arg Asn Phe Phe Ser Pro Gln Ile Ile
       1085                1090                1095

Thr Thr Asp Asn Thr Phe Val Ser Gly Ser Cys Asp Val Val Ile
       1100                1105                1110

Gly Ile Ile Asn Asn Thr Val Tyr Asp Pro Leu Gln Pro Glu Leu
       1115                1120                1125

Asp Ser Phe Lys Glu Glu Leu Asp Lys Tyr Phe Lys Asn His Thr
       1130                1135                1140

Ser Pro Asp Val Asp Leu Gly Asp Ile Ser Gly Ile Asn Ala Ser
       1145                1150                1155

Val Val Asn Ile Gln Lys Glu Ile Asp Arg Leu Asn Glu Val Ala
       1160                1165                1170

Lys Asn Leu Asn Glu Ser Leu Ile Asp Leu Gln Glu Leu Gly Lys
       1175                1180                1185

Tyr Glu Gln Tyr Ile Lys Trp Pro Trp Tyr Val Trp Leu Gly Phe
       1190                1195                1200

Ile Ala Gly Leu Ile Ala Ile Val Met Val Thr Ile Leu Leu Cys
       1205                1210                1215

Cys Met Thr Ser Cys Cys Ser Cys Leu Lys Gly Ala Cys Ser Cys
       1220                1225                1230
```

-continued

```
Gly Ser Cys Cys Lys Phe Asp Glu Asp Asp Ser Glu Pro Val Leu
    1235                1240                1245

Lys Gly Val Lys Leu His Tyr Thr
    1250                1255

<210> SEQ ID NO 15
<211> LENGTH: 1191
<212> TYPE: PRT
<213> ORGANISM: Artificial Sequence
<220> FEATURE:
<223> OTHER INFORMATION: recombinant coronavirus spike protein

<400> SEQUENCE: 15

Met Lys Leu Leu Val Leu Val Phe Ala Thr Leu Val Ser Ser Tyr Thr
1               5                   10                  15

Ile Glu Lys Cys Leu Asp Phe Asp Asp Arg Thr Pro Pro Ala Asn Thr
            20                  25                  30

Gln Phe Leu Ser Ser His Arg Gly Val Tyr Tyr Pro Asp Asp Ile Phe
        35                  40                  45

Arg Ser Asn Val Leu His Leu Val Gln Asp His Phe Leu Pro Phe Asp
    50                  55                  60

Ser Asn Val Thr Arg Phe Ile Thr Phe Gly Leu Asn Phe Asp Asn Pro
65                  70                  75                  80

Ile Ile Pro Phe Lys Asp Gly Ile Tyr Phe Ala Ala Thr Glu Lys Ser
                85                  90                  95

Asn Val Ile Arg Gly Trp Val Phe Gly Ser Thr Met Asn Asn Lys Ser
            100                 105                 110

Gln Ser Val Ile Ile Met Asn Asn Ser Thr Asn Leu Val Ile Arg Ala
        115                 120                 125

Cys Asn Phe Glu Leu Cys Asp Asn Pro Phe Phe Val Val Leu Lys Ser
    130                 135                 140

Asn Asn Thr Gln Ile Pro Ser Tyr Ile Phe Asn Asn Ala Phe Asn Cys
145                 150                 155                 160

Thr Phe Glu Tyr Val Ser Lys Asp Phe Asn Leu Asp Leu Gly Glu Lys
                165                 170                 175

Pro Gly Asn Phe Lys Asp Leu Arg Glu Phe Val Phe Arg Asn Lys Asp
            180                 185                 190

Gly Phe Leu His Val Tyr Ser Gly Tyr Gln Pro Ile Ser Ala Ala Ser
        195                 200                 205

Gly Leu Pro Thr Gly Phe Asn Ala Leu Lys Pro Ile Phe Lys Leu Pro
    210                 215                 220

Leu Gly Ile Asn Ile Thr Asn Phe Arg Thr Leu Leu Thr Ala Phe Pro
225                 230                 235                 240

Pro Arg Pro Asp Tyr Trp Gly Thr Ser Ala Ala Ala Tyr Phe Val Gly
                245                 250                 255

Tyr Leu Lys Pro Thr Thr Phe Met Leu Lys Tyr Asp Glu Asn Gly Thr
            260                 265                 270

Ile Thr Asp Ala Val Asp Cys Ser Gln Asn Pro Leu Ala Glu Leu Lys
        275                 280                 285

Cys Ser Val Lys Ser Phe Glu Ile Asp Lys Gly Ile Tyr Gln Thr Ser
    290                 295                 300

Asn Phe Arg Val Ala Pro Ser Lys Glu Val Val Arg Phe Pro Asn Ile
305                 310                 315                 320

Thr Asn Leu Cys Pro Phe Gly Glu Val Phe Asn Ala Thr Thr Phe Pro
                325                 330                 335
```

```
Ser Val Tyr Ala Trp Glu Arg Lys Arg Ile Ser Asn Cys Val Ala Asp
            340                 345                 350

Tyr Ser Val Leu Tyr Asn Ser Thr Ser Phe Ser Thr Phe Lys Cys Tyr
            355                 360                 365

Gly Val Ser Ala Thr Lys Leu Asn Asp Leu Cys Phe Ser Asn Val Tyr
370                 375                 380

Ala Asp Ser Phe Val Val Lys Gly Asp Val Arg Gln Ile Ala Pro
385                 390                 395                 400

Gly Gln Thr Gly Val Ile Ala Asp Tyr Asn Tyr Lys Leu Pro Asp Asp
                405                 410                 415

Phe Thr Gly Cys Val Leu Ala Trp Asn Thr Arg Asn Ile Asp Ala Thr
            420                 425                 430

Gln Thr Gly Asn Tyr Asn Tyr Lys Tyr Arg Ser Leu Arg His Gly Lys
            435                 440                 445

Leu Arg Pro Phe Glu Arg Asp Ile Ser Asn Val Pro Phe Ser Pro Asp
    450                 455                 460

Gly Lys Pro Cys Thr Pro Pro Ala Phe Asn Cys Tyr Trp Pro Leu Asn
465                 470                 475                 480

Asp Tyr Gly Phe Tyr Ile Thr Asn Gly Ile Gly Tyr Gln Pro Tyr Arg
                485                 490                 495

Val Val Val Leu Ser Phe Glu Leu Leu Asn Ala Pro Ala Thr Val Cys
                500                 505                 510

Gly Pro Lys Leu Ser Thr Asp Leu Ile Lys Asn Gln Cys Val Asn Phe
            515                 520                 525

Asn Phe Asn Gly Leu Thr Gly Thr Gly Val Leu Thr Pro Ser Ser Lys
    530                 535                 540

Arg Phe Gln Pro Phe Gln Gln Phe Gly Arg Asp Val Ser Asp Phe Thr
545                 550                 555                 560

Asp Ser Val Arg Asp Pro Lys Thr Ser Glu Ile Leu Asp Ile Ser Pro
                565                 570                 575

Cys Ser Phe Gly Gly Val Ser Val Ile Thr Pro Gly Thr Asn Thr Ser
                580                 585                 590

Ser Glu Val Ala Val Leu Tyr Gln Asp Val Asn Cys Thr Asp Val Pro
            595                 600                 605

Val Ala Ile His Ala Asp Gln Leu Thr Pro Ser Trp Arg Val His Ser
    610                 615                 620

Thr Gly Asn Asn Val Phe Gln Thr Gln Ala Gly Cys Leu Ile Gly Ala
625                 630                 635                 640

Glu His Val Asp Thr Ser Tyr Glu Cys Asp Ile Pro Ile Gly Ala Gly
                645                 650                 655

Ile Cys Ala Ser Tyr His Thr Val Ser Ser Leu Arg Ser Thr Ser Gln
            660                 665                 670

Lys Ser Ile Val Ala Tyr Thr Met Ser Leu Gly Ala Asp Ser Ser Ile
    675                 680                 685

Ala Tyr Ser Asn Asn Thr Ile Ala Ile Pro Thr Asn Phe Ser Ile Ser
            690                 695                 700

Ile Thr Thr Glu Val Met Pro Val Ser Met Ala Lys Thr Ser Val Asp
705                 710                 715                 720

Cys Asn Met Tyr Ile Cys Gly Asp Ser Thr Glu Cys Ala Asn Leu Leu
                725                 730                 735

Leu Gln Tyr Gly Ser Phe Cys Thr Gln Leu Asn Arg Ala Leu Ser Gly
            740                 745                 750
```

```
Ile Ala Val Glu Gln Asp Arg Asn Thr Arg Glu Val Phe Ala Gln Val
            755                 760                 765

Lys Gln Met Tyr Lys Thr Pro Thr Leu Lys Asp Phe Gly Gly Phe Asn
        770                 775                 780

Phe Ser Gln Ile Leu Pro Asp Pro Leu Lys Pro Thr Lys Arg Ser Phe
785                 790                 795                 800

Ile Glu Asp Leu Leu Phe Asn Lys Val Thr Leu Ala Asp Ala Gly Phe
                805                 810                 815

Met Lys Gln Tyr Gly Glu Cys Leu Gly Asp Ile Asn Ala Arg Asp Leu
            820                 825                 830

Ile Cys Ala Gln Lys Phe Asn Gly Leu Thr Val Leu Pro Pro Leu Leu
        835                 840                 845

Thr Asp Asp Met Ile Ala Ala Tyr Thr Ala Ala Leu Val Ser Gly Thr
850                 855                 860

Ala Thr Ala Gly Trp Thr Phe Gly Ala Gly Ala Ala Leu Gln Ile Pro
865                 870                 875                 880

Phe Ala Met Gln Met Ala Tyr Arg Phe Asn Gly Ile Gly Val Thr Gln
                885                 890                 895

Asn Val Leu Tyr Glu Asn Gln Lys Gln Ile Ala Asn Gln Phe Asn Lys
            900                 905                 910

Ala Ile Ser Gln Ile Gln Glu Ser Leu Thr Thr Thr Ser Thr Ala Leu
        915                 920                 925

Gly Lys Leu Gln Asp Val Val Asn Gln Asn Ala Gln Ala Leu Asn Thr
930                 935                 940

Leu Val Lys Gln Leu Ser Ser Asn Phe Gly Ala Ile Ser Ser Val Leu
945                 950                 955                 960

Asn Asp Ile Leu Ser Arg Leu Asp Pro Pro Glu Ala Glu Val Gln Ile
                965                 970                 975

Asp Arg Leu Ile Thr Gly Arg Leu Gln Ser Leu Gln Thr Tyr Val Thr
            980                 985                 990

Gln Gln Leu Ile Arg Ala Ala Glu Ile Arg Ala Ser Ala Asn Leu Ala
        995                1000                1005

Ala Thr Lys Met Ser Glu Cys Val Leu Gly Gln Ser Lys Arg Val
       1010                1015                1020

Asp Phe Cys Gly Lys Gly Tyr His Leu Met Ser Phe Pro Gln Ala
       1025                1030                1035

Ala Pro His Gly Val Val Phe Leu His Val Thr Tyr Val Pro Ser
       1040                1045                1050

Gln Glu Arg Asn Phe Thr Thr Ala Pro Ala Ile Cys His Glu Gly
       1055                1060                1065

Lys Ala Tyr Phe Pro Arg Glu Gly Val Phe Val Phe Asn Gly Thr
       1070                1075                1080

Ser Trp Phe Ile Thr Gln Arg Asn Phe Phe Ser Pro Gln Ile Ile
       1085                1090                1095

Thr Thr Asp Asn Thr Phe Val Ser Gly Ser Cys Asp Val Val Ile
       1100                1105                1110

Gly Ile Ile Asn Asn Thr Val Tyr Asp Pro Leu Gln Pro Glu Leu
       1115                1120                1125

Asp Ser Phe Lys Glu Glu Leu Asp Lys Tyr Phe Lys Asn His Thr
       1130                1135                1140

Ser Pro Asp Val Asp Leu Gly Asp Ile Ser Gly Ile Asn Ala Ser
       1145                1150                1155

Val Val Asn Ile Gln Lys Glu Ile Asp Arg Leu Asn Glu Val Ala
```

-continued

```
                1160               1165               1170
Lys Asn Leu Asn Glu Ser Leu Ile Asp Leu Gln Glu Leu Gly Lys
       1175               1180               1185
Tyr Glu Gln
   1190

<210> SEQ ID NO 16
<211> LENGTH: 1361
<212> TYPE: PRT
<213> ORGANISM: Artificial Sequence
<220> FEATURE:
<223> OTHER INFORMATION: recombinant coronavirus spike protein

<400> SEQUENCE: 16

Met Leu Ser Val Phe Ile Leu Phe Leu Pro Ser Cys Leu Gly Tyr Ile
1               5                   10                  15

Gly Asp Phe Arg Cys Ile Asn Leu Val Asn Thr Asp Thr Ser Asn Ala
            20                  25                  30

Ser Ala Pro Ser Val Ser Thr Glu Val Val Asp Val Ser Lys Gly Ile
        35                  40                  45

Gly Thr Tyr Tyr Val Leu Asp Arg Val Tyr Leu Asn Ala Thr Leu Leu
    50                  55                  60

Leu Thr Gly Tyr Tyr Pro Val Asp Gly Ser Asn Tyr Arg Asn Leu Ala
65                  70                  75                  80

Leu Thr Gly Thr Asn Thr Leu Ser Leu Asn Trp Tyr Lys Pro Pro Phe
                85                  90                  95

Leu Ser Glu Phe Asn Asp Gly Ile Phe Ala Lys Val Lys Asn Leu Lys
            100                 105                 110

Ala Ser Leu Pro Lys Asp Ser Thr Ser Tyr Phe Pro Thr Ile Val Ile
        115                 120                 125

Gly Ser Asn Phe Val Thr Thr Ser Tyr Thr Val Val Leu Glu Pro Tyr
    130                 135                 140

Asn Gly Ile Ile Met Ala Ser Ile Cys Gln Tyr Thr Ile Cys Leu Leu
145                 150                 155                 160

Pro Tyr Thr Asp Cys Lys Pro Asn Thr Gly Gly Asn Lys Leu Ile Gly
                165                 170                 175

Phe Trp His Ile Asp Leu Lys Ser Pro Val Cys Ile Leu Lys Arg Asn
            180                 185                 190

Phe Thr Phe Asn Val Asn Ala Asp Trp Leu Tyr Phe His Phe Tyr Gln
        195                 200                 205

Gln Gly Gly Thr Phe Tyr Ala Tyr Tyr Ala Asp Ala Gly Ser Ala Thr
    210                 215                 220

Thr Phe Leu Phe Ser Ser Tyr Ile Gly Asp Val Leu Thr Gln Tyr Phe
225                 230                 235                 240

Val Leu Pro Phe Val Cys Thr Pro Thr Thr Gly Val Phe Ser Pro
                245                 250                 255

Gln Tyr Trp Val Thr Pro Leu Val Lys Arg Gln Tyr Leu Phe Asn Phe
            260                 265                 270

Asn Gln Lys Gly Thr Ile Thr Ser Ala Val Asp Cys Ala Ser Ser Tyr
        275                 280                 285

Thr Ser Glu Ile Lys Cys Lys Thr Gln Ser Met Asn Pro Asn Thr Gly
    290                 295                 300

Val Tyr Asp Leu Ser Gly Tyr Thr Val Gln Pro Val Gly Leu Val Tyr
305                 310                 315                 320

Arg Arg Val Arg Asn Leu Pro Asp Cys Arg Ile Glu Asp Trp Leu Ala
```

-continued

```
                325                 330                 335
Ala Lys Thr Val Pro Ser Pro Leu Asn Trp Glu Arg Lys Thr Phe Gln
            340                 345                 350
Asn Cys Asn Phe Asn Leu Ser Ser Leu Leu Arg Leu Val Gln Ala Gly
            355                 360                 365
Ser Leu Ser Cys Ser Asn Ile Asp Ala Ala Lys Val Tyr Gly Met Cys
            370                 375                 380
Phe Gly Ser Met Ser Ile Asp Lys Phe Ala Ile Pro Asn Ser Arg Arg
385                 390                 395                 400
Val Asp Leu Gln Leu Gly Asn Ser Gly Phe Leu Gln Ser Phe Asn Tyr
            405                 410                 415
Lys Ile Asp Thr Arg Ala Thr Ser Cys Gln Leu Tyr Tyr Ser Leu Ala
            420                 425                 430
Gln Ser Asn Val Thr Val Asn Asn His Asn Pro Ser Ser Trp Asn Arg
            435                 440                 445
Arg Tyr Gly Phe Asn Asp Val Ala Thr Phe Gly Arg Gly Lys His Asp
            450                 455                 460
Val Ala Tyr Ala Glu Ala Cys Phe Thr Val Gly Ala Ser Tyr Cys Pro
465                 470                 475                 480
Cys Ala Asn Pro Ser Ile Val Ser Pro Cys Thr Thr Gly Lys Pro Lys
            485                 490                 495
Phe Ala Asn Cys Pro Thr Gly Thr Thr Asn Arg Glu Cys Asn Val Leu
            500                 505                 510
Ala Leu Gly Ser Asn Leu Phe Lys Cys Asp Cys Thr Cys Asn Pro Ser
            515                 520                 525
Pro Leu Thr Thr Tyr Asp Leu Arg Cys Leu Gln Gly Arg Ser Met Leu
            530                 535                 540
Gly Val Gly Asp His Cys Glu Gly Leu Gly Val Leu Glu Asp Lys Cys
545                 550                 555                 560
Gly Gly Ser Asn Thr Cys Asn Cys Ser Ala Asp Ala Phe Val Gly Trp
            565                 570                 575
Ala Lys Asp Ser Cys Leu Ser Asn Gly Arg Cys His Ile Phe Ser Asn
            580                 585                 590
Leu Met Leu Asn Gly Ile Asn Ser Gly Thr Thr Cys Ser Thr Asp Leu
            595                 600                 605
Gln Leu Pro Asn Thr Glu Val Val Thr Gly Ile Cys Val Lys Tyr Asp
            610                 615                 620
Leu Tyr Gly Ile Thr Gly Gln Gly Val Phe Lys Glu Val Lys Ala Asp
625                 630                 635                 640
Tyr Tyr Asn Ser Trp Gln Asn Leu Leu Tyr Asp Val Asn Gly Asn Leu
            645                 650                 655
Asn Gly Phe Arg Asp Ile Val Thr Asn Lys Thr Tyr Leu Thr Arg Ser
            660                 665                 670
Cys Tyr Ser Gly Arg Val Ser Ala Ala Tyr His Gln Asp Ala Pro Glu
            675                 680                 685
Pro Ala Leu Leu Tyr Arg Asn Leu Lys Cys Asp Tyr Val Phe Asn Asn
            690                 695                 700
Asn Ile Phe Arg Glu Glu Thr Pro Leu Asn Tyr Phe Asp Ser Tyr Leu
705                 710                 715                 720
Gly Cys Val Val Asn Ala Asp Asn Ser Thr Glu Gln Ala Val Asp Ala
            725                 730                 735
Cys Asp Leu Arg Met Gly Ser Gly Leu Cys Val Asn Tyr Ser Thr Ala
            740                 745                 750
```

-continued

```
His Arg Ala Arg Thr Ser Val Ser Thr Gly Tyr Lys Leu Thr Thr Phe
            755                 760                 765
Glu Pro Phe Thr Val Ser Ile Val Asn Asp Ser Val Glu Ser Val Gly
            770                 775                 780
Gly Leu Tyr Glu Met Gln Ile Pro Thr Asn Phe Thr Ile Ala Ser His
785                 790                 795                 800
Gln Glu Phe Ile Gln Thr Arg Ala Pro Lys Val Thr Ile Asp Cys Ala
                805                 810                 815
Ala Phe Val Cys Gly Asp Tyr Thr Thr Cys Arg Gln Gln Leu Val Glu
            820                 825                 830
Tyr Gly Ser Phe Cys Asp Asn Ile Asn Ala Ile Leu Gly Glu Val Asn
            835                 840                 845
Asn Leu Ile Asp Thr Met Gln Leu Gln Val Ala Ser Ala Leu Ile Gln
    850                 855                 860
Gly Val Thr Leu Ser Ser Arg Leu Ala Asp Gly Ile Ser Gly Gln Ile
865                 870                 875                 880
Asp Asp Ile Asn Phe Ser Pro Leu Leu Gly Cys Leu Gly Ser Gln Cys
                885                 890                 895
Ser Glu Gly Thr Met Ala Ala Gln Gly Arg Ser Thr Val Glu Asp Leu
            900                 905                 910
Leu Phe Asp Lys Val Lys Leu Ser Asp Val Gly Phe Val Glu Ala Tyr
            915                 920                 925
Asn Asn Cys Thr Gly Gly Gln Glu Val Arg Asp Leu Leu Cys Val Gln
    930                 935                 940
Ser Phe Asn Gly Ile Lys Val Leu Pro Pro Val Leu Ser Glu Asn Gln
945                 950                 955                 960
Val Ser Gly Tyr Thr Ala Gly Ala Thr Ala Ser Ser Met Phe Pro Pro
                965                 970                 975
Trp Ser Ala Ala Ala Gly Val Pro Phe Ser Leu Ser Val Gln Tyr Arg
            980                 985                 990
Ile Asn Gly Leu Gly Val Thr Met  Asn Val Leu Ser Glu  Asn Gln Lys
            995                 1000                1005
Met Ile  Ala Ser Ala Phe Asn  Asn Ala Ile Gly Ala  Ile Gln Glu
    1010                1015                1020
Gly Phe  Asp Ala Thr Asn Ser  Ala Leu Ala Lys Ile  Gln Ser Val
    1025                1030                1035
Val Asn  Ala Asn Ala Glu Ala  Leu Asn Asn Leu Leu  Asn Gln Leu
    1040                1045                1050
Ser Asn  Arg Phe Gly Ala Ile  Ser Ala Ser Leu Gln  Glu Ile Leu
    1055                1060                1065
Ser Arg  Leu Asp Ala Leu Glu  Ala Gln Ala Gln Ile  Asp Arg Leu
    1070                1075                1080
Ile Asn  Gly Arg Leu Thr Ala  Leu Asn Ala Tyr Val  Ser Lys Gln
    1085                1090                1095
Leu Ser  Asp Met Thr Leu Ile  Lys Val Ser Ala Ala  Gln Ala Ile
    1100                1105                1110
Glu Lys  Val Asn Glu Cys Val  Lys Ser Gln Ser Pro  Arg Ile Asn
    1115                1120                1125
Phe Cys  Gly Asn Gly Asn His  Ile Leu Ser Leu Val  Gln Asn Ala
    1130                1135                1140
Pro Tyr  Gly Leu Tyr Phe Leu  His Phe Ser Tyr Val  Pro Thr Ser
    1145                1150                1155
```

```
Phe Thr Thr Ala Asn Val Ser Pro Gly Leu Cys Ile Ser Gly Asp
    1160                1165                1170

Arg Gly Leu Ala Pro Lys Ala Gly Tyr Phe Val Gln Asp Asp Gly
1175                1180                1185

Glu Trp Lys Phe Thr Gly Ser Asn Tyr Tyr Tyr Pro Glu Pro Ile
    1190                1195                1200

Thr Asp Lys Asn Ser Val Val Met Ser Ser Cys Ala Val Asn Tyr
1205                1210                1215

Thr Lys Ala Pro Glu Val Phe Leu Asn Thr Ser Ile Ser Asn Leu
    1220                1225                1230

Pro Asp Phe Lys Glu Glu Leu Asp Lys Trp Phe Lys Asn Gln Thr
1235                1240                1245

Ser Val Ala Pro Asp Leu Ser Leu Asp Phe Glu Lys Leu Asn Val
    1250                1255                1260

Thr Phe Leu Asp Leu Ser Asp Glu Met Asn Arg Ile Gln Glu Ala
1265                1270                1275

Ile Lys Lys Leu Asn Glu Ser Tyr Ile Asn Leu Lys Glu Ile Gly
    1280                1285                1290

Thr Tyr Glu Met Tyr Val Lys Trp Pro Trp Tyr Val Trp Leu Leu
1295                1300                1305

Ile Gly Leu Ala Gly Val Ala Val Cys Val Leu Leu Phe Phe Ile
    1310                1315                1320

Cys Cys Cys Thr Gly Cys Gly Ser Cys Cys Phe Lys Lys Cys Gly
1325                1330                1335

Asn Cys Cys Asp Glu Tyr Gly Gly His Gln Asp Ser Ile Val Ile
    1340                1345                1350

His Asn Ile Ser Ser His Glu Asp
1355                1360

<210> SEQ ID NO 17
<211> LENGTH: 1297
<212> TYPE: PRT
<213> ORGANISM: Artificial Sequence
<220> FEATURE:
<223> OTHER INFORMATION: recombinant coronavirus spike protein

<400> SEQUENCE: 17

Met Leu Ser Val Phe Ile Leu Phe Leu Pro Ser Cys Leu Gly Tyr Ile
1               5                   10                  15

Gly Asp Phe Arg Cys Ile Asn Leu Val Asn Thr Asp Thr Ser Asn Ala
                20                  25                  30

Ser Ala Pro Ser Val Ser Thr Glu Val Val Asp Val Ser Lys Gly Ile
            35                  40                  45

Gly Thr Tyr Tyr Val Leu Asp Arg Val Tyr Leu Asn Ala Thr Leu Leu
50                  55                  60

Leu Thr Gly Tyr Tyr Pro Val Asp Gly Ser Asn Tyr Arg Asn Leu Ala
65                  70                  75                  80

Leu Thr Gly Thr Asn Thr Leu Ser Leu Asn Trp Tyr Lys Pro Pro Phe
                85                  90                  95

Leu Ser Glu Phe Asn Asp Gly Ile Phe Ala Lys Val Lys Asn Leu Lys
            100                 105                 110

Ala Ser Leu Pro Lys Asp Ser Thr Ser Tyr Phe Pro Thr Ile Val Ile
        115                 120                 125

Gly Ser Asn Phe Val Thr Thr Ser Tyr Thr Val Val Leu Glu Pro Tyr
    130                 135                 140
```

```
Asn Gly Ile Ile Met Ala Ser Ile Cys Gln Tyr Thr Ile Cys Leu Leu
145                 150                 155                 160

Pro Tyr Thr Asp Cys Lys Pro Asn Thr Gly Asn Lys Leu Ile Gly
                165                 170                 175

Phe Trp His Ile Asp Leu Lys Ser Pro Val Cys Ile Leu Lys Arg Asn
            180                 185                 190

Phe Thr Phe Asn Val Asn Ala Asp Trp Leu Tyr Phe His Phe Tyr Gln
        195                 200                 205

Gln Gly Gly Thr Phe Tyr Ala Tyr Tyr Ala Asp Ala Gly Ser Ala Thr
    210                 215                 220

Thr Phe Leu Phe Ser Ser Tyr Ile Gly Asp Val Leu Thr Gln Tyr Phe
225                 230                 235                 240

Val Leu Pro Phe Val Cys Thr Pro Thr Thr Gly Val Phe Ser Pro
                245                 250                 255

Gln Tyr Trp Val Thr Pro Leu Val Lys Arg Gln Tyr Leu Phe Asn Phe
            260                 265                 270

Asn Gln Lys Gly Thr Ile Thr Ser Ala Val Asp Cys Ala Ser Ser Tyr
        275                 280                 285

Thr Ser Glu Ile Lys Cys Lys Thr Gln Ser Met Asn Pro Asn Thr Gly
290                 295                 300

Val Tyr Asp Leu Ser Gly Tyr Thr Val Gln Pro Val Gly Leu Val Tyr
305                 310                 315                 320

Arg Arg Val Arg Asn Leu Pro Asp Cys Arg Ile Glu Asp Trp Leu Ala
                325                 330                 335

Ala Lys Thr Val Pro Ser Pro Leu Asn Trp Glu Arg Lys Thr Phe Gln
            340                 345                 350

Asn Cys Asn Phe Asn Leu Ser Ser Leu Leu Arg Leu Val Gln Ala Gly
        355                 360                 365

Ser Leu Ser Cys Ser Asn Ile Asp Ala Ala Lys Val Tyr Gly Met Cys
370                 375                 380

Phe Gly Ser Met Ser Ile Asp Lys Phe Ala Ile Pro Asn Ser Arg Arg
385                 390                 395                 400

Val Asp Leu Gln Leu Gly Asn Ser Gly Phe Leu Gln Ser Phe Asn Tyr
                405                 410                 415

Lys Ile Asp Thr Arg Ala Thr Ser Cys Gln Leu Tyr Tyr Ser Leu Ala
            420                 425                 430

Gln Ser Asn Val Thr Val Asn Asn His Asn Pro Ser Ser Trp Asn Arg
        435                 440                 445

Arg Tyr Gly Phe Asn Asp Val Ala Thr Phe Gly Arg Gly Lys His Asp
450                 455                 460

Val Ala Tyr Ala Glu Ala Cys Phe Thr Val Gly Ala Ser Tyr Cys Pro
465                 470                 475                 480

Cys Ala Asn Pro Ser Ile Val Ser Pro Cys Thr Thr Gly Lys Pro Lys
                485                 490                 495

Phe Ala Asn Cys Pro Thr Gly Thr Thr Asn Arg Glu Cys Asn Val Leu
            500                 505                 510

Ala Leu Gly Ser Asn Leu Phe Lys Cys Asp Cys Thr Cys Asn Pro Ser
        515                 520                 525

Pro Leu Thr Thr Tyr Asp Leu Arg Cys Leu Gln Gly Arg Ser Met Leu
530                 535                 540

Gly Val Gly Asp His Cys Glu Gly Leu Gly Val Leu Glu Asp Lys Cys
545                 550                 555                 560

Gly Gly Ser Asn Thr Cys Asn Cys Ser Ala Asp Ala Phe Val Gly Trp
```

```
                565                 570                 575
Ala Lys Asp Ser Cys Leu Ser Asn Gly Arg Cys His Ile Phe Ser Asn
            580                 585                 590

Leu Met Leu Asn Gly Ile Asn Ser Gly Thr Thr Cys Ser Thr Asp Leu
            595                 600                 605

Gln Leu Pro Asn Thr Glu Val Val Thr Gly Ile Cys Val Lys Tyr Asp
            610                 615                 620

Leu Tyr Gly Ile Thr Gly Gln Gly Val Phe Lys Glu Val Lys Ala Asp
625                 630                 635                 640

Tyr Tyr Asn Ser Trp Gln Asn Leu Leu Tyr Asp Val Asn Gly Asn Leu
            645                 650                 655

Asn Gly Phe Arg Asp Ile Val Thr Asn Lys Thr Tyr Leu Thr Arg Ser
            660                 665                 670

Cys Tyr Ser Gly Arg Val Ser Ala Ala Tyr His Gln Asp Ala Pro Glu
            675                 680                 685

Pro Ala Leu Leu Tyr Arg Asn Leu Lys Cys Asp Tyr Val Phe Asn Asn
            690                 695                 700

Asn Ile Phe Arg Glu Glu Thr Pro Leu Asn Tyr Phe Asp Ser Tyr Leu
705                 710                 715                 720

Gly Cys Val Val Asn Ala Asp Asn Ser Thr Glu Gln Ala Val Asp Ala
                725                 730                 735

Cys Asp Leu Arg Met Gly Ser Gly Leu Cys Val Asn Tyr Ser Thr Ala
            740                 745                 750

His Arg Ala Arg Thr Ser Val Ser Thr Gly Tyr Lys Leu Thr Thr Phe
            755                 760                 765

Glu Pro Phe Thr Val Ser Ile Val Asn Asp Ser Val Glu Ser Val Gly
            770                 775                 780

Gly Leu Tyr Glu Met Gln Ile Pro Thr Asn Phe Thr Ile Ala Ser His
785                 790                 795                 800

Gln Glu Phe Ile Gln Thr Arg Ala Pro Lys Val Thr Ile Asp Cys Ala
            805                 810                 815

Ala Phe Val Cys Gly Asp Tyr Thr Thr Cys Arg Gln Gln Leu Val Glu
            820                 825                 830

Tyr Gly Ser Phe Cys Asp Asn Ile Asn Ala Ile Leu Gly Glu Val Asn
            835                 840                 845

Asn Leu Ile Asp Thr Met Gln Leu Gln Val Ala Ser Ala Leu Ile Gln
            850                 855                 860

Gly Val Thr Leu Ser Ser Arg Leu Ala Asp Gly Ile Ser Gly Gln Ile
865                 870                 875                 880

Asp Asp Ile Asn Phe Ser Pro Leu Leu Gly Cys Leu Gly Ser Gln Cys
                885                 890                 895

Ser Glu Gly Thr Met Ala Ala Gln Gly Arg Ser Thr Val Glu Asp Leu
            900                 905                 910

Leu Phe Asp Lys Val Lys Leu Ser Asp Val Gly Phe Val Glu Ala Tyr
            915                 920                 925

Asn Asn Cys Thr Gly Gly Gln Glu Val Arg Asp Leu Leu Cys Val Gln
            930                 935                 940

Ser Phe Asn Gly Ile Lys Val Leu Pro Pro Val Leu Ser Glu Asn Gln
945                 950                 955                 960

Val Ser Gly Tyr Thr Ala Gly Ala Thr Ala Ser Ser Met Phe Pro Pro
                965                 970                 975

Trp Ser Ala Ala Ala Gly Val Pro Phe Ser Leu Ser Val Gln Tyr Arg
            980                 985                 990
```

```
Ile Asn Gly Leu Gly Val Thr Met Asn Val Leu Ser Glu Asn Gln Lys
        995                 1000                1005

Met Ile Ala Ser Ala Phe Asn Asn Ala Ile Gly Ala Ile Gln Glu
    1010                1015                1020

Gly Phe Asp Ala Thr Asn Ser Ala Leu Ala Lys Ile Gln Ser Val
    1025                1030                1035

Val Asn Ala Asn Ala Glu Ala Leu Asn Asn Leu Leu Asn Gln Leu
    1040                1045                1050

Ser Asn Arg Phe Gly Ala Ile Ser Ala Ser Leu Gln Glu Ile Leu
    1055                1060                1065

Ser Arg Leu Asp Pro Pro Glu Ala Gln Ala Gln Ile Asp Arg Leu
    1070                1075                1080

Ile Asn Gly Arg Leu Thr Ala Leu Asn Ala Tyr Val Ser Lys Gln
    1085                1090                1095

Leu Ser Asp Met Thr Leu Ile Lys Val Ser Ala Ala Gln Ala Ile
    1100                1105                1110

Glu Lys Val Asn Glu Cys Val Lys Ser Gln Ser Pro Arg Ile Asn
    1115                1120                1125

Phe Cys Gly Asn Gly Asn His Ile Leu Ser Leu Val Gln Asn Ala
    1130                1135                1140

Pro Tyr Gly Leu Tyr Phe Leu His Phe Ser Tyr Val Pro Thr Ser
    1145                1150                1155

Phe Thr Thr Ala Asn Val Ser Pro Gly Leu Cys Ile Ser Gly Asp
    1160                1165                1170

Arg Gly Leu Ala Pro Lys Ala Gly Tyr Phe Val Gln Asp Asp Gly
    1175                1180                1185

Glu Trp Lys Phe Thr Gly Ser Asn Tyr Tyr Tyr Pro Glu Pro Ile
    1190                1195                1200

Thr Asp Lys Asn Ser Val Val Met Ser Ser Cys Ala Val Asn Tyr
    1205                1210                1215

Thr Lys Ala Pro Glu Val Phe Leu Asn Thr Ser Ile Ser Asn Leu
    1220                1225                1230

Pro Asp Phe Lys Glu Glu Leu Asp Lys Trp Phe Lys Asn Gln Thr
    1235                1240                1245

Ser Val Ala Pro Asp Leu Ser Leu Asp Phe Glu Lys Leu Asn Val
    1250                1255                1260

Thr Phe Leu Asp Leu Ser Asp Glu Met Asn Arg Ile Gln Glu Ala
    1265                1270                1275

Ile Lys Lys Leu Asn Glu Ser Tyr Ile Asn Leu Lys Glu Ile Gly
    1280                1285                1290

Thr Tyr Glu Met
    1295

<210> SEQ ID NO 18
<211> LENGTH: 1356
<212> TYPE: PRT
<213> ORGANISM: Artificial Sequence
<220> FEATURE:
<223> OTHER INFORMATION: recombinant coronavirus spike protein

<400> SEQUENCE: 18

Met Lys Leu Phe Leu Ile Leu Leu Val Leu Pro Leu Ala Ser Cys Phe
1               5                   10                  15

Phe Thr Cys Asn Ser Asn Ala Asn Leu Ser Met Leu Gln Leu Gly Val
            20                  25                  30
```

```
Pro Asp Asn Ser Ser Thr Ile Val Thr Gly Leu Leu Pro Thr His Trp
         35                  40                  45

Phe Cys Ala Asn Gln Ser Thr Ser Val Tyr Ser Ala Asn Gly Phe Phe
     50                  55                  60

Tyr Ile Asp Val Gly Asn His Arg Ser Ala Phe Ala Leu His Thr Gly
 65                  70                  75                  80

Tyr Tyr Asp Ala Asn Gln Tyr Tyr Ile Tyr Val Thr Asn Glu Ile Gly
                 85                  90                  95

Leu Asn Ala Ser Val Thr Leu Lys Ile Cys Lys Phe Ser Arg Asn Thr
                100                 105                 110

Thr Phe Asp Phe Leu Ser Asn Ala Ser Ser Ser Phe Asp Cys Ile Val
            115                 120                 125

Asn Leu Leu Phe Thr Glu Gln Leu Gly Ala Pro Leu Gly Ile Thr Ile
            130                 135                 140

Ser Gly Glu Thr Val Arg Leu His Leu Tyr Asn Val Thr Arg Thr Phe
145                 150                 155                 160

Tyr Val Pro Ala Ala Tyr Lys Leu Thr Lys Leu Ser Val Lys Cys Tyr
                165                 170                 175

Phe Asn Tyr Ser Cys Val Phe Ser Val Val Asn Ala Thr Val Thr Val
            180                 185                 190

Asn Val Thr Thr His Asn Gly Arg Val Val Asn Tyr Thr Val Cys Asp
            195                 200                 205

Asp Cys Asn Gly Tyr Thr Asp Asn Ile Phe Ser Val Gln Gln Asp Gly
        210                 215                 220

Arg Ile Pro Asn Gly Phe Pro Phe Asn Asn Trp Phe Leu Leu Thr Asn
225                 230                 235                 240

Gly Ser Thr Leu Val Asp Gly Val Ser Arg Leu Tyr Gln Pro Leu Arg
                245                 250                 255

Leu Thr Cys Leu Trp Pro Val Pro Gly Leu Lys Ser Ser Thr Gly Phe
            260                 265                 270

Val Tyr Phe Asn Ala Thr Gly Ser Asp Val Asn Cys Asn Gly Tyr Gln
        275                 280                 285

His Asn Ser Val Val Asp Val Met Arg Tyr Asn Leu Asn Phe Ser Ala
        290                 295                 300

Asn Ser Leu Asp Asn Leu Lys Ser Gly Val Ile Val Phe Lys Thr Leu
305                 310                 315                 320

Gln Tyr Asp Val Leu Phe Tyr Cys Ser Asn Ser Ser Ser Gly Val Leu
                325                 330                 335

Asp Thr Thr Ile Pro Phe Gly Pro Ser Ser Gln Pro Tyr Tyr Cys Phe
            340                 345                 350

Ile Asn Ser Thr Ile Asn Thr Thr His Val Ser Thr Phe Val Gly Ile
        355                 360                 365

Leu Pro Pro Thr Val Arg Glu Ile Val Val Ala Arg Thr Gly Gln Phe
        370                 375                 380

Tyr Ile Asn Gly Phe Lys Tyr Phe Asp Leu Gly Phe Ile Glu Ala Val
385                 390                 395                 400

Asn Phe Asn Val Thr Thr Ala Ser Ala Thr Asp Phe Trp Thr Val Ala
                405                 410                 415

Phe Ala Thr Phe Val Asp Val Leu Val Asn Val Ser Ala Thr Asn Ile
            420                 425                 430

Gln Asn Leu Leu Tyr Cys Asp Ser Pro Phe Glu Lys Leu Gln Cys Glu
        435                 440                 445
```

-continued

His Leu Gln Phe Gly Leu Gln Asp Gly Phe Tyr Ser Ala Asn Phe Leu
    450                 455                 460

Asp Asp Asn Val Leu Pro Glu Thr Tyr Val Ala Leu Pro Ile Tyr Tyr
465                 470                 475                 480

Gln His Thr Asp Ile Asn Phe Thr Ala Thr Ala Ser Phe Gly Gly Ser
                485                 490                 495

Cys Tyr Val Cys Lys Pro His Gln Val Asn Ile Ser Leu Asn Gly Asn
                500                 505                 510

Thr Ser Val Cys Val Arg Thr Ser His Phe Ser Ile Arg Tyr Ile Tyr
            515                 520                 525

Asn Arg Val Lys Ser Gly Ser Pro Gly Asp Ser Ser Trp His Ile Tyr
530                 535                 540

Leu Lys Ser Gly Thr Cys Pro Phe Ser Phe Ser Lys Leu Asn Asn Phe
545                 550                 555                 560

Gln Lys Phe Lys Thr Ile Cys Phe Ser Thr Val Glu Val Pro Gly Ser
                565                 570                 575

Cys Asn Phe Pro Leu Glu Ala Thr Trp His Tyr Thr Ser Tyr Thr Ile
                580                 585                 590

Val Gly Ala Leu Tyr Val Thr Trp Ser Glu Gly Asn Ser Ile Thr Gly
            595                 600                 605

Val Pro Tyr Pro Val Ser Gly Ile Arg Glu Phe Ser Asn Leu Val Leu
    610                 615                 620

Asn Asn Cys Thr Lys Tyr Asn Ile Tyr Asp Tyr Val Gly Thr Gly Ile
625                 630                 635                 640

Ile Arg Ser Ser Asn Gln Ser Leu Ala Gly Gly Ile Thr Tyr Val Ser
                645                 650                 655

Asn Ser Gly Asn Leu Leu Gly Phe Lys Asn Val Ser Thr Gly Asn Ile
                660                 665                 670

Phe Ile Val Thr Pro Cys Asn Gln Pro Asp Gln Val Ala Val Tyr Gln
            675                 680                 685

Gln Ser Ile Ile Gly Ala Met Thr Ala Val Asn Glu Ser Arg Tyr Gly
    690                 695                 700

Leu Gln Asn Leu Leu Gln Leu Pro Asn Phe Tyr Tyr Val Ser Asn Gly
705                 710                 715                 720

Gly Asn Asn Cys Thr Thr Ala Val Met Thr Tyr Ser Asn Phe Gly Ile
                725                 730                 735

Cys Ala Asp Gly Ser Leu Ile Pro Val Arg Pro Arg Asn Ser Ser Asp
                740                 745                 750

Asn Gly Ile Ser Ala Ile Ile Thr Ala Asn Leu Ser Ile Pro Ser Asn
            755                 760                 765

Trp Thr Thr Ser Val Gln Val Glu Tyr Leu Gln Ile Thr Ser Thr Pro
    770                 775                 780

Ile Val Val Asp Cys Ala Thr Tyr Val Cys Asn Gly Asn Pro Arg Cys
785                 790                 795                 800

Lys Asn Leu Leu Lys Gln Tyr Thr Ser Ala Cys Lys Thr Ile Glu Asp
                805                 810                 815

Ala Leu Arg Leu Ser Ala His Leu Glu Thr Asn Asp Val Ser Ser Met
                820                 825                 830

Leu Thr Phe Asp Ser Asn Ala Phe Ser Leu Ala Asn Val Thr Ser Phe
            835                 840                 845

Gly Asp Tyr Asn Leu Ser Ser Val Leu Pro Gln Arg Asn Ile Arg Ser
850                 855                 860

Ser Arg Ile Ala Gly Arg Ser Ala Leu Glu Asp Leu Leu Phe Ser Lys

```
                865                 870                 875                 880
        Val Val Thr Ser Gly Leu Gly Thr Val Asp Val Asp Tyr Lys Ser Cys
                        885                 890                 895

Thr Lys Gly Leu Ser Ile Ala Asp Leu Ala Cys Ala Gln Tyr Tyr Asn
                        900                 905                 910

Gly Ile Met Val Leu Pro Gly Val Ala Asp Ala Glu Arg Met Ala Met
                        915                 920                 925

Tyr Thr Gly Ser Leu Ile Gly Gly Met Val Leu Gly Gly Leu Thr Ser
                        930                 935                 940

Ala Ala Ala Ile Pro Phe Ser Leu Ala Leu Gln Ala Arg Leu Asn Tyr
        945                 950                 955                 960

Val Ala Leu Gln Thr Asp Val Leu Gln Glu Asn Gln Lys Ile Leu Ala
                        965                 970                 975

Ala Ser Phe Asn Lys Ala Ile Asn Asn Ile Val Ala Ser Phe Ser Ser
                        980                 985                 990

Val Asn Asp Ala Ile Thr Gln Thr Ala Glu Ala Ile His Thr Val Thr
                        995                 1000                1005

Ile Ala Leu Asn Lys Ile Gln Asp Val Val Asn Gln Gln Gly Ser
                        1010                1015                1020

Ala Leu Asn His Leu Thr Ser Gln Leu Arg His Asn Phe Gln Ala
                        1025                1030                1035

Ile Ser Asn Ser Ile Gln Ala Ile Tyr Asp Arg Leu Asp Ser Ile
                        1040                1045                1050

Gln Ala Asp Gln Gln Val Asp Arg Leu Ile Thr Gly Arg Leu Ala
                        1055                1060                1065

Ala Leu Asn Ala Phe Val Ser Gln Val Leu Asn Lys Tyr Thr Glu
                        1070                1075                1080

Val Arg Gly Ser Arg Arg Leu Ala Gln Gln Lys Ile Asn Glu Cys
                        1085                1090                1095

Val Lys Ser Gln Ser Asn Arg Tyr Gly Phe Cys Gly Asn Gly Thr
                        1100                1105                1110

His Ile Phe Ser Ile Val Asn Ser Ala Pro Asp Gly Leu Leu Phe
                        1115                1120                1125

Leu His Thr Val Leu Leu Pro Thr Asp Tyr Lys Asn Val Lys Ala
                        1130                1135                1140

Trp Ser Gly Ile Cys Val Asp Gly Ile Tyr Gly Tyr Val Leu Arg
                        1145                1150                1155

Gln Pro Asn Leu Val Leu Tyr Ser Asp Asn Gly Val Phe Arg Val
                        1160                1165                1170

Thr Ser Arg Ile Met Phe Gln Pro Arg Leu Pro Val Leu Ser Asp
                        1175                1180                1185

Phe Val Gln Ile Tyr Asn Cys Asn Val Thr Phe Val Asn Ile Ser
                        1190                1195                1200

Arg Val Glu Leu His Thr Val Ile Pro Asp Tyr Val Asp Val Asn
                        1205                1210                1215

Lys Thr Leu Gln Glu Phe Ala Gln Asn Leu Pro Lys Tyr Val Lys
                        1220                1225                1230

Pro Asn Phe Asp Leu Thr Pro Phe Asn Leu Thr Tyr Leu Asn Leu
                        1235                1240                1245

Ser Ser Glu Leu Lys Gln Leu Glu Ala Lys Thr Ala Ser Leu Phe
                        1250                1255                1260

Gln Thr Thr Val Glu Leu Gln Gly Leu Ile Asp Gln Ile Asn Ser
                        1265                1270                1275
```

```
Thr Tyr Val Asp Leu Lys Leu Leu Asn Arg Phe Glu Asn Tyr Ile
    1280            1285            1290

Lys Trp Pro Trp Trp Val Trp Leu Ile Ile Ser Val Val Phe Val
1295            1300            1305

Val Leu Leu Ser Leu Leu Val Phe Cys Cys Leu Ser Thr Gly Cys
    1310            1315            1320

Cys Gly Cys Cys Asn Cys Leu Thr Ser Ser Met Arg Gly Cys Cys
    1325            1330            1335

Asp Cys Gly Ser Thr Lys Leu Pro Tyr Tyr Glu Phe Glu Lys Val
    1340            1345            1350

His Val Gln
    1355

<210> SEQ ID NO 19
<211> LENGTH: 1291
<212> TYPE: PRT
<213> ORGANISM: Artificial Sequence
<220> FEATURE:
<223> OTHER INFORMATION: recombinant coronavirus spike protein

<400> SEQUENCE: 19

Met Lys Leu Phe Leu Ile Leu Val Leu Pro Leu Ala Ser Cys Phe
1               5               10              15

Phe Thr Cys Asn Ser Asn Ala Asn Leu Ser Met Leu Gln Leu Gly Val
            20              25              30

Pro Asp Asn Ser Ser Thr Ile Val Thr Gly Leu Leu Pro Thr His Trp
            35              40              45

Phe Cys Ala Asn Gln Ser Thr Ser Val Tyr Ser Ala Asn Gly Phe Phe
50              55              60

Tyr Ile Asp Val Gly Asn His Arg Ser Ala Phe Ala Leu His Thr Gly
65              70              75              80

Tyr Tyr Asp Ala Asn Gln Tyr Tyr Ile Tyr Val Thr Asn Glu Ile Gly
            85              90              95

Leu Asn Ala Ser Val Thr Leu Lys Ile Cys Lys Phe Ser Arg Asn Thr
            100             105             110

Thr Phe Asp Phe Leu Ser Asn Ala Ser Ser Ser Phe Asp Cys Ile Val
            115             120             125

Asn Leu Leu Phe Thr Glu Gln Leu Gly Ala Pro Leu Gly Ile Thr Ile
            130             135             140

Ser Gly Glu Thr Val Arg Leu His Leu Tyr Asn Val Thr Arg Thr Phe
145             150             155             160

Tyr Val Pro Ala Ala Tyr Lys Leu Thr Lys Leu Ser Val Lys Cys Tyr
                165             170             175

Phe Asn Tyr Ser Cys Val Phe Ser Val Val Asn Ala Thr Val Thr Val
            180             185             190

Asn Val Thr Thr His Asn Gly Arg Val Val Asn Tyr Thr Val Cys Asp
            195             200             205

Asp Cys Asn Gly Tyr Thr Asp Asn Ile Phe Ser Val Gln Gln Asp Gly
            210             215             220

Arg Ile Pro Asn Gly Phe Pro Phe Asn Asn Trp Phe Leu Leu Thr Asn
225             230             235             240

Gly Ser Thr Leu Val Asp Gly Val Ser Arg Leu Tyr Gln Pro Leu Arg
            245             250             255

Leu Thr Cys Leu Trp Pro Val Pro Gly Leu Lys Ser Ser Thr Gly Phe
            260             265             270
```

```
Val Tyr Phe Asn Ala Thr Gly Ser Asp Val Asn Cys Asn Gly Tyr Gln
            275                 280                 285

His Asn Ser Val Val Asp Val Met Arg Tyr Asn Leu Asn Phe Ser Ala
    290                 295                 300

Asn Ser Leu Asp Asn Leu Lys Ser Gly Val Ile Val Phe Lys Thr Leu
305                 310                 315                 320

Gln Tyr Asp Val Leu Phe Tyr Cys Ser Asn Ser Ser Gly Val Leu
                325                 330                 335

Asp Thr Thr Ile Pro Phe Gly Pro Ser Ser Gln Pro Tyr Tyr Cys Phe
                340                 345                 350

Ile Asn Ser Thr Ile Asn Thr Thr His Val Ser Thr Phe Val Gly Ile
            355                 360                 365

Leu Pro Pro Thr Val Arg Glu Ile Val Val Ala Arg Thr Gly Gln Phe
            370                 375                 380

Tyr Ile Asn Gly Phe Lys Tyr Phe Asp Leu Gly Phe Ile Glu Ala Val
385                 390                 395                 400

Asn Phe Asn Val Thr Thr Ala Ser Ala Thr Asp Phe Trp Thr Val Ala
                405                 410                 415

Phe Ala Thr Phe Val Asp Val Leu Val Asn Val Ser Ala Thr Asn Ile
                420                 425                 430

Gln Asn Leu Leu Tyr Cys Asp Ser Pro Phe Glu Lys Leu Gln Cys Glu
            435                 440                 445

His Leu Gln Phe Gly Leu Gln Asp Gly Phe Tyr Ser Ala Asn Phe Leu
    450                 455                 460

Asp Asp Asn Val Leu Pro Glu Thr Tyr Val Ala Leu Pro Ile Tyr Tyr
465                 470                 475                 480

Gln His Thr Asp Ile Asn Phe Thr Ala Thr Ala Ser Phe Gly Gly Ser
                485                 490                 495

Cys Tyr Val Cys Lys Pro His Gln Val Asn Ile Ser Leu Asn Gly Asn
                500                 505                 510

Thr Ser Val Cys Val Arg Thr Ser His Phe Ser Ile Arg Tyr Ile Tyr
            515                 520                 525

Asn Arg Val Lys Ser Gly Ser Pro Gly Asp Ser Ser Trp His Ile Tyr
    530                 535                 540

Leu Lys Ser Gly Thr Cys Pro Phe Ser Phe Ser Lys Leu Asn Asn Phe
545                 550                 555                 560

Gln Lys Phe Lys Thr Ile Cys Phe Ser Thr Val Glu Val Pro Gly Ser
                565                 570                 575

Cys Asn Phe Pro Leu Glu Ala Thr Trp His Tyr Thr Ser Tyr Thr Ile
                580                 585                 590

Val Gly Ala Leu Tyr Val Thr Trp Ser Glu Gly Asn Ser Ile Thr Gly
            595                 600                 605

Val Pro Tyr Pro Val Ser Gly Ile Arg Glu Phe Ser Asn Leu Val Leu
            610                 615                 620

Asn Asn Cys Thr Lys Tyr Asn Ile Tyr Asp Tyr Val Gly Thr Gly Ile
625                 630                 635                 640

Ile Arg Ser Ser Asn Gln Ser Leu Ala Gly Gly Ile Thr Tyr Val Ser
                645                 650                 655

Asn Ser Gly Asn Leu Leu Gly Phe Lys Asn Val Ser Thr Gly Asn Ile
            660                 665                 670

Phe Ile Val Thr Pro Cys Asn Gln Pro Asp Gln Val Ala Val Tyr Gln
            675                 680                 685
```

```
Gln Ser Ile Ile Gly Ala Met Thr Ala Val Asn Glu Ser Arg Tyr Gly
    690             695             700
Leu Gln Asn Leu Leu Gln Leu Pro Asn Phe Tyr Tyr Val Ser Asn Gly
705             710             715             720
Gly Asn Asn Cys Thr Thr Ala Val Met Thr Tyr Ser Asn Phe Gly Ile
            725             730             735
Cys Ala Asp Gly Ser Leu Ile Pro Val Arg Pro Arg Asn Ser Ser Asp
            740             745             750
Asn Gly Ile Ser Ala Ile Ile Thr Ala Asn Leu Ser Ile Pro Ser Asn
            755             760             765
Trp Thr Thr Ser Val Gln Val Glu Tyr Leu Gln Ile Thr Ser Thr Pro
770             775             780
Ile Val Val Asp Cys Ala Thr Tyr Val Cys Asn Gly Asn Pro Arg Cys
785             790             795             800
Lys Asn Leu Leu Lys Gln Tyr Thr Ser Ala Cys Lys Thr Ile Glu Asp
            805             810             815
Ala Leu Arg Leu Ser Ala His Leu Glu Thr Asn Asp Val Ser Ser Met
            820             825             830
Leu Thr Phe Asp Ser Asn Ala Phe Ser Leu Ala Asn Val Thr Ser Phe
            835             840             845
Gly Asp Tyr Asn Leu Ser Ser Val Leu Pro Gln Arg Asn Ile Arg Ser
850             855             860
Ser Arg Ile Ala Gly Arg Ser Ala Leu Glu Asp Leu Leu Phe Ser Lys
865             870             875             880
Val Val Thr Ser Gly Leu Gly Thr Val Asp Val Asp Tyr Lys Ser Cys
            885             890             895
Thr Lys Gly Leu Ser Ile Ala Asp Leu Ala Cys Ala Gln Tyr Tyr Asn
            900             905             910
Gly Ile Met Val Leu Pro Gly Val Ala Asp Ala Glu Arg Met Ala Met
            915             920             925
Tyr Thr Gly Ser Leu Ile Gly Gly Met Val Leu Gly Gly Leu Thr Ser
930             935             940
Ala Ala Ala Ile Pro Phe Ser Leu Ala Leu Gln Ala Arg Leu Asn Tyr
945             950             955             960
Val Ala Leu Gln Thr Asp Val Leu Gln Glu Asn Gln Lys Ile Leu Ala
            965             970             975
Ala Ser Phe Asn Lys Ala Ile Asn Asn Ile Val Ala Ser Phe Ser Ser
            980             985             990
Val Asn Asp Ala Ile Thr Gln Thr Ala Glu Ala Ile His Thr Val Thr
            995             1000            1005
Ile Ala Leu Asn Lys Ile Gln Asp Val Val Asn Gln Gln Gly Ser
    1010            1015            1020
Ala Leu Asn His Leu Thr Ser Gln Leu Arg His Asn Phe Gln Ala
    1025            1030            1035
Ile Ser Asn Ser Ile Gln Ala Ile Tyr Asp Arg Leu Asp Pro Pro
    1040            1045            1050
Gln Ala Asp Gln Gln Val Asp Arg Leu Ile Thr Gly Arg Leu Ala
    1055            1060            1065
Ala Leu Asn Ala Phe Val Ser Gln Val Leu Asn Lys Tyr Thr Glu
    1070            1075            1080
Val Arg Gly Ser Arg Arg Leu Ala Gln Gln Lys Ile Asn Glu Cys
    1085            1090            1095
Val Lys Ser Gln Ser Asn Arg Tyr Gly Phe Cys Gly Asn Gly Thr
```

```
                1100                1105                1110
His Ile Phe Ser Ile Val Asn Ser Ala Pro Asp Gly Leu Leu Phe
    1115                1120                1125

Leu His Thr Val Leu Leu Pro Thr Asp Tyr Lys Asn Val Lys Ala
    1130                1135                1140

Trp Ser Gly Ile Cys Val Asp Gly Ile Tyr Gly Tyr Val Leu Arg
    1145                1150                1155

Gln Pro Asn Leu Val Leu Tyr Ser Asp Asn Gly Val Phe Arg Val
    1160                1165                1170

Thr Ser Arg Ile Met Phe Gln Pro Arg Leu Pro Val Leu Ser Asp
    1175                1180                1185

Phe Val Gln Ile Tyr Asn Cys Asn Val Thr Phe Val Asn Ile Ser
    1190                1195                1200

Arg Val Glu Leu His Thr Val Ile Pro Asp Tyr Val Asp Val Asn
    1205                1210                1215

Lys Thr Leu Gln Glu Phe Ala Gln Asn Leu Pro Lys Tyr Val Lys
    1220                1225                1230

Pro Asn Phe Asp Leu Thr Pro Phe Asn Leu Thr Tyr Leu Asn Leu
    1235                1240                1245

Ser Ser Glu Leu Lys Gln Leu Glu Ala Lys Thr Ala Ser Leu Phe
    1250                1255                1260

Gln Thr Thr Val Glu Leu Gln Gly Leu Ile Asp Gln Ile Asn Ser
    1265                1270                1275

Thr Tyr Val Asp Leu Lys Leu Leu Asn Arg Phe Glu Asn
    1280                1285                1290

<210> SEQ ID NO 20
<211> LENGTH: 1171
<212> TYPE: PRT
<213> ORGANISM: Artificial Sequence
<220> FEATURE:
<223> OTHER INFORMATION: recombinant coronavirus spike protein

<400> SEQUENCE: 20

Met Phe Val Leu Leu Val Ala Tyr Ala Leu Leu His Ile Ala Gly Cys
1               5                   10                  15

Gln Thr Thr Asn Gly Thr Asn Thr Ser His Ser Val Cys Asn Gly Cys
                20                  25                  30

Val Gly His Ser Glu Asn Val Phe Ala Val Glu Ser Gly Gly Tyr Ile
            35                  40                  45

Pro Ser Asn Phe Ala Phe Asn Asn Trp Phe Leu Leu Thr Asn Thr Ser
        50                  55                  60

Ser Val Val Asp Gly Val Val Arg Ser Phe Gln Pro Leu Leu Leu Asn
65                  70                  75                  80

Cys Leu Trp Ser Val Ser Gly Ser Gln Phe Thr Thr Gly Phe Val Tyr
                85                  90                  95

Phe Asn Gly Thr Gly Arg Gly Ala Cys Lys Gly Phe Tyr Ser Asn Ala
                100                 105                 110

Ser Ser Asp Val Ile Arg Tyr Asn Ile Asn Phe Glu Glu Asn Leu Arg
            115                 120                 125

Arg Gly Thr Ile Leu Phe Lys Thr Ser Tyr Gly Ala Val Val Phe Tyr
        130                 135                 140

Cys Thr Asn Asn Thr Leu Val Ser Gly Asp Ala His Ile Pro Ser Gly
145                 150                 155                 160

Thr Val Leu Gly Asn Phe Tyr Cys Phe Val Asn Thr Thr Ile Gly Asn
```

```
                165                 170                 175
Glu Thr Thr Ser Ala Phe Val Gly Ala Leu Pro Lys Thr Val Arg Glu
            180                 185                 190

Phe Val Ile Ser Arg Thr Gly His Phe Tyr Ile Asn Gly Tyr Arg Tyr
            195                 200                 205

Phe Ser Leu Gly Asp Val Glu Ala Val Asn Phe Asn Val Thr Asn Ala
            210                 215                 220

Ala Thr Val Cys Thr Val Ala Leu Ala Ser Tyr Ala Asp Val Leu
225             230                 235                 240

Val Asn Val Ser Gln Thr Ala Ile Ala Asn Ile Ile Tyr Cys Asn Ser
                245                 250                 255

Val Ile Asn Arg Leu Arg Cys Asp Gln Leu Ser Phe Asp Val Pro Asp
                260                 265                 270

Gly Phe Tyr Ser Thr Ser Pro Ile Gln Pro Val Glu Leu Pro Val Ser
                275                 280                 285

Ile Val Ser Leu Pro Val Tyr His Lys His Thr Phe Ile Val Leu Tyr
            290                 295                 300

Val Asn Phe Glu His Arg Arg Gly Pro Gly Lys Cys Tyr Asn Cys Arg
305             310                 315                 320

Pro Ala Val Ile Asn Ile Thr Leu Ala Asn Phe Asn Glu Thr Lys Gly
                325                 330                 335

Pro Leu Cys Val Asp Thr Ser His Phe Thr Thr Gln Phe Val Asp Asn
            340                 345                 350

Val Lys Leu Ala Arg Trp Ser Ala Ser Ile Asn Thr Gly Asn Cys Pro
355             360                 365

Phe Ser Phe Gly Lys Val Asn Asn Phe Val Lys Phe Gly Ser Val Cys
            370                 375                 380

Phe Ser Leu Lys Asp Ile Pro Gly Gly Cys Ala Met Pro Ile Met Ala
385             390                 395                 400

Asn Leu Val Asn Ser Lys Ser His Asn Ile Gly Ser Leu Tyr Val Ser
                405                 410                 415

Trp Ser Asp Gly Asp Val Ile Thr Gly Val Pro Lys Pro Val Glu Gly
                420                 425                 430

Val Ser Ser Phe Met Asn Val Thr Leu Asn Lys Cys Thr Lys Tyr Asn
            435                 440                 445

Ile Tyr Asp Val Ser Gly Val Gly Val Ile Arg Ile Ser Asn Asp Thr
            450                 455                 460

Phe Leu Asn Gly Ile Thr Tyr Thr Ser Thr Ser Gly Asn Leu Leu Gly
465             470                 475                 480

Phe Lys Asp Val Thr Asn Gly Thr Ile Tyr Ser Ile Thr Pro Cys Asn
                485                 490                 495

Pro Pro Asp Gln Leu Val Val Tyr Gln Gln Ala Val Val Gly Ala Met
            500                 505                 510

Leu Ser Glu Asn Phe Thr Ser Tyr Gly Phe Ser Asn Val Val Glu Met
            515                 520                 525

Pro Lys Phe Phe Tyr Ala Ser Asn Gly Thr Tyr Asn Cys Thr Asp Ala
            530                 535                 540

Val Leu Thr Tyr Ser Ser Phe Gly Val Cys Ala Asp Gly Ser Ile Ile
545             550                 555                 560

Ala Val Gln Pro Arg Asn Val Ser Tyr Asp Ser Val Ser Ala Ile Val
                565                 570                 575

Thr Ala Asn Leu Ser Ile Pro Phe Asn Trp Thr Thr Ser Val Gln Val
                580                 585                 590
```

```
Glu Tyr Leu Gln Ile Thr Ser Thr Pro Ile Val Val Asp Cys Ser Thr
            595                 600                 605

Tyr Val Cys Asn Gly Asn Val Arg Cys Val Glu Leu Leu Lys Gln Tyr
    610                 615                 620

Thr Ser Ala Cys Lys Thr Ile Glu Asp Ala Leu Arg Asn Ser Ala Met
625                 630                 635                 640

Leu Glu Ser Ala Asp Val Ser Glu Met Leu Thr Phe Asp Lys Lys Ala
                645                 650                 655

Phe Thr Leu Ala Asn Val Ser Ser Phe Gly Asp Tyr Asn Leu Ser Ser
            660                 665                 670

Val Ile Pro Ser Leu Pro Arg Ser Gly Ser Arg Val Ala Gly Arg Ser
        675                 680                 685

Ala Ile Glu Asp Ile Leu Phe Ser Lys Leu Val Thr Ser Gly Leu Gly
    690                 695                 700

Thr Val Asp Ala Asp Tyr Lys Lys Cys Thr Lys Gly Leu Ser Ile Ala
705                 710                 715                 720

Asp Leu Ala Cys Ala Gln Tyr Tyr Asn Gly Ile Met Val Leu Pro Gly
                725                 730                 735

Val Ala Asp Ala Glu Arg Met Ala Met Tyr Thr Gly Ser Leu Ile Gly
            740                 745                 750

Gly Ile Ala Leu Gly Gly Leu Thr Ser Ala Ala Ser Ile Pro Phe Ser
        755                 760                 765

Leu Ala Ile Gln Ser Arg Leu Asn Tyr Val Ala Leu Gln Thr Asp Val
770                 775                 780

Leu Gln Glu Asn Gln Arg Ile Leu Ala Ala Ser Phe Asn Lys Ala Met
785                 790                 795                 800

Thr Asn Ile Val Asp Ala Phe Thr Gly Val Asn Asp Ala Ile Thr Gln
                805                 810                 815

Thr Ser Gln Ala Leu Gln Thr Val Ala Thr Ala Leu Asn Lys Ile Gln
            820                 825                 830

Asp Val Val Asn Gln Gln Gly Asn Ser Leu Asn His Leu Thr Ser Gln
        835                 840                 845

Leu Arg Gln Asn Phe Gln Ala Ile Ser Ser Ser Ile Gln Ala Ile Tyr
850                 855                 860

Asp Arg Leu Asp Ile Ile Gln Ala Asp Gln Gln Val Asp Arg Leu Ile
865                 870                 875                 880

Thr Gly Arg Leu Ala Ala Leu Asn Val Phe Val Ser His Thr Leu Thr
                885                 890                 895

Lys Tyr Thr Glu Val Arg Ala Ser Arg Gln Leu Ala Gln Gln Lys Val
            900                 905                 910

Asn Glu Cys Val Lys Ser Gln Ser Lys Arg Tyr Gly Phe Cys Gly Asn
        915                 920                 925

Gly Thr His Ile Phe Ser Leu Val Asn Ala Ala Pro Glu Gly Leu Val
    930                 935                 940

Phe Leu His Thr Val Leu Leu Pro Thr Gln Tyr Lys Asp Val Glu Ala
945                 950                 955                 960

Trp Ser Gly Leu Cys Val Asp Gly Ile Asn Gly Tyr Val Leu Arg Gln
                965                 970                 975

Pro Asn Leu Ala Leu Tyr Lys Glu Gly Asn Tyr Tyr Arg Ile Thr Ser
            980                 985                 990

Arg Ile Met Phe Glu Pro Arg Ile  Pro Thr Ile Ala Asp  Phe Val Gln
        995                 1000                1005
```

```
Ile Glu Asn Cys Asn Val Thr Phe Val Asn Ile Ser Arg Ser Glu
    1010                1015                1020

Leu Gln Thr Ile Val Pro Glu Tyr Ile Asp Val Asn Lys Thr Leu
    1025                1030                1035

Gln Glu Leu Ser Tyr Lys Leu Pro Asn Tyr Thr Val Pro Asp Leu
    1040                1045                1050

Val Val Glu Gln Tyr Asn Gln Thr Ile Leu Asn Leu Thr Ser Glu
    1055                1060                1065

Ile Ser Thr Leu Glu Asn Lys Ser Ala Glu Leu Asn Tyr Thr Val
    1070                1075                1080

Gln Lys Leu Gln Thr Leu Ile Asp Asn Ile Asn Ser Thr Leu Val
    1085                1090                1095

Asp Leu Lys Trp Leu Asn Arg Val Glu Thr Tyr Ile Lys Trp Pro
    1100                1105                1110

Trp Trp Val Trp Leu Cys Ile Ser Val Val Leu Ile Phe Val Val
    1115                1120                1125

Ser Met Leu Leu Leu Cys Cys Cys Ser Thr Gly Cys Cys Gly Phe
    1130                1135                1140

Phe Ser Cys Phe Ala Ser Ser Ile Arg Gly Cys Cys Glu Ser Thr
    1145                1150                1155

Lys Leu Pro Tyr Tyr Asp Val Glu Lys Ile His Ile Gln
    1160                1165                1170

<210> SEQ ID NO 21
<211> LENGTH: 1108
<212> TYPE: PRT
<213> ORGANISM: Artificial Sequence
<220> FEATURE:
<223> OTHER INFORMATION: recombinant coronavirus spike protein

<400> SEQUENCE: 21

Met Phe Val Leu Leu Val Ala Tyr Ala Leu Leu His Ile Ala Gly Cys
1               5                   10                  15

Gln Thr Thr Asn Gly Thr Asn Thr Ser His Ser Val Cys Asn Gly Cys
                20                  25                  30

Val Gly His Ser Glu Asn Val Phe Ala Val Glu Ser Gly Gly Tyr Ile
            35                  40                  45

Pro Ser Asn Phe Ala Phe Asn Asn Trp Phe Leu Leu Thr Asn Thr Ser
50                  55                  60

Ser Val Val Asp Gly Val Val Arg Ser Phe Gln Pro Leu Leu Leu Asn
65                  70                  75                  80

Cys Leu Trp Ser Val Ser Gly Ser Gln Phe Thr Thr Gly Phe Val Tyr
                85                  90                  95

Phe Asn Gly Thr Gly Arg Gly Ala Cys Lys Gly Phe Tyr Ser Asn Ala
            100                 105                 110

Ser Ser Asp Val Ile Arg Tyr Asn Ile Asn Phe Glu Glu Asn Leu Arg
        115                 120                 125

Arg Gly Thr Ile Leu Phe Lys Thr Ser Tyr Gly Ala Val Val Phe Tyr
    130                 135                 140

Cys Thr Asn Asn Thr Leu Val Ser Gly Asp Ala His Ile Pro Ser Gly
145                 150                 155                 160

Thr Val Leu Gly Asn Phe Tyr Cys Phe Val Asn Thr Thr Ile Gly Asn
                165                 170                 175

Glu Thr Thr Ser Ala Phe Val Gly Ala Leu Pro Lys Thr Val Arg Glu
            180                 185                 190
```

```
Phe Val Ile Ser Arg Thr Gly His Phe Tyr Ile Asn Gly Tyr Arg Tyr
            195                 200                 205

Phe Ser Leu Gly Asp Val Glu Ala Val Asn Phe Asn Val Thr Asn Ala
        210                 215                 220

Ala Thr Thr Val Cys Thr Val Ala Leu Ala Ser Tyr Ala Asp Val Leu
225                 230                 235                 240

Val Asn Val Ser Gln Thr Ala Ile Ala Asn Ile Ile Tyr Cys Asn Ser
                245                 250                 255

Val Ile Asn Arg Leu Arg Cys Asp Gln Leu Ser Phe Asp Val Pro Asp
            260                 265                 270

Gly Phe Tyr Ser Thr Ser Pro Ile Gln Pro Val Glu Leu Pro Val Ser
        275                 280                 285

Ile Val Ser Leu Pro Val Tyr His Lys His Thr Phe Ile Val Leu Tyr
    290                 295                 300

Val Asn Phe Glu His Arg Arg Gly Pro Gly Lys Cys Tyr Asn Cys Arg
305                 310                 315                 320

Pro Ala Val Ile Asn Ile Thr Leu Ala Asn Phe Asn Glu Thr Lys Gly
                325                 330                 335

Pro Leu Cys Val Asp Thr Ser His Phe Thr Thr Gln Phe Val Asp Asn
            340                 345                 350

Val Lys Leu Ala Arg Trp Ser Ala Ser Ile Asn Thr Gly Asn Cys Pro
        355                 360                 365

Phe Ser Phe Gly Lys Val Asn Asn Phe Val Lys Phe Gly Ser Val Cys
    370                 375                 380

Phe Ser Leu Lys Asp Ile Pro Gly Gly Cys Ala Met Pro Ile Met Ala
385                 390                 395                 400

Asn Leu Val Asn Ser Lys Ser His Asn Ile Gly Ser Leu Tyr Val Ser
                405                 410                 415

Trp Ser Asp Gly Asp Val Ile Thr Gly Val Pro Lys Pro Val Glu Gly
            420                 425                 430

Val Ser Ser Phe Met Asn Val Thr Leu Asn Lys Cys Thr Lys Tyr Asn
        435                 440                 445

Ile Tyr Asp Val Ser Gly Val Gly Val Ile Arg Ile Ser Asn Asp Thr
    450                 455                 460

Phe Leu Asn Gly Ile Thr Tyr Thr Ser Thr Ser Gly Asn Leu Leu Gly
465                 470                 475                 480

Phe Lys Asp Val Thr Asn Gly Thr Ile Tyr Ser Ile Thr Pro Cys Asn
                485                 490                 495

Pro Pro Asp Gln Leu Val Val Tyr Gln Gln Ala Val Val Gly Ala Met
            500                 505                 510

Leu Ser Glu Asn Phe Thr Ser Tyr Gly Phe Ser Asn Val Val Glu Met
        515                 520                 525

Pro Lys Phe Phe Tyr Ala Ser Asn Gly Thr Tyr Asn Cys Thr Asp Ala
    530                 535                 540

Val Leu Thr Tyr Ser Ser Phe Gly Val Cys Ala Asp Gly Ser Ile Ile
545                 550                 555                 560

Ala Val Gln Pro Arg Asn Val Ser Tyr Asp Ser Val Ser Ala Ile Val
                565                 570                 575

Thr Ala Asn Leu Ser Ile Pro Phe Asn Trp Thr Thr Ser Val Gln Val
            580                 585                 590

Glu Tyr Leu Gln Ile Thr Ser Thr Pro Ile Val Val Asp Cys Ser Thr
        595                 600                 605

Tyr Val Cys Asn Gly Asn Val Arg Cys Val Glu Leu Leu Lys Gln Tyr
```

```
            610                 615                 620
Thr Ser Ala Cys Lys Thr Ile Glu Asp Ala Leu Arg Asn Ser Ala Met
625                 630                 635                 640

Leu Glu Ser Ala Asp Val Ser Glu Met Leu Thr Phe Asp Lys Lys Ala
                645                 650                 655

Phe Thr Leu Ala Asn Val Ser Ser Phe Gly Asp Tyr Asn Leu Ser Ser
                660                 665                 670

Val Ile Pro Ser Leu Pro Arg Ser Gly Ser Arg Val Ala Gly Arg Ser
            675                 680                 685

Ala Ile Glu Asp Ile Leu Phe Ser Lys Leu Val Thr Ser Gly Leu Gly
            690                 695                 700

Thr Val Asp Ala Asp Tyr Lys Lys Cys Thr Lys Gly Leu Ser Ile Ala
705                 710                 715                 720

Asp Leu Ala Cys Ala Gln Tyr Tyr Asn Gly Ile Met Val Leu Pro Gly
                725                 730                 735

Val Ala Asp Ala Glu Arg Met Ala Met Tyr Thr Gly Ser Leu Ile Gly
                740                 745                 750

Gly Ile Ala Leu Gly Gly Leu Thr Ser Ala Ala Ser Ile Pro Phe Ser
            755                 760                 765

Leu Ala Ile Gln Ser Arg Leu Asn Tyr Val Ala Leu Gln Thr Asp Val
770                 775                 780

Leu Gln Glu Asn Gln Arg Ile Leu Ala Ala Ser Phe Asn Lys Ala Met
785                 790                 795                 800

Thr Asn Ile Val Asp Ala Phe Thr Gly Val Asn Asp Ala Ile Thr Gln
                805                 810                 815

Thr Ser Gln Ala Leu Gln Thr Val Ala Thr Ala Leu Asn Lys Ile Gln
                820                 825                 830

Asp Val Val Asn Gln Gln Gly Asn Ser Leu Asn His Leu Thr Ser Gln
            835                 840                 845

Leu Arg Gln Asn Phe Gln Ala Ile Ser Ser Ser Ile Gln Ala Ile Tyr
850                 855                 860

Asp Arg Leu Asp Pro Pro Gln Ala Asp Gln Gln Val Asp Arg Leu Ile
865                 870                 875                 880

Thr Gly Arg Leu Ala Ala Leu Asn Val Phe Val Ser His Thr Leu Thr
                885                 890                 895

Lys Tyr Thr Glu Val Arg Ala Ser Arg Gln Leu Ala Gln Gln Lys Val
                900                 905                 910

Asn Glu Cys Val Lys Ser Gln Ser Lys Arg Tyr Gly Phe Cys Gly Asn
            915                 920                 925

Gly Thr His Ile Phe Ser Leu Val Asn Ala Ala Pro Glu Gly Leu Val
            930                 935                 940

Phe Leu His Thr Val Leu Leu Pro Thr Gln Tyr Lys Asp Val Glu Ala
945                 950                 955                 960

Trp Ser Gly Leu Cys Val Asp Gly Ile Asn Gly Tyr Val Leu Arg Gln
                965                 970                 975

Pro Asn Leu Ala Leu Tyr Lys Glu Gly Asn Tyr Tyr Arg Ile Thr Ser
                980                 985                 990

Arg Ile Met Phe Glu Pro Arg Ile Pro Thr Ile Ala Asp Phe Val Gln
            995                 1000                1005

Ile Glu Asn Cys Asn Val Thr Phe Val Asn Ile Ser Arg Ser Glu
            1010                1015                1020

Leu Gln Thr Ile Val Pro Glu Tyr Ile Asp Val Asn Lys Thr Leu
            1025                1030                1035
```

```
Gln Glu Leu Ser Tyr Lys Leu Pro Asn Tyr Thr Val Pro Asp Leu
        1040                1045                1050

Val Val Glu Gln Tyr Asn Gln Thr Ile Leu Asn Leu Thr Ser Glu
    1055                1060                1065

Ile Ser Thr Leu Glu Asn Lys Ser Ala Glu Leu Asn Tyr Thr Val
    1070                1075                1080

Gln Lys Leu Gln Thr Leu Ile Asp Asn Ile Asn Ser Thr Leu Val
    1085                1090                1095

Asp Leu Lys Trp Leu Asn Arg Val Glu Thr
    1100                1105
```

<210> SEQ ID NO 22
<211> LENGTH: 26
<212> TYPE: PRT
<213> ORGANISM: Artificial Sequence
<220> FEATURE:
<223> OTHER INFORMATION: GCN4 trimerization domain

<400> SEQUENCE: 22

```
Gly Tyr Ile Pro Glu Ala Pro Arg Asp Gly Gln Ala Tyr Val Arg Lys
1               5                   10                  15

Asp Gly Glu Trp Val Leu Leu Ser Thr Phe
            20                  25
```

<210> SEQ ID NO 23
<211> LENGTH: 173
<212> TYPE: PRT
<213> ORGANISM: Artificial Sequence
<220> FEATURE:
<223> OTHER INFORMATION: self-assembling protein nanoparticle sequence

<400> SEQUENCE: 23

```
Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30

Met Ser Ser Trp Cys Tyr Thr His Ser Leu Asp Gly Ala Gly Leu Phe
        35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170
```

<210> SEQ ID NO 24
<211> LENGTH: 154
<212> TYPE: PRT

-continued

<213> ORGANISM: Artificial Sequence
<220> FEATURE:
<223> OTHER INFORMATION: self-assembling protein nanoparticle sequence

<400> SEQUENCE: 24

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150

<210> SEQ ID NO 25
<211> LENGTH: 265
<212> TYPE: PRT
<213> ORGANISM: Artificial Sequence
<220> FEATURE:
<223> OTHER INFORMATION: self-assembling protein nanoparticle sequence

<400> SEQUENCE: 25

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
            195                 200                 205

Ile Glu Asp Ala Leu Val Val Ser Glu Arg Gly Gly Asp Phe Lys Leu
        210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265

<210> SEQ ID NO 26
<211> LENGTH: 265
<212> TYPE: PRT
<213> ORGANISM: Artificial Sequence
<220> FEATURE:
<223> OTHER INFORMATION: self-assembling protein nanoparticle sequence

<400> SEQUENCE: 26

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
            195                 200                 205

Ile Glu Asp Ala Leu Val Val Ser Glu Arg Gly Gly Asp Phe Lys Leu
        210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265

<210> SEQ ID NO 27
<211> LENGTH: 26
<212> TYPE: PRT
<213> ORGANISM: Artificial Sequence
<220> FEATURE:
<223> OTHER INFORMATION: GCN4 trimerization domain

<400> SEQUENCE: 27

```
Gly Tyr Ile Pro Glu Ala Pro Arg Asp Gly Gln Ala Tyr Val Arg Lys
1               5                   10                  15

Asp Gly Glu Trp Val Leu Leu Ser Thr Phe
            20                  25
```

<210> SEQ ID NO 28
<211> LENGTH: 1318
<212> TYPE: PRT
<213> ORGANISM: Artificial Sequence
<220> FEATURE:
<223> OTHER INFORMATION: recombinant coronavirus spike protein

<400> SEQUENCE: 28

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285
```

-continued

```
Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Phe Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700
```

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
            725                 730                 735

Ala Leu Pro Asp Thr Pro Ser Thr Leu Thr Pro Ala Ser Val Gly Ser
            740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
            805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
            885                 890                 895

Lys Val Thr Ile Ala Asp Pro Gly Tyr Met Gln Gly Tyr Asp Asp Cys
        900                 905                 910

Met Gln Gln Gly Pro Ala Ser Ala Arg Asp Leu Ile Cys Ala Gln Tyr
    915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
            965                 970                 975

Phe Tyr Arg Leu Asn Gly Val Gly Ile Thr Gln Gln Val Leu Ser Glu
            980                 985                 990

Asn Gln Lys Leu Ile Ala Asn Lys Phe Asn Gln Ala Leu Gly Ala Met
        995                 1000                1005

Gln Thr Gly Phe Thr Thr Thr Asn Glu Ala Phe His Lys Val Gln
    1010                1015                1020

Asp Ala Val Asn Asn Asn Ala Gln Ala Leu Ser Lys Leu Ala Ser
    1025                1030                1035

Glu Leu Ser Asn Thr Phe Gly Ala Ile Ser Ala Ser Ile Gly Asp
    1040                1045                1050

Ile Ile Gln Arg Leu Asp Pro Pro Glu Gln Asp Ala Gln Ile Asp
    1055                1060                1065

Arg Leu Ile Asn Gly Arg Leu Thr Thr Leu Asn Ala Phe Val Ala
    1070                1075                1080

Gln Gln Leu Val Arg Ser Glu Ser Ala Ala Leu Ser Ala Gln Leu
    1085                1090                1095

Ala Lys Asp Lys Val Asn Glu Cys Val Lys Ala Gln Ser Lys Arg
    1100                1105                1110

Ser Gly Phe Cys Gly Gln Gly Thr His Ile Val Ser Phe Val Val

```
                      1115                1120                1125

Asn Ala  Pro Asn Gly Leu Tyr  Phe Met His Val Gly  Tyr Tyr Pro
         1130                1135                1140

Ser Asn  His Ile Glu Val Val  Ser Ala Tyr Gly Leu  Cys Asp Ala
         1145                1150                1155

Ala Asn  Pro Thr Asn Cys Ile  Ala Pro Val Asn Gly  Tyr Phe Ile
         1160                1165                1170

Lys Thr  Asn Asn Thr Arg Ile  Val Asp Glu Trp Ser  Tyr Thr Gly
         1175                1180                1185

Ser Ser  Phe Tyr Ala Pro Glu  Pro Ile Thr Ser Leu  Asn Thr Lys
         1190                1195                1200

Tyr Val  Ala Pro Gln Val Thr  Tyr Gln Asn Ile Ser  Thr Asn Leu
         1205                1210                1215

Pro Pro  Pro Leu Leu Gly Asn  Ser Thr Gly Ile Asp  Phe Gln Asp
         1220                1225                1230

Glu Leu  Asp Glu Phe Phe Lys  Asn Val Ser Thr Ser  Ile Pro Asn
         1235                1240                1245

Phe Gly  Ser Leu Thr Gln Ile  Asn Thr Thr Leu Leu  Asp Leu Thr
         1250                1255                1260

Tyr Glu  Met Leu Ser Leu Gln  Gln Val Val Lys Ala  Leu Asn Glu
         1265                1270                1275

Ser Tyr  Ile Asp Leu Lys Glu  Leu Gly Asn Tyr Thr  Tyr Gly Gly
         1280                1285                1290

Tyr Ile  Pro Glu Ala Pro Arg  Asp Gly Gln Ala Tyr  Val Arg Lys
         1295                1300                1305

Asp Gly  Glu Trp Val Leu Leu  Ser Thr Phe
         1310                1315

<210> SEQ ID NO 29
<211> LENGTH: 1318
<212> TYPE: PRT
<213> ORGANISM: Artificial Sequence
<220> FEATURE:
<223> OTHER INFORMATION: recombinant coronavirus spike protein

<400> SEQUENCE: 29

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
```

-continued

```
            145                 150                 155                 160
        Met Gly Arg Phe Phe Asn His Thr Leu Val Leu Leu Pro Asp Gly Cys
                        165                 170                 175

Gly Thr Leu Leu Arg Ala Phe Tyr Cys Ile Leu Glu Pro Arg Ser Gly
                        180                 185                 190

Asn His Cys Pro Ala Gly Asn Ser Tyr Thr Ser Phe Ala Thr Tyr His
                        195                 200                 205

Thr Pro Ala Thr Asp Cys Ser Asp Gly Asn Tyr Asn Arg Asn Ala Ser
                        210                 215                 220

Leu Asn Ser Phe Lys Glu Tyr Phe Asn Leu Arg Asn Cys Thr Phe Met
        225                 230                 235                 240

Tyr Thr Tyr Asn Ile Thr Glu Asp Glu Ile Leu Glu Trp Phe Gly Ile
                            245                 250                 255

Thr Gln Thr Ala Gln Gly Val His Leu Phe Ser Ser Arg Tyr Val Asp
                        260                 265                 270

Leu Tyr Gly Gly Asn Met Phe Gln Phe Ala Thr Leu Pro Val Tyr Asp
                        275                 280                 285

Thr Ile Lys Tyr Tyr Ser Ile Ile Pro His Ser Ile Arg Ser Ile Gln
                        290                 295                 300

Ser Asp Arg Lys Ala Trp Ala Ala Phe Tyr Val Tyr Lys Leu Gln Pro
        305                 310                 315                 320

Leu Thr Phe Leu Leu Asp Phe Ser Val Asp Gly Tyr Ile Arg Arg Ala
                        325                 330                 335

Ile Asp Cys Gly Phe Asn Asp Leu Ser Gln Leu His Cys Ser Tyr Glu
                        340                 345                 350

Ser Phe Asp Val Glu Ser Gly Val Tyr Ser Val Ser Ser Phe Glu Ala
                        355                 360                 365

Lys Pro Ser Gly Ser Val Val Glu Gln Ala Glu Gly Val Glu Cys Asp
                        370                 375                 380

Phe Ser Pro Leu Leu Ser Gly Thr Pro Pro Gln Val Tyr Asn Phe Lys
        385                 390                 395                 400

Arg Leu Val Phe Thr Asn Cys Asn Tyr Asn Leu Thr Lys Leu Leu Ser
                        405                 410                 415

Leu Phe Ser Val Asn Asp Phe Thr Cys Ser Gln Ile Ser Pro Ala Ala
                        420                 425                 430

Ile Ala Ser Asn Cys Tyr Ser Ser Leu Ile Leu Asp Tyr Phe Ser Tyr
                        435                 440                 445

Pro Leu Ser Met Lys Ser Asp Leu Ser Val Ser Ser Ala Gly Pro Ile
        450                 455                 460

Ser Gln Phe Asn Tyr Lys Gln Ser Phe Ser Asn Pro Thr Cys Leu Ile
        465                 470                 475                 480

Leu Ala Thr Val Pro His Asn Leu Thr Thr Ile Thr Lys Pro Leu Lys
                        485                 490                 495

Tyr Ser Tyr Ile Asn Lys Cys Ser Arg Phe Leu Ser Asp Asp Arg Thr
                        500                 505                 510

Glu Val Pro Gln Leu Val Asn Ala Asn Gln Tyr Ser Pro Cys Val Ser
                        515                 520                 525

Ile Val Pro Ser Thr Val Trp Glu Asp Gly Asp Tyr Tyr Arg Lys Gln
                        530                 535                 540

Leu Ser Pro Leu Glu Gly Gly Gly Trp Leu Val Ala Ser Gly Ser Thr
        545                 550                 555                 560

Val Ala Met Thr Glu Gln Leu Gln Met Gly Phe Gly Ile Thr Val Gln
                        565                 570                 575
```

```
Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Ala Ser Val Gly Ser
            740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Ser Val Arg Asn
    835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Gly Ser Ala Gly Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990
```

Asn Gln Lys Leu Ile Ala Asn Lys Phe Asn Gln Ala Leu Gly Ala Met
            995                 1000                1005

Gln Thr Gly Phe Thr Thr Thr Asn Glu Ala Phe His Lys Val Gln
        1010                1015                1020

Asp Ala Val Asn Asn Asn Ala Gln Ala Leu Ser Lys Leu Ala Ser
        1025                1030                1035

Glu Leu Ser Asn Thr Phe Gly Ala Ile Ser Ala Ser Ile Gly Asp
        1040                1045                1050

Ile Ile Gln Arg Leu Asp Pro Pro Glu Gln Asp Ala Gln Ile Asp
        1055                1060                1065

Arg Leu Ile Asn Gly Arg Leu Thr Thr Leu Asn Ala Phe Val Ala
        1070                1075                1080

Gln Gln Leu Val Arg Ser Glu Ser Ala Ala Leu Ser Ala Gln Leu
        1085                1090                1095

Ala Lys Asp Lys Val Asn Glu Cys Val Lys Ala Gln Ser Lys Arg
        1100                1105                1110

Ser Gly Phe Cys Gly Gln Gly Thr His Ile Val Ser Phe Val Val
        1115                1120                1125

Asn Ala Pro Asn Gly Leu Tyr Phe Met His Val Gly Tyr Tyr Pro
        1130                1135                1140

Ser Asn His Ile Glu Val Val Ser Ala Tyr Gly Leu Cys Asp Ala
        1145                1150                1155

Ala Asn Pro Thr Asn Cys Ile Ala Pro Val Asn Gly Tyr Phe Ile
        1160                1165                1170

Lys Thr Asn Asn Thr Arg Ile Val Asp Glu Trp Ser Tyr Thr Gly
        1175                1180                1185

Ser Ser Phe Tyr Ala Pro Glu Pro Ile Thr Ser Leu Asn Thr Lys
        1190                1195                1200

Tyr Val Ala Pro Gln Val Thr Tyr Gln Asn Ile Ser Thr Asn Leu
        1205                1210                1215

Pro Pro Pro Leu Leu Gly Asn Ser Thr Gly Ile Asp Phe Gln Asp
        1220                1225                1230

Glu Leu Asp Glu Phe Phe Lys Asn Val Ser Thr Ser Ile Pro Asn
        1235                1240                1245

Phe Gly Ser Leu Thr Gln Ile Asn Thr Thr Leu Leu Asp Leu Thr
        1250                1255                1260

Tyr Glu Met Leu Ser Leu Gln Gln Val Val Lys Ala Leu Asn Glu
        1265                1270                1275

Ser Tyr Ile Asp Leu Lys Glu Leu Gly Asn Tyr Thr Tyr Gly Gly
        1280                1285                1290

Tyr Ile Pro Glu Ala Pro Arg Asp Gly Gln Ala Tyr Val Arg Lys
        1295                1300                1305

Asp Gly Glu Trp Val Leu Leu Ser Thr Phe
        1310                1315

<210> SEQ ID NO 30
<211> LENGTH: 1217
<212> TYPE: PRT
<213> ORGANISM: Artificial Sequence
<220> FEATURE:
<223> OTHER INFORMATION: recombinant coronavirus spike protein

<400> SEQUENCE: 30

Met Phe Ile Phe Leu Leu Phe Leu Thr Leu Thr Ser Gly Ser Asp Leu
1               5                   10                  15

```
Asp Arg Cys Thr Thr Phe Asp Val Gln Ala Pro Asn Tyr Thr Gln
             20                  25                  30

His Thr Ser Ser Met Arg Gly Val Tyr Tyr Pro Asp Glu Ile Phe Arg
         35                  40                  45

Ser Asp Thr Leu Tyr Leu Thr Gln Asp Leu Phe Leu Pro Phe Tyr Ser
     50                  55                  60

Asn Val Thr Gly Phe His Thr Ile Asn His Thr Phe Gly Asn Pro Val
 65                  70                  75                  80

Ile Pro Phe Lys Asp Gly Ile Tyr Phe Ala Ala Thr Glu Lys Ser Asn
             85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
            115                 120                 125

Asn Phe Glu Leu Cys Asp Asn Pro Phe Phe Ala Val Ser Lys Pro Met
            130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
            165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
            195                 200                 205

Leu Pro Ser Gly Phe Asn Thr Leu Lys Pro Ile Phe Lys Leu Pro Leu
210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
            275                 280                 285

Ser Val Lys Ser Phe Glu Ile Asp Lys Gly Ile Tyr Gln Thr Ser Asn
290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
            355                 360                 365

Val Ser Ala Thr Lys Leu Asn Asp Leu Cys Phe Ser Asn Val Tyr Ala
            370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
```

```
            435                 440                 445
Arg Pro Phe Glu Arg Asp Ile Ser Asn Val Pro Phe Ser Pro Asp Gly
450                 455                 460
Lys Pro Cys Thr Pro Pro Ala Leu Asn Cys Tyr Trp Pro Leu Asn Asp
465                 470                 475                 480
Tyr Gly Phe Tyr Thr Thr Gly Ile Gly Tyr Gln Pro Tyr Arg Val
                485                 490                 495
Val Val Leu Ser Phe Glu Leu Leu Asn Ala Pro Ala Thr Val Cys Gly
                500                 505                 510
Pro Lys Leu Ser Thr Asp Leu Ile Lys Asn Gln Cys Val Asn Phe Asn
            515                 520                 525
Phe Asn Gly Leu Thr Gly Thr Gly Val Leu Thr Pro Ser Ser Lys Arg
        530                 535                 540
Phe Gln Pro Phe Gln Gln Phe Gly Arg Asp Val Ser Asp Phe Thr Asp
545                 550                 555                 560
Ser Val Arg Asp Pro Lys Thr Ser Glu Ile Leu Asp Ile Ser Pro Cys
                565                 570                 575
Ala Phe Gly Gly Val Ser Val Ile Thr Pro Gly Thr Asn Ala Ser Ser
                580                 585                 590
Glu Val Ala Val Leu Tyr Gln Asp Val Asn Cys Thr Asp Val Ser Thr
            595                 600                 605
Ala Ile His Ala Asp Gln Leu Thr Pro Ala Trp Arg Ile Tyr Ser Thr
        610                 615                 620
Gly Asn Asn Val Phe Gln Thr Gln Ala Gly Cys Leu Ile Gly Ala Glu
625                 630                 635                 640
His Val Asp Thr Ser Tyr Glu Cys Asp Ile Pro Ile Gly Ala Gly Ile
                645                 650                 655
Cys Ala Ser Tyr His Thr Val Ser Leu Leu Arg Ser Thr Ser Gln Lys
                660                 665                 670
Ser Ile Val Ala Tyr Thr Met Ser Leu Gly Ala Asp Ser Ser Ile Ala
            675                 680                 685
Tyr Ser Asn Asn Thr Ile Ala Ile Pro Thr Asn Phe Ser Ile Ser Ile
        690                 695                 700
Thr Thr Glu Val Met Pro Val Ser Met Ala Lys Thr Ser Val Asp Cys
705                 710                 715                 720
Asn Met Tyr Ile Cys Gly Asp Ser Thr Glu Cys Ala Asn Leu Leu Leu
                725                 730                 735
Gln Tyr Gly Ser Phe Cys Thr Gln Leu Asn Arg Ala Leu Ser Gly Ile
                740                 745                 750
Ala Ala Glu Gln Asp Arg Asn Thr Arg Glu Val Phe Ala Gln Val Lys
            755                 760                 765
Gln Met Tyr Lys Thr Pro Thr Leu Lys Tyr Phe Gly Gly Phe Asn Phe
        770                 775                 780
Ser Gln Ile Leu Pro Asp Pro Leu Lys Pro Thr Lys Arg Ser Phe Ile
785                 790                 795                 800
Glu Asp Leu Leu Phe Asn Lys Val Thr Leu Ala Asp Ala Gly Phe Met
                805                 810                 815
Lys Gln Tyr Gly Glu Cys Leu Gly Asp Ile Asn Ala Arg Asp Leu Ile
                820                 825                 830
Cys Ala Gln Lys Phe Asn Gly Leu Thr Val Leu Pro Pro Leu Leu Thr
            835                 840                 845
Asp Asp Met Ile Ala Ala Tyr Thr Ala Ala Leu Val Ser Gly Thr Ala
        850                 855                 860
```

```
Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
            885                 890                 895

Val Leu Tyr Glu Asn Gln Lys Gln Ile Ala Asn Gln Phe Asn Lys Ala
        900                 905                 910

Ile Ser Gln Ile Gln Glu Ser Leu Thr Thr Thr Ser Thr Ala Leu Gly
    915                 920                 925

Lys Leu Gln Asp Val Val Asn Gln Asn Ala Gln Ala Leu Asn Thr Leu
930                 935                 940

Val Lys Gln Leu Ser Ser Asn Phe Gly Ala Ile Ser Ser Val Leu Asn
945                 950                 955                 960

Asp Ile Leu Ser Arg Leu Asp Pro Pro Glu Ala Glu Val Gln Ile Asp
            965                 970                 975

Arg Leu Ile Thr Gly Arg Leu Gln Ser Leu Gln Thr Tyr Val Thr Gln
        980                 985                 990

Gln Leu Ile Arg Ala Ala Glu Ile Arg Ala Ser Ala Asn Leu Ala Ala
    995                 1000                1005

Thr Lys Met Ser Glu Cys Val Leu Gly Gln Ser Lys Arg Val Asp
    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Gly Gly Tyr Ile Pro Glu Ala Pro Arg Asp Gly Gln Ala
    1190                1195                1200

Tyr Val Arg Lys Asp Gly Glu Trp Val Leu Leu Ser Thr Phe
    1205                1210                1215

<210> SEQ ID NO 31
<211> LENGTH: 1303
<212> TYPE: PRT
<213> ORGANISM: Artificial Sequence
<220> FEATURE:
<223> OTHER INFORMATION: recombinant coronavirus spike protein

<400> SEQUENCE: 31
```

```
Met Phe Leu Ile Ile Phe Ile Leu Pro Thr Thr Leu Ala Val Ile Gly
1               5                   10                  15

Asp Phe Asn Cys Thr Asn Ser Phe Ile Asn Asp Tyr Asn Lys Thr Ile
                20                  25                  30

Pro Arg Ile Ser Glu Asp Val Val Asp Val Ser Leu Gly Leu Gly Thr
            35                  40                  45

Tyr Tyr Val Leu Asn Arg Val Tyr Leu Asn Thr Thr Leu Leu Phe Thr
    50                  55                  60

Gly Tyr Phe Pro Lys Ser Gly Ala Asn Phe Arg Asp Leu Ala Leu Lys
65                  70                  75                  80

Gly Ser Ile Tyr Leu Ser Thr Leu Trp Tyr Lys Pro Pro Phe Leu Ser
                85                  90                  95

Asp Phe Asn Asn Gly Ile Phe Ser Lys Val Lys Asn Thr Lys Leu Tyr
                100                 105                 110

Val Asn Asn Thr Leu Tyr Ser Glu Phe Ser Thr Ile Val Ile Gly Ser
            115                 120                 125

Val Phe Val Asn Thr Ser Tyr Thr Ile Val Val Gln Pro His Asn Gly
    130                 135                 140

Ile Leu Glu Ile Thr Ala Cys Gln Tyr Thr Met Cys Glu Tyr Pro His
145                 150                 155                 160

Thr Val Cys Lys Ser Lys Gly Ser Ile Arg Asn Glu Ser Trp His Ile
                165                 170                 175

Asp Ser Ser Glu Pro Leu Cys Leu Phe Lys Lys Asn Phe Thr Tyr Asn
                180                 185                 190

Val Ser Ala Asp Trp Leu Tyr Phe His Phe Tyr Gln Glu Arg Gly Val
            195                 200                 205

Phe Tyr Ala Tyr Tyr Ala Asp Val Gly Met Pro Thr Thr Phe Leu Phe
    210                 215                 220

Ser Leu Tyr Leu Gly Thr Ile Leu Ser His Tyr Tyr Val Met Pro Leu
225                 230                 235                 240

Thr Cys Asn Ala Ile Ser Ser Asn Thr Asp Asn Glu Thr Leu Glu Tyr
                245                 250                 255

Trp Val Thr Pro Leu Ser Arg Arg Gln Tyr Leu Leu Asn Phe Asp Glu
                260                 265                 270

His Gly Val Ile Thr Asn Ala Val Asp Cys Ser Ser Ser Phe Leu Ser
            275                 280                 285

Glu Ile Gln Cys Lys Thr Gln Ser Phe Ala Pro Asn Thr Gly Val Tyr
    290                 295                 300

Asp Leu Ser Gly Phe Thr Val Lys Pro Val Ala Thr Val Tyr Arg Arg
305                 310                 315                 320

Ile Pro Asn Leu Pro Asp Cys Asp Ile Asp Asn Trp Leu Asn Asn Val
                325                 330                 335

Ser Val Pro Ser Pro Leu Asn Trp Glu Arg Arg Ile Phe Ser Asn Cys
                340                 345                 350

Asn Phe Asn Leu Ser Thr Leu Leu Arg Leu Val His Val Asp Ser Phe
            355                 360                 365

Ser Cys Asn Asn Leu Asp Lys Ser Lys Ile Phe Gly Ser Cys Phe Asn
    370                 375                 380

Ser Ile Thr Val Asp Lys Phe Ala Ile Pro Asn Arg Arg Arg Asp Asp
385                 390                 395                 400

Leu Gln Leu Gly Ser Ser Gly Phe Leu Gln Ser Ser Asn Tyr Lys Ile
                405                 410                 415
```

-continued

Asp Ile Ser Ser Ser Ser Cys Gln Leu Tyr Tyr Ser Leu Pro Leu Val
            420                 425                 430

Asn Val Thr Ile Asn Asn Phe Asn Pro Ser Ser Trp Asn Arg Arg Tyr
            435                 440                 445

Gly Phe Gly Ser Phe Asn Leu Ser Ser Tyr Asp Val Val Tyr Ser Asp
        450                 455                 460

His Cys Phe Ser Val Asn Ser Asp Phe Cys Pro Cys Ala Asp Pro Ser
465                 470                 475                 480

Val Val Asn Ser Cys Ala Lys Ser Lys Pro Pro Ser Ala Ile Cys Pro
                485                 490                 495

Ala Gly Thr Lys Tyr Arg His Cys Asp Leu Asp Thr Thr Leu Tyr Val
            500                 505                 510

Lys Asn Trp Cys Arg Cys Ser Cys Leu Pro Asp Pro Ile Ser Thr Tyr
            515                 520                 525

Ser Pro Asn Thr Cys Pro Gln Lys Lys Val Val Gly Ile Gly Glu
        530                 535                 540

His Cys Pro Gly Leu Gly Ile Asn Glu Glu Lys Cys Gly Thr Gln Leu
545                 550                 555                 560

Asn His Ser Ser Cys Phe Cys Ser Pro Asp Ala Phe Leu Gly Trp Ser
                565                 570                 575

Phe Asp Ser Cys Ile Ser Asn Asn Arg Cys Asn Ile Phe Ser Asn Phe
            580                 585                 590

Ile Phe Asn Gly Ile Asn Ser Gly Thr Thr Cys Ser Asn Asp Leu Leu
            595                 600                 605

Tyr Ser Asn Thr Glu Ile Ser Thr Gly Val Cys Val Asn Tyr Asp Leu
        610                 615                 620

Tyr Gly Ile Thr Gly Gln Gly Ile Phe Lys Glu Val Ser Ala Ala Tyr
625                 630                 635                 640

Tyr Asn Asn Trp Gln Asn Leu Leu Tyr Asp Ser Asn Gly Asn Ile Ile
            645                 650                 655

Gly Phe Lys Asp Phe Leu Thr Asn Lys Thr Tyr Thr Ile Leu Pro Cys
            660                 665                 670

Tyr Ser Gly Arg Val Ser Ala Ala Phe Tyr Gln Asn Ser Ser Ser Pro
        675                 680                 685

Ala Leu Leu Tyr Arg Asn Leu Lys Cys Ser Tyr Val Leu Asn Asn Ile
        690                 695                 700

Ser Phe Ile Ser Gln Pro Phe Tyr Phe Asp Ser Tyr Leu Gly Cys Val
705                 710                 715                 720

Leu Asn Ala Val Asn Leu Thr Ser Tyr Ser Val Ser Ser Cys Asp Leu
            725                 730                 735

Arg Met Gly Ser Gly Phe Cys Ile Asp Tyr Ala Leu Pro Ser Ser Gly
            740                 745                 750

Gly Ser Gly Ser Gly Ile Ser Ser Pro Tyr Arg Phe Val Thr Phe Glu
        755                 760                 765

Pro Phe Asn Val Ser Phe Val Asn Asp Ser Val Glu Thr Val Gly Gly
        770                 775                 780

Leu Phe Glu Ile Gln Ile Pro Thr Asn Phe Thr Ile Ala Gly His Glu
785                 790                 795                 800

Glu Phe Ile Gln Thr Ser Ser Pro Lys Val Thr Ile Asp Cys Ser Ala
                805                 810                 815

Phe Val Cys Ser Asn Tyr Ala Ala Cys His Asp Leu Leu Ser Glu Tyr
            820                 825                 830

Gly Thr Phe Cys Asp Asn Ile Asn Ser Ile Leu Asn Glu Val Asn Asp

```
                835                 840                 845
Leu Leu Asp Ile Thr Gln Leu Gln Val Ala Asn Ala Leu Met Gln Gly
            850                 855                 860

Val Thr Leu Ser Ser Asn Leu Asn Thr Asn Leu His Ser Asp Val Asp
865                 870                 875                 880

Asn Ile Asp Phe Lys Ser Leu Leu Gly Cys Leu Gly Ser Gln Cys Gly
                885                 890                 895

Ser Ser Ser Arg Ser Leu Leu Glu Asp Leu Leu Phe Asn Lys Val Lys
            900                 905                 910

Leu Ser Asp Val Gly Phe Val Glu Ala Tyr Asn Asn Cys Thr Gly Gly
            915                 920                 925

Ser Glu Ile Arg Asp Leu Leu Cys Val Gln Ser Phe Asn Gly Ile Lys
            930                 935                 940

Val Leu Pro Pro Ile Leu Ser Glu Thr Gln Ile Ser Gly Tyr Thr Thr
945                 950                 955                 960

Ala Ala Thr Val Ala Ala Met Phe Pro Pro Trp Ser Ala Ala Ala Gly
                965                 970                 975

Val Pro Phe Ser Leu Asn Val Gln Tyr Arg Ile Asn Gly Leu Gly Val
            980                 985                 990

Thr Met Asp Val Leu Asn Lys Asn Gln Lys Leu Ile Ala Asn Ala Phe
            995                 1000                1005

Asn Lys Ala Leu Leu Ser Ile Gln Asn Gly Phe Thr Ala Thr Asn
    1010                1015                1020

Ser Ala Leu Ala Lys Ile Gln Ser Val Val Asn Ala Asn Ala Gln
    1025                1030                1035

Ala Leu Asn Ser Leu Leu Gln Gln Leu Phe Asn Lys Phe Gly Ala
    1040                1045                1050

Ile Ser Ser Ser Leu Gln Glu Ile Leu Ser Arg Leu Asp Pro Pro
    1055                1060                1065

Glu Ala Gln Val Gln Ile Asp Arg Leu Ile Asn Gly Arg Leu Thr
    1070                1075                1080

Ala Leu Asn Ala Tyr Val Ser Gln Gln Leu Ser Asp Ile Thr Leu
    1085                1090                1095

Ile Lys Ala Gly Ala Ser Arg Ala Ile Glu Lys Val Asn Glu Cys
    1100                1105                1110

Val Lys Ser Gln Ser Pro Arg Ile Asn Phe Cys Gly Asn Gly Asn
    1115                1120                1125

His Ile Leu Ser Leu Val Gln Asn Ala Pro Tyr Gly Leu Leu Phe
    1130                1135                1140

Ile His Phe Ser Tyr Lys Pro Thr Ser Phe Lys Thr Val Leu Val
    1145                1150                1155

Ser Pro Gly Leu Cys Leu Ser Gly Asp Arg Gly Ile Ala Pro Lys
    1160                1165                1170

Gln Gly Tyr Phe Ile Lys Gln Asn Asp Ser Trp Met Phe Thr Gly
    1175                1180                1185

Ser Ser Tyr Tyr Tyr Pro Glu Pro Ile Ser Asp Lys Asn Val Val
    1190                1195                1200

Phe Met Asn Ser Cys Ser Val Asn Phe Thr Lys Ala Pro Phe Ile
    1205                1210                1215

Tyr Leu Asn Asn Ser Ile Pro Asn Leu Ser Asp Phe Glu Ala Glu
    1220                1225                1230

Leu Ser Leu Trp Phe Lys Asn His Thr Ser Ile Ala Pro Asn Leu
    1235                1240                1245
```

-continued

Thr Phe Asn Ser His Ile Asn Ala Thr Phe Leu Asp Leu Tyr Tyr
    1250                1255                1260

Glu Met Asn Val Ile Gln Glu Ser Ile Lys Ser Leu Asn Gly Gly
    1265                1270                1275

Tyr Ile Pro Glu Ala Pro Arg Asp Gly Gln Ala Tyr Val Arg Lys
    1280                1285                1290

Asp Gly Glu Trp Val Leu Leu Ser Thr Phe
    1295                1300

<210> SEQ ID NO 32
<211> LENGTH: 1234
<212> TYPE: PRT
<213> ORGANISM: Artificial Sequence
<220> FEATURE:
<223> OTHER INFORMATION: recombinant coronavirus spike protein

<400> SEQUENCE: 32

Met Leu Leu Ile Leu Val Leu Gly Val Ser Leu Ala Ala Ala Ser Arg
1               5                   10                  15

Pro Glu Cys Phe Asn Pro Arg Phe Thr Leu Thr Pro Leu Asn His Thr
                20                  25                  30

Leu Asn Tyr Thr Ser Ile Lys Ala Lys Val Ser Asn Val Leu Leu Pro
            35                  40                  45

Asp Pro Tyr Ile Ala Tyr Ser Gly Gln Thr Leu Arg Gln Asn Leu Phe
        50                  55                  60

Met Ala Asp Met Ser Asn Thr Ile Leu Tyr Pro Val Thr Pro Pro Ala
65                  70                  75                  80

Asn Gly Ala Asn Gly Gly Phe Ile Tyr Asn Thr Ser Ile Ile Pro Val
                85                  90                  95

Ser Ala Gly Leu Phe Val Asn Thr Trp Met Tyr Arg Gln Pro Ala Ser
            100                 105                 110

Ser Arg Ala Tyr Cys Gln Glu Pro Phe Gly Val Ala Phe Gly Asp Thr
        115                 120                 125

Phe Glu Asn Asp Arg Ile Ala Ile Leu Ile Met Ala Pro Asp Asn Leu
    130                 135                 140

Gly Ser Trp Ser Ala Val Ala Pro Arg Asn Gln Thr Asn Ile Tyr Leu
145                 150                 155                 160

Leu Val Cys Ser Asn Ala Thr Leu Cys Ile Asn Pro Gly Phe Asn Arg
                165                 170                 175

Trp Gly Pro Ala Gly Ser Phe Ile Ala Pro Asp Ala Leu Val Asp His
            180                 185                 190

Ser Asn Ser Cys Phe Val Asn Asn Thr Phe Ser Val Asn Ile Ser Thr
        195                 200                 205

Ser Arg Ile Ser Leu Ala Phe Leu Phe Lys Asp Gly Asp Leu Leu Ile
    210                 215                 220

Tyr His Ser Gly Trp Leu Pro Thr Ser Asn Phe Glu His Gly Phe Ser
225                 230                 235                 240

Arg Gly Ser His Pro Met Thr Tyr Phe Met Ser Leu Pro Val Gly Gly
                245                 250                 255

Asn Leu Pro Arg Ala Gln Phe Phe Gln Ser Ile Val Arg Ser Asn Ala
            260                 265                 270

Ile Asp Lys Gly Asp Gly Met Cys Thr Asn Phe Asp Val Asn Leu His
        275                 280                 285

Val Ala His Leu Ile Asn Arg Asp Leu Leu Val Ser Tyr Phe Asn Asn
    290                 295                 300

```
Gly Ser Val Ala Asn Ala Ala Asp Cys Ala Asp Ser Ala Glu Glu
305                 310                 315                 320

Leu Tyr Cys Val Thr Gly Ser Phe Asp Pro Pro Thr Gly Val Tyr Pro
            325                 330                 335

Leu Ser Arg Tyr Arg Ala Gln Val Ala Gly Phe Val Arg Val Thr Gln
            340                 345                 350

Arg Gly Ser Tyr Cys Thr Pro Pro Tyr Ser Val Leu Gln Asp Pro Pro
            355                 360                 365

Gln Pro Val Val Trp Arg Arg Tyr Met Leu Tyr Asp Cys Val Phe Asp
370                 375                 380

Phe Thr Val Val Asp Ser Leu Pro Thr His Gln Leu Gln Cys Tyr
385                 390                 395                 400

Gly Val Ser Pro Arg Arg Leu Ala Ser Met Cys Tyr Gly Ser Val Thr
            405                 410                 415

Leu Asp Val Met Arg Ile Asn Glu Thr His Leu Asn Asn Leu Phe Asn
            420                 425                 430

Arg Val Pro Asp Thr Phe Ser Leu Tyr Asn Tyr Ala Leu Pro Asp Asn
            435                 440                 445

Phe Tyr Gly Cys Leu His Ala Phe Tyr Leu Asn Ser Thr Ala Pro Tyr
450                 455                 460

Ala Val Ala Asn Arg Phe Pro Ile Lys Pro Gly Gly Arg Gln Ser Asn
465                 470                 475                 480

Ser Ala Phe Ile Asp Thr Val Ile Asn Ala Ala His Tyr Ser Pro Phe
            485                 490                 495

Ser Tyr Val Tyr Gly Leu Ala Val Ile Thr Leu Lys Pro Ala Ala Gly
            500                 505                 510

Ser Lys Leu Val Cys Pro Val Ala Asn Asp Thr Val Val Ile Thr Asp
            515                 520                 525

Arg Cys Val Gln Tyr Asn Leu Tyr Gly Tyr Thr Gly Thr Gly Val Leu
530                 535                 540

Ser Lys Asn Thr Ser Leu Val Ile Pro Asp Gly Lys Val Phe Thr Ala
545                 550                 555                 560

Ser Ser Thr Gly Thr Ile Ile Gly Val Ser Ile Asn Ser Thr Thr Tyr
            565                 570                 575

Ser Ile Met Pro Cys Val Thr Val Pro Val Ser Val Gly Tyr His Pro
            580                 585                 590

Asn Phe Glu Arg Ala Leu Leu Phe Asn Gly Leu Ser Cys Ser Gln Arg
            595                 600                 605

Ser Arg Ala Val Thr Glu Pro Val Ser Val Leu Trp Ser Ala Ser Ala
            610                 615                 620

Thr Ala Gln Asp Ala Phe Asp Thr Pro Ser Gly Cys Val Val Asn Val
625                 630                 635                 640

Glu Leu Arg Asn Thr Thr Ile Val Asn Thr Cys Ala Met Pro Ile Gly
            645                 650                 655

Asn Ser Leu Cys Phe Ile Asn Gly Ser Ile Ala Thr Ala Asn Ala Asp
            660                 665                 670

Ser Leu Pro Arg Leu Gln Leu Val Asn Tyr Asp Pro Leu Tyr Asp Asn
            675                 680                 685

Ser Thr Ala Thr Pro Met Thr Pro Val Tyr Trp Val Lys Val Pro Thr
            690                 695                 700

Asn Phe Thr Leu Ser Ala Thr Glu Glu Tyr Ile Gln Thr Thr Ala Pro
705                 710                 715                 720
```

-continued

Lys Ile Thr Ile Asp Cys Ala Arg Tyr Leu Cys Gly Asp Ser Ser Arg
            725                 730                 735

Cys Leu Asn Val Leu Leu His Tyr Gly Thr Phe Cys Asn Asp Ile Asn
            740                 745                 750

Lys Ala Leu Ser Arg Val Ser Thr Ile Leu Asp Ser Ala Leu Leu Ser
            755                 760                 765

Leu Val Lys Glu Leu Ser Ile Asn Thr Arg Asp Glu Val Thr Thr Phe
            770                 775                 780

Ser Phe Asp Gly Asp Tyr Asn Phe Thr Gly Leu Met Gly Cys Leu Gly
785                 790                 795                 800

Pro Asn Cys Gly Ala Thr Thr Tyr Arg Ser Ala Phe Ser Asp Leu Leu
            805                 810                 815

Tyr Asp Lys Val Arg Ile Thr Asp Pro Gly Phe Met Gln Ser Tyr Gln
            820                 825                 830

Lys Cys Ile Asp Ser Gln Trp Gly Gly Ser Ile Arg Asp Leu Leu Cys
            835                 840                 845

Thr Gln Thr Tyr Asn Gly Ile Ala Val Leu Pro Pro Ile Val Ser Pro
            850                 855                 860

Ala Met Gln Ala Leu Tyr Thr Ser Leu Leu Val Gly Ala Val Ala Ser
865                 870                 875                 880

Ser Gly Tyr Thr Phe Gly Ile Thr Ser Ala Gly Val Ile Pro Phe Ala
            885                 890                 895

Thr Gln Leu Gln Phe Arg Leu Asn Gly Ile Gly Val Thr Thr Gln Val
            900                 905                 910

Leu Val Glu Asn Gln Lys Leu Ile Ala Ser Ser Phe Asn Asn Ala Leu
            915                 920                 925

Val Asn Ile Gln Lys Gly Phe Thr Glu Thr Ser Ile Ala Leu Ser Lys
            930                 935                 940

Met Gln Asp Val Ile Asn Gln His Ala Ala Gln Leu His Thr Leu Val
945                 950                 955                 960

Val Gln Leu Gly Asn Ser Phe Gly Ala Ile Ser Ser Ser Ile Asn Glu
            965                 970                 975

Ile Phe Ser Arg Leu Glu Pro Pro Ala Ala Asn Ala Glu Val Asp Arg
            980                 985                 990

Leu Ile Asn Gly Arg Met Met Val Leu Asn Thr Tyr Val Thr Gln Leu
            995                 1000                1005

Leu Ile Gln Ala Ser Glu Ala Lys Ala Gln Asn Ala Leu Ala Ala
            1010                1015                1020

Gln Lys Ile Ser Glu Cys Val Lys Ala Gln Ser Leu Arg Asn Asp
            1025                1030                1035

Phe Cys Gly Asn Gly Thr His Val Leu Ser Ile Pro Gln Leu Ala
            1040                1045                1050

Pro Asn Gly Val Leu Phe Ile His Tyr Ala Tyr Thr Pro Thr Glu
            1055                1060                1065

Tyr Ala Phe Val Gln Thr Ser Ala Gly Leu Cys His Asn Gly Thr
            1070                1075                1080

Gly Tyr Ala Pro Arg Gln Gly Met Phe Val Leu Pro Asn Asn Thr
            1085                1090                1095

Asn Met Trp His Phe Thr Thr Met Gln Phe Tyr Asn Pro Val Asn
            1100                1105                1110

Ile Ser Ala Ser Asn Thr Gln Val Leu Thr Ser Cys Ser Val Asn
            1115                1120                1125

Tyr Thr Ser Val Asn Tyr Thr Val Leu Glu Pro Ser Val Pro Gly

-continued

```
                1130                1135                1140
Asp Tyr Asp Phe Gln Lys Glu Phe Asp Lys Phe Tyr Lys Asn Leu
        1145                1150                1155

Ser Thr Ile Phe Asn Asn Thr Phe Asn Pro Asn Asp Phe Asn Phe
    1160                1165                1170

Ser Thr Val Asp Val Thr Ala Gln Ile Lys Ser Leu His Asp Val
    1175                1180                1185

Val Asn Gln Leu Asn Gln Ser Phe Ile Asp Leu Lys Lys Leu Asn
    1190                1195                1200

Val Tyr Glu Lys Gly Gly Tyr Ile Pro Glu Ala Pro Arg Asp Gly
    1205                1210                1215

Gln Ala Tyr Val Arg Lys Asp Gly Glu Trp Val Leu Leu Ser Thr
    1220                1225                1230

Phe

<210> SEQ ID NO 33
<211> LENGTH: 1314
<212> TYPE: PRT
<213> ORGANISM: Artificial Sequence
<220> FEATURE:
<223> OTHER INFORMATION: recombinant coronavirus spike protein

<400> SEQUENCE: 33

Met Phe Leu Ile Leu Leu Ile Ser Leu Pro Thr Ala Phe Ala Val Ile
1               5                   10                  15

Gly Asp Leu Lys Cys Pro Leu Asp Ser Arg Thr Gly Ser Leu Asn Asn
            20                  25                  30

Ile Asp Thr Gly Pro Pro Ser Ile Ser Thr Ala Thr Val Asp Val Thr
        35                  40                  45

Asn Gly Leu Gly Thr Tyr Tyr Val Leu Asp Arg Val Tyr Leu Asn Thr
    50                  55                  60

Thr Leu Phe Leu Asn Gly Tyr Tyr Pro Thr Ser Gly Ser Thr Tyr Arg
65                  70                  75                  80

Asn Met Ala Leu Lys Gly Thr Asp Lys Leu Ser Thr Leu Trp Phe Lys
                85                  90                  95

Pro Pro Phe Leu Ser Asp Phe Ile Asn Gly Ile Phe Ala Lys Val Lys
            100                 105                 110

Asn Thr Lys Val Phe Lys Asp Gly Val Met Tyr Ser Glu Phe Pro Ala
        115                 120                 125

Ile Thr Ile Gly Ser Thr Phe Val Asn Thr Ser Tyr Ser Val Val Val
    130                 135                 140

Gln Pro Arg Thr Ile Asn Ser Thr Gln Asp Gly Val Asn Lys Leu Gln
145                 150                 155                 160

Gly Leu Leu Glu Val Ser Val Cys Gln Tyr Asn Met Cys Glu Tyr Pro
                165                 170                 175

His Thr Ile Cys His Pro Lys Leu Gly Asn His Phe Lys Glu Leu Trp
            180                 185                 190

His Met Asp Thr Gly Val Val Ser Cys Leu Tyr Lys Arg Asn Phe Thr
        195                 200                 205

Tyr Asp Val Asn Ala Thr Tyr Leu Tyr Phe His Phe Tyr Gln Glu Gly
    210                 215                 220

Gly Thr Phe Tyr Ala Tyr Phe Thr Asp Thr Gly Val Val Thr Lys Phe
225                 230                 235                 240

Leu Phe Asn Val Tyr Leu Gly Met Ala Leu Ser His Tyr Tyr Val Met
                245                 250                 255
```

```
Pro Leu Thr Cys Ile Ser Arg Arg Asp Ile Gly Phe Thr Leu Glu Tyr
        260                 265                 270

Trp Val Thr Pro Leu Thr Ser Arg Gln Tyr Leu Leu Ala Phe Asn Gln
            275                 280                 285

Asp Gly Ile Ile Phe Asn Ala Val Asp Cys Met Ser Asp Phe Met Ser
290                 295                 300

Glu Ile Lys Cys Lys Thr Gln Ser Ile Ala Pro Pro Thr Gly Val Tyr
305                 310                 315                 320

Glu Leu Asn Gly Tyr Thr Val Gln Pro Ile Ala Asp Val Tyr Arg Arg
                325                 330                 335

Lys Pro Asp Leu Pro Asn Cys Asn Ile Glu Ala Trp Leu Asn Asp Lys
            340                 345                 350

Ser Val Pro Ser Pro Leu Asn Trp Glu Arg Lys Thr Phe Ser Asn Cys
            355                 360                 365

Asn Phe Asn Met Ser Ser Leu Met Ser Phe Ile Gln Ala Asp Ser Phe
370                 375                 380

Thr Cys Asn Asn Ile Asp Ala Ala Lys Ile Tyr Gly Met Cys Phe Ser
385                 390                 395                 400

Ser Ile Thr Ile Asp Lys Phe Ala Ile Pro Asn Gly Arg Lys Val Asp
                405                 410                 415

Leu Gln Leu Gly Asn Leu Gly Tyr Leu Gln Ser Phe Asn Tyr Arg Ile
            420                 425                 430

Asp Thr Thr Ala Thr Ser Cys Gln Leu Tyr Tyr Asn Leu Pro Ala Ala
            435                 440                 445

Asn Val Ser Val Ser Arg Phe Asn Pro Ser Thr Trp Asn Lys Arg Phe
            450                 455                 460

Gly Phe Ile Glu Asn Ser Val Phe Lys Pro Gln Pro Ala Gly Val Leu
465                 470                 475                 480

Thr Asn His Asp Val Val Tyr Ala Gln His Cys Phe Lys Ala Pro Lys
                485                 490                 495

Asn Phe Cys Pro Cys Lys Leu Asn Ser Ser Leu Cys Val Gly Ser Gly
            500                 505                 510

Pro Gly Lys Asn Asn Gly Ile Gly Thr Cys Pro Ala Gly Thr Asn Tyr
            515                 520                 525

Leu Thr Cys His Asn Leu Cys Asn Pro Asp Pro Ile Thr Phe Thr Gly
530                 535                 540

Pro Tyr Lys Cys Pro Gln Thr Lys Ser Leu Val Gly Ile Gly Glu His
545                 550                 555                 560

Cys Ser Gly Leu Ala Val Lys Ser Asp Tyr Cys Gly Gly Asn Pro Cys
                565                 570                 575

Thr Cys Gln Pro Gln Ala Phe Leu Gly Trp Ser Ala Asp Ser Cys Leu
            580                 585                 590

Gln Gly Asp Lys Cys Asn Ile Phe Ala Asn Leu Ile Leu His Asp Val
            595                 600                 605

Asn Ser Gly Leu Thr Cys Ser Thr Asp Leu Gln Lys Ala Asn Thr Asp
            610                 615                 620

Ile Lys Leu Gly Val Cys Val Asn Tyr Asp Leu Tyr Gly Ile Ser Gly
625                 630                 635                 640

Gln Gly Ile Phe Val Glu Val Asn Ala Thr Tyr Tyr Asn Ser Trp Gln
                645                 650                 655

Asn Leu Leu Tyr Asp Ser Asn Gly Asn Leu Tyr Gly Phe Arg Asp Tyr
            660                 665                 670
```

```
Ile Thr Asn Arg Thr Phe Met Ile Arg Ser Cys Tyr Ser Gly Arg Val
        675                 680                 685

Ser Ala Ala Phe His Ala Asn Ser Ser Glu Pro Ala Leu Leu Phe Arg
    690                 695                 700

Asn Ile Lys Cys Asn Tyr Val Phe Asn Asn Ser Leu Ile Arg Gln Leu
705                 710                 715                 720

Gln Pro Ile Asn Tyr Phe Asp Ser Tyr Leu Gly Cys Val Val Asn Ala
            725                 730                 735

Tyr Asn Ser Thr Ala Ile Ser Val Gln Thr Cys Asp Leu Thr Val Gly
            740                 745                 750

Ser Gly Tyr Cys Val Asp Tyr Ser Lys Asn Gly Gly Ser Gly Ser Ala
        755                 760                 765

Ile Thr Thr Gly Tyr Arg Phe Thr Asn Phe Glu Pro Phe Thr Val Asn
    770                 775                 780

Ser Val Asn Asp Ser Leu Glu Pro Val Gly Gly Leu Tyr Glu Ile Gln
785                 790                 795                 800

Ile Pro Ser Glu Phe Thr Ile Gly Asn Met Glu Glu Phe Ile Gln Thr
            805                 810                 815

Ser Ser Pro Lys Val Thr Ile Asp Cys Ala Ala Phe Val Cys Gly Asp
            820                 825                 830

Tyr Ala Ala Cys Lys Ser Gln Leu Val Glu Tyr Gly Ser Phe Cys Asp
        835                 840                 845

Asn Ile Asn Ala Ile Leu Thr Glu Val Asn Glu Leu Leu Asp Thr Thr
    850                 855                 860

Gln Leu Gln Val Ala Asn Ser Leu Met Asn Gly Val Thr Leu Ser Thr
865                 870                 875                 880

Lys Leu Lys Asp Gly Val Asn Phe Asn Val Asp Asp Ile Asn Phe Ser
            885                 890                 895

Ser Val Leu Gly Cys Leu Gly Ser Glu Cys Ser Lys Ala Ser Ser Arg
            900                 905                 910

Ser Ala Ile Glu Asp Leu Leu Phe Asp Lys Val Lys Leu Ser Asp Val
        915                 920                 925

Gly Phe Val Ala Ala Tyr Asn Asn Cys Thr Gly Gly Ala Glu Ile Arg
    930                 935                 940

Asp Leu Ile Cys Val Gln Ser Tyr Lys Gly Ile Lys Val Leu Pro Pro
945                 950                 955                 960

Leu Leu Ser Glu Asn Gln Ile Ser Gly Tyr Thr Leu Ala Ala Thr Ser
            965                 970                 975

Ala Ser Leu Phe Pro Pro Trp Thr Ala Ala Gly Val Pro Phe Tyr
            980                 985                 990

Leu Asn Val Gln Tyr Arg Ile Asn Gly Leu Gly Val Thr Met Asp Val
        995                 1000                1005

Leu Ser Gln Asn Gln Lys Leu Ile Ala Asn Ala Phe Asn Asn Ala
    1010                1015                1020

Leu Asp Ala Ile Gln Glu Gly Phe Asp Ala Thr Asn Ser Ala Leu
    1025                1030                1035

Val Lys Ile Gln Ala Val Val Asn Ala Asn Ala Glu Ala Leu Asn
    1040                1045                1050

Asn Leu Leu Gln Gln Leu Ser Asn Arg Phe Gly Ala Ile Ser Ser
    1055                1060                1065

Ser Leu Gln Glu Ile Leu Ser Arg Leu Asp Pro Pro Glu Ala Glu
    1070                1075                1080

Ala Gln Ile Asp Arg Leu Ile Asn Gly Arg Leu Thr Ala Leu Asn
```

```
                1085                1090                1095

Ala Tyr Val Ser Gln Gln Leu Ser Asp Ser Thr Leu Val Lys Phe
        1100                1105                1110

Ser Ala Ala Gln Ala Met Glu Lys Val Asn Glu Cys Val Lys Ser
    1115                1120                1125

Gln Ser Ser Arg Ile Asn Phe Cys Gly Asn Gly Asn His Ile Ile
    1130                1135                1140

Ser Leu Val Gln Asn Ala Pro Tyr Gly Leu Tyr Phe Ile His Phe
    1145                1150                1155

Ser Tyr Val Pro Thr Lys Tyr Val Thr Ala Lys Val Ser Pro Gly
    1160                1165                1170

Leu Cys Ile Ala Gly Asp Arg Gly Ile Ala Pro Lys Ser Gly Tyr
    1175                1180                1185

Phe Val Asn Val Asn Asn Thr Trp Met Tyr Thr Gly Ser Gly Tyr
    1190                1195                1200

Tyr Tyr Pro Glu Pro Ile Thr Glu Asn Asn Val Val Val Met Ser
    1205                1210                1215

Thr Cys Ala Val Asn Tyr Thr Lys Ala Pro Tyr Val Met Leu Asn
    1220                1225                1230

Thr Ser Thr Pro Asn Leu Pro Asp Phe Arg Glu Glu Leu Asp Gln
    1235                1240                1245

Trp Phe Lys Asn Gln Thr Ser Val Ala Pro Asp Leu Ser Leu Asp
    1250                1255                1260

Tyr Ile Asn Val Thr Phe Leu Asp Leu Gln Val Glu Met Asn Arg
    1265                1270                1275

Leu Gln Glu Ala Ile Lys Val Leu Asn Gly Gly Tyr Ile Pro Glu
    1280                1285                1290

Ala Pro Arg Asp Gly Gln Ala Tyr Val Arg Lys Asp Gly Glu Trp
    1295                1300                1305

Val Leu Leu Ser Thr Phe
    1310

<210> SEQ ID NO 34
<211> LENGTH: 1218
<212> TYPE: PRT
<213> ORGANISM: Artificial Sequence
<220> FEATURE:
<223> OTHER INFORMATION: recombinant coronavirus spike protein

<400> SEQUENCE: 34

Met Lys Leu Leu Val Leu Val Phe Ala Thr Leu Val Ser Ser Tyr Thr
1               5                   10                  15

Ile Glu Lys Cys Leu Asp Phe Asp Asp Arg Thr Pro Pro Ala Asn Thr
                20                  25                  30

Gln Phe Leu Ser Ser His Arg Gly Val Tyr Tyr Pro Asp Asp Ile Phe
        35                  40                  45

Arg Ser Asn Val Leu His Leu Val Gln Asp His Phe Leu Pro Phe Asp
    50                  55                  60

Ser Asn Val Thr Arg Phe Ile Thr Phe Gly Leu Asn Phe Asp Asn Pro
65                  70                  75                  80

Ile Ile Pro Phe Lys Asp Gly Ile Tyr Phe Ala Ala Thr Glu Lys Ser
                85                  90                  95

Asn Val Ile Arg Gly Trp Val Phe Gly Ser Thr Met Asn Asn Lys Ser
                100                 105                 110

Gln Ser Val Ile Ile Met Asn Asn Ser Thr Asn Leu Val Ile Arg Ala
```

```
              115                 120                 125
Cys Asn Phe Glu Leu Cys Asp Asn Pro Phe Val Val Leu Lys Ser
        130                 135                 140

Asn Asn Thr Gln Ile Pro Ser Tyr Ile Phe Asn Asn Ala Phe Asn Cys
145                 150                 155                 160

Thr Phe Glu Tyr Val Ser Lys Asp Phe Asn Leu Asp Leu Gly Glu Lys
                    165                 170                 175

Pro Gly Asn Phe Lys Asp Leu Arg Glu Phe Val Phe Arg Asn Lys Asp
                180                 185                 190

Gly Phe Leu His Val Tyr Ser Gly Tyr Gln Pro Ile Ser Ala Ala Ser
            195                 200                 205

Gly Leu Pro Thr Gly Phe Asn Ala Leu Lys Pro Ile Phe Lys Leu Pro
        210                 215                 220

Leu Gly Ile Asn Ile Thr Asn Phe Arg Thr Leu Leu Thr Ala Phe Pro
225                 230                 235                 240

Pro Arg Pro Asp Tyr Trp Gly Thr Ser Ala Ala Tyr Phe Val Gly
                    245                 250                 255

Tyr Leu Lys Pro Thr Thr Phe Met Leu Lys Tyr Asp Glu Asn Gly Thr
                260                 265                 270

Ile Thr Asp Ala Val Asp Cys Ser Gln Asn Pro Leu Ala Glu Leu Lys
            275                 280                 285

Cys Ser Val Lys Ser Phe Glu Ile Asp Lys Gly Ile Tyr Gln Thr Ser
        290                 295                 300

Asn Phe Arg Val Ala Pro Ser Lys Glu Val Val Arg Phe Pro Asn Ile
305                 310                 315                 320

Thr Asn Leu Cys Pro Phe Gly Glu Val Phe Asn Ala Thr Thr Phe Pro
                    325                 330                 335

Ser Val Tyr Ala Trp Glu Arg Lys Arg Ile Ser Asn Cys Val Ala Asp
                340                 345                 350

Tyr Ser Val Leu Tyr Asn Ser Thr Ser Phe Ser Thr Phe Lys Cys Tyr
            355                 360                 365

Gly Val Ser Ala Thr Lys Leu Asn Asp Leu Cys Phe Ser Asn Val Tyr
        370                 375                 380

Ala Asp Ser Phe Val Val Lys Gly Asp Asp Val Arg Gln Ile Ala Pro
385                 390                 395                 400

Gly Gln Thr Gly Val Ile Ala Asp Tyr Asn Tyr Lys Leu Pro Asp Asp
                    405                 410                 415

Phe Thr Gly Cys Val Leu Ala Trp Asn Thr Arg Asn Ile Asp Ala Thr
                420                 425                 430

Gln Thr Gly Asn Tyr Asn Tyr Lys Tyr Arg Ser Leu Arg His Gly Lys
            435                 440                 445

Leu Arg Pro Phe Glu Arg Asp Ile Ser Asn Val Pro Phe Ser Pro Asp
        450                 455                 460

Gly Lys Pro Cys Thr Pro Pro Ala Phe Asn Cys Tyr Trp Pro Leu Asn
465                 470                 475                 480

Asp Tyr Gly Phe Tyr Ile Thr Asn Gly Ile Gly Tyr Gln Pro Tyr Arg
                    485                 490                 495

Val Val Val Leu Ser Phe Glu Leu Leu Asn Ala Pro Ala Thr Val Cys
                500                 505                 510

Gly Pro Lys Leu Ser Thr Asp Leu Ile Lys Asn Gln Cys Val Asn Phe
            515                 520                 525

Asn Phe Asn Gly Leu Thr Gly Thr Gly Val Leu Thr Pro Ser Ser Lys
        530                 535                 540
```

-continued

```
Arg Phe Gln Pro Phe Gln Gln Phe Gly Arg Asp Val Ser Asp Phe Thr
545                 550                 555                 560

Asp Ser Val Arg Asp Pro Lys Thr Ser Glu Ile Leu Asp Ile Ser Pro
            565                 570                 575

Cys Ser Phe Gly Gly Val Ser Val Ile Thr Pro Gly Thr Asn Thr Ser
        580                 585                 590

Ser Glu Val Ala Val Leu Tyr Gln Asp Val Asn Cys Thr Asp Val Pro
    595                 600                 605

Val Ala Ile His Ala Asp Gln Leu Thr Pro Ser Trp Arg Val His Ser
610                 615                 620

Thr Gly Asn Asn Val Phe Gln Thr Gln Ala Gly Cys Leu Ile Gly Ala
625                 630                 635                 640

Glu His Val Asp Thr Ser Tyr Glu Cys Asp Ile Pro Ile Gly Ala Gly
                645                 650                 655

Ile Cys Ala Ser Tyr His Thr Val Ser Ser Leu Arg Ser Thr Ser Gln
            660                 665                 670

Lys Ser Ile Val Ala Tyr Thr Met Ser Leu Gly Ala Asp Ser Ser Ile
        675                 680                 685

Ala Tyr Ser Asn Asn Thr Ile Ala Ile Pro Thr Asn Phe Ser Ile Ser
690                 695                 700

Ile Thr Thr Glu Val Met Pro Val Ser Met Ala Lys Thr Ser Val Asp
705                 710                 715                 720

Cys Asn Met Tyr Ile Cys Gly Asp Ser Thr Glu Cys Ala Asn Leu Leu
                725                 730                 735

Leu Gln Tyr Gly Ser Phe Cys Thr Gln Leu Asn Arg Ala Leu Ser Gly
            740                 745                 750

Ile Ala Val Glu Gln Asp Arg Asn Thr Arg Glu Val Phe Ala Gln Val
        755                 760                 765

Lys Gln Met Tyr Lys Thr Pro Thr Leu Lys Asp Phe Gly Gly Phe Asn
770                 775                 780

Phe Ser Gln Ile Leu Pro Asp Pro Leu Lys Pro Thr Lys Arg Ser Phe
785                 790                 795                 800

Ile Glu Asp Leu Leu Phe Asn Lys Val Thr Leu Ala Asp Ala Gly Phe
                805                 810                 815

Met Lys Gln Tyr Gly Glu Cys Leu Gly Asp Ile Asn Ala Arg Asp Leu
            820                 825                 830

Ile Cys Ala Gln Lys Phe Asn Gly Leu Thr Val Leu Pro Pro Leu Leu
        835                 840                 845

Thr Asp Asp Met Ile Ala Ala Tyr Thr Ala Ala Leu Val Ser Gly Thr
850                 855                 860

Ala Thr Ala Gly Trp Thr Phe Gly Ala Gly Ala Ala Leu Gln Ile Pro
865                 870                 875                 880

Phe Ala Met Gln Met Ala Tyr Arg Phe Asn Gly Ile Gly Val Thr Gln
                885                 890                 895

Asn Val Leu Tyr Glu Asn Gln Lys Gln Ile Ala Asn Gln Phe Asn Lys
            900                 905                 910

Ala Ile Ser Gln Ile Gln Glu Ser Leu Thr Thr Thr Ser Thr Ala Leu
        915                 920                 925

Gly Lys Leu Gln Asp Val Val Asn Gln Asn Ala Gln Ala Leu Asn Thr
930                 935                 940

Leu Val Lys Gln Leu Ser Ser Asn Phe Gly Ala Ile Ser Ser Val Leu
945                 950                 955                 960
```

Asn Asp Ile Leu Ser Arg Leu Asp Pro Pro Glu Ala Glu Val Gln Ile
            965                 970                 975

Asp Arg Leu Ile Thr Gly Arg Leu Gln Ser Leu Gln Thr Tyr Val Thr
        980                 985                 990

Gln Gln Leu Ile Arg Ala Ala Glu Ile Arg Ala Ser Ala Asn Leu Ala
            995                 1000                1005

Ala Thr Lys Met Ser Glu Cys Val Leu Gly Gln Ser Lys Arg Val
    1010                1015                1020

Asp Phe Cys Gly Lys Gly Tyr His Leu Met Ser Phe Pro Gln Ala
    1025                1030                1035

Ala Pro His Gly Val Val Phe Leu His Val Thr Tyr Val Pro Ser
    1040                1045                1050

Gln Glu Arg Asn Phe Thr Thr Ala Pro Ala Ile Cys His Glu Gly
    1055                1060                1065

Lys Ala Tyr Phe Pro Arg Glu Gly Val Phe Val Phe Asn Gly Thr
    1070                1075                1080

Ser Trp Phe Ile Thr Gln Arg Asn Phe Phe Ser Pro Gln Ile Ile
    1085                1090                1095

Thr Thr Asp Asn Thr Phe Val Ser Gly Ser Cys Asp Val Val Ile
    1100                1105                1110

Gly Ile Ile Asn Asn Thr Val Tyr Asp Pro Leu Gln Pro Glu Leu
    1115                1120                1125

Asp Ser Phe Lys Glu Glu Leu Asp Lys Tyr Phe Lys Asn His Thr
    1130                1135                1140

Ser Pro Asp Val Asp Leu Gly Asp Ile Ser Gly Ile Asn Ala Ser
    1145                1150                1155

Val Val Asn Ile Gln Lys Glu Ile Asp Arg Leu Asn Glu Val Ala
    1160                1165                1170

Lys Asn Leu Asn Glu Ser Leu Ile Asp Leu Gln Glu Leu Gly Lys
    1175                1180                1185

Tyr Glu Gln Gly Gly Tyr Ile Pro Glu Ala Pro Arg Asp Gly Gln
    1190                1195                1200

Ala Tyr Val Arg Lys Asp Gly Glu Trp Val Leu Leu Ser Thr Phe
    1205                1210                1215

<210> SEQ ID NO 35
<211> LENGTH: 1324
<212> TYPE: PRT
<213> ORGANISM: Artificial Sequence
<220> FEATURE:
<223> OTHER INFORMATION: recombinant coronavirus spike protein

<400> SEQUENCE: 35

Met Leu Ser Val Phe Ile Leu Phe Leu Pro Ser Cys Leu Gly Tyr Ile
1               5                   10                  15

Gly Asp Phe Arg Cys Ile Asn Leu Val Asn Thr Asp Thr Ser Asn Ala
            20                  25                  30

Ser Ala Pro Ser Val Ser Thr Glu Val Val Asp Val Ser Lys Gly Ile
        35                  40                  45

Gly Thr Tyr Tyr Val Leu Asp Arg Val Tyr Leu Asn Ala Thr Leu Leu
    50                  55                  60

Leu Thr Gly Tyr Tyr Pro Val Asp Gly Ser Asn Tyr Arg Asn Leu Ala
65                  70                  75                  80

Leu Thr Gly Thr Asn Thr Leu Ser Leu Asn Trp Tyr Lys Pro Pro Phe
                85                  90                  95

-continued

Leu Ser Glu Phe Asn Asp Gly Ile Phe Ala Lys Val Lys Asn Leu Lys
            100                 105                 110

Ala Ser Leu Pro Lys Asp Ser Thr Ser Tyr Phe Pro Thr Ile Val Ile
        115                 120                 125

Gly Ser Asn Phe Val Thr Thr Ser Tyr Thr Val Leu Glu Pro Tyr
    130                 135                 140

Asn Gly Ile Ile Met Ala Ser Ile Cys Gln Tyr Thr Ile Cys Leu Leu
145                 150                 155                 160

Pro Tyr Thr Asp Cys Lys Pro Asn Thr Gly Asn Lys Leu Ile Gly
                165                 170                 175

Phe Trp His Ile Asp Leu Lys Ser Pro Val Cys Ile Leu Lys Arg Asn
            180                 185                 190

Phe Thr Phe Asn Val Asn Ala Asp Trp Leu Tyr Phe His Phe Tyr Gln
        195                 200                 205

Gln Gly Gly Thr Phe Tyr Ala Tyr Tyr Ala Asp Ala Gly Ser Ala Thr
    210                 215                 220

Thr Phe Leu Phe Ser Ser Tyr Ile Gly Asp Val Leu Thr Gln Tyr Phe
225                 230                 235                 240

Val Leu Pro Phe Val Cys Thr Pro Thr Thr Gly Val Phe Ser Pro
                245                 250                 255

Gln Tyr Trp Val Thr Pro Leu Val Lys Arg Gln Tyr Leu Phe Asn Phe
            260                 265                 270

Asn Gln Lys Gly Thr Ile Thr Ser Ala Val Asp Cys Ala Ser Ser Tyr
        275                 280                 285

Thr Ser Glu Ile Lys Cys Lys Thr Gln Ser Met Asn Pro Asn Thr Gly
    290                 295                 300

Val Tyr Asp Leu Ser Gly Tyr Thr Val Gln Pro Val Gly Leu Val Tyr
305                 310                 315                 320

Arg Arg Val Arg Asn Leu Pro Asp Cys Arg Ile Glu Asp Trp Leu Ala
                325                 330                 335

Ala Lys Thr Val Pro Ser Pro Leu Asn Trp Glu Arg Lys Thr Phe Gln
            340                 345                 350

Asn Cys Asn Phe Asn Leu Ser Ser Leu Leu Arg Leu Val Gln Ala Gly
        355                 360                 365

Ser Leu Ser Cys Ser Asn Ile Asp Ala Ala Lys Val Tyr Gly Met Cys
    370                 375                 380

Phe Gly Ser Met Ser Ile Asp Lys Phe Ala Ile Pro Asn Ser Arg Arg
385                 390                 395                 400

Val Asp Leu Gln Leu Gly Asn Ser Gly Phe Leu Gln Ser Phe Asn Tyr
                405                 410                 415

Lys Ile Asp Thr Arg Ala Thr Ser Cys Gln Leu Tyr Tyr Ser Leu Ala
            420                 425                 430

Gln Ser Asn Val Thr Val Asn Asn His Asn Pro Ser Ser Trp Asn Arg
        435                 440                 445

Arg Tyr Gly Phe Asn Asp Val Ala Thr Phe Gly Arg Gly Lys His Asp
    450                 455                 460

Val Ala Tyr Ala Glu Ala Cys Phe Thr Val Gly Ala Ser Tyr Cys Pro
465                 470                 475                 480

Cys Ala Asn Pro Ser Ile Val Ser Pro Cys Thr Thr Gly Lys Pro Lys
                485                 490                 495

Phe Ala Asn Cys Pro Thr Gly Thr Thr Asn Arg Glu Cys Asn Val Leu
            500                 505                 510

Ala Leu Gly Ser Asn Leu Phe Lys Cys Asp Cys Thr Cys Asn Pro Ser

```
              515                 520                 525
    Pro Leu Thr Thr Tyr Asp Leu Arg Cys Leu Gln Gly Arg Ser Met Leu
        530                 535                 540

Gly Val Gly Asp His Cys Glu Gly Leu Gly Val Leu Glu Asp Lys Cys
    545                 550                 555                 560

Gly Gly Ser Asn Thr Cys Asn Cys Ser Ala Asp Ala Phe Val Gly Trp
                    565                 570                 575

Ala Lys Asp Ser Cys Leu Ser Asn Gly Arg Cys His Ile Phe Ser Asn
                580                 585                 590

Leu Met Leu Asn Gly Ile Asn Ser Gly Thr Thr Cys Ser Thr Asp Leu
                595                 600                 605

Gln Leu Pro Asn Thr Glu Val Val Thr Gly Ile Cys Val Lys Tyr Asp
        610                 615                 620

Leu Tyr Gly Ile Thr Gly Gln Gly Val Phe Lys Glu Val Lys Ala Asp
    625                 630                 635                 640

Tyr Tyr Asn Ser Trp Gln Asn Leu Leu Tyr Asp Val Asn Gly Asn Leu
                    645                 650                 655

Asn Gly Phe Arg Asp Ile Val Thr Asn Lys Thr Tyr Leu Thr Arg Ser
                660                 665                 670

Cys Tyr Ser Gly Arg Val Ser Ala Ala Tyr His Gln Asp Ala Pro Glu
                675                 680                 685

Pro Ala Leu Leu Tyr Arg Asn Leu Lys Cys Asp Tyr Val Phe Asn Asn
        690                 695                 700

Asn Ile Phe Arg Glu Glu Thr Pro Leu Asn Tyr Phe Asp Ser Tyr Leu
    705                 710                 715                 720

Gly Cys Val Val Asn Ala Asp Asn Ser Thr Glu Gln Ala Val Asp Ala
                    725                 730                 735

Cys Asp Leu Arg Met Gly Ser Gly Leu Cys Val Asn Tyr Ser Thr Ala
                740                 745                 750

His Arg Ala Arg Thr Ser Val Ser Thr Gly Tyr Lys Leu Thr Thr Phe
                755                 760                 765

Glu Pro Phe Thr Val Ser Ile Val Asn Asp Ser Val Glu Ser Val Gly
        770                 775                 780

Gly Leu Tyr Glu Met Gln Ile Pro Thr Asn Phe Thr Ile Ala Ser His
    785                 790                 795                 800

Gln Glu Phe Ile Gln Thr Arg Ala Pro Lys Val Thr Ile Asp Cys Ala
                    805                 810                 815

Ala Phe Val Cys Gly Asp Tyr Thr Thr Cys Arg Gln Gln Leu Val Glu
                820                 825                 830

Tyr Gly Ser Phe Cys Asp Asn Ile Asn Ala Ile Leu Gly Glu Val Asn
                835                 840                 845

Asn Leu Ile Asp Thr Met Gln Leu Gln Val Ala Ser Ala Leu Ile Gln
        850                 855                 860

Gly Val Thr Leu Ser Ser Arg Leu Ala Asp Gly Ile Ser Gly Gln Ile
    865                 870                 875                 880

Asp Asp Ile Asn Phe Ser Pro Leu Leu Gly Cys Leu Gly Ser Gln Cys
                    885                 890                 895

Ser Glu Gly Thr Met Ala Ala Gln Gly Arg Ser Thr Val Glu Asp Leu
                900                 905                 910

Leu Phe Asp Lys Val Lys Leu Ser Asp Val Gly Phe Val Glu Ala Tyr
                915                 920                 925

Asn Asn Cys Thr Gly Gly Gln Glu Val Arg Asp Leu Leu Cys Val Gln
        930                 935                 940
```

```
Ser Phe Asn Gly Ile Lys Val Leu Pro Pro Val Leu Ser Glu Asn Gln
945                 950                 955                 960

Val Ser Gly Tyr Thr Ala Gly Ala Thr Ala Ser Ser Met Phe Pro Pro
                965                 970                 975

Trp Ser Ala Ala Ala Gly Val Pro Phe Ser Leu Ser Val Gln Tyr Arg
                980                 985                 990

Ile Asn Gly Leu Gly Val Thr Met Asn Val Leu Ser Glu Asn Gln Lys
            995                 1000                1005

Met Ile Ala Ser Ala Phe Asn Asn Ala Ile Gly Ala Ile Gln Glu
    1010            1015                1020

Gly Phe Asp Ala Thr Asn Ser Ala Leu Ala Lys Ile Gln Ser Val
    1025            1030                1035

Val Asn Ala Asn Ala Glu Ala Leu Asn Asn Leu Leu Asn Gln Leu
    1040            1045                1050

Ser Asn Arg Phe Gly Ala Ile Ser Ala Ser Leu Gln Glu Ile Leu
    1055            1060                1065

Ser Arg Leu Asp Pro Pro Glu Ala Gln Ala Gln Ile Asp Arg Leu
    1070            1075                1080

Ile Asn Gly Arg Leu Thr Ala Leu Asn Ala Tyr Val Ser Lys Gln
    1085            1090                1095

Leu Ser Asp Met Thr Leu Ile Lys Val Ser Ala Ala Gln Ala Ile
    1100            1105                1110

Glu Lys Val Asn Glu Cys Val Lys Ser Gln Ser Pro Arg Ile Asn
    1115            1120                1125

Phe Cys Gly Asn Gly Asn His Ile Leu Ser Leu Val Gln Asn Ala
    1130            1135                1140

Pro Tyr Gly Leu Tyr Phe Leu His Phe Ser Tyr Val Pro Thr Ser
    1145            1150                1155

Phe Thr Thr Ala Asn Val Ser Pro Gly Leu Cys Ile Ser Gly Asp
    1160            1165                1170

Arg Gly Leu Ala Pro Lys Ala Gly Tyr Phe Val Gln Asp Asp Gly
    1175            1180                1185

Glu Trp Lys Phe Thr Gly Ser Asn Tyr Tyr Tyr Pro Glu Pro Ile
    1190            1195                1200

Thr Asp Lys Asn Ser Val Val Met Ser Ser Cys Ala Val Asn Tyr
    1205            1210                1215

Thr Lys Ala Pro Glu Val Phe Leu Asn Thr Ser Ile Ser Asn Leu
    1220            1225                1230

Pro Asp Phe Lys Glu Glu Leu Asp Lys Trp Phe Lys Asn Gln Thr
    1235            1240                1245

Ser Val Ala Pro Asp Leu Ser Leu Asp Phe Glu Lys Leu Asn Val
    1250            1255                1260

Thr Phe Leu Asp Leu Ser Asp Glu Met Asn Arg Ile Gln Glu Ala
    1265            1270                1275

Ile Lys Lys Leu Asn Glu Ser Tyr Ile Asn Leu Lys Glu Ile Gly
    1280            1285                1290

Thr Tyr Glu Met Gly Gly Tyr Ile Pro Glu Ala Pro Arg Asp Gly
    1295            1300                1305

Gln Ala Tyr Val Arg Lys Asp Gly Glu Trp Val Leu Leu Ser Thr
    1310            1315                1320

Phe
```

```
<210> SEQ ID NO 36
<211> LENGTH: 1318
<212> TYPE: PRT
<213> ORGANISM: Artificial Sequence
<220> FEATURE:
<223> OTHER INFORMATION: recombinant coronavirus spike protein

<400> SEQUENCE: 36
```

| | | | | | | | | | | | | | | |
|---|---|---|---|---|---|---|---|---|---|---|---|---|---|---|
| Met | Lys | Leu | Phe | Leu | Ile | Leu | Val | Leu | Pro | Leu | Ala | Ser | Cys | Phe |
| 1 | | | | 5 | | | | | 10 | | | | | 15 |
| Phe | Thr | Cys | Asn | Ser | Asn | Ala | Asn | Leu | Ser | Met | Leu | Gln | Leu | Gly | Val |
| | | | 20 | | | | | 25 | | | | | 30 | | |
| Pro | Asp | Asn | Ser | Ser | Thr | Ile | Val | Thr | Gly | Leu | Leu | Pro | Thr | His | Trp |
| | | | 35 | | | | | 40 | | | | | 45 | | |
| Phe | Cys | Ala | Asn | Gln | Ser | Thr | Ser | Val | Tyr | Ser | Ala | Asn | Gly | Phe | Phe |
| | | | 50 | | | | | 55 | | | | | 60 | | |
| Tyr | Ile | Asp | Val | Gly | Asn | His | Arg | Ser | Ala | Phe | Ala | Leu | His | Thr | Gly |
| 65 | | | | | 70 | | | | | 75 | | | | | 80 |
| Tyr | Tyr | Asp | Ala | Asn | Gln | Tyr | Tyr | Ile | Tyr | Val | Thr | Asn | Glu | Ile | Gly |
| | | | | 85 | | | | | 90 | | | | | 95 | |
| Leu | Asn | Ala | Ser | Val | Thr | Leu | Lys | Ile | Cys | Lys | Phe | Ser | Arg | Asn | Thr |
| | | | | 100 | | | | | 105 | | | | | 110 | |
| Thr | Phe | Asp | Phe | Leu | Ser | Asn | Ala | Ser | Ser | Ser | Phe | Asp | Cys | Ile | Val |
| | | | 115 | | | | | 120 | | | | | 125 | | |
| Asn | Leu | Leu | Phe | Thr | Glu | Gln | Leu | Gly | Ala | Pro | Leu | Gly | Ile | Thr | Ile |
| | 130 | | | | | 135 | | | | | 140 | | | | |
| Ser | Gly | Glu | Thr | Val | Arg | Leu | His | Leu | Tyr | Asn | Val | Thr | Arg | Thr | Phe |
| 145 | | | | | 150 | | | | | 155 | | | | | 160 |
| Tyr | Val | Pro | Ala | Ala | Tyr | Lys | Leu | Thr | Lys | Leu | Ser | Val | Lys | Cys | Tyr |
| | | | | 165 | | | | | 170 | | | | | 175 | |
| Phe | Asn | Tyr | Ser | Cys | Val | Phe | Ser | Val | Val | Asn | Ala | Thr | Val | Thr | Val |
| | | | | 180 | | | | | 185 | | | | | 190 | |
| Asn | Val | Thr | Thr | His | Asn | Gly | Arg | Val | Val | Asn | Tyr | Thr | Val | Cys | Asp |
| | | | 195 | | | | | 200 | | | | | 205 | | |
| Asp | Cys | Asn | Gly | Tyr | Thr | Asp | Asn | Ile | Phe | Ser | Val | Gln | Gln | Asp | Gly |
| | 210 | | | | | 215 | | | | | 220 | | | | |
| Arg | Ile | Pro | Asn | Gly | Phe | Pro | Phe | Asn | Asn | Trp | Phe | Leu | Leu | Thr | Asn |
| 225 | | | | | 230 | | | | | 235 | | | | | 240 |
| Gly | Ser | Thr | Leu | Val | Asp | Gly | Val | Ser | Arg | Leu | Tyr | Gln | Pro | Leu | Arg |
| | | | | 245 | | | | | 250 | | | | | 255 | |
| Leu | Thr | Cys | Leu | Trp | Pro | Val | Pro | Gly | Leu | Lys | Ser | Ser | Thr | Gly | Phe |
| | | | | 260 | | | | | 265 | | | | | 270 | |
| Val | Tyr | Phe | Asn | Ala | Thr | Gly | Ser | Asp | Val | Asn | Cys | Asn | Gly | Tyr | Gln |
| | | | 275 | | | | | 280 | | | | | 285 | | |
| His | Asn | Ser | Val | Val | Asp | Val | Met | Arg | Tyr | Asn | Leu | Asn | Phe | Ser | Ala |
| | 290 | | | | | 295 | | | | | 300 | | | | |
| Asn | Ser | Leu | Asp | Asn | Leu | Lys | Ser | Gly | Val | Ile | Val | Phe | Lys | Thr | Leu |
| 305 | | | | | 310 | | | | | 315 | | | | | 320 |
| Gln | Tyr | Asp | Val | Leu | Phe | Tyr | Cys | Ser | Asn | Ser | Ser | Gly | Val | Leu |
| | | | | 325 | | | | | 330 | | | | | 335 |
| Asp | Thr | Thr | Ile | Pro | Phe | Gly | Pro | Ser | Ser | Gln | Pro | Tyr | Tyr | Cys | Phe |
| | | | 340 | | | | | 345 | | | | | 350 | | |
| Ile | Asn | Ser | Thr | Ile | Asn | Thr | Thr | His | Val | Ser | Thr | Phe | Val | Gly | Ile |
| | | | 355 | | | | | 360 | | | | | 365 | | |
| Leu | Pro | Pro | Thr | Val | Arg | Glu | Ile | Val | Val | Ala | Arg | Thr | Gly | Gln | Phe |

```
            370                 375                 380
Tyr Ile Asn Gly Phe Lys Tyr Phe Asp Leu Gly Phe Ile Glu Ala Val
385                 390                 395                 400

Asn Phe Asn Val Thr Thr Ala Ser Ala Thr Asp Phe Trp Thr Val Ala
                405                 410                 415

Phe Ala Thr Phe Val Asp Val Leu Val Asn Val Ser Ala Thr Asn Ile
                420                 425                 430

Gln Asn Leu Leu Tyr Cys Asp Ser Pro Phe Glu Lys Leu Gln Cys Glu
            435                 440                 445

His Leu Gln Phe Gly Leu Gln Asp Gly Phe Tyr Ser Ala Asn Phe Leu
        450                 455                 460

Asp Asp Asn Val Leu Pro Glu Thr Tyr Val Ala Leu Pro Ile Tyr Tyr
465                 470                 475                 480

Gln His Thr Asp Ile Asn Phe Thr Ala Thr Ala Ser Phe Gly Gly Ser
                485                 490                 495

Cys Tyr Val Cys Lys Pro His Gln Val Asn Ile Ser Leu Asn Gly Asn
                500                 505                 510

Thr Ser Val Cys Val Arg Thr Ser His Phe Ser Ile Arg Tyr Ile Tyr
            515                 520                 525

Asn Arg Val Lys Ser Gly Ser Pro Gly Asp Ser Ser Trp His Ile Tyr
        530                 535                 540

Leu Lys Ser Gly Thr Cys Pro Phe Ser Phe Ser Lys Leu Asn Asn Phe
545                 550                 555                 560

Gln Lys Phe Lys Thr Ile Cys Phe Ser Thr Val Glu Val Pro Gly Ser
                565                 570                 575

Cys Asn Phe Pro Leu Glu Ala Thr Trp His Tyr Thr Ser Tyr Thr Ile
            580                 585                 590

Val Gly Ala Leu Tyr Val Thr Trp Ser Glu Gly Asn Ser Ile Thr Gly
        595                 600                 605

Val Pro Tyr Pro Val Ser Gly Ile Arg Glu Phe Ser Asn Leu Val Leu
        610                 615                 620

Asn Asn Cys Thr Lys Tyr Asn Ile Tyr Asp Tyr Val Gly Thr Gly Ile
625                 630                 635                 640

Ile Arg Ser Ser Asn Gln Ser Leu Ala Gly Gly Ile Thr Tyr Val Ser
                645                 650                 655

Asn Ser Gly Asn Leu Leu Gly Phe Lys Asn Val Ser Thr Gly Asn Ile
            660                 665                 670

Phe Ile Val Thr Pro Cys Asn Gln Pro Asp Gln Val Ala Val Tyr Gln
        675                 680                 685

Gln Ser Ile Ile Gly Ala Met Thr Ala Val Asn Glu Ser Arg Tyr Gly
        690                 695                 700

Leu Gln Asn Leu Leu Gln Leu Pro Asn Phe Tyr Tyr Val Ser Asn Gly
705                 710                 715                 720

Gly Asn Asn Cys Thr Thr Ala Val Met Thr Tyr Ser Asn Phe Gly Ile
                725                 730                 735

Cys Ala Asp Gly Ser Leu Ile Pro Val Arg Pro Arg Asn Ser Ser Asp
            740                 745                 750

Asn Gly Ile Ser Ala Ile Thr Ala Asn Leu Ser Ile Pro Ser Asn
        755                 760                 765

Trp Thr Thr Ser Val Gln Val Glu Tyr Leu Gln Ile Thr Ser Thr Pro
        770                 775                 780

Ile Val Val Asp Cys Ala Thr Tyr Val Cys Asn Gly Asn Pro Arg Cys
785                 790                 795                 800
```

Lys Asn Leu Leu Lys Gln Tyr Thr Ser Ala Cys Lys Thr Ile Glu Asp
            805                 810                 815

Ala Leu Arg Leu Ser Ala His Leu Glu Thr Asn Asp Val Ser Ser Met
            820                 825                 830

Leu Thr Phe Asp Ser Asn Ala Phe Ser Leu Ala Asn Val Thr Ser Phe
            835                 840                 845

Gly Asp Tyr Asn Leu Ser Ser Val Leu Pro Gln Arg Asn Ile Arg Ser
            850                 855                 860

Ser Arg Ile Ala Gly Arg Ser Ala Leu Glu Asp Leu Leu Phe Ser Lys
865                 870                 875                 880

Val Val Thr Ser Gly Leu Gly Thr Val Asp Val Asp Tyr Lys Ser Cys
            885                 890                 895

Thr Lys Gly Leu Ser Ile Ala Asp Leu Ala Cys Ala Gln Tyr Tyr Asn
            900                 905                 910

Gly Ile Met Val Leu Pro Gly Val Ala Asp Ala Glu Arg Met Ala Met
            915                 920                 925

Tyr Thr Gly Ser Leu Ile Gly Gly Met Val Leu Gly Gly Leu Thr Ser
            930                 935                 940

Ala Ala Ala Ile Pro Phe Ser Leu Ala Leu Gln Ala Arg Leu Asn Tyr
945                 950                 955                 960

Val Ala Leu Gln Thr Asp Val Leu Gln Glu Asn Gln Lys Ile Leu Ala
            965                 970                 975

Ala Ser Phe Asn Lys Ala Ile Asn Asn Ile Val Ala Ser Phe Ser Ser
            980                 985                 990

Val Asn Asp Ala Ile Thr Gln Thr Ala Glu Ala Ile His Thr Val Thr
            995                 1000                1005

Ile Ala Leu Asn Lys Ile Gln Asp Val Val Asn Gln Gln Gly Ser
        1010                1015                1020

Ala Leu Asn His Leu Thr Ser Gln Leu Arg His Asn Phe Gln Ala
        1025                1030                1035

Ile Ser Asn Ser Ile Gln Ala Ile Tyr Asp Arg Leu Asp Pro Pro
        1040                1045                1050

Gln Ala Asp Gln Gln Val Asp Arg Leu Ile Thr Gly Arg Leu Ala
        1055                1060                1065

Ala Leu Asn Ala Phe Val Ser Gln Val Leu Asn Lys Tyr Thr Glu
        1070                1075                1080

Val Arg Gly Ser Arg Arg Leu Ala Gln Gln Lys Ile Asn Glu Cys
        1085                1090                1095

Val Lys Ser Gln Ser Asn Arg Tyr Gly Phe Cys Gly Asn Gly Thr
        1100                1105                1110

His Ile Phe Ser Ile Val Asn Ser Ala Pro Asp Gly Leu Leu Phe
        1115                1120                1125

Leu His Thr Val Leu Leu Pro Thr Asp Tyr Lys Asn Val Lys Ala
        1130                1135                1140

Trp Ser Gly Ile Cys Val Asp Gly Ile Tyr Gly Tyr Val Leu Arg
        1145                1150                1155

Gln Pro Asn Leu Val Leu Tyr Ser Asp Asn Gly Val Phe Arg Val
        1160                1165                1170

Thr Ser Arg Ile Met Phe Gln Pro Arg Leu Pro Val Leu Ser Asp
        1175                1180                1185

Phe Val Gln Ile Tyr Asn Cys Asn Val Thr Phe Val Asn Ile Ser
        1190                1195                1200

```
Arg Val Glu Leu His Thr Val Ile Pro Asp Tyr Val Asp Val Asn
    1205                1210                1215

Lys Thr Leu Gln Glu Phe Ala Gln Asn Leu Pro Lys Tyr Val Lys
    1220                1225                1230

Pro Asn Phe Asp Leu Thr Pro Phe Asn Leu Thr Tyr Leu Asn Leu
    1235                1240                1245

Ser Ser Glu Leu Lys Gln Leu Glu Ala Lys Thr Ala Ser Leu Phe
    1250                1255                1260

Gln Thr Thr Val Glu Leu Gln Gly Leu Ile Asp Gln Ile Asn Ser
    1265                1270                1275

Thr Tyr Val Asp Leu Lys Leu Leu Asn Arg Phe Glu Asn Gly Gly
    1280                1285                1290

Tyr Ile Pro Glu Ala Pro Arg Asp Gly Gln Ala Tyr Val Arg Lys
    1295                1300                1305

Asp Gly Glu Trp Val Leu Leu Ser Thr Phe
    1310                1315

<210> SEQ ID NO 37
<211> LENGTH: 1135
<212> TYPE: PRT
<213> ORGANISM: Artificial Sequence
<220> FEATURE:
<223> OTHER INFORMATION: recombinant coronavirus spike protein

<400> SEQUENCE: 37

Met Phe Val Leu Leu Val Ala Tyr Ala Leu Leu His Ile Ala Gly Cys
1               5                   10                  15

Gln Thr Thr Asn Gly Thr Asn Thr Ser His Ser Val Cys Asn Gly Cys
            20                  25                  30

Val Gly His Ser Glu Asn Val Phe Ala Val Glu Ser Gly Gly Tyr Ile
        35                  40                  45

Pro Ser Asn Phe Ala Phe Asn Asn Trp Phe Leu Leu Thr Asn Thr Ser
    50                  55                  60

Ser Val Val Asp Gly Val Val Arg Ser Phe Gln Pro Leu Leu Leu Asn
65                  70                  75                  80

Cys Leu Trp Ser Val Ser Gly Ser Gln Phe Thr Thr Gly Phe Val Tyr
                85                  90                  95

Phe Asn Gly Thr Gly Arg Gly Ala Cys Lys Gly Phe Tyr Ser Asn Ala
            100                 105                 110

Ser Ser Asp Val Ile Arg Tyr Asn Ile Asn Phe Glu Glu Asn Leu Arg
        115                 120                 125

Arg Gly Thr Ile Leu Phe Lys Thr Ser Tyr Gly Ala Val Val Phe Tyr
    130                 135                 140

Cys Thr Asn Asn Thr Leu Val Ser Gly Asp Ala His Ile Pro Ser Gly
145                 150                 155                 160

Thr Val Leu Gly Asn Phe Tyr Cys Phe Val Asn Thr Thr Ile Gly Asn
                165                 170                 175

Glu Thr Thr Ser Ala Phe Val Gly Ala Leu Pro Lys Thr Val Arg Glu
            180                 185                 190

Phe Val Ile Ser Arg Thr Gly His Phe Tyr Ile Asn Gly Tyr Arg Tyr
        195                 200                 205

Phe Ser Leu Gly Asp Val Glu Ala Val Asn Phe Asn Val Thr Asn Ala
    210                 215                 220

Ala Thr Thr Val Cys Thr Val Ala Leu Ala Ser Tyr Ala Asp Val Leu
225                 230                 235                 240
```

-continued

```
Val Asn Val Ser Gln Thr Ala Ile Ala Asn Ile Ile Tyr Cys Asn Ser
                245                 250                 255

Val Ile Asn Arg Leu Arg Cys Asp Gln Leu Ser Phe Asp Val Pro Asp
            260                 265                 270

Gly Phe Tyr Ser Thr Ser Pro Ile Gln Pro Val Glu Leu Pro Val Ser
        275                 280                 285

Ile Val Ser Leu Pro Val Tyr His Lys His Thr Phe Ile Val Leu Tyr
    290                 295                 300

Val Asn Phe Glu His Arg Arg Gly Pro Gly Lys Cys Tyr Asn Cys Arg
305                 310                 315                 320

Pro Ala Val Ile Asn Ile Thr Leu Ala Asn Phe Asn Glu Thr Lys Gly
                325                 330                 335

Pro Leu Cys Val Asp Thr Ser His Phe Thr Thr Gln Phe Val Asp Asn
            340                 345                 350

Val Lys Leu Ala Arg Trp Ser Ala Ser Ile Asn Thr Gly Asn Cys Pro
        355                 360                 365

Phe Ser Phe Gly Lys Val Asn Asn Phe Val Lys Phe Gly Ser Val Cys
    370                 375                 380

Phe Ser Leu Lys Asp Ile Pro Gly Gly Cys Ala Met Pro Ile Met Ala
385                 390                 395                 400

Asn Leu Val Asn Ser Lys Ser His Asn Ile Gly Ser Leu Tyr Val Ser
                405                 410                 415

Trp Ser Asp Gly Asp Val Ile Thr Gly Val Pro Lys Pro Val Glu Gly
            420                 425                 430

Val Ser Ser Phe Met Asn Val Thr Leu Asn Lys Cys Thr Lys Tyr Asn
        435                 440                 445

Ile Tyr Asp Val Ser Gly Val Gly Val Ile Arg Ile Ser Asn Asp Thr
    450                 455                 460

Phe Leu Asn Gly Ile Thr Tyr Thr Ser Thr Ser Gly Asn Leu Leu Gly
465                 470                 475                 480

Phe Lys Asp Val Thr Asn Gly Thr Ile Tyr Ser Ile Thr Pro Cys Asn
                485                 490                 495

Pro Pro Asp Gln Leu Val Val Tyr Gln Gln Ala Val Val Gly Ala Met
            500                 505                 510

Leu Ser Glu Asn Phe Thr Ser Tyr Gly Phe Ser Asn Val Val Glu Met
        515                 520                 525

Pro Lys Phe Phe Tyr Ala Ser Asn Gly Thr Tyr Asn Cys Thr Asp Ala
    530                 535                 540

Val Leu Thr Tyr Ser Ser Phe Gly Val Cys Ala Asp Gly Ser Ile Ile
545                 550                 555                 560

Ala Val Gln Pro Arg Asn Val Ser Tyr Asp Ser Val Ser Ala Ile Val
                565                 570                 575

Thr Ala Asn Leu Ser Ile Pro Phe Asn Trp Thr Thr Ser Val Gln Val
            580                 585                 590

Glu Tyr Leu Gln Ile Thr Ser Thr Pro Ile Val Val Asp Cys Ser Thr
        595                 600                 605

Tyr Val Cys Asn Gly Asn Val Arg Cys Val Glu Leu Leu Lys Gln Tyr
    610                 615                 620

Thr Ser Ala Cys Lys Thr Ile Glu Asp Ala Leu Arg Asn Ser Ala Met
625                 630                 635                 640

Leu Glu Ser Ala Asp Val Ser Glu Met Leu Thr Phe Asp Lys Lys Ala
                645                 650                 655

Phe Thr Leu Ala Asn Val Ser Ser Phe Gly Asp Tyr Asn Leu Ser Ser
```

```
                    660                 665                 670
Val Ile Pro Ser Leu Pro Arg Ser Gly Ser Arg Val Ala Gly Arg Ser
                675                 680                 685

Ala Ile Glu Asp Ile Leu Phe Ser Lys Leu Val Thr Ser Gly Leu Gly
            690                 695                 700

Thr Val Asp Ala Asp Tyr Lys Lys Cys Thr Lys Gly Leu Ser Ile Ala
705                 710                 715                 720

Asp Leu Ala Cys Ala Gln Tyr Tyr Asn Gly Ile Met Val Leu Pro Gly
                725                 730                 735

Val Ala Asp Ala Glu Arg Met Ala Met Tyr Thr Gly Ser Leu Ile Gly
            740                 745                 750

Gly Ile Ala Leu Gly Gly Leu Thr Ser Ala Ala Ser Ile Pro Phe Ser
        755                 760                 765

Leu Ala Ile Gln Ser Arg Leu Asn Tyr Val Ala Leu Gln Thr Asp Val
        770                 775                 780

Leu Gln Glu Asn Gln Arg Ile Leu Ala Ala Ser Phe Asn Lys Ala Met
785                 790                 795                 800

Thr Asn Ile Val Asp Ala Phe Thr Gly Val Asn Asp Ala Ile Thr Gln
                805                 810                 815

Thr Ser Gln Ala Leu Gln Thr Val Ala Thr Ala Leu Asn Lys Ile Gln
                820                 825                 830

Asp Val Val Asn Gln Gln Gly Asn Ser Leu Asn His Leu Thr Ser Gln
            835                 840                 845

Leu Arg Gln Asn Phe Gln Ala Ile Ser Ser Ser Ile Gln Ala Ile Tyr
        850                 855                 860

Asp Arg Leu Asp Pro Pro Gln Ala Asp Gln Gln Val Asp Arg Leu Ile
865                 870                 875                 880

Thr Gly Arg Leu Ala Ala Leu Asn Val Phe Val Ser His Thr Leu Thr
                885                 890                 895

Lys Tyr Thr Glu Val Arg Ala Ser Arg Gln Leu Ala Gln Gln Lys Val
            900                 905                 910

Asn Glu Cys Val Lys Ser Gln Ser Lys Arg Tyr Gly Phe Cys Gly Asn
        915                 920                 925

Gly Thr His Ile Phe Ser Leu Val Asn Ala Ala Pro Glu Gly Leu Val
        930                 935                 940

Phe Leu His Thr Val Leu Leu Pro Thr Gln Tyr Lys Asp Val Glu Ala
945                 950                 955                 960

Trp Ser Gly Leu Cys Val Asp Gly Ile Asn Gly Tyr Val Leu Arg Gln
                965                 970                 975

Pro Asn Leu Ala Leu Tyr Lys Glu Gly Asn Tyr Tyr Arg Ile Thr Ser
            980                 985                 990

Arg Ile Met Phe Glu Pro Arg Ile Pro Thr Ile Ala Asp Phe Val Gln
        995                 1000                1005

Ile Glu Asn Cys Asn Val Thr Phe Val Asn Ile Ser Arg Ser Glu
        1010                1015                1020

Leu Gln Thr Ile Val Pro Glu Tyr Ile Asp Val Asn Lys Thr Leu
        1025                1030                1035

Gln Glu Leu Ser Tyr Lys Leu Pro Asn Tyr Thr Val Pro Asp Leu
        1040                1045                1050

Val Val Glu Gln Tyr Asn Gln Thr Ile Leu Asn Leu Thr Ser Glu
        1055                1060                1065

Ile Ser Thr Leu Glu Asn Lys Ser Ala Glu Leu Asn Tyr Thr Val
        1070                1075                1080
```

```
Gln Lys Leu Gln Thr Leu Ile Asp Asn Ile Asn Ser Thr Leu Val
    1085            1090                1095

Asp Leu Lys Trp Leu Asn Arg Val Glu Thr Gly Gly Tyr Ile Pro
    1100            1105                1110

Glu Ala Pro Arg Asp Gly Gln Ala Tyr Val Arg Lys Asp Gly Glu
    1115            1120                1125

Trp Val Leu Leu Ser Thr Phe
    1130            1135

<210> SEQ ID NO 38
<211> LENGTH: 1386
<212> TYPE: PRT
<213> ORGANISM: Artificial Sequence
<220> FEATURE:
<223> OTHER INFORMATION: recombinant coronavirus spike protein

<400> SEQUENCE: 38

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ile Gly Glu Asn Gln Gly Val Asn Ser Thr
50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
            115                 120                 125

Pro Ser Ile Lys Thr Leu Gly Pro Thr Ala Asn Asn Asp Val Thr Thr
130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
            195                 200                 205

Glu Pro Thr Tyr Tyr Met Leu Asn Val Thr Ser Ala Gly Glu Asp Gly
        210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu His Gly Lys
            260                 265                 270

Val Val Ser Asn Gln Pro Leu Leu Val Asn Cys Leu Leu Ala Ile Pro
            275                 280                 285

Lys Ile Tyr Gly Leu Gly Gln Phe Phe Ser Phe Asn Gln Thr Ile Asp
            290                 295                 300
```

```
Gly Val Cys Asn Gly Ala Ala Val Gln Arg Ala Pro Glu Ala Leu Arg
305                 310                 315                 320

Phe Asn Ile Asn Asp Ile Ser Val Ile Leu Ala Glu Gly Ser Ile Val
            325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
            355                 360                 365

Val Pro Tyr Tyr Cys Phe Phe Lys Val Asp Thr Tyr Asn Ser Thr Val
370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
                420                 425                 430

Asp Asp Val Ser Gly Phe Trp Thr Ile Ala Ser Thr Asn Phe Val Asp
            435                 440                 445

Ala Leu Ile Glu Val Gln Gly Thr Ala Ile Gln Arg Ile Leu Tyr Cys
450                 455                 460

Asp Asp Pro Val Ser Gln Leu Lys Cys Ser Gln Val Ala Phe Asp Leu
465                 470                 475                 480

Asp Asp Gly Phe Tyr Thr Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
            515                 520                 525

Leu Ile Ala Ser Asp Thr Thr Ile Asn Gly Phe Ser Ser Phe Cys Val
530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
            595                 600                 605

Phe Gly Ser Gly Val Lys Phe Thr Ser Leu Tyr Phe Gln Phe Thr Lys
610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
                660                 665                 670

Gly Val Tyr Tyr Thr Ser Asp Ser Gly Gln Leu Leu Ala Phe Lys Asn
            675                 680                 685

Val Thr Ser Gly Ala Val Tyr Ser Val Thr Pro Cys Ser Phe Ser Glu
            690                 695                 700

Gln Ala Ala Tyr Val Asp Asp Ile Val Gly Val Ile Ser Ser Leu
705                 710                 715                 720
```

```
Ser Ser Ser Thr Phe Asn Ser Thr Arg Glu Leu Pro Gly Phe Phe Tyr
            725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
            755                 760                 765

Ser Gly Gln Val Lys Ile Ala Pro Thr Val Thr Gly Asn Ile Ser Ile
            770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
            805                 810                 815

Ser Arg Cys Lys Gln Leu Leu Thr Gln Tyr Thr Ala Ala Cys Lys Thr
            820                 825                 830

Ile Glu Ser Ala Leu Gln Leu Ser Ala Arg Leu Glu Ser Val Glu Val
            835                 840                 845

Asn Ser Met Leu Thr Ile Ser Asp Glu Ala Leu Gln Leu Ala Thr Ile
            850                 855                 860

Ser Ser Phe Asn Gly Asp Gly Tyr Asn Phe Thr Asn Val Leu Gly Val
865                 870                 875                 880

Ser Val Tyr Asp Pro Ala Ser Arg Arg Val Val Gln Lys Arg Ser Phe
            885                 890                 895

Ile Glu Asp Leu Leu Phe Asn Lys Val Val Thr Asn Gly Leu Gly Thr
            900                 905                 910

Val Asp Glu Asp Tyr Lys Arg Cys Ser Asn Gly Arg Ser Val Ala Asp
            915                 920                 925

Leu Val Cys Ala Gln Tyr Tyr Ser Gly Val Met Val Leu Pro Gly Val
            930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
            965                 970                 975

Ala Val Gln Ala Arg Leu Asn Tyr Leu Ala Leu Gln Thr Asp Val Leu
            980                 985                 990

Gln Arg Asn Gln Gln Leu Leu Ala Glu Ser Phe Asn Ser Ala Ile Gly
            995                 1000                1005

Asn Ile Thr Ser Ala Phe Glu Ser Val Lys Glu Ala Ile Ser Gln
            1010                1015                1020

Thr Ser Lys Gly Leu Asn Thr Val Ala His Ala Leu Thr Lys Val
            1025                1030                1035

Gln Glu Val Val Asn Ser Gly Ala Ala Leu Thr Gln Leu Thr
            1040                1045                1050

Val Gln Leu Gln His Asn Phe Gln Ala Ile Ser Ser Ser Ile Asp
            1055                1060                1065

Asp Ile Tyr Ser Arg Leu Asp Ile Leu Ser Ala Asp Ala Gln Val
            1070                1075                1080

Asp Arg Leu Ile Thr Gly Arg Leu Ser Ala Leu Asn Ala Phe Val
            1085                1090                1095

Ala Gln Thr Leu Thr Lys Tyr Thr Glu Val Gln Ala Ser Arg Lys
            1100                1105                1110

Leu Ala Gln Gln Lys Val Asn Glu Cys Val Lys Ser Gln Ser Gln
            1115                1120                1125

Arg Tyr Gly Phe Cys Gly Gly Asp Gly Glu His Ile Phe Ser Leu
```

```
                1130                1135                1140
Val Gln Ala Ala Pro Gln Gly Leu Leu Phe Leu His Thr Val Leu
        1145                1150                1155
Val Pro Ser Asp Phe Val Asp Val Ile Ala Ile Ala Gly Leu Cys
        1160                1165                1170
Val Asn Asp Glu Ile Ala Leu Thr Leu Arg Glu Pro Gly Leu Val
        1175                1180                1185
Leu Phe Thr His Glu Leu Gln Asn His Thr Ala Thr Glu Tyr Phe
        1190                1195                1200
Val Ser Ser Arg Arg Met Phe Glu Pro Arg Lys Pro Thr Val Ser
        1205                1210                1215
Asp Phe Val Gln Ile Glu Ser Cys Val Val Thr Tyr Val Asn Leu
        1220                1225                1230
Thr Arg Asp Gln Leu Pro Asp Val Ile Pro Asp Tyr Ile Asp Val
        1235                1240                1245
Asn Lys Thr Leu Tyr Glu Ile Leu Ala Ser Leu Pro Asn Arg Thr
        1250                1255                1260
Gly Pro Ser Leu Pro Leu Asp Val Phe Asn Ala Thr Tyr Leu Asn
        1265                1270                1275
Leu Thr Gly Glu Ile Ala Asp Leu Glu Gln Arg Ser Glu Ser Leu
        1280                1285                1290
Arg Asn Thr Thr Glu Glu Leu Gln Ser Leu Ile Tyr Asn Ile Asn
        1295                1300                1305
Asn Thr Leu Val Asp Leu Glu Trp Leu Asn Arg Val Glu Thr Tyr
        1310                1315                1320
Ile Lys Trp Pro Trp Trp Val Trp Leu Ile Ile Phe Ile Val Leu
        1325                1330                1335
Ile Phe Val Val Ser Leu Leu Val Phe Cys Cys Ile Ser Thr Gly
        1340                1345                1350
Cys Cys Gly Cys Cys Gly Cys Cys Ala Cys Phe Ser Gly Cys
        1355                1360                1365
Cys Arg Gly Pro Arg Leu Gln Pro Tyr Glu Val Phe Glu Lys Val
        1370                1375                1380
His Val Gln
        1385

<210> SEQ ID NO 39
<211> LENGTH: 1322
<212> TYPE: PRT
<213> ORGANISM: Artificial Sequence
<220> FEATURE:
<223> OTHER INFORMATION: recombinant coronavirus spike protein

<400> SEQUENCE: 39

Met Lys Ser Leu Thr Tyr Phe Trp Leu Phe Leu Pro Val Leu Ser Thr
1               5                   10                  15
Leu Ser Leu Pro Gln Asp Val Thr Arg Cys Ser Ala Asn Thr Asn Phe
            20                  25                  30
Arg Arg Phe Phe Ser Lys Phe Asn Val Gln Ala Pro Ala Val Val Val
        35                  40                  45
Leu Gly Gly Tyr Leu Pro Ile Gly Glu Asn Gln Gly Val Asn Ser Thr
    50                  55                  60
Trp Tyr Cys Ala Gly Gln His Pro Thr Ala Ser Gly Val His Gly Ile
65                  70                  75                  80
Phe Val Ser His Ile Arg Gly Gly His Gly Phe Glu Ile Gly Ile Ser
```

```
            85                  90                  95
Gln Glu Pro Phe Asp Pro Ser Gly Tyr Gln Leu Tyr Leu His Lys Ala
            100                 105                 110
Thr Asn Gly Asn Thr Asn Ala Thr Ala Arg Leu Arg Ile Cys Gln Phe
            115                 120                 125
Pro Ser Ile Lys Thr Leu Gly Pro Thr Ala Asn Asn Asp Val Thr Thr
            130                 135                 140
Gly Arg Asn Cys Leu Phe Asn Lys Ala Ile Pro Ala His Met Ser Glu
145                 150                 155                 160
His Ser Val Val Gly Ile Thr Trp Asp Asn Asp Arg Val Thr Val Phe
                    165                 170                 175
Ser Asp Lys Ile Tyr Tyr Phe Tyr Lys Asn Asp Trp Ser Arg Val
                    180                 185                 190
Ala Thr Lys Cys Tyr Asn Ser Gly Gly Cys Ala Met Gln Tyr Val Tyr
                    195                 200                 205
Glu Pro Thr Tyr Tyr Met Leu Asn Val Thr Ser Ala Gly Glu Asp Gly
            210                 215                 220
Ile Ser Tyr Gln Pro Cys Thr Ala Asn Cys Ile Gly Tyr Ala Ala Asn
225                 230                 235                 240
Val Phe Ala Thr Glu Pro Asn Gly His Ile Pro Glu Gly Phe Ser Phe
                    245                 250                 255
Asn Asn Trp Phe Leu Leu Ser Asn Asp Ser Thr Leu Val His Gly Lys
                    260                 265                 270
Val Val Ser Asn Gln Pro Leu Leu Val Asn Cys Leu Leu Ala Ile Pro
                    275                 280                 285
Lys Ile Tyr Gly Leu Gly Gln Phe Phe Ser Phe Asn Gln Thr Ile Asp
            290                 295                 300
Gly Val Cys Asn Gly Ala Ala Val Gln Arg Ala Pro Glu Ala Leu Arg
305                 310                 315                 320
Phe Asn Ile Asn Asp Ile Ser Val Ile Leu Ala Glu Gly Ser Ile Val
                    325                 330                 335
Leu His Thr Ala Leu Gly Thr Asn Phe Ser Phe Val Cys Ser Asn Ser
                    340                 345                 350
Ser Asn Pro His Leu Ala Thr Phe Ala Ile Pro Leu Gly Ala Thr Gln
            355                 360                 365
Val Pro Tyr Tyr Cys Phe Phe Lys Val Asp Thr Tyr Asn Ser Thr Val
            370                 375                 380
Tyr Lys Phe Leu Ala Val Leu Pro Pro Thr Val Arg Glu Ile Val Ile
385                 390                 395                 400
Thr Lys Tyr Gly Asp Val Tyr Val Asn Gly Phe Gly Tyr Leu His Leu
                    405                 410                 415
Gly Leu Leu Asp Ala Val Thr Ile Asn Phe Thr Gly His Gly Thr Asp
                    420                 425                 430
Asp Asp Val Ser Gly Phe Trp Thr Ile Ala Ser Thr Asn Phe Val Asp
                    435                 440                 445
Ala Leu Ile Glu Val Gln Gly Thr Ala Ile Gln Arg Ile Leu Tyr Cys
            450                 455                 460
Asp Asp Pro Val Ser Gln Leu Lys Cys Ser Gln Val Ala Phe Asp Leu
465                 470                 475                 480
Asp Asp Gly Phe Tyr Thr Ile Ser Ser Arg Asn Leu Leu Ser His Glu
                    485                 490                 495
Gln Pro Ile Ser Phe Val Thr Leu Pro Ser Phe Asn Asp His Ser Phe
            500                 505                 510
```

-continued

```
Val Asn Ile Thr Val Ser Ala Ser Phe Gly Gly His Ser Gly Ala Asn
        515                 520                 525
Leu Ile Ala Ser Asp Thr Thr Ile Asn Gly Phe Ser Ser Phe Cys Val
530             535                 540
Asp Thr Arg Gln Phe Thr Ile Ser Leu Phe Tyr Asn Val Thr Asn Ser
545                 550                 555                 560
Tyr Gly Tyr Val Ser Lys Ser Gln Asp Ser Asn Cys Pro Phe Thr Leu
                565                 570                 575
Gln Ser Val Asn Asp Tyr Leu Ser Phe Ser Lys Phe Cys Val Ser Thr
            580                 585                 590
Ser Leu Leu Ala Ser Ala Cys Thr Ile Asp Leu Phe Gly Tyr Pro Glu
        595                 600                 605
Phe Gly Ser Gly Val Lys Phe Thr Ser Leu Tyr Phe Gln Phe Thr Lys
    610                 615                 620
Gly Glu Leu Ile Thr Gly Thr Pro Lys Pro Leu Glu Gly Val Thr Asp
625                 630                 635                 640
Val Ser Phe Met Thr Leu Asp Val Cys Thr Lys Tyr Thr Ile Tyr Gly
                645                 650                 655
Phe Lys Gly Glu Gly Ile Ile Thr Leu Thr Asn Ser Ser Phe Leu Ala
            660                 665                 670
Gly Val Tyr Tyr Thr Ser Asp Ser Gly Gln Leu Leu Ala Phe Lys Asn
        675                 680                 685
Val Thr Ser Gly Ala Val Tyr Ser Val Thr Pro Cys Ser Phe Ser Glu
    690                 695                 700
Gln Ala Ala Tyr Val Asp Asp Ile Val Gly Val Ile Ser Ser Leu
705                 710                 715                 720
Ser Ser Ser Thr Phe Asn Ser Thr Arg Glu Leu Pro Gly Phe Phe Tyr
                725                 730                 735
His Ser Asn Asp Gly Ser Asn Cys Thr Glu Pro Val Leu Val Tyr Ser
            740                 745                 750
Asn Ile Gly Val Cys Lys Ser Gly Ser Ile Gly Tyr Val Pro Ser Gln
        755                 760                 765
Ser Gly Gln Val Lys Ile Ala Pro Thr Val Thr Gly Asn Ile Ser Ile
    770                 775                 780
Pro Thr Asn Phe Ser Met Ser Ile Arg Thr Glu Tyr Leu Gln Leu Tyr
785                 790                 795                 800
Asn Thr Pro Val Ser Val Asp Cys Ala Thr Tyr Val Cys Asn Gly Asn
                805                 810                 815
Ser Arg Cys Lys Gln Leu Leu Thr Gln Tyr Thr Ala Ala Cys Lys Thr
            820                 825                 830
Ile Glu Ser Ala Leu Gln Leu Ser Ala Arg Leu Glu Ser Val Glu Val
        835                 840                 845
Asn Ser Met Leu Thr Ile Ser Asp Glu Ala Leu Gln Leu Ala Thr Ile
    850                 855                 860
Ser Ser Phe Asn Gly Asp Gly Tyr Asn Phe Thr Asn Val Leu Gly Val
865                 870                 875                 880
Ser Val Tyr Asp Pro Ala Ser Arg Arg Val Gln Lys Arg Ser Phe
                885                 890                 895
Ile Glu Asp Leu Leu Phe Asn Lys Val Val Thr Asn Gly Leu Gly Thr
            900                 905                 910
Val Asp Glu Asp Tyr Lys Arg Cys Ser Asn Gly Arg Ser Val Ala Asp
    915                 920                 925
```

-continued

```
Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
            980                 985                 990

Gln Arg Asn Gln Gln Leu Leu Ala Glu Ser Phe Asn Ser Ala Ile Gly
        995                 1000                1005

Asn Ile Thr Ser Ala Phe Glu Ser Val Lys Glu Ala Ile Ser Gln
    1010                1015                1020

Thr Ser Lys Gly Leu Asn Thr Val Ala His Ala Leu Thr Lys Val
    1025                1030                1035

Gln Glu Val Val Asn Ser Gln Gly Ala Ala Leu Thr Gln Leu Thr
    1040                1045                1050

Val Gln Leu Gln His Asn Phe Gln Ala Ile Ser Ser Ser Ile Asp
    1055                1060                1065

Asp Ile Tyr Ser Arg Leu Asp Pro Pro Ser Ala Asp Ala Gln Val
    1070                1075                1080

Asp Arg Leu Ile Thr Gly Arg Leu Ser Ala Leu Asn Ala Phe Val
    1085                1090                1095

Ala Gln Thr Leu Thr Lys Tyr Thr Glu Val Gln Ala Ser Arg Lys
    1100                1105                1110

Leu Ala Gln Gln Lys Val Asn Glu Cys Val Lys Ser Gln Ser Gln
    1115                1120                1125

Arg Tyr Gly Phe Cys Gly Gly Asp Gly Glu His Ile Phe Ser Leu
    1130                1135                1140

Val Gln Ala Ala Pro Gln Gly Leu Leu Phe Leu His Thr Val Leu
    1145                1150                1155

Val Pro Ser Asp Phe Val Asp Val Ile Ala Ile Ala Gly Leu Cys
    1160                1165                1170

Val Asn Asp Glu Ile Ala Leu Thr Leu Arg Glu Pro Gly Leu Val
    1175                1180                1185

Leu Phe Thr His Glu Leu Gln Asn His Thr Ala Thr Glu Tyr Phe
    1190                1195                1200

Val Ser Ser Arg Arg Met Phe Glu Pro Arg Lys Pro Thr Val Ser
    1205                1210                1215

Asp Phe Val Gln Ile Glu Ser Cys Val Val Thr Tyr Val Asn Leu
    1220                1225                1230

Thr Arg Asp Gln Leu Pro Asp Val Ile Pro Asp Tyr Ile Asp Val
    1235                1240                1245

Asn Lys Thr Leu Tyr Glu Ile Leu Ala Ser Leu Pro Asn Arg Thr
    1250                1255                1260

Gly Pro Ser Leu Pro Leu Asp Val Phe Asn Ala Thr Tyr Leu Asn
    1265                1270                1275

Leu Thr Gly Glu Ile Ala Asp Leu Glu Gln Arg Ser Glu Ser Leu
    1280                1285                1290

Arg Asn Thr Thr Glu Glu Leu Gln Ser Leu Ile Tyr Asn Ile Asn
    1295                1300                1305

Asn Thr Leu Val Asp Leu Glu Trp Leu Asn Arg Val Glu Thr
    1310                1315                1320
```

```
<210> SEQ ID NO 40
<211> LENGTH: 1349
<212> TYPE: PRT
<213> ORGANISM: Artificial Sequence
<220> FEATURE:
<223> OTHER INFORMATION: recombinant coronavirus spike protein

<400> SEQUENCE: 40
```

| Met | Lys | Ser | Leu | Thr | Tyr | Phe | Trp | Leu | Phe | Leu | Pro | Val | Leu | Ser | Thr |
|---|---|---|---|---|---|---|---|---|---|---|---|---|---|---|---|
| 1 | | | | 5 | | | | | 10 | | | | | 15 | |

| Leu | Ser | Leu | Pro | Gln | Asp | Val | Thr | Arg | Cys | Ser | Ala | Asn | Thr | Asn | Phe |
| | | | 20 | | | | | 25 | | | | | 30 | | |

| Arg | Arg | Phe | Phe | Ser | Lys | Phe | Asn | Val | Gln | Ala | Pro | Ala | Val | Val | Val |
| | | | 35 | | | | | 40 | | | | | 45 | | |

| Leu | Gly | Gly | Tyr | Leu | Pro | Ile | Gly | Glu | Asn | Gln | Gly | Val | Asn | Ser | Thr |
| | | 50 | | | | | 55 | | | | | 60 | | | |

| Trp | Tyr | Cys | Ala | Gly | Gln | His | Pro | Thr | Ala | Ser | Gly | Val | His | Gly | Ile |
| 65 | | | | | 70 | | | | | 75 | | | | | 80 |

| Phe | Val | Ser | His | Ile | Arg | Gly | Gly | His | Gly | Phe | Glu | Ile | Gly | Ile | Ser |
| | | | | 85 | | | | | 90 | | | | | 95 | |

| Gln | Glu | Pro | Phe | Asp | Pro | Ser | Gly | Tyr | Gln | Leu | Tyr | Leu | His | Lys | Ala |
| | | | 100 | | | | | 105 | | | | | 110 | | |

| Thr | Asn | Gly | Asn | Thr | Asn | Ala | Thr | Ala | Arg | Leu | Arg | Ile | Cys | Gln | Phe |
| | | | 115 | | | | | 120 | | | | | 125 | | |

| Pro | Ser | Ile | Lys | Thr | Leu | Gly | Pro | Thr | Ala | Asn | Asn | Asp | Val | Thr | Thr |
| | | 130 | | | | | 135 | | | | | 140 | | | |

| Gly | Arg | Asn | Cys | Leu | Phe | Asn | Lys | Ala | Ile | Pro | Ala | His | Met | Ser | Glu |
| 145 | | | | | 150 | | | | | 155 | | | | | 160 |

| His | Ser | Val | Val | Gly | Ile | Thr | Trp | Asp | Asn | Asp | Arg | Val | Thr | Val | Phe |
| | | | | 165 | | | | | 170 | | | | | 175 | |

| Ser | Asp | Lys | Ile | Tyr | Tyr | Phe | Tyr | Phe | Lys | Asn | Asp | Trp | Ser | Arg | Val |
| | | | 180 | | | | | 185 | | | | | 190 | | |

| Ala | Thr | Lys | Cys | Tyr | Asn | Ser | Gly | Gly | Cys | Ala | Met | Gln | Tyr | Val | Tyr |
| | | | 195 | | | | | 200 | | | | | 205 | | |

| Glu | Pro | Thr | Tyr | Tyr | Met | Leu | Asn | Val | Thr | Ser | Ala | Gly | Glu | Asp | Gly |
| | | 210 | | | | | 215 | | | | | 220 | | | |

| Ile | Ser | Tyr | Gln | Pro | Cys | Thr | Ala | Asn | Cys | Ile | Gly | Tyr | Ala | Ala | Asn |
| 225 | | | | | 230 | | | | | 235 | | | | | 240 |

| Val | Phe | Ala | Thr | Glu | Pro | Asn | Gly | His | Ile | Pro | Glu | Gly | Phe | Ser | Phe |
| | | | | 245 | | | | | 250 | | | | | 255 | |

| Asn | Asn | Trp | Phe | Leu | Leu | Ser | Asn | Asp | Ser | Thr | Leu | Val | His | Gly | Lys |
| | | | 260 | | | | | 265 | | | | | 270 | | |

| Val | Val | Ser | Asn | Gln | Pro | Leu | Leu | Val | Asn | Cys | Leu | Leu | Ala | Ile | Pro |
| | | | 275 | | | | | 280 | | | | | 285 | | |

| Lys | Ile | Tyr | Gly | Leu | Gly | Gln | Phe | Phe | Ser | Phe | Asn | Gln | Thr | Ile | Asp |
| | | 290 | | | | | 295 | | | | | 300 | | | |

| Gly | Val | Cys | Asn | Gly | Ala | Ala | Val | Gln | Arg | Ala | Pro | Glu | Ala | Leu | Arg |
| 305 | | | | | 310 | | | | | 315 | | | | | 320 |

| Phe | Asn | Ile | Asn | Asp | Ile | Ser | Val | Ile | Leu | Ala | Glu | Gly | Ser | Ile | Val |
| | | | | 325 | | | | | 330 | | | | | 335 | |

| Leu | His | Thr | Ala | Leu | Gly | Thr | Asn | Phe | Ser | Phe | Val | Cys | Ser | Asn | Ser |
| | | | 340 | | | | | 345 | | | | | 350 | | |

| Ser | Asn | Pro | His | Leu | Ala | Thr | Phe | Ala | Ile | Pro | Leu | Gly | Ala | Thr | Gln |
| | | | 355 | | | | | 360 | | | | | 365 | | |

| Val | Pro | Tyr | Tyr | Cys | Phe | Phe | Lys | Val | Asp | Thr | Tyr | Asn | Ser | Thr | Val |

```
            370                 375                 380
Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
            405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
            435                 440                 445

Ala Leu Ile Glu Val Gln Gly Thr Ala Ile Gln Arg Ile Leu Tyr Cys
            450                 455                 460

Asp Asp Pro Val Ser Gln Leu Lys Cys Ser Gln Val Ala Phe Asp Leu
465                 470                 475                 480

Asp Asp Gly Phe Tyr Thr Ile Ser Ser Arg Asn Leu Leu Ser His Glu
            485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
            515                 520                 525

Leu Ile Ala Ser Asp Thr Thr Ile Asn Gly Phe Ser Ser Phe Cys Val
            530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
            565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
            595                 600                 605

Phe Gly Ser Gly Val Lys Phe Thr Ser Leu Tyr Phe Gln Phe Thr Lys
            610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
            645                 650                 655

Phe Lys Gly Glu Gly Ile Ile Thr Leu Thr Asn Ser Ser Phe Leu Ala
            660                 665                 670

Gly Val Tyr Tyr Thr Ser Asp Ser Gly Gln Leu Leu Ala Phe Lys Asn
            675                 680                 685

Val Thr Ser Gly Ala Val Tyr Ser Val Thr Pro Cys Ser Phe Ser Glu
            690                 695                 700

Gln Ala Ala Tyr Val Asp Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
            725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
            755                 760                 765

Ser Gly Gln Val Lys Ile Ala Pro Thr Val Thr Gly Asn Ile Ser Ile
            770                 775                 780

Pro Thr Asn Phe Ser Met Ser Ile Arg Thr Glu Tyr Leu Gln Leu Tyr
785                 790                 795                 800
```

```
Asn Thr Pro Val Ser Val Asp Cys Ala Thr Tyr Val Cys Asn Gly Asn
            805                 810                 815

Ser Arg Cys Lys Gln Leu Leu Thr Gln Tyr Thr Ala Ala Cys Lys Thr
            820                 825                 830

Ile Glu Ser Ala Leu Gln Leu Ser Ala Arg Leu Glu Ser Val Glu Val
            835                 840                 845

Asn Ser Met Leu Thr Ile Ser Asp Glu Ala Leu Gln Leu Ala Thr Ile
            850                 855                 860

Ser Ser Phe Asn Gly Asp Gly Tyr Asn Phe Thr Asn Val Leu Gly Val
865                 870                 875                 880

Ser Val Tyr Asp Pro Ala Ser Arg Arg Val Val Gln Lys Arg Ser Phe
            885                 890                 895

Ile Glu Asp Leu Leu Phe Asn Lys Val Val Thr Asn Gly Leu Gly Thr
            900                 905                 910

Val Asp Glu Asp Tyr Lys Arg Cys Ser Asn Gly Arg Ser Val Ala Asp
            915                 920                 925

Leu Val Cys Ala Gln Tyr Tyr Ser Gly Val Met Val Leu Pro Gly Val
            930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
            965                 970                 975

Ala Val Gln Ala Arg Leu Asn Tyr Leu Ala Leu Gln Thr Asp Val Leu
            980                 985                 990

Gln Arg Asn Gln Gln Leu Leu Ala Glu Ser Phe Asn Ser Ala Ile Gly
            995                 1000                1005

Asn Ile Thr Ser Ala Phe Glu Ser Val Lys Glu Ala Ile Ser Gln
        1010                1015                1020

Thr Ser Lys Gly Leu Asn Thr Val Ala His Ala Leu Thr Lys Val
        1025                1030                1035

Gln Glu Val Val Asn Ser Gln Gly Ala Ala Leu Thr Gln Leu Thr
        1040                1045                1050

Val Gln Leu Gln His Asn Phe Gln Ala Ile Ser Ser Ser Ile Asp
        1055                1060                1065

Asp Ile Tyr Ser Arg Leu Asp Pro Pro Ser Ala Asp Ala Gln Val
        1070                1075                1080

Asp Arg Leu Ile Thr Gly Arg Leu Ser Ala Leu Asn Ala Phe Val
        1085                1090                1095

Ala Gln Thr Leu Thr Lys Tyr Thr Glu Val Gln Ala Ser Arg Lys
        1100                1105                1110

Leu Ala Gln Gln Lys Val Asn Glu Cys Val Lys Ser Gln Ser Gln
        1115                1120                1125

Arg Tyr Gly Phe Cys Gly Gly Asp Gly Glu His Ile Phe Ser Leu
        1130                1135                1140

Val Gln Ala Ala Pro Gln Gly Leu Leu Phe Leu His Thr Val Leu
        1145                1150                1155

Val Pro Ser Asp Phe Val Asp Val Ile Ala Ile Ala Gly Leu Cys
        1160                1165                1170

Val Asn Asp Glu Ile Ala Leu Thr Leu Arg Glu Pro Gly Leu Val
        1175                1180                1185

Leu Phe Thr His Glu Leu Gln Asn His Thr Ala Thr Glu Tyr Phe
        1190                1195                1200
```

```
Val Ser Ser Arg Arg Met Phe Glu Pro Arg Lys Pro Thr Val Ser
    1205                1210                1215

Asp Phe Val Gln Ile Glu Ser Cys Val Val Thr Tyr Val Asn Leu
    1220                1225                1230

Thr Arg Asp Gln Leu Pro Asp Val Ile Pro Asp Tyr Ile Asp Val
    1235                1240                1245

Asn Lys Thr Leu Tyr Glu Ile Leu Ala Ser Leu Pro Asn Arg Thr
    1250                1255                1260

Gly Pro Ser Leu Pro Leu Asp Val Phe Asn Ala Thr Tyr Leu Asn
    1265                1270                1275

Leu Thr Gly Glu Ile Ala Asp Leu Glu Gln Arg Ser Glu Ser Leu
    1280                1285                1290

Arg Asn Thr Thr Glu Glu Leu Gln Ser Leu Ile Tyr Asn Ile Asn
    1295                1300                1305

Asn Thr Leu Val Asp Leu Glu Trp Leu Asn Arg Val Glu Thr Gly
    1310                1315                1320

Gly Tyr Ile Pro Glu Ala Pro Arg Asp Gly Gln Ala Tyr Val Arg
    1325                1330                1335

Lys Asp Gly Glu Trp Val Leu Leu Ser Thr Phe
    1340                1345

<210> SEQ ID NO 41
<211> LENGTH: 1160
<212> TYPE: PRT
<213> ORGANISM: Swine deltacoronovirus

<400> SEQUENCE: 41

Met Gln Arg Ala Leu Leu Ile Met Thr Leu Leu Cys Leu Ala Arg Ala
1               5                   10                  15

Lys Phe Ala Asp Asp Leu Leu Asp Leu Leu Thr Phe Pro Gly Ala His
                20                  25                  30

Arg Phe Leu His Lys Pro Thr Arg Asn Asp Ser Ile Leu Tyr Ser Arg
            35                  40                  45

Ala Asn Asn Asn Phe Asp Val Gly Val Leu Pro Gly Tyr Pro Thr Lys
        50                  55                  60

Asn Val Asn Leu Phe Ser Pro Leu Thr Asn Ser Thr Leu Pro Ile Asn
65                  70                  75                  80

Gly Leu His Arg Ser Tyr Gln Pro Leu Met Leu Asn Cys Leu Thr Lys
                85                  90                  95

Ile Thr Asn Gln Thr Leu Ser Met Tyr Leu Gln Pro Ser Glu Ile Gln
                100                 105                 110

Thr Tyr Ser Cys Gly Gly Ala Met Val Lys Tyr Gln Thr His Asp Ala
            115                 120                 125

Val Arg Ile Ile Leu Asp Leu Ile Ala Thr Asp Arg Ile Ser Val Glu
        130                 135                 140

Val Val Gly Gln Ala Gly Glu Asn Tyr Val Phe Val Cys Ser Asp Gln
145                 150                 155                 160

Phe Asn Tyr Thr Thr Ala Leu His Asn Ser Thr Phe Phe Ser Leu Asn
                165                 170                 175

Ser Gln Leu Tyr Cys Phe Thr Asn Asn Thr Tyr Leu Gly Ile Leu Pro
                180                 185                 190

Pro Asp Leu Thr Asp Phe Thr Val Tyr Arg Thr Gly Gln Phe Tyr Ala
            195                 200                 205

Asn Gly Tyr Leu Leu Gly Thr Leu Pro Ile Thr Val Asn Tyr Val Arg
        210                 215                 220
```

```
Leu Tyr Arg Gly Gln Leu Ser Ala Asn Ser Ala His Phe Ala Leu Ala
225                 230                 235                 240

Asn Leu Thr Asp Thr Leu Ile Thr Leu Thr Asn Thr Thr Ile Ser Gln
            245                 250                 255

Ile Thr Tyr Cys Asp Lys Ser Val Val Asp Ser Ile Ala Cys Gln Arg
                260                 265                 270

Ser Ser His Gln Val Glu Asp Gly Phe Tyr Ser Asp Pro Lys Ser Ala
            275                 280                 285

Val Arg Ala Arg Gln Arg Thr Ile Val Thr Leu Pro Lys Leu Pro Glu
290                 295                 300

Leu Glu Val Val Gln Leu Asn Ile Ser Ala His Met Asp Phe Gly Glu
305                 310                 315                 320

Ala Arg Leu Asp Ser Val Thr Ile Asn Gly Asn Thr Ser Tyr Cys Val
                325                 330                 335

Thr Lys Pro Tyr Phe Arg Leu Glu Thr Asn Phe Leu Cys Arg Gly Cys
            340                 345                 350

Thr Met Asn Leu Arg Thr Asp Thr Cys Ser Phe Asp Leu Ser Ala Val
            355                 360                 365

Asn Asn Gly Met Ser Phe Ser Gln Phe Cys Leu Ser Thr Glu Ser Gly
370                 375                 380

Ala Cys Glu Met Lys Ile Ile Val Thr Tyr Val Trp Asn Tyr Leu Leu
385                 390                 395                 400

Arg Gln Arg Leu Tyr Val Thr Ala Val Glu Gly Gln Thr His Thr Gly
                405                 410                 415

Thr Thr Ser Val His Ala Thr Asp Thr Ser Ser Val Ile Thr Asp Val
            420                 425                 430

Cys Thr Asp Tyr Thr Ile Tyr Gly Val Ser Gly Thr Gly Ile Ile Lys
            435                 440                 445

Pro Ser Asp Leu Leu His Asn Gly Ile Ala Phe Thr Ser Pro Thr
            450                 455                 460

Gly Glu Leu Tyr Ala Phe Lys Asn Ile Thr Thr Gly Lys Thr Leu Gln
465                 470                 475                 480

Val Leu Pro Cys Glu Thr Pro Ser Gln Leu Ile Val Ile Asn Asn Thr
                485                 490                 495

Val Val Gly Ala Ile Thr Ser Ser Asn Ser Thr Glu Asn Asn Arg Phe
            500                 505                 510

Thr Thr Thr Ile Val Thr Pro Thr Phe Phe Tyr Ser Thr Asn Ala Thr
            515                 520                 525

Thr Leu Asn Cys Thr Lys Pro Val Leu Ser Tyr Gly Pro Ile Ser Val
530                 535                 540

Cys Ser Asp Gly Ala Ile Ala Gly Thr Ser Thr Leu Gln Asn Thr Arg
545                 550                 555                 560

Pro Ser Ile Val Ser Leu Tyr Asp Gly Glu Ile Glu Ile Pro Ser Ala
            565                 570                 575

Phe Ser Leu Ser Val Gln Thr Glu Tyr Leu Gln Val Gln Ala Glu Gln
            580                 585                 590

Val Ile Val Asp Cys Pro Gln Tyr Val Cys Asn Gly Asn Ser Arg Cys
            595                 600                 605

Leu Gln Leu Leu Ala Gln Tyr Thr Ser Ala Cys Ser Asn Ile Glu Val
610                 615                 620

Ala Leu His Ser Ser Ala Gln Leu Asp Ser Arg Glu Ile Ile Ser Met
625                 630                 635                 640
```

-continued

Phe Lys Thr Ser Thr Gln Ser Leu Gln Leu Ala Asn Ile Thr Asn Phe
                    645                 650                 655

Lys Gly Asp Tyr Asn Phe Ser Ser Ile Leu Thr Ser Arg Val Gly Gly
            660                 665                 670

Arg Ser Ala Ile Glu Asp Leu Leu Phe Asn Lys Val Val Thr Ser Gly
            675                 680                 685

Leu Gly Thr Val Asp Gln Asp Tyr Lys Ser Cys Ser Arg Asn Met Ala
        690                 695                 700

Ile Ala Asp Leu Val Cys Ser Gln Tyr Tyr Asn Gly Ile Met Val Leu
705                 710                 715                 720

Pro Gly Val Val Asp Ala Glu Lys Met Ala Met Tyr Thr Gly Ser Leu
                725                 730                 735

Thr Gly Ala Met Val Phe Gly Gly Leu Thr Ala Ala Ala Ile Pro
            740                 745                 750

Phe Ala Thr Ala Val Gln Ala Arg Leu Asn Tyr Val Ala Leu Gln Thr
            755                 760                 765

Asn Val Leu Gln Glu Asn Gln Lys Ile Leu Ala Glu Ser Phe Asn Gln
    770                 775                 780

Ala Val Gly Asn Ile Ser Leu Ala Leu Ser Ser Val Asn Asp Ala Ile
785                 790                 795                 800

Gln Gln Thr Ser Glu Ala Leu Asn Thr Val Ala Ile Ala Ile Lys Lys
                805                 810                 815

Ile Gln Thr Val Val Asn Gln Gln Gly Glu Ala Leu Ser His Leu Thr
                820                 825                 830

Ala Gln Leu Ser Asn Asn Phe Gln Ala Ile Ser Thr Ser Ile Gln Asp
            835                 840                 845

Ile Tyr Asn Arg Leu Glu Glu Val Glu Ala Asn Gln Gln Val Asp Arg
    850                 855                 860

Leu Ile Asn Gly Arg Leu Ala Ala Leu Asn Ala Tyr Val Thr Gln Leu
865                 870                 875                 880

Leu Asn Gln Met Ser Gln Ile Arg Gln Ser Arg Leu Leu Ala Gln Gln
                885                 890                 895

Lys Ile Asn Glu Cys Val Lys Ser Gln Ser Pro Arg Tyr Gly Phe Cys
            900                 905                 910

Gly Asn Gly Thr His Ile Phe Ser Leu Thr Gln Thr Ala Pro Asn Gly
        915                 920                 925

Ile Phe Phe Met His Ala Val Leu Val Pro Asn Lys Phe Thr Arg Val
    930                 935                 940

Asn Ala Ser Ala Gly Ile Cys Val Asp Asn Thr Arg Gly Tyr Ser Leu
945                 950                 955                 960

Gln Pro Gln Leu Ile Leu Tyr Gln Phe Asn Asn Ser Trp Arg Val Thr
                965                 970                 975

Pro Arg Asn Met Tyr Glu Pro Arg Leu Pro Arg Gln Ala Asp Phe Ile
            980                 985                 990

Gln Leu Thr Asp Cys Ser Val Thr Phe Tyr Asn Thr Thr Ala Ala Asn
            995                 1000                1005

Leu Pro Asn Ile Ile Pro Asp Val Ile Asp Val Asn Gln Thr Val
        1010                1015                1020

Ser Asp Ile Ile Asp Asn Leu Pro Thr Ala Thr Pro Pro Gln Trp
    1025                1030                1035

Asp Val Gly Ile Tyr Asn Asn Thr Ile Leu Asn Leu Thr Val Glu
    1040                1045                1050

Ile Asn Asp Leu Gln Glu Arg Ser Lys Asn Leu Ser Gln Ile Ala

-continued

```
                1055                1060                1065

Asp Arg Leu Gln Asn Tyr Ile Asp Asn Leu Asn Thr Leu Val
            1070                1075                1080

Asp Leu Glu Trp Leu Asn Arg Val Glu Thr Tyr Leu Lys Trp Pro
        1085                1090                1095

Trp Tyr Ile Trp Leu Ala Ile Ala Leu Ala Leu Ile Ala Phe Val
    1100                1105                1110

Thr Ile Leu Ile Thr Ile Phe Leu Cys Thr Gly Cys Cys Gly Gly
        1115                1120                1125

Cys Phe Gly Cys Cys Gly Gly Cys Phe Gly Leu Phe Ser Lys Lys
        1130                1135                1140

Lys Arg Tyr Thr Asp Asp Gln Pro Thr Pro Ser Phe Lys Phe Lys
    1145                1150                1155

Glu Trp
    1160
```

<210> SEQ ID NO 42
<211> LENGTH: 1093
<212> TYPE: PRT
<213> ORGANISM: Artificial Sequence
<220> FEATURE:
<223> OTHER INFORMATION: recombinant coronavirus S protein

<400> SEQUENCE: 42

```
Met Gln Arg Ala Leu Leu Ile Met Thr Leu Leu Cys Leu Ala Arg Ala
1               5                   10                  15

Lys Phe Ala Asp Asp Leu Leu Asp Leu Leu Thr Phe Pro Gly Ala His
            20                  25                  30

Arg Phe Leu His Lys Pro Thr Arg Asn Asp Ser Ile Leu Tyr Ser Arg
        35                  40                  45

Ala Asn Asn Asn Phe Asp Val Gly Val Leu Pro Gly Tyr Pro Thr Lys
    50                  55                  60

Asn Val Asn Leu Phe Ser Pro Leu Thr Asn Ser Thr Leu Pro Ile Asn
65                  70                  75                  80

Gly Leu His Arg Ser Tyr Gln Pro Leu Met Leu Asn Cys Leu Thr Lys
                85                  90                  95

Ile Thr Asn Gln Thr Leu Ser Met Tyr Leu Gln Pro Ser Glu Ile Gln
            100                 105                 110

Thr Tyr Ser Cys Gly Gly Ala Met Val Lys Tyr Gln Thr His Asp Ala
        115                 120                 125

Val Arg Ile Ile Leu Asp Leu Ile Ala Thr Asp Arg Ile Ser Val Glu
    130                 135                 140

Val Val Gly Gln Ala Gly Glu Asn Tyr Val Phe Val Cys Ser Asp Gln
145                 150                 155                 160

Phe Asn Tyr Thr Thr Ala Leu His Asn Ser Thr Phe Phe Ser Leu Asn
                165                 170                 175

Ser Gln Leu Tyr Cys Phe Thr Asn Asn Thr Tyr Leu Gly Ile Leu Pro
            180                 185                 190

Pro Asp Leu Thr Asp Phe Thr Val Tyr Arg Thr Gly Gln Phe Tyr Ala
        195                 200                 205

Asn Gly Tyr Leu Leu Gly Thr Leu Pro Ile Thr Val Asn Tyr Val Arg
    210                 215                 220

Leu Tyr Arg Gly Gln Leu Ser Ala Asn Ser Ala His Phe Ala Leu Ala
225                 230                 235                 240

Asn Leu Thr Asp Thr Leu Ile Thr Leu Thr Asn Thr Thr Ile Ser Gln
```

```
                    245                 250                 255
Ile Thr Tyr Cys Asp Lys Ser Val Val Asp Ser Ile Ala Cys Gln Arg
                260                 265                 270

Ser Ser His Gln Val Glu Asp Gly Phe Tyr Ser Asp Pro Lys Ser Ala
            275                 280                 285

Val Arg Ala Arg Gln Arg Thr Ile Val Thr Leu Pro Lys Leu Pro Glu
        290                 295                 300

Leu Glu Val Val Gln Leu Asn Ile Ser Ala His Met Asp Phe Gly Glu
305                 310                 315                 320

Ala Arg Leu Asp Ser Val Thr Ile Asn Gly Asn Thr Ser Tyr Cys Val
                325                 330                 335

Thr Lys Pro Tyr Phe Arg Leu Glu Thr Asn Phe Leu Cys Arg Gly Cys
            340                 345                 350

Thr Met Asn Leu Arg Thr Asp Thr Cys Ser Phe Asp Leu Ser Ala Val
        355                 360                 365

Asn Asn Gly Met Ser Phe Ser Gln Phe Cys Leu Ser Thr Glu Ser Gly
370                 375                 380

Ala Cys Glu Met Lys Ile Ile Val Thr Tyr Val Trp Asn Tyr Leu Leu
385                 390                 395                 400

Arg Gln Arg Leu Tyr Val Thr Ala Val Glu Gly Gln Thr His Thr Gly
                405                 410                 415

Thr Thr Ser Val His Ala Thr Asp Thr Ser Ser Val Ile Thr Asp Val
            420                 425                 430

Cys Thr Asp Tyr Thr Ile Tyr Gly Val Ser Gly Thr Gly Ile Ile Lys
        435                 440                 445

Pro Ser Asp Leu Leu His Asn Gly Ile Ala Phe Thr Ser Pro Thr
450                 455                 460

Gly Glu Leu Tyr Ala Phe Lys Asn Ile Thr Thr Gly Lys Thr Leu Gln
465                 470                 475                 480

Val Leu Pro Cys Glu Thr Pro Ser Gln Leu Ile Val Ile Asn Asn Thr
                485                 490                 495

Val Val Gly Ala Ile Thr Ser Ser Asn Ser Thr Glu Asn Asn Arg Phe
            500                 505                 510

Thr Thr Thr Ile Val Thr Pro Thr Phe Phe Tyr Ser Thr Asn Ala Thr
        515                 520                 525

Thr Leu Asn Cys Thr Lys Pro Val Leu Ser Tyr Gly Pro Ile Ser Val
530                 535                 540

Cys Ser Asp Gly Ala Ile Ala Gly Thr Ser Thr Leu Gln Asn Thr Arg
545                 550                 555                 560

Pro Ser Ile Val Ser Leu Tyr Asp Gly Glu Ile Glu Ile Pro Ser Ala
                565                 570                 575

Phe Ser Leu Ser Val Gln Thr Glu Tyr Leu Gln Val Gln Ala Glu Gln
            580                 585                 590

Val Ile Val Asp Cys Pro Gln Tyr Val Cys Asn Gly Asn Ser Arg Cys
        595                 600                 605

Leu Gln Leu Leu Ala Gln Tyr Thr Ser Ala Cys Ser Asn Ile Glu Val
610                 615                 620

Ala Leu His Ser Ser Ala Gln Leu Asp Ser Arg Glu Ile Ile Ser Met
625                 630                 635                 640

Phe Lys Thr Ser Thr Gln Ser Leu Gln Leu Ala Asn Ile Thr Asn Phe
                645                 650                 655

Lys Gly Asp Tyr Asn Phe Ser Ser Ile Leu Thr Ser Arg Val Gly Gly
            660                 665                 670
```

```
Arg Ser Ala Ile Glu Asp Leu Leu Phe Asn Lys Val Thr Ser Gly
        675                 680                 685

Leu Gly Thr Val Asp Gln Asp Tyr Lys Ser Cys Ser Arg Asn Met Ala
    690                 695                 700

Ile Ala Asp Leu Val Cys Ser Gln Tyr Tyr Asn Gly Ile Met Val Leu
705                 710                 715                 720

Pro Gly Val Val Asp Ala Glu Lys Met Ala Met Tyr Thr Gly Ser Leu
                725                 730                 735

Thr Gly Ala Met Val Phe Gly Gly Leu Thr Ala Ala Ala Ile Pro
            740                 745                 750

Phe Ala Thr Ala Val Gln Ala Arg Leu Asn Tyr Val Ala Leu Gln Thr
                755                 760                 765

Asn Val Leu Gln Glu Asn Gln Lys Ile Leu Ala Glu Ser Phe Asn Gln
770                 775                 780

Ala Val Gly Asn Ile Ser Leu Ala Leu Ser Ser Val Asn Asp Ala Ile
785                 790                 795                 800

Gln Gln Thr Ser Glu Ala Leu Asn Thr Val Ala Ile Ala Ile Lys Lys
                805                 810                 815

Ile Gln Thr Val Val Asn Gln Gln Gly Glu Ala Leu Ser His Leu Thr
                820                 825                 830

Ala Gln Leu Ser Asn Asn Phe Gln Ala Ile Ser Thr Ser Ile Gln Asp
            835                 840                 845

Ile Tyr Asn Arg Leu Glu Pro Pro Glu Ala Asn Gln Gln Val Asp Arg
            850                 855                 860

Leu Ile Asn Gly Arg Leu Ala Ala Leu Asn Ala Tyr Val Thr Gln Leu
865                 870                 875                 880

Leu Asn Gln Met Ser Gln Ile Arg Gln Ser Arg Leu Leu Ala Gln Gln
                885                 890                 895

Lys Ile Asn Glu Cys Val Lys Ser Gln Ser Pro Arg Tyr Gly Phe Cys
            900                 905                 910

Gly Asn Gly Thr His Ile Phe Ser Leu Thr Gln Thr Ala Pro Asn Gly
        915                 920                 925

Ile Phe Phe Met His Ala Val Leu Val Pro Asn Lys Phe Thr Arg Val
    930                 935                 940

Asn Ala Ser Ala Gly Ile Cys Val Asp Asn Thr Arg Gly Tyr Ser Leu
945                 950                 955                 960

Gln Pro Gln Leu Ile Leu Tyr Gln Phe Asn Asn Ser Trp Arg Val Thr
                965                 970                 975

Pro Arg Asn Met Tyr Glu Pro Arg Leu Pro Arg Gln Ala Asp Phe Ile
            980                 985                 990

Gln Leu Thr Asp Cys Ser Val Thr  Phe Tyr Asn Thr Thr  Ala Ala Asn
        995                 1000                1005

Leu Pro Asn Ile Ile Pro Asp Val Ile Asp Val Asn  Gln Thr Val
    1010                1015                1020

Ser Asp Ile Ile Asp Asn Leu  Pro Thr Ala Thr Pro  Pro Gln Trp
    1025                1030                1035

Asp Val Gly Ile Tyr Asn Asn  Thr Ile Leu Asn Leu  Thr Val Glu
    1040                1045                1050

Ile Asn Asp Leu Gln Glu Arg  Ser Lys Asn Leu Ser  Gln Ile Ala
    1055                1060                1065

Asp Arg Leu Gln Asn Tyr Ile  Asp Asn Leu Asn Asn  Thr Leu Val
    1070                1075                1080
```

```
Asp Leu Glu Trp Leu Asn Arg Val Glu Thr
    1085                1090

<210> SEQ ID NO 43
<211> LENGTH: 1120
<212> TYPE: PRT
<213> ORGANISM: Artificial Sequence
<220> FEATURE:
<223> OTHER INFORMATION: recombinant coronavirus S protein

<400> SEQUENCE: 43

Met Gln Arg Ala Leu Leu Ile Met Thr Leu Leu Cys Leu Ala Arg Ala
1               5                   10                  15

Lys Phe Ala Asp Asp Leu Leu Asp Leu Leu Thr Phe Pro Gly Ala His
            20                  25                  30

Arg Phe Leu His Lys Pro Thr Arg Asn Asp Ser Ile Leu Tyr Ser Arg
        35                  40                  45

Ala Asn Asn Asn Phe Asp Val Gly Val Leu Pro Gly Tyr Pro Thr Lys
    50                  55                  60

Asn Val Asn Leu Phe Ser Pro Leu Thr Asn Ser Thr Leu Pro Ile Asn
65                  70                  75                  80

Gly Leu His Arg Ser Tyr Gln Pro Leu Met Leu Asn Cys Leu Thr Lys
                85                  90                  95

Ile Thr Asn Gln Thr Leu Ser Met Tyr Leu Gln Pro Ser Glu Ile Gln
            100                 105                 110

Thr Tyr Ser Cys Gly Gly Ala Met Val Lys Tyr Gln Thr His Asp Ala
        115                 120                 125

Val Arg Ile Ile Leu Asp Leu Ile Ala Thr Asp Arg Ile Ser Val Glu
    130                 135                 140

Val Val Gly Gln Ala Gly Glu Asn Tyr Val Phe Val Cys Ser Asp Gln
145                 150                 155                 160

Phe Asn Tyr Thr Thr Ala Leu His Asn Ser Thr Phe Phe Ser Leu Asn
                165                 170                 175

Ser Gln Leu Tyr Cys Phe Thr Asn Asn Thr Tyr Leu Gly Ile Leu Pro
            180                 185                 190

Pro Asp Leu Thr Asp Phe Thr Val Tyr Arg Thr Gly Gln Phe Tyr Ala
        195                 200                 205

Asn Gly Tyr Leu Leu Gly Thr Leu Pro Ile Thr Val Asn Tyr Val Arg
    210                 215                 220

Leu Tyr Arg Gly Gln Leu Ser Ala Asn Ser Ala His Phe Ala Leu Ala
225                 230                 235                 240

Asn Leu Thr Asp Thr Leu Ile Thr Leu Thr Asn Thr Thr Ile Ser Gln
                245                 250                 255

Ile Thr Tyr Cys Asp Lys Ser Val Val Asp Ser Ile Ala Cys Gln Arg
            260                 265                 270

Ser Ser His Gln Val Glu Asp Gly Phe Tyr Ser Asp Pro Lys Ser Ala
        275                 280                 285

Val Arg Ala Arg Gln Arg Thr Ile Val Thr Leu Pro Lys Leu Pro Glu
    290                 295                 300

Leu Glu Val Val Gln Leu Asn Ile Ser Ala His Met Asp Phe Gly Glu
305                 310                 315                 320

Ala Arg Leu Asp Ser Val Thr Ile Asn Gly Asn Thr Ser Tyr Cys Val
                325                 330                 335

Thr Lys Pro Tyr Phe Arg Leu Glu Thr Asn Phe Leu Cys Arg Gly Cys
            340                 345                 350
```

-continued

```
Thr Met Asn Leu Arg Thr Asp Thr Cys Ser Phe Asp Leu Ser Ala Val
            355                 360                 365

Asn Asn Gly Met Ser Phe Ser Gln Phe Cys Leu Ser Thr Glu Ser Gly
370                 375                 380

Ala Cys Glu Met Lys Ile Ile Val Thr Val Trp Asn Tyr Leu Leu
385                 390                 395                 400

Arg Gln Arg Leu Tyr Val Thr Ala Val Glu Gly Gln Thr His Thr Gly
                405                 410                 415

Thr Thr Ser Val His Ala Thr Asp Thr Ser Ser Val Ile Thr Asp Val
                420                 425                 430

Cys Thr Asp Tyr Thr Ile Tyr Gly Val Ser Gly Thr Gly Ile Ile Lys
            435                 440                 445

Pro Ser Asp Leu Leu Leu His Asn Gly Ile Ala Phe Thr Ser Pro Thr
            450                 455                 460

Gly Glu Leu Tyr Ala Phe Lys Asn Ile Thr Thr Gly Lys Thr Leu Gln
465                 470                 475                 480

Val Leu Pro Cys Glu Thr Pro Ser Gln Leu Ile Val Ile Asn Asn Thr
                485                 490                 495

Val Val Gly Ala Ile Thr Ser Ser Asn Ser Thr Glu Asn Asn Arg Phe
            500                 505                 510

Thr Thr Thr Ile Val Thr Pro Thr Phe Phe Tyr Ser Thr Asn Ala Thr
            515                 520                 525

Thr Leu Asn Cys Thr Lys Pro Val Leu Ser Tyr Gly Pro Ile Ser Val
            530                 535                 540

Cys Ser Asp Gly Ala Ile Ala Gly Thr Ser Thr Leu Gln Asn Thr Arg
545                 550                 555                 560

Pro Ser Ile Val Ser Leu Tyr Asp Gly Glu Ile Glu Ile Pro Ser Ala
                565                 570                 575

Phe Ser Leu Ser Val Gln Thr Glu Tyr Leu Gln Val Gln Ala Glu Gln
            580                 585                 590

Val Ile Val Asp Cys Pro Gln Tyr Val Cys Asn Gly Asn Ser Arg Cys
            595                 600                 605

Leu Gln Leu Leu Ala Gln Tyr Thr Ser Ala Cys Ser Asn Ile Glu Val
610                 615                 620

Ala Leu His Ser Ser Ala Gln Leu Asp Ser Arg Glu Ile Ile Ser Met
625                 630                 635                 640

Phe Lys Thr Ser Thr Gln Ser Leu Gln Leu Ala Asn Ile Thr Asn Phe
                645                 650                 655

Lys Gly Asp Tyr Asn Phe Ser Ser Ile Leu Thr Ser Arg Val Gly Gly
            660                 665                 670

Arg Ser Ala Ile Glu Asp Leu Leu Phe Asn Lys Val Val Thr Ser Gly
            675                 680                 685

Leu Gly Thr Val Asp Gln Asp Tyr Lys Ser Cys Ser Arg Asn Met Ala
690                 695                 700

Ile Ala Asp Leu Val Cys Ser Gln Tyr Tyr Asn Gly Ile Met Val Leu
705                 710                 715                 720

Pro Gly Val Val Asp Ala Glu Lys Met Ala Met Tyr Thr Gly Ser Leu
                725                 730                 735

Thr Gly Ala Met Val Phe Gly Gly Leu Thr Ala Ala Ala Ile Pro
            740                 745                 750

Phe Ala Thr Ala Val Gln Ala Arg Leu Asn Tyr Val Ala Leu Gln Thr
            755                 760                 765

Asn Val Leu Gln Glu Asn Gln Lys Ile Leu Ala Glu Ser Phe Asn Gln
```

```
            770             775             780
Ala Val Gly Asn Ile Ser Leu Ala Leu Ser Val Asn Asp Ala Ile
785             790             795             800

Gln Gln Thr Ser Glu Ala Leu Asn Thr Val Ala Ile Ala Ile Lys Lys
            805             810             815

Ile Gln Thr Val Val Asn Gln Gln Gly Glu Ala Leu Ser His Leu Thr
            820             825             830

Ala Gln Leu Ser Asn Asn Phe Gln Ala Ile Ser Thr Ser Ile Gln Asp
            835             840             845

Ile Tyr Asn Arg Leu Glu Pro Pro Glu Ala Asn Gln Gln Val Asp Arg
850             855             860

Leu Ile Asn Gly Arg Leu Ala Ala Leu Asn Ala Tyr Val Thr Gln Leu
865             870             875             880

Leu Asn Gln Met Ser Gln Ile Arg Gln Ser Arg Leu Leu Ala Gln Gln
            885             890             895

Lys Ile Asn Glu Cys Val Lys Ser Gln Ser Pro Arg Tyr Gly Phe Cys
            900             905             910

Gly Asn Gly Thr His Ile Phe Ser Leu Thr Gln Thr Ala Pro Asn Gly
            915             920             925

Ile Phe Phe Met His Ala Val Leu Val Pro Asn Lys Phe Thr Arg Val
            930             935             940

Asn Ala Ser Ala Gly Ile Cys Val Asp Asn Thr Arg Gly Tyr Ser Leu
945             950             955             960

Gln Pro Gln Leu Ile Leu Tyr Gln Phe Asn Asn Ser Trp Arg Val Thr
            965             970             975

Pro Arg Asn Met Tyr Glu Pro Arg Leu Pro Arg Gln Ala Asp Phe Ile
            980             985             990

Gln Leu Thr Asp Cys Ser Val Thr Phe Tyr Asn Thr Thr Ala Ala Asn
            995             1000            1005

Leu Pro Asn Ile Ile Pro Asp Val Ile Asp Val Asn Gln Thr Val
    1010            1015            1020

Ser Asp Ile Ile Asp Asn Leu Pro Thr Ala Thr Pro Pro Gln Trp
    1025            1030            1035

Asp Val Gly Ile Tyr Asn Asn Thr Ile Leu Asn Leu Thr Val Glu
    1040            1045            1050

Ile Asn Asp Leu Gln Glu Arg Ser Lys Asn Leu Ser Gln Ile Ala
    1055            1060            1065

Asp Arg Leu Gln Asn Tyr Ile Asp Asn Leu Asn Asn Thr Leu Val
    1070            1075            1080

Asp Leu Glu Trp Leu Asn Arg Val Glu Thr Gly Gly Tyr Ile Pro
    1085            1090            1095

Glu Ala Pro Arg Asp Gly Gln Ala Tyr Val Arg Lys Asp Gly Glu
    1100            1105            1110

Trp Val Leu Leu Ser Thr Phe
    1115            1120
```

PREFUSION CORONAVIRUS SPIKE PROTEINS AND THEIR USE

CROSS REFERENCE TO RELATED APPLICATIONS

This is a continuation of U.S. patent application Ser. No. 16/344,774, filed on Apr. 24, 2019, which is the U.S. National Stage of International Application No. PCT/US2017/058370, filed Oct. 25, 2017, which was published in English under PCT Article 21(2), which in turn claims the benefit of U.S. Provisional Application No. 62/412,703, filed Oct. 25, 2016. Each of the prior patent applications is herein incorporated by reference in its entirety.

FIELD OF THE DISCLOSURE

This disclosure relates to recombinant coronavirus spike (S) proteins, such as Middle East respiratory syndrome coronavirus (MERS-CoV) and severe acute respiratory syndrome coronavirus (SARS-CoV) S proteins, that are stabilized in a prefusion conformation by one or more amino acid substitutions, and their use as immunogens.

BACKGROUND

Coronaviruses are enveloped, positive-sense single-stranded RNA viruses. They have the largest genomes (26-32 kb) among known RNA viruses, and are phylogenetically divided into four genera (α, β, γ, δ), with betacoronaviruses further subdivided into four lineages (A, B, C, D). Coronaviruses infect a wide range of avian and mammalian species, including humans. Of the six known human coronaviruses, four of them (HCoV-OC43, HCoV-229E, HCoV-HKU1 and HCoV-NL63) circulate annually in humans and generally cause mild respiratory diseases, although severity can be greater in infants, elderly, and the immunocompromised. In contrast, the Middle East respiratory syndrome coronavirus (MERS-CoV) and the severe acute respiratory syndrome coronavirus (SARS-CoV), belonging to betacoronavirus lineages C and B, respectively, are highly pathogenic. Both viruses emerged into the human population from animal reservoirs within the last 15 years and caused outbreaks with high case-fatality rates.

MERS-CoV was isolated in 2012 from a patient in Saudi Arabia and is still circulating across the Arabian Peninsula. Primary transmission, most likely from camels, is now considered to be the most common route of transmission, and camels are thought to be a secondary or intermediate reservoir for MERS-CoV, with bats serving as the primary reservoir. Human-to-human transmission, especially as a result of close contact between patients and hospital workers within health care settings, is another important route of transmission, and was responsible for an outbreak of MERS-CoV in South Korea. The high pathogenicity and airborne transmissibility of SARS-CoV and MERS-CoV have raised concern about the potential for another coronavirus pandemic. The high case-fatality rate, vaguely defined epidemiology, and absence of prophylactic or therapeutic measures against coronaviruses have created an urgent need for an effective vaccine and related therapeutic agents.

SUMMARY

Disclosed herein are recombinant coronavirus S ectodomain trimers comprising protomers comprising one or more proline substitution(s) that stabilize the S protein trimer in the prefusion conformation. One class of mutation, comprising one or more (such as two) proline substitutions at or near the boundary between a Heptad Repeat 1 (HR1) and a central helix of the protomers of the coronavirus S ectodomain trimer was found to be surprisingly effective for stabilization of coronavirus S protein trimers in the prefusion conformation. Embodiments of such prefusion-stabilized coronavirus S ectodomain trimers are demonstrated to produce a superior immune response in an animal model compared to corresponding coronavirus S ectodomain trimers that are not stabilized in the prefusion conformation.

In some embodiments, an immunogen is provided that comprises a recombinant alphacoronavirus or betacoronavirus S ectodomain trimer comprising protomers comprising one or two proline substitutions at or near a junction between a heptad repeat 1 (HR1) and a central helix that stabilize the S ectodomain trimer in a prefusion conformation. The one or two proline substitutions can comprise two consecutive proline substitutions (a "double proline substitution"). In some embodiments, the recombinant alphacoronavirus or betacoronavirus S ectodomain trimer comprises S ectodomains from a NL63-CoV, 229E-CoV, OC43-CoV, SARS-CoV, MERS-CoV, HKU1-CoV, WIV1-CoV, mouse hepatitis virus (MHV), or HKU9-CoV, that comprise the one or two proline substitutions.

In some embodiments, the recombinant alphacoronavirus or betacoronavirus S ectodomain trimer comprises: a recombinant HKU1-CoV S ectodomain trimer, and the double proline substitution is between residues 1050 to 1070 of the protomers in the trimer (for example, N1067P and L1068P substitutions); a recombinant SARS-CoV S ectodomain trimer, and the double proline substitution is between residues 951 to 971 of the protomers in the trimer (for example, K968P and V969P substitutions); a recombinant MERS-CoV S ectodomain trimer, and the double proline substitution is between residues 1050 to 1069 of the protomers in the trimer (for example, V1060P and L1061P substitutions); a recombinant OC43-CoV S ectodomain trimer, and the double proline substitution is between residues 1062 to 1082 of the protomers in the trimer (for example, A1079P and L1080P substitutions); a recombinant HKU9-CoV S ectodomain trimer, and the double proline substitution is between residues 966 to 986 of the protomers in the trimer (for example, G1018P and L1019P substitutions); a recombinant NL63-CoV S ectodomain trimer, and the double proline substitution is between residues 1035 to 1055 of the protomers in the trimer (for example, S1052P and I1053P substitutions); a recombinant 229E-CoV S ectodomain trimer, and the double proline substitution is between residues 852 to 872 of the protomers in the trimer (for example, I869P and I870P substitutions); a recombinant WIV1-CoV S ectodomain trimer, and the double proline substitution is between residues 952 to 972 of the protomers in the trimer (for example, K969P and V970P substitutions); or a recombinant MHV S ectodomain trimer, and the double proline substitution is between residues 852 to 872 of the protomers in the trimer (for example, I869P and I870P substitutions).

In some embodiments, the protomers of the recombinant alphacoronavirus or betacoronavirus S ectodomain trimer further comprise one or more additional amino acid substitutions or deletions, such as amino acid substitutions that stabilize the recombinant alphacoronavirus or betacoronavirus S ectodomain trimer in the prefusion conformation, or amino acid substitutions to inhibit or prevent protease cleavage at a S1/S2 protease cleavage site and/or a S2' protease cleave site of the S ectodomain.

In some embodiments, the protomers of the recombinant alphacoronavirus or betacoronavirus S ectodomain trimer can be linked to a trimerization domain (such as T4 Fibritin trimerization domain) In additional embodiments, the protomers of the recombinant alphacoronavirus or betacoronavirus S ectodomain trimer can be linked to a transmembrane domain.

In additional embodiments, the recombinant coronavirus S ectodomain trimer can be included on a protein nanoparticle, such as a ferritin protein nanoparticle. Nucleic acid molecules encoding a protomer of the disclosed recombinant coronavirus S ectodomain trimers are also provided, as are vectors including the nucleic acid molecules, and methods of producing the disclosed coronavirus S ectodomain trimers.

Immunogenic compositions including the recombinant coronavirus S ectodomain trimer that are suitable for administration to a subject are also provided, and may also be contained in a unit dosage form. The compositions can further include an adjuvant. The recombinant coronavirus S ectodomain trimers may also be conjugated to a carrier to facilitate presentation to the immune system.

Methods of inducing an immune response in a subject are disclosed, as are methods of treating, inhibiting or preventing a coronavirus infection in a subject, by administering to the subject an effective amount of a disclosed recombinant coronavirus S ectodomain trimer, nucleic acid molecule, or vector.

The foregoing and other features and advantages of this disclosure will become more apparent from the following detailed description of several embodiments which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-1C illustrate the structure of the HKU1-CoV prefusion spike ectodomain. (1A) A single protomer of the trimeric S protein is shown in cartoon representation colored as a rainbow from the N to C terminus (blue to red) with the reconstructed EM density of remaining protomers shown in white and grey. (1B) The S1 subunit is composed of the N-terminal domain (NTD) and C-terminal domain (CTD) as well as two sub-domains (SD-1 and SD-2). The S2 subunit contains the coronavirus fusion machinery and is primarily α-helical. (1C) Domain architecture of the HKU1-CoV S protein colored as in (1A).

FIGS. 2A-2D Illustrate the Architecture of the HKU1-CoV S1 Subunit. (2A) EM Density corresponding to each S1 protomer is shown. The putative glycan-binding and protein-receptor-binding sites are indicated with dashed shapes on the NTD and CTD, respectively. (2B) The HKU1-CoV S1 CTD forms quaternary interactions with an adjacent CTD using a surface similar to that used by SARS-CoV CTD to bind its receptor, ACE2. (2C) SD-1 is composed of amino acid residues before and after the S1 CTD. (2D) SD-2 is composed of S1 sequence C-terminal to the CTD, a short peptide following the NTD, and the N-terminal strand of S2, which follows the S1/S2 furin-cleavage site.

FIGS. 3A-3C illustrate the HKU1-CoV S2 subunit fusion machinery. (3A) The HKU1-CoV S2 subunit is colored like a rainbow from the N-terminal β-strand (blue), which participates in S1 sub-domain 2, to the C terminus (red) before HR2. (3B) The HKU1-CoV S2 structure contains the fusion peptide (FP) and a HR1. Protease-recognition sites are indicated within disordered regions of the protein (dashed lines). (3C) A comparison of coronavirus S2 HR1 in the pre- and post-fusion conformations. Five HR1α-helices are labelled and colored like a rainbow from blue to red, N to C terminus, respectively. The structures are oriented to position similar portions of the central helix (red).

FIGS. 4A-4C illustrate stabilization of MERS-CoV S protein in a prefusion conformation by V1060P ("Top 3") and L1061P ("Top 4") amino acid substitutions. (4A) Location of various stabilization design conceptions. V1060P and L1061P (red circle) are located at the top of S2 HR1 and the S2 central helix. MERS-CoV S ectodomains with V1060P and L1061P mutations were expressed individually and in combination and purified. Protein expression levels and purity were determined by (4B) gel electrophoresis and (4C) size-exclusion chromatography.

FIGS. 5A-5B are a set of graphs showing results from neutralization assays using sera from mice immunized with the MERS-CoV S prefusion stabilized (2P) ectodomain trimer. Mice (N=5/group) were immunized with 0.1 μg of MERS-CoV wild-type S ectodomain trimer or MERS-CoV prefusion-stabilized S ectodomain trimer intramuscularly with Sigma Adjuvant System at weeks 0 and 3. Control mice were given PBS. Two weeks following the last immunization, serum was collected and tested for neutralizing antibodies against various MERS pseudovirus strains: England1, Florida USA2, Bisha1, Korea002, JordanN3, Buraidah1, and Indiana USA1. (FIG. 5A) Reciprocal serum $IC_{90}$ neutralizing activity against autologous MERS England1 pseudotyped lentivirus reporter plotted against vaccine dose. (FIG. 5B) Reciprocal serum $IC_{90}$ neutralizing activity against multiple homologous MERS-CoV pseudoviruses of sera from mice immunized with 0.1 μg of purified MERS-CoV S ectodomain trimer. For both panels, the geometric mean $IC_{90}$ titer (GMT) of each group is represented by (FIG. 5A) symbols or (FIG. 5B) bars. Error bars represent geometric SDs. P values denoted as *$P<0.05$ and **$P<0.01$. The limit of detection for the assay is represented by dotted lines; for sera below the limit of detection a reciprocal $IC_{90}$ titer of 10 was assigned.

FIGS. 6A and 6B shows results from the dissection of binding and neutralizing antibodies elicited by MERS S-2P. Serum from mice immunized with (A) MERS S1, (B) MERS S WT ectodomain trimer, and MERS S-2P ectodomain trimer were depleted of MERS RBD, MERS S1, and MERS S-2P ectodomain trimer specific antibodies by magnetic bead depletion. The resulting depleted serum was then tested for (FIG. 6A) MERS S-2P ectodomain trimer specific antibodies by ELISA or (FIG. 6B) neutralizing antibodies against MERS England1 pseudovirus. For the binding assays, endpoint ELISA titers were determined, and % binding retained was calculated as a measure of endpoint titers for each serum depleted with MERS protein compared to binding after depletion with a nonspecific protein. For the neutralization assays, IC50 titers were determined, and % neutralization retained was calculated as a measure of neutralization each serum depleted with MERS protein compared to binding after depletion with a nonspecific protein. Bars represent the mean of each group; error bars represent SD.

Figure 9C:
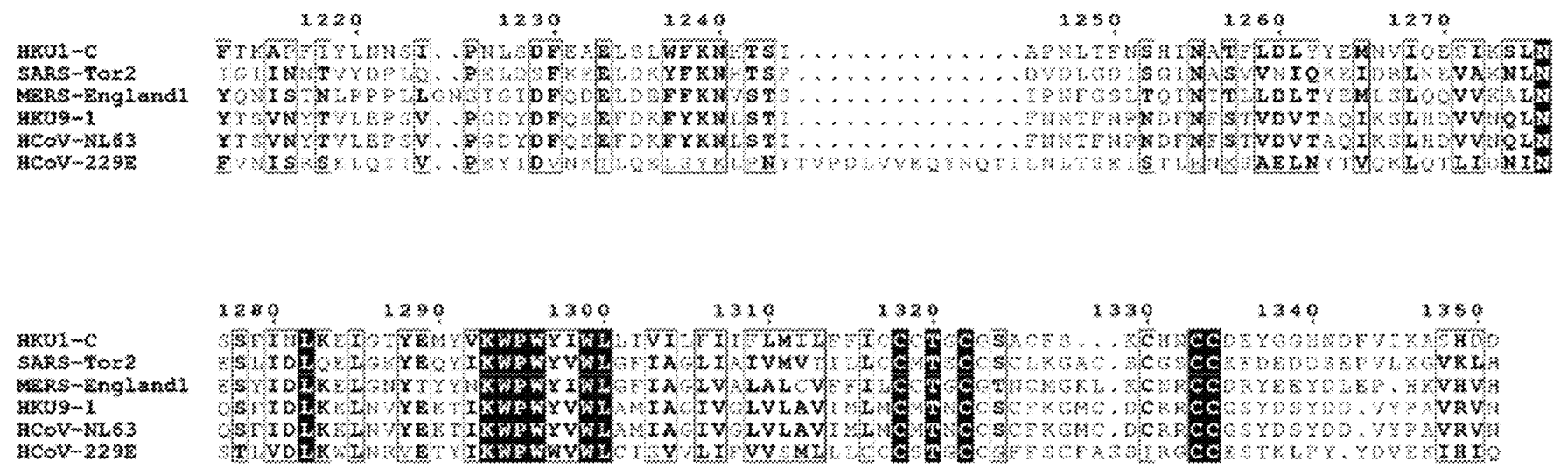

FIGS. 9A-9C show a sequence alignment of the S2 subunit of the HKU1-CoV (SEQ ID NO: 8), SARS-CoV (SEQ ID NO: 6), MERS-CoV (SEQ ID NO: 1), HKU9-CoV (SEQ ID NO: 12), NL63-CoV (SEQ ID NO: 18), and 229E-CoV (SEQ ID NO: 20) S proteins, showing relevant sequence homology.

FIG. 11 shows a Coomassie-stained polyacrylamide gel illustrating that the SARS-CoV S ectodomain with K968P and V969P substitutions (SARS-S-2P) has higher thermal stability than corresponding SARS-CoV S ectodomain having native sequence (SARS-S-WT).

FIG. 12 shows a set of graphs illustrating gel chromatography results of purified SARS-CoV, MERS-CoV, and HKU1-CoV S ectodomains having native (S-WT) sequence or double proline substitutions noted above (S-2P).

FIGS. 14A-14G show low-resolution negative-stain reconstructions of S trimer constructs from (14A) HKU1-CoV S 2P ectodomain trimer, (14B) MERS-CoV S 2P ectodomain trimer, (14C) SARS-CoV S 2P ectodomain trimer, (14D) OC43 S-2P ectodomain trimer, (14E) WIV1-CoV S 2P ectodomain trimer, (14F) PEDV-CoV S 2P ectodomain trimer, and (14G) 229E-CoV S 2P ectodomain trimer that were obtained from the negative-stain electron microscopy data shown in FIG. 13. The particles all formed homogeneous trimeric spike protein structures.

FIG. 15 is a graph showing results of immunogenicity assays of HKU1-CoV S 2P ectodomain trimer and SARS S-2P ectodomain trimer in mice. Reciprocal serum $IC_{90}$ neutralizing activity against autologous pseudotyped lentivirus reporter (SARS Urbani for the SARS immunization) plotted against vaccine dose. The geometric mean $IC_{90}$ titer (GMT) of each group is represented by symbols. Error bars represent geometric SDs. The limit of detection for the assay is represented by dotted lines; for sera below the limit of detection a reciprocal $IC_{90}$ titer of 10 was assigned.

SEQUENCE LISTING

Figure 5B:
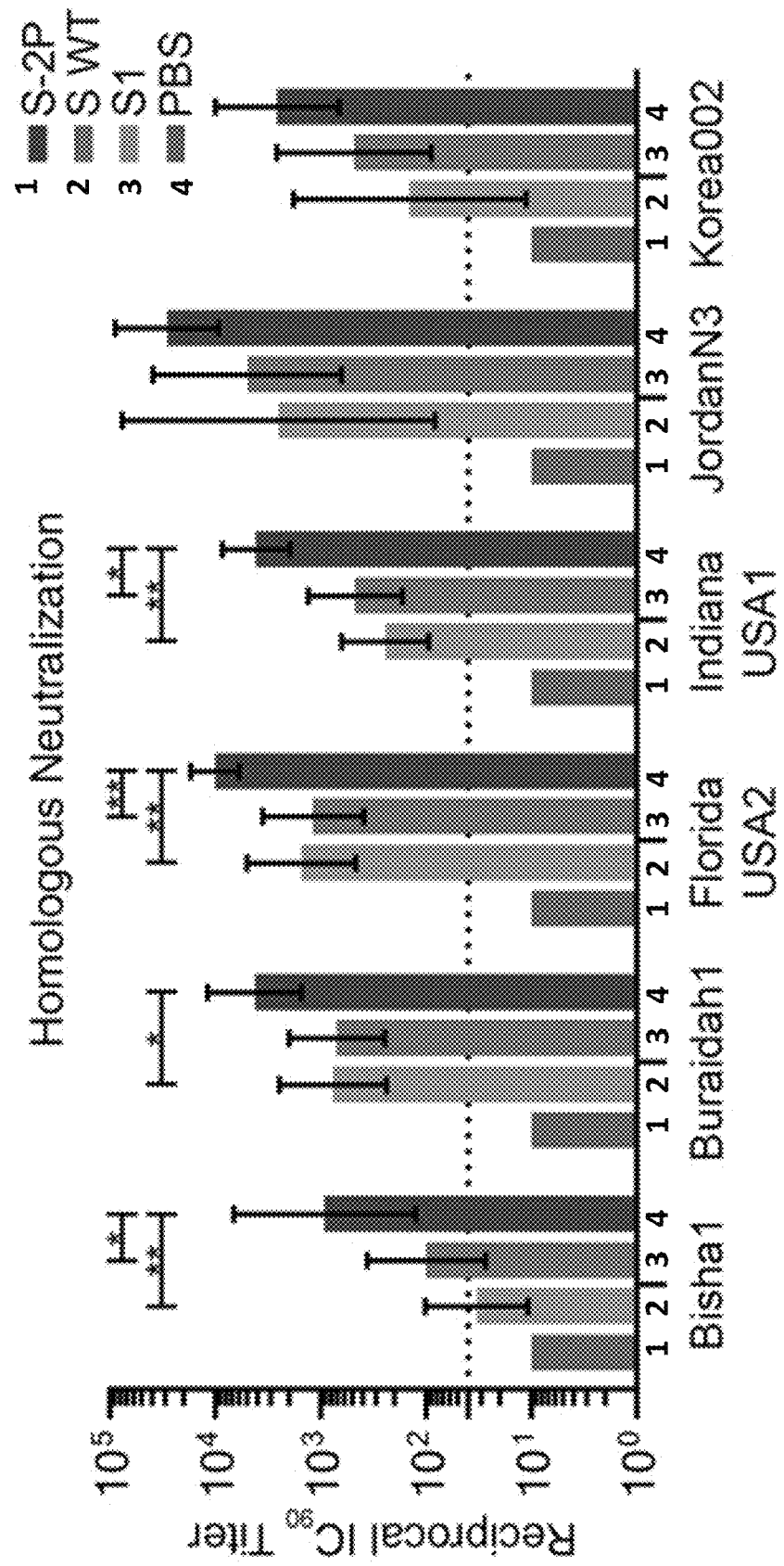

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~404 kb), which was created on Jan. 8, 2021, and which is incorporated by reference herein.

DETAILED DESCRIPTION

Past efforts to develop coronavirus vaccines have used whole-inactivated virus, live-attenuated virus, recombinant protein subunit, or genetic approaches (Graham et al., Nature reviews. Microbiology 11, 836, 2013). This disclosure provides CoV Spike glycoprotein (S) ectodomain trimers that are stabilized in the prefusion conformation and which are shown to elicit a neutralizing immune response in animal models.

I. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. In some embodiments, an adjuvant can include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). In some embodiments, the adjuvant used in a disclosed immunogenic composition is a combination of lecithin and carbomer homopolymer (such as the ADJUPLEX™ adjuvant available from Advanced BioAdjuvants, LLC, see also Wegmann, Clin Vaccine Immunol, 22(9): 1004-1012, 2015). Additional adjuvants for use in the disclosed immunogenic compositions include the QS21 purified plant extract, Matrix M, ASO1, MF59, and ALFQ adjuvants Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL and toll-like receptor (TLR) agonists, such as TLR-9 agonists. Additional description of adjuvants can be found, for example, in Singh (ed.) Vaccine Adjuvants and Delivery Systems. Wiley-Interscience, 2007). Adjuvants can be used in combination with the disclosed immunogens.

Administration: The introduction of an agent, such as a disclosed immunogen, into a subject by a chosen route. Administration can be local or systemic. For example, if the chosen route is intranasal, the agent (such as an immunogen comprising a recombinant coronavirus S ectodomain trimer stabilized in a prefusion conformation) is administered by introducing the composition into the nasal passages of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in a polypeptide with a different amino acid.

Antibody: An immunoglobulin, antigen-binding fragment, or derivative thereof, that specifically binds and recognizes an analyte (antigen) such as a coronavirus S protein, an antigenic fragment thereof, or a dimer or multimer of the antigen. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010). Carrier: An immunogenic molecule to which an antigen can be linked. When linked to a carrier, the antigen may become more immunogenic. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached.

Cavity-filling amino acid substitution: An amino acid substitution that fills a cavity within the protein core of a protein, such as a coronavirus S protein ectodomain Cavities are essentially voids within a folded protein where amino acids or amino acid side chains are not present. In several embodiments, a cavity-filling amino acid substitution is introduced to fill a cavity present in the prefusion conformation of a coronavirus S ectodomain core that collapses (e.g., has reduced volume) after transition to the postfusion conformation.

Conservative variants: "Conservative" amino acid substitutions are those substitutions that do not substantially affect or decrease a function of a protein, such as the ability of the protein to induce an immune response when administered to a subject. The term conservative variation also includes the use of a substituted amino acid in place of an unsubstituted parent amino acid. Furthermore, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the recombinant coronavirus S ectodomain trimer, such as the ability to induce an immune response when administered to a subject. For instance, if an amino acid residue is essential for a function of the protein, even an otherwise conservative substitution may disrupt that activity. Thus, a conservative substitution does not alter the basic function of a protein of interest.

Control: A reference standard. In some embodiments, the control is a negative control sample obtained from a healthy patient. In other embodiments, the control is a positive control sample obtained from a patient diagnosed with a coronavirus infection, such as MERS-CoV or SARS-CoV. In still other embodiments, the control is a historical control or standard reference value or range of values (such as a previously tested control sample, such as a group of patients infected with a coronavirus with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Coronavirus: A family of positive-sense, single-stranded RNA viruses that are known to cause severe respiratory illness. Viruses currently known to infect human from the coronavirus family are from the alphacoronavirus and beta-coronavirus genera. Additionally, it is believed that the gammacoronavirus and deltacoronavirus genera may infect humans in the future.

Non-limiting examples of betacoronaviruses include Middle East respiratory syndrome coronavirus (MERS-CoV), Severe Acute Respiratory Syndrome coronavirus (SARS-CoV), Human coronavirus HKU1 (HKU1-CoV), Human coronavirus OC43 (OC43-CoV), Murine Hepatitis Virus (MHV-CoV), Bat SARS-like coronavirus WIV1 (WIV1-CoV), and Human coronavirus HKU9 (HKU9-CoV). Non-limiting examples of alphacoronaviruses include human coronavirus 229E (229E-CoV), human coronavirus NL63 (NL63-CoV), porcine epidemic diarrhea virus (PEDV), and Transmissible gastroenteritis coronavirus (TGEV). A non-limiting example of a deltacoronaviruses is the Swine Delta Coronavirus (SDCV). Exemplary sequences of the ectodomains of S proteins from these viruses are provided herein.

The viral genome is capped, polyadenylated, and covered with nucleocapsid proteins. The coronavirus virion includes a viral envelope containing type I fusion glycoproteins referred to as the spike (S) protein. Most coronaviruses have a common genome organization with the replicase gene included in the 5'-portion of the genome, and structural genes included in the 3'-portion of the genome.

Coronavirus Spike (S) protein: A class I fusion glycoprotein initially synthesized as a precursor protein. Individual precursor S polypeptides form a homotrimer and undergo glycosylation within the Golgi apparatus as well as processing to remove the signal peptide, and cleavage by a cellular protease to generate separate S1 and S2 polypeptide chains, which remain associated as S1/S2 protomers within the homotrimer and is therefore a trimer of heterodimers. The S1 subunit is distal to the virus membrane and contains the receptor-binding domain (RBD) that mediates virus attachment to its host receptor. The S2 subunit contains fusion protein machinery, such as the fusion peptide, two heptad-repeat sequences (HR1 and HR2) and a central helix typical of fusion glycoproteins, a transmembrane domain, and the cytosolic tail domain.

Coronavirus Spike (S) protein prefusion conformation: A structural conformation adopted by the ectodomain of the coronavirus S protein following processing into a mature coronavirus S protein in the secretory system, and prior to triggering of the fusogenic event that leads to transition of coronavirus S to the postfusion conformation. The three-dimensional structure of an exemplary coronavirus S protein (HKU1-CoV) in a prefusion conformation is disclosed herein (see Example 1) and provided in Kirchdoerfer et al., "Pre-fusion structure of a human coronavirus spike protein," Nature, 531: 118-121, 2016 (incorporated by reference herein).

A coronavirus S ectodomain trimer "stabilized in a prefusion conformation" comprises one or more amino acid substitutions, deletions, or insertions compared to a native coronavirus S sequence that provide for increased retention of the prefusion conformation compared to coronavirus S ectodomain trimers formed from a corresponding native coronavirus S sequence. The "stabilization" of the prefusion conformation by the one or more amino acid substitutions, deletions, or insertions can be, for example, energetic stabilization (for example, reducing the energy of the prefusion conformation relative to the post-fusion open conformation) and/or kinetic stabilization (for example, reducing the rate of transition from the prefusion conformation to the postfusion conformation). Additionally, stabilization of the coronavirus S ectodomain trimer in the prefusion conformation can include an increase in resistance to denaturation compared to a corresponding native coronavirus S sequence. Methods of determining if a coronavirus S ectodomain trimer is in the prefusion conformation are provided herein, and include (but are not limited to) negative-stain electron microscopy and antibody binding assays using a prefusion-conformation-specific antibody.

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Effective amount: An amount of agent, such as an immunogen, that is sufficient to elicit a desired response, such as an immune response in a subject. It is understood that to obtain a protective immune response against an antigen of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to elicit a protective immune response.

In one example, a desired response is to inhibit or reduce or prevent CoV (such as MERS-CoV) infection. The CoV infection does not need to be completely eliminated or reduced or prevented for the method to be effective. For example, administration of an effective amount of the immunogen can induce an immune response that decreases the CoV infection (for example, as measured by infection of cells, or by number or percentage of subjects infected by the CoV) by a desired amount, for example by at least 50%, at least 60%, at least 70%, at least 80%, at least 90%, at least 95%, at least 98%, or even at least 100% (elimination or prevention of detectable CoV infection), as compared to a suitable control.

Epitope: An antigenic determinant. These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on coronavirus S ectodomain, such as a MERS-CoV S ectodomain Epitopes can be formed both from contiguous amino acids or noncontiguous amino acids juxtaposed by tertiary folding of a protein.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., Methods in Enzymology 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Glycosylation site: An amino acid sequence on the surface of a polypeptide, such as a protein, which accommodates the attachment of a glycan. An N-linked glycosylation site is triplet sequence of NX(S/T) in which N is asparagine, X is any residues except proline, and (S/T) is a serine or threonine residue. A glycan is a polysaccharide or oligosaccharide. Glycan may also be used to refer to the carbohydrate portion of a glycoconjugate, such as a glycoprotein, glycolipid, or a proteoglycan.

Heterologous: Originating from a different genetic source. A nucleic acid molecule that is heterologous to a cell originated from a genetic source other than the cell in which it is expressed. In one specific, non-limiting example, a heterologous nucleic acid molecule encoding a recombinant coronavirus S ectodomain is expressed in a cell, such as a mammalian cell. Methods for introducing a heterologous nucleic acid molecule in a cell or organism are well known in the art, for example transformation with a nucleic acid, including electroporation, lipofection, particle gun acceleration, and homologous recombination.

Ferritin: A protein that stores iron and releases it in a controlled fashion. The protein is produced by almost all living organisms. Ferritin polypeptides assemble into a globular protein complex of 24 protein subunits, and each of the 24 subunits includes a single ferritin polypeptide. In some examples, ferritin is used to form a nanoparticle presenting antigens on its surface, for example, a coronavirus S ectodomain trimer.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogen: A compound, composition, or substance (for example, a recombinant coronavirus S ectodomain trimer) that can elicit an immune response in an animal, including compositions that are injected or absorbed into an animal Administration of an immunogen to a subject can lead to protective immunity against a pathogen of interest.

Immunogenic composition: A composition comprising a disclosed recombinant coronavirus S ectodomain trimer that induces a measurable CTL response against the coronavirus, or induces a measurable B cell response (such as production of antibodies) against the coronavirus, when administered to a subject. It further refers to isolated nucleic acid molecules and vectors encoding a protomer of a disclosed recombinant coronavirus S ectodomain trimer that can be used to express the protomer (and thus be used to elicit an immune response against recombinant coronavirus S ectodomain trimer). For in vivo use, the immunogenic composition will typically include the recombinant coronavirus S ectodomain trimer or a nucleic acid molecule encoding a protomer of the recombinant coronavirus S ectodomain trimer in a pharmaceutically acceptable carrier and may also include other agents, such as an adjuvant.

Inhibiting or treating a disease: Inhibiting the full development of a disease or condition, for example, in a subject who is at risk for a disease such as a CoV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. Inhibiting a disease can include preventing or reducing the risk of the disease, such as preventing or reducing the risk of viral infection. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linker and Linked: A bi-functional molecule that can be used to link two molecules into one contiguous molecule. Non-limiting examples of peptide linkers include glycine-serine peptide linkers. Unless context indicates otherwise, reference to "linking" a first polypeptide and a second polypeptide, or to two polypeptides "linked" together, or to a first polypeptide having a "linkage" to a second polypeptide, refers to covalent linkage by peptide bond (for example via a peptide linker) such that the first and second polypeptides form a contiguous polypeptide chain. If a peptide linker is involved, the covalent linkage of the first and second polypeptides can be to the N- and C-termini of the peptide linker. Typically, such linkage is accomplished using molecular biology techniques to genetically manipulate DNA encoding the first polypeptide linked to the second polypeptide by the peptide linker.

Native protein, sequence, or disulfide bond: A polypeptide, sequence or disulfide bond that has not been modified, for example, by selective mutation. For example, selective mutation to focus the antigenicity of the antigen to a target epitope, or to introduce a disulfide bond into a protein that does not occur in the native protein. Native protein or native sequence are also referred to as wild-type protein or wild-type sequence. A non-native disulfide bond is a disulfide bond that is not present in a native protein, for example, a disulfide bond that forms in a protein due to introduction of one or more cysteine residues into the protein by genetic engineering.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as immunogenic compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Prime-boost vaccination: An immunotherapy including administration of a first immunogenic composition (the primary vaccine) followed by administration of a second immunogenic composition (the booster vaccine) to a subject to induce an immune response. The priming vaccine and/or the booster vaccine include a vector (such as a viral vector, RNA, or DNA vector) expressing the antigen to which the immune response is directed. The booster vaccine is administered to the subject after the priming vaccine; a suitable time interval between administration of the priming vaccine and the booster vaccine, and examples of such timeframes are disclosed herein. In some embodiments, the priming vaccine, the booster vaccine, or both primer vaccine and the booster vaccine additionally include an adjuvant. In one non-limiting example, the priming vaccine is a DNA-based vaccine (or other vaccine based on gene delivery), and the booster vaccine is a protein subunit or protein nanoparticle based vaccine.

Protein nanoparticle: A multi-subunit, self-assembling, protein-based polyhedron shaped structure. The subunits are each composed of proteins (for example a glycosylated polypeptide), and, optionally of single or multiple features of the following: nucleic acids, prosthetic groups, organic and inorganic compounds. In some embodiments, protomers of the disclosed trimeric spike proteins can be fused to the subunits of the protein nanoparticles to provide multiple copies of the trimeric spike on each protein nanoparticle. Non-limiting examples of protein nanoparticles include ferritin nanoparticles (see, e.g., Zhang, Y. Int. J. Mol. Sci., 12:5406-5421, 2011, incorporated by reference herein), encapsulin nanoparticles (see, e.g., Sutter et al., Nature Struct. and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., *J. Mol. Biol.,* 306: 1099-1114, 2001), and pyruvate dehydrogenase nanoparticles (see, e.g., Izard et al., PNAS 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. Additional protein nanoparticle structures are described by Heinze et al., J Phys Chem B., 120(26):5945-52, 2016; Hsia et al., Nature, 535 (7610):136-9, 2016; and King et al., Nature, 510(7503):103-8, 2014; each of which is incorporated by reference herein.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant virus is one that includes a genome that includes a recombinant nucleic acid molecule. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, CABIOS 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Homologs and variants of a polypeptide (such as a coronavirus S ectodomain) are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" or similar language refers to "at least 90%, at least 91%, at least 92%, at least 93%, at least 94%, at least 95%, at least 96%, at least 97%, at least 98%, at least 99%, or even 100% identity" to a specified reference sequence.

Signal Peptide: A short amino acid sequence (e.g., approximately 10-35 amino acids in length) that directs newly synthesized secretory or membrane proteins to and through membranes (for example, the endoplasmic reticulum membrane). Signal peptides are typically located at the N-terminus of a polypeptide and are removed by signal peptidases. Signal peptide sequences typically contain three common structural features: an N-terminal polar basic region (n-region), a hydrophobic core, and a hydrophilic c-region).

Single chain coronavirus S ectodomain: A recombinant coronavirus S ectodomain including the coronavirus S1 and S2 proteins in a single contiguous polypeptide chain. Single chain coronavirus S ectodomain can trimerize to form a coronavirus S ectodomain trimer. A single coronavirus S ectodomain includes mutations to prevent protease cleavage at the $S_1/S_2$ cleavage site and the S2' cleavage site in the S ectodomain Therefore, when produced in cells, the S polypeptide is not cleaved into separate S1 and S2 polypeptide chains.

Soluble protein: A protein capable of dissolving in aqueous liquid at room temperature and remaining dissolved. The solubility of a protein may change depending on the concentration of the protein in the water-based liquid, the buffering condition of the liquid, the concentration of other solutes in the liquid, for example salt and protein concentrations, and the heat of the liquid. In several embodiments, a soluble protein is one that dissolves to a concentration of at least 0.5 mg/ml in phosphate buffered saline (pH 7.4) at room temperature and remains dissolved for at least 48 hours.

Subject: Living multi-cellular vertebrate organisms, a category that includes human and non-human mammals, such as non-human primates, pigs, camels, bats, sheep, cows, dogs, cats, rodents, and the like. In an example, a subject is a human. In a particular example, the subject is a camel or a bat. The subject can be a domestic animal (such as a dog or a cat) or a farm animal (such as a cow or a pig). In an additional example, a subject is selected that is in need of inhibiting of a coronavirus infection, such as a SARS-CoV or MERS-CoV infection. For example, the subject is either uninfected and at risk of the coronavirus infection or is infected and in need of treatment.

T4 Fibritin trimerization domain: Also referred to as a "foldon" domain, the T4 Fibritin trimerization domain comprises an amino acid sequence that naturally forms a trimeric structure. In some examples, a T4 Fibritin trimerization domain can be linked to the C-terminus of a disclosed recombinant coronavirus S protein ectodomain. In one example, a T4 Fibritin trimerization domain comprises the amino acid sequence set forth as (GYIPEAPRDGQAYVRKDGEWVLLSTF (SEQ ID NO: 22). In some embodiments, a protease cleavage site (such as a thrombin cleavage site) can be included between the C-terminus of the recombinant coronavirus ectodomain and the T4 Fibritin trimerization domain to facilitate removal of the trimerization domain as needed, for example, following expression and purification of the recombinant coronavirus S ectodomain.

Transmembrane domain: An amino acid sequence that inserts into a lipid bilayer, such as the lipid bilayer of a cell or virus or virus-like particle. A transmembrane domain can be used to anchor an antigen to a membrane. In some examples a transmembrane domain is a coronavirus S transmembrane domain, such as a MERS-CoV or SARS-CoV S transmembrane domain.

Vaccine: A pharmaceutical composition that induces a prophylactic or therapeutic immune response in a subject. In some cases, the immune response is a protective immune response. Typically, a vaccine induces an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In a non-limiting example, a vaccine induces an immune response that reduces the severity of the symptoms associated with a coronavirus infection (such as a SARS-CoV or MERS-CoV infection) and/or decreases the viral load compared to a control. In another non-limiting example, a vaccine induces an immune response that reduces and/or prevents a coronavirus infection (such as a SARS-CoV or MERS-CoV infection) compared to a control.

Vector: An entity containing a DNA or RNA molecule bearing a promoter(s) that is operationally linked to the coding sequence of an antigen(s) of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses.

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60:1445-1456; and Hagensee et al. (1994) J. Virol. 68:4503-4505; Vincente, *J Invertebr Pathol.*, 2011; Schneider-Ohrum and Ross, *Curr. Top. Microbiol. Immunol.*, 354: 53073, 2012).

II. Immunogens

Disclosed herein are recombinant coronavirus (such as alphacoronavirus or betacoronavirus) S ectodomain trimers comprising protomers comprising one or more proline substitution(s). The proline substitutions inhibit a conformational change in the S protein from the prefusion conformation to the postfusion conformation, and therefore stabilize the S ectodomain trimer in the prefusion conformation. In some embodiments, the recombinant coronavirus (such as alphacoronavirus or betacoronavirus) S ectodomain trimer comprises protomers comprising one or more (such as two) proline substitutions at or near the boundary between a HR1 domain and a central helix domain of the protomers. In some embodiments, the one or more (such as two, for example two consecutive) proline substitutions that stabilize the protomers of the S ectodomain in the prefusion conformation are located between a position 15 amino acids N-terminal of a C-terminal residue of the HR1 and a position 5 amino acids C-terminal of a N-terminal residue of the central helix. Exemplary embodiments are shown to produce a superior immune response in an animal model compared to corresponding coronavirus S ectodomain trimers that are not stabilized in the prefusion conformation.

In some embodiments, the recombinant S ectodomain trimer comprises recombinant S ectodomain protomers from an alphacoronavirus, such as NL63-CoV or 229E-CoV, that have been mutated to include the one or more proline substitutions for stabilization in the prefusion conformation. In some embodiments, the recombinant S ectodomain trimers comprise S ectodomain protomers from a betacoronavirus, such as OC43-CoV, SARS-CoV, MERS-CoV, HKU1-CoV, WIV1-CoV, mouse hepatitis virus (MHV), or HKU9-CoV, that have been mutated to include the one or more proline substitutions for stabilization in the prefusion conformation. Additional description is provided below.

A. MERS-CoV

In some embodiments, the immunogen comprises a recombinant MERS-CoV S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions that stabilize the MERS-CoV S ectodomain trimer in the prefusion conformation are located between residues 1050 to 1069 (such as between residues 1053 to 1063, or between residues 1058 to 1063) of the S ectodomain protomers in the trimer. In some embodiments, the MERS-CoV S ectodomain trimer is stabilized in the prefusion conformation by one or two of: L1058P, D1059P, V1060P, and L1061P substitutions in the S ectodomain protomers in the trimer. In some embodiments, the MERS-CoV S ectodomain trimer is stabilized in the prefusion conformation by V1060P and L1061P substitutions ("2P") in the S ectodomain protomers in the trimer. The amino acid numbering for MERS-CoV S proteins is with reference to the MERS-CoV S sequence provided as SEQ ID NO: 1.

In some embodiments, the recombinant MERS-CoV S ectodomain trimer stabilized in the prefusion conformation comprises protomers of single-chain S ectodomains comprising mutations to the S1/S2 and/or S2' protease cleavage sites to prevent protease cleavage at these sites. Non-limiting examples of such mutations include 748-RSVR-751 (residues 748-751 of SEQ ID NO: 1) to 748-ASVG-751 (residues 748-751 of SEQ ID NO: 3) substitutions to inhibit cleavage at the S1/S2 cleavage site, and 884-RSAR-887 (residues 884-887 of SEQ ID NO: 1) to 884-GSAG-887 (residues 884-887 of SEQ ID NO: 3) substitutions to inhibit cleavage at the S2' site.

In some embodiments, the recombinant MERS-CoV S ectodomain trimer comprising protomers stabilized in the prefusion conformation by the one or more proline substitutions (such as V1060P and L1061P substitutions) comprises additional modifications for stabilization in the prefusion conformation. In some embodiments, the recombinant MERS-CoV S ectodomain trimer comprising protomers stabilized in the prefusion conformation by the one or more proline substitutions (such as V1060P and L1061P substitutions) further comprises cavity filling substitutions to stabilize the S ectodomain the prefusion conformation, such as one of: N1072F and A1083I; N1072F and L1086F; N1072F and V1087I; N1072F and E1090I; T1076F and A1083I; T1076F and L1086F; T1076F and V1087I; T1076F and E1090I; T1076I and A1083I; T1076I and L1086F; T1076I and V1087I; T1076I and E1090I; A1018V; or A1018I.

In some embodiments, the recombinant MERS-CoV S ectodomain trimer stabilized in the prefusion conformation by the one or more proline substitutions (such as V1060P and L1061P substitutions) further comprises a repacking substitution to stabilize the S ectodomain the prefusion conformation, such as one of: E793M and K1102F; E793M, K1102F, and H1138F; D1068M and R1069W; A1083L; A1083L and V1087I; A1083L, V1087, and E1090L; A834L and Q1084M; Q1066M; S454F; R921W; S612F and G1052F; or P476V, T477A, and R1057W.

In some embodiments, the recombinant MERS-CoV S ectodomain trimer stabilized in the prefusion conformation by the one or more proline substitutions (such as V1060P and L1061P substitutions) further comprises one of A1083S, E1090I, Q1097I, D1101F, or A653W to stabilize the S ectodomain the prefusion conformation.

In some embodiments, the recombinant MERS-CoV S ectodomain trimer stabilized in the prefusion conformation by the one or more proline substitutions (such as V1060P and L1061P substitutions) further comprises a non-native disulfide bond formed between cysteines introduced by one of: T63C and V631C; T63C and Q638C; Q733C and D940C; S676C and D910C; V1087C (which forms a disulfide bond with a cysteine present in the native sequence); A432C and L1058C; or A432C and D1059C to stabilize the S ectodomain the prefusion conformation.

In some embodiments, the recombinant MERS-CoV S ectodomain trimer stabilized in the prefusion conformation by the one or more proline substitutions (such as V1060P and L1061P substitutions) further comprises an additional proline substitution to stabilize the S ectodomain the prefusion conformation, such as one of: K801P; V802P; T803P; V804P; S919P; A920P; A968P; A969P; I970P; F972P; A973P; T1014P; N1042P; T1043P; F1044P; G1045P; A1046P; I1047P; or A1049P.

Any of the substitutions described above can be combined in the MERS-CoV S ectodomain trimer, as long as the trimer is stabilized in the prefusion conformation and can be used to generate a neutralizing immune response to MERS-CoV in a subject.

With reference to the MERS-CoV S protein sequence provided as SEQ ID NO: 1, the ectodomain of the MERS-CoV S protein includes about residues 18-1291. Residues 1-17 are the signal peptide, which is removed during cellular processing. The S1/S2 cleavage site is located at about position 751/752. The S2' cleavage site is located at about position 887/888. The HR1 is located at about residues 989-1057. The central helix is located at about residues 1062-1103. The HR2 is located at about 1246-1277. The C-terminal end of the S2 ectodomain is located at about residue 1291. In some embodiments, the protomers of the prefusion-stabilized MERS-CoV S ectodomain trimer can have a C-terminal residue (which can be linked to a trimerization domain, or a transmembrane domain, for example) of the C-terminal residue of the HR2 (e.g., position 1277), or the ectodomain (e.g., position 1291) or from one of positions 1277-1291. The position numbering of the S protein may vary between MERS-CoV stains, but the sequences can be aligned to determine relevant structural domains and cleavage sites. It will be appreciated that a few residues (such as up to 10) on the N and C-terminal ends of the ectodomain can be removed or modified in the disclosed immunogens without decreasing the utility of the S ectodomain trimer as an immunogen.

Exemplary MERS-CoV S protein sequences are provided below. Any of the MERS-CoV S protein mutations (such as V1060P and L1061P, and/or modifications to generate a single chain) can be incorporated in the MERS-CoV S protein sequences.

An exemplary sequence of MERS-CoV S protein including the ectodomain and TM and CT domains) England1 strain is provided as SEQ ID NO: 1:

MIHSVFLLMFLLTPTESYVDVGPDSVKSACIEVDIQQTFFDKTWPRPIDV

SKADGIIYPQGRTYSNITITYQGLFPYQGDHGDMYVYSAGHATGTTPQKL

FVANYSQDVKQFANGFVVRIGAAANSIGTVIISPSTSATIRKIYPAFMLG

SSVGNFSDGKMGRFFNHTLVLLPDGCGTLLRAFYCILEPRSGNHCPAGNS

YTSFATYHTPATDCSDGNYNRNASLNSFKEYFNLRNCTEMYTYNITEDEI

LEWFGITQTAQGVHLFSSRYVDLYGGNMFQFATLPVYDTIKYYSIIPHSI

RSIQSDRKAWAAFYVYKLQPLTFLLDFSVDGYIRRAIDCGENDLSQLHCS

YESFDVESGVYSVSSFEAKPSGSVVEQAEGVECDFSPLLSGTPPQVYNEK

RLVFTNCNYNLTKLLSLFSVNDFTCSQISPAAIASNCYSSLILDYFSYPL

SMKSDLSVSSAGPISQFNYKQSFSNPTCLILATVPHNLTTITKPLKYSYI

NKCSRFLSDDRTEVPQLVNANQYSPCVSIVPSTVWEDGDYYRKQLSPLEG

GGWLVASGSTVAMTEQLQMGFGITVQYGTDTNSVCPKLEFANDTKIASQL

GNCVEYSLYGVSGRGVFQNCTAVGVRQQRFVYDAYQNLVGYYSDDGNYYC

LRACVSVPVSVIYDKETKTHATLFGSVACEHISSTMSQYSRSTRSMLKRR

DSTYGPLQTPVGCVLGLVNSSLFVEDCKLPLGQSLCALPDTPSTLTPRSV

RSVPGEMRLASIAFNHPIQVDQLNSSYFKLSIPTNFSFGVTQEYIQTTIQ

KVTVDCKQYVCNGFQKCEQLLREYGQFCSKINQALHGANLRQDDSVRNLF

ASVKSSQSSPIIPGFGGDENLILLEPVSISTGSRSARSAIEDLLFDKVTI

ADPGYMQGYDDCMQQGPASARDLICAQYVAGYKVLPPLMDVNMEAAYTSS

LLGSIAGVGWTAGLSSFAAIPFAQSIFYRLNGVGITQQVLSENQKLIANK

ENQALGAMQTGFTTTNEAFHKVQDAVNNNAQALSKLASELSNTFGAISAS

IGDIIQRLDVLEQDAQIDRLINGRLTTLNAFVAQQLVRSESAALSAQLAK

DKVNECVKAQSKRSGFCGQGTHIVSFVVNAPNGLYFMHVGYYPSNHIEVV

SAYGLCDAANPTNCIAPVNGYFIKINNTRIVDEWSYTGSSFYAPEPITSL

NTKYVAPQVTYQNISTNLPPPLLGNSTGIDFQDELDEFFKNVSTSIPNFG

SLTQINTTLLDLTYEMLSLQQVVKALNESYIDLKELGNYTYYNKWPWYIW

LGFIAGLVALALCVFFILCCTGCGTNCMGKLKCNRCCDRYEEYDLEPHKV

HVH

An exemplary sequence of MERS-CoV S ectodomain England1 strain including V1060P and L1061P substitutions is provided as SEQ ID NO: 2:

MIHSVFLLMFLLTPTESYVDVGPDSVKSACIEVDIQQTFFDKTWPRPIDV

SKADGIIYPQGRTYSNITITYQGLFPYQGDHGDMYVYSAGHATGTTPQKL

FVANYSQDVKQFANGFVVRIGAAANSTGTVIISPSTSATIRKIYPAFMLG

SSVGNFSDGKMGRFFNHTLVLLPDGCGTLLRAFYCILEPRSGNHCPAGNS

YTSFATYHTPATDCSDGNYNRNASLNSFKEYFNLRNCTEMYTYNITEDEI

LEWFGITQTAQGVHLFSSRYVDLYGGNMFQFATLPVYDTIKYYSIIPHSI

RSIQSDRKAWAAFYVYKLQPLTFLLDFSVDGYIRRAIDCGENDLSQLHCS

YESFDVESGVYSVSSFEAKPSGSVVEQAEGVECDFSPLLSGTPPQVYNFK

RLVFTNCNYNLTKLLSLFSVNDFTCSQISPAAIASNCYSSLILDYFSYPL

SMKSDLSVSSAGPISQFNYKQSFSNPTCLILATVPHNLTTITKPLKYSYI

NKCSRFLSDDRTEVPQLVNANQYSPCVSIVPSTVWEDGDYYRKQLSPLEG

GGWLVASGSTVAMTEQLQMGFGITVQYGTDTNSVCPKLEFANDTKIASQL

GNCVEYSLYGVSGRGVFQNCTAVGVRQQRFVYDAYQNLVGYYSDDGNYYC

LRACVSVPVSVIYDKETKTHATLFGSVACEHISSTMSQYSRSTRSMLKRR

DSTYGPLQTPVGCVLGLVNSSLFVEDCKLPLGQSLCALPDTPSTLTPRSV

RSVPGEMRLASIAFNHPIQVDQLNSSYFKLSIPTNFSFGVTQEYIQTTIQ

KVTVDCKQYVCNGFQKCEQLLREYGQFCSKINQALHGANLRQDDSVRNLF

ASVKSSQSSPIIPGFGGDENLILLEPVSISTGSRSARSAIEDLLFDKVTI

ADPGYMQGYDDCMQQGPASARDLICAQYVAGYKVLPPLMDVNMEAAYTSS

LLGSIAGVGWTAGLSSFAAIPFAQSIFYRLNGVGITQQVLSENQKLIANK

ENQALGAMQTGFTTTNEAFHKVQDAVNNNAQALSKLASELSNTFGAISAS

IGDIIQRLDPPEQDAQIDRLINGRLTTLNAFVAQQLVRSESAALSAQLAK

DKVNECVKAQSKRSGFCGQGTHIVSFVVNAPNGLYFMHVGYYPSNHIEVV

SAYGLCDAANPTNCIAPVNGYFIKTNNTRIVDEWSYTGSSFYAPEPITSL

NTKYVAPQVTYQNISTNLPPPLLGNSTGIDFQDELDEFFKNVSTSIPNFG

SLTQINTTLLDLTYEMLSLQQVVKALNESYIDLKELGNYTY

An exemplary sequence of MERS-CoV S ectodomain England1 strain including V1060P and L1061P substitutions and 748-RSVR-751 (residues 748-751 of SEQ ID NO: 1) to 748-ASVG-751 (residues 748-751 of SEQ ID NO: 3) substitutions to remove the S1/S2 cleavage site is provided as SEQ ID NO: 3:

MIHSVFLLMFLLTPTESYVDVGPDSVKSACIEVDIQQTFFDKTWPRPIDV

SKADGIIYPQGRTYSNITITYQGLFPYQGDHGDMYVYSAGHATGTTPQKL

FVANYSQDVKQFANGFVVRIGAAANSTGTVIISPSTSATIRKIYPAFMLG

SSVGNFSDGKMGRFFNHTLVLLPDGCGTLLRAFYCILEPRSGNHCPAGNS

YTSFATYHTPATDCSDGNYNRNASLNSFKEYFNLRNCTEMYTYNITEDEI

LEWFGITQTAQGVHLFSSRYVDLYGGNMFQFATLPVYDTIKYYSIIPHSI

RSIQSDRKAWAAFYVYKLQPLTFLLDFSVDGYIRRAIDCGENDLSQLHCS

YESFDVESGVYSVSSFEAKPSGSVVEQAEGVECDFSPLLSGTPPQVYNEK

RLVFTNCNYNLTKLLSLFSVNDFTCSQISPAAIASNCYSSLILDYFSYPL

SMKSDLSVSSAGPISQFNYKQSFSNPTCLILATVPHNLTTITKPLKYSYI

NKCSRFLSDDRTEVPQLVNANQYSPCVSIVPSTVWEDGDYYRKQLSPLEG

GGWLVASGSTVAMTEQLQMGFGITVQYGTDTNSVCPKLEFANDTKIASQL

GNCVEYSLYGVSGRGVFQNCTAVGVRQQRFVYDAYQNLVGYYSDDGNYYC

LRACVSVPVSVIYDKETKTHATLFGSVACEHISSTMSQYSRSTRSMLKRR

DSTYGPLQTPVGCVLGLVNSSLFVEDCKLPLGQSLCALPDTPSTLTPASV

GSVPGEMRLASIAFNHPIQVDQLNSSYFKLSIPTNFSFGVTQEYIQTTIQ

KVTVDCKQYVCNGFQKCEQLLREYGQFCSKINQALHGANLRQDDSVRNLF

ASVKSSQSSPIIPGFGGDENLTLLEPVSISTGSRSARSAIEDLLEDKVTI

ADPGYMQGYDDCMQQGPASARDLICAQYVAGYKVLPPLMDVNMEAAYTSS

LLGSIAGVGWTAGLSSFAAIPFAQSIFYRLNGVGITQQVLSENQKLIANK

ENQALGAMQTGFTTTNEAFHKVQDAVNNNAQALSKLASELSNTFGAISAS

IGDIIQRLDPPEQDAQIDRLINGRLTTLNAFVAQQLVRSESAALSAQLAK

DKVNECVKAQSKRSGFCGQGTHIVSFVVNAPNGLYFMHVGYYPSNHIEVV

SAYGLCDAANPTNCIAPVNGYFIKTNNTRIVDEWSYTGSSFYAPEPITSL

NTKYVAPQVTYQNISTNLPPPLLGNSTGIDFQDELDEFFKNVSTSIPNFG

SLTQINTTLLDLTYEMLSLQQVVKALNESYIDLKELGNYTY

An exemplary sequence of MERS-CoV S ectodomain England1 strain including V1060P and L1061P substitutions and 748-RSVR-751 (residues 748-751 of SEQ ID NO: 1) to 748-ASVG-751 (residues 748-751 of SEQ ID NO: 3) and 884-RSAR-887 (residues 884-887 of SEQ ID NO: 1) to 884-GSAG-887 (residues 884-887 of SEQ ID NO: 3) substitutions to remove the S1/S2 cleavage site and the S2' cleavage site is provided as SEQ ID NO: 4:

MIHSVFLLMFLLTPTESYVDVGPDSVKSACIEVDIQQTFFDKTWPRPIDV
SKADGIIYPQGRTYSNITITYQGLFPYQGDHGDMYVYSAGHATGTTPQKL
FVANYSQDVKQFANGFVVRIGAAANSTGTVIISPSTSATIRKIYPAFMLG
SSVGNFSDGKMGRFFNHTLVLLPDGCGTLLRAFYCILEPRSGNHCPAGNS
YTSFATYHTPATDCSDGNYNRNASLNSFKEYFNLRNCTEMYTYNITEDEI
LEWFGITQTAQGVHLFSSRYVDLYGGNMFQFATLPVYDTIKYYSIIPHSI
RSIQSDRKAWAAFYVYKLQPLTFLLDESVDGYIRRAIDCGENDLSQLHCS
YESFDVESGVYSVSSFEAKPSGSVVEQAEGVECDFSPLLSGTPPQVYNFK
RLVFTNCNYNLTKLLSLESVNDFTCSQISPAAIASNCYSSLILDYFSYPL
SMKSDLSVSSAGPISQFNYKQSFSNPTCLILATVPHNLTTITKPLKYSYI
NKCSRFLSDDRTEVPQLVNANQYSPCVSIVPSTVWEDGDYYRKQLSPLEG
GGWLVASGSTVAMTEQLQMGFGITVQYGTDTNSVCPKLEFANDTKIASQL
GNCVEYSLYGVSGRGVFQNCTAVGVRQQRFVYDAYQNLVGYYSDDGNYYC
LRACVSVPVSVIYDKETKTHATLEGSVACEHISSTMSQYSRSTRSMLKRR
DSTYGPLQTPVGCVLGLVNSSLFVEDCKLPLGQSLCALPDTPSTLTPASV
GSVPGEMRLASIAFNHPIQVDQLNSSYFKLSIPTNFSFGVTQEYIQTTIQ
KVTVDCKQYVCNGFQKCEQLLREYGQFCSKINQALHGANLRQDDSVRNLF
ASVKSSQSSPIIPGFGGDENLILLEPVSISTGSGSAGSAIEDLLEDKVTI
ADPGYMQGYDDCMQQGPASARDLICAQYVAGYKVLPPLMDVNMEAAYTSS
LLGSIAGVGWTAGLSSFAAIPFAQSIFYRLNGVGITQQVLSENQKLIANK
ENQALGAMQTGFTTTNEAFHKVQDAVNNNAQALSKLASELSNTFGAISAS
IGDIIQRLDPPEQDAQIDRLINGRLTTLNAFVAQQLVRSESAALSAQLAK
DKVNECVKAQSKRSGFCGQGTHIVSFVVNAPNGLYFMHVGYYPSNHIEVV
SAYGLCDAANPTNCIAPVNGYFIKTNNTRIVDEWSYTGSSFYAPEPITSL
NTKYVAPQVTYQNISTNLPPPLLGNSTGIDFQDELDEFFKNVSTSIPNFG
SLTQINTTLLDLTYEMLSLQQVVKALNESYIDLKELGNYTY

A C-terminal trimerization domain can be added to the protomers of the MERS-CoV S ectodomains trimer to promote trimerization of the ectodomain.

An exemplary sequence of MERS-CoV S ectodomain England1 strain including V1060P and L1061P substitutions and 748-RSVR-751 (residues 748-751 of SEQ ID NO: 1) to 748-ASVG-751 (residues 748-751 of SEQ ID NO: 3) substitutions to remove the S1/S2 cleavage site, and a T4 fibritin trimerization domain is provided as SEQ ID NO: 28:

MIHSVFLLMFLLTPTESYVDVGPDSVKSACIEVDIQQTFFDKTWPRPIDV
SKADGIIYPQGRTYSNITITYQGLFPYQGDHGDMYVYSAGHATGTTPQKL
FVANYSQDVKQFANGFVVRIGAAANSTGTVIISPSTSATIRKIYPAFMLG
SSVGNFSDGKMGRFFNHTLVLLPDGCGTLLRAFYCILEPRSGNHCPAGNS
YTSFATYHTPATDCSDGNYNRNASLNSFKEYFNLRNCTEMYTYNITEDEI
LEWFGITQTAQGVHLFSSRYVDLYGGNMFQFATLPVYDTIKYYSIIPHSI
RSIQSDRKAWAAFYVYKLQPLTFLLDFSVDGYIRRAIDCGENDLSQLHCS
YESFDVESGVYSVSSFEAKPSGSVVEQAEGVECDFSPLLSGTPPQVYNEK
RLVFTNCNYNLTKLLSLESVNDFTCSQISPAAIASNCYSSLILDYFSYPL
SMKSDLSVSSAGPISQFNYKQSFSNPTCLILATVPHNLTTITKPLKYSYI
NKCSRFLSDDRTEVPQLVNANQYSPCVSIVPSTVWEDGDYYRKQLSPLEG
GGWLVASGSTVAMTEQLQMGFGITVQYGTDTNSVCPKLEFANDTKIASQL
GNCVEYSLYGVSGRGVFQNCTAVGVRQQRFVYDAYQNLVGYYSDDGNYYC
LRACVSVPVSVIYDKETKTHATLEGSVACEHISSTMSQYSRSTRSMLKRR
DSTYGPLQTPVGCVLGLVNSSLFVEDCKLPLGQSLCALPDTPSTLTPASV
GSVPGEMRLASIAFNHPIQVDQLNSSYFKLSIPTNFSFGVTQEYIQTTIQ
KVTVDCKQYVCNGFQKCEQLLREYGQFCSKINQALHGANLRQDDSVRNLF
ASVKSSQSSPIIPGFGGDENLILLEPVSISTGSRSARSAIEDLLFDKVTI
ADPGYMQGYDDCMQQGPASARDLICAQYVAGYKVLPPLMDVNMEAAYTSS
LLGSIAGVGWTAGLSSFAAIPFAQSIFYRLNGVGITQQVLSENQKLIANK
ENQALGAMQTGFTTTNEAFHKVQDAVNNNAQALSKLASELSNTFGAISAS
IGDIIQRLDPPEQDAQIDRLINGRLTTLNAFVAQQLVRSESAALSAQLAK
DKVNECVKAQSKRSGFCGQGTHIVSFVVNAPNGLYFMHVGYYPSNHIEVV
SAYGLCDAANPTNCIAPVNGYFIKTNNTRIVDEWSYTGSSFYAPEPITSL
NTKYVAPQVTYQNISTNLPPPLLGNSTGIDFQDELDEFFKNVSTSIPNFG
SLTQINTTLLDLTYEMLSLQQVVKALNESYIDLKELGNYTYGGYIPEAPR
DGQAYVRKDGEWVLLSTF

An exemplary sequence of MERS-CoV S ectodomain England1 strain including V1060P and L1061P substitutions and 748-RSVR-751 to 748-ASVG-751 and 884-RSAR-887 (residues 884-887 of SEQ ID NO: 1) to 884-GSAG-887 (residues 884-887 of SEQ ID NO: 3) substitutions to remove the S1/S2 cleavage site and the S2' cleavage site, and a T4 fibritin trimerization domain is provided as SEQ ID NO: 29:

MIHSVFLLMFLLTPTESYVDVGPDSVKSACIEVDIQQTFFDKTWPRPIDV
SKADGIIYPQGRTYSNITITYQGLFPYQGDHGDMYVYSAGHATGTTPQKL
FVANYSQDVKQFANGFVVRIGAAANSTGTVIISPSTSATIRKIYPAFMLG
SSVGNFSDGKMGRFFNHTLVLLPDGCGTLLRAFYCILEPRSGNHCPAGNS
YTSFATYHTPATDCSDGNYNRNASLNSFKEYFNLRNCTEMYTYNITEDEI
LEWFGITQTAQGVHLFSSRYVDLYGGNMFQFATLPVYDTIKYYSIIPHSI
RSIQSDRKAWAAFYVYKLQPLTFLLDFSVDGYIRRAIDCGENDLSQLHCS
YESFDVESGVYSVSSFEAKPSGSVVEQAEGVECDFSPLLSGTPPQVYNEK
RLVFTNCNYNLTKLLSLESVNDFTCSQISPAAIASNCYSSLILDYFSYPL
SMKSDLSVSSAGPISQFNYKQSFSNPTCLILATVPHNLTTITKPLKYSYI
NKCSRFLSDDRTEVPQLVNANQYSPCVSIVPSTVWEDGDYYRKQLSPLEG
GGWLVASGSTVAMTEQLQMGFGITVQYGTDTNSVCPKLEFANDTKIASQL
GNCVEYSLYGVSGRGVFQNCTAVGVRQQRFVYDAYQNLVGYYSDDGNYYC
LRACVSVPVSVIYDKETKTHATLEGSVACEHISSTMSQYSRSTRSMLKRR

-continued

DSTYGPLQTPVGCVLGLVNSSLFVEDCKLPLGQSLCALPDTPSTLTPASV

GSVPGEMRLASIAFNHPIQVDQLNSSYFKLSIPTNFSFGVTQEYIQTTIQ

KVTVDCKQYVCNGFQKCEQLLREYGQFCSKINQALHGANLRQDDSVRNLF

ASVKSSQSSPIIPGFGGDENLILLEPVSISTGSGSAGSAIEDLLFDKVTI

ADPGYMQGYDDCMQQGPASARDLICAQYVAGYKVLPPLMDVNMEAAYTSS

LLGSIAGVGWTAGLSSFAAIPFAQSIFYRLNGVGITQQVLSENQKLIANK

ENQALGAMQTGFTTTNEAFHKVQDAVNNNAQALSKLASELSNTFGAISAS

IGDIIQRLDPPEQDAQIDRLINGRLTTLNAFVAQQLVRSESAALSAQLAK

DKVNECVKAQSKRSGFCGQGTHIVSFVVNAPNGLYFMHVGYYPSNHIEVV

SAYGLCDAANPTNCIAPVNGYFIKTNNTRIVDEWSYTGSSFYAPEPITSL

NTKYVAPQVTYQNISTNLPPPLLGNSTGIDFQDELDEFFKNVSTSIPNFG

SLTQINTILLDLTYEMLSLQQVVKALNESYIDLKELGNYTYGGYIPEAPR

DGQAYVRKDGEWVLLSTF

In some embodiments, the recombinant MERS-CoV S ectodomain trimer comprises protomers comprising the ectodomain sequence of any one of SEQ ID NOs: 2-4 and 29. In some embodiments, the recombinant MERS-CoV S ectodomain trimer comprises protomers comprising residues 18-1291 of any one of SEQ ID NOs: 2-4 or residues 18-1318 of SEQ ID NO: 29. In some embodiments, the recombinant MERS-CoV S ectodomain trimer comprises protomers comprising an ectodomain sequence at least 90% identical to the ectodomain sequence of any one of SEQ ID NOs: 2-4, wherein the MERS-CoV S ectodomain trimer is stabilized in the prefusion conformation and comprises the "2P" substitution and/or modifications to remove the S1/S2 cleavage site and the S2' cleavage site of the protomers. In some embodiments, the recombinant MERS-CoV S ectodomain trimer comprises protomers comprising an amino acid sequence at least 90% identical to residues 18-1291 of any one of SEQ ID NOs: 2-4 or residues 18-1318 of SEQ ID NO: 29, wherein the MERS-CoV S ectodomain trimer is stabilized in the prefusion conformation and comprises the "2P" substitution and/or modifications to remove the S1/S2 cleavage site and the S2' cleavage site of the protomers.

B. SARS-CoV

In some embodiments, the immunogen comprises a recombinant SARS-CoV S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions that stabilize the SARS-CoV S ectodomain trimer in the prefusion conformation are located between residues 951 to 971 (such as between residues 961 to 971 or between residues 966 to 971) of the S ectodomain protomers in the trimer. In some embodiments, the SARS-CoV S ectodomain trimer is stabilized in the prefusion conformation by K968P and V969P substitutions ("2P") in the S ectodomain protomers in the trimer. The amino acid numbering for SARS-CoV S proteins is with reference to the SARS-CoV S sequence provided as SEQ ID NO: 6.

In some embodiments, the recombinant SARS-CoV S ectodomain trimer stabilized in the prefusion conformation comprises single-chain S ectodomain protomers comprising mutations to the S1/S2 and/or S2' protease cleavage sites to prevent protease cleavage at these sites.

In some embodiments, the protomers of the recombinant SARS-CoV S ectodomain trimer stabilized in the prefusion conformation by the one or more proline substitutions (such as K968P and V969P substitutions) comprises additional modifications for stabilization in the prefusion conformation.

With reference to the SARS-CoV S protein sequence provided as SEQ ID NO: 6, the ectodomain of the SARS-CoV S protein includes about residues 14-1190. Residues 1-13 are the signal peptide, which is removed during cellular processing. The S1/S2 cleavage site is located at position 667/668 or 678/679. The S2' cleavage site is located at about position 797/798. The HR1 is located at about residues 897-965. The central helix is located at about residues 970-1011. The HR2 is located at about 1145-1176. The C-terminal end of the S2 ectodomain is located at about residue 1190. In some embodiments, the protomers of the prefusion-stabilized SARS-CoV S ectodomain trimer can have a C-terminal residue (which can be linked to a trimerization domain, or a transmembrane domain, for example) of the C-terminal residue of the HR2 (e.g., position 1176), or the ectodomain (e.g., position 1190), or from one of positions 1176-1190. The position numbering of the S protein may vary between SARS-CoV stains, but the sequences can be aligned to determine relevant structural domains and cleavage sites. It will be appreciated that a few residues (such as up to 10) on the N and C-terminal ends of the ectodomain can be removed or modified in the disclosed immunogens without decreasing the utility of the S ectodomain trimer as an immunogen.

Exemplary SARS-CoV S protein sequences are provided below. The prefusion stabilizing substitutions disclosed herein (and other modifications, such as substitutions to generate a single chain) can be incorporated into SARS-CoV S protein sequences.

An exemplary sequence of SARS-CoV S protein (including the ectodomain and TM and CT domains) is provided as SEQ ID NO: 6 (GenBank GI: 30795145, incorporated by reference herein):

MFIFLLFLTLTSGSDLDRCTTFDDVQAPNYTQHTSSMRGVYYPDEIFRSD

TLYLTQDLFLPFYSNVTGFHTINHTFGNPVIPFKDGIYFAATEKSNVVRG

WVFGSTMNNKSQSVIIINNSTNVVIRACNFELCDNPFFAVSKPMGTQTHT

MIFDNAFNCTFEYISDAFSLDVSEKSGNFKHLREFVFKNKDGFLYVYKGY

QPIDVVRDLPSGFNTLKPIFKLPLGINIINFRAILTAFSPAQDIWGTSAA

AYFVGYLKPTTFMLKYDENGTITDAVDCSQNPLAELKCSVKSFEIDKGIY

QTSNFRVVPSGDVVRFPNITNLCPFGEVENATKFPSVYAWERKKISNCVA

DYSVLYNSTFFSTFKCYGVSATKLNDLCFSNVYADSFVVKGDDVRQIAPG

QTGVIADYNYKLPDDFMGCVLAWNTRNIDATSTGNYNYKYRYLRHGKLRP

FERDISNVPFSPDGKPCTPPALNCYWPLNDYGFYTTTGIGYQPYRVVVLS

FELLNAPATVCGPKLSTDLIKNQCVNFNFNGLTGTGVLTPSSKRFQPFQQ

-continued

```
FGRDVSDFTDSVRDPKTSEILDISPCAFGGVSVITPGTNASSEVAVLYQD

VNCTDVSTAIHADQLTPAWRIYSTGNNVFQTQAGCLIGAEHVDTSYECDI

PIGAGICASYHTVSLLRSTSQKSIVAYTMSLGADSSIAYSNNTIAIPTNF

SISITTEVMPVSMAKTSVDCNMYICGDSTECANLLLQYGSFCTQLNRALS

GIAAEQDRNTREVFAQVKQMYKTPTLKYFGGFNFSQILPDPLKPTKRSFI

EDLLFNKVTLADAGFMKQYGECLGDINARDLICAQKENGLTVLPPLLTDD

MIAAYTAALVSGTATAGWTFGAGAALQIPFAMQMAYRENGIGVTQNVLYE

NQKQIANQFNKAISQIQESLTTTSTALGKLQDVVNQNAQALNTLVKQLSS

NFGAISSVLNDILSRLDKVEAEVQIDRLITGRLQSLQTYVTQQLIRAAEI

RASANLAATKMSECVLGQSKRVDFCGKGYHLMSFPQAAPHGVVFLHVTYV

PSQERNFTTAPAICHEGKAYFPREGVFVENGTSWFITQRNFFSPQIITTD

NTFVSGNCDVVIGIINNTVYDPLQPELDSFKEELDKYFKNHTSPDVDLGD

ISGINASVVNIQKEIDRLNEVAKNLNESLIDLQELGKYEQYIKWPWYVWL

GFIAGLIAIVMVTILLCCMTSCCSCLKGACSCGSCCKFDEDDSEPVLKGV

KLHYT
```

An exemplary sequence of SARS-CoV S ectodomain (TOR2 strain) including a double proline substitution for stabilization in the prefusion conformation is provided as SEQ ID NO: 7:

```
MFIFLLFLTLTSGSDLDRCTTFDDVQAPNYTQHTSSMRGVYYPDEIFRSD

TLYLTQDLFLPFYSNVTGFHTINHTFGNPVIPFKDGIYFAATEKSNVVRG

WVFGSTMNNKSQSVIIINNSTNVVIRACNFELCDNPFFAVSKPMGTQTHT

MIFDNAFNCTFEYISDAFSLDVSEKSGNFKHLREFVFKNKDGFLYVYKGY

QPIDVVRDLPSGENTLKPIFKLPLGINIINFRAILTAFSPAQDIWGTSAA

AYFVGYLKPTTFMLKYDENGTITDAVDCSQNPLAELKCSVKSFEIDKGIY

QTSNFRVVPSGDVVRFPNITNLCPFGEVENATKFPSVYAWERKKISNCVA

DYSVLYNSTFFSTFKCYGVSATKLNDLCFSNVYADSFVVKGDDVRQIAPG

QTGVIADYNYKLPDDFMGCVLAWNTRNIDATSTGNYNYKYRYLRHGKLRP

FERDISNVPFSPDGKPCTPPALNCYWPLNDYGFYTTTGIGYQPYRVVVLS

FELLNAPATVCGPKLSTDLIKNQCVNFNFNGLTGTGVLTPSSKRFQPFQQ

FGRDVSDFTDSVRDPKTSEILDISPCAFGGVSVITPGTNASSEVAVLYQD

VNCTDVSTAIHADQLTPAWRIYSTGNNVFQTQAGCLIGAEHVDTSYECDI

PIGAGICASYHTVSLLRSTSQKSIVAYTMSLGADSSIAYSNNTIAIPTNF

SISITTEVMPVSMAKTSVDCNMYICGDSTECANLLLQYGSFCTQLNRALS

GIAAEQDRNTREVFAQVKQMYKTPTLKYFGGFNFSQILPDPLKPTKRSFI

EDLLFNKVTLADAGFMKQYGECLGDINARDLICAQKENGLTVLPPLLTDD

MIAAYTAALVSGTATAGWTFGAGAALQIPFAMQMAYRFNGIGVTQNVLYE

NQKQIANQFNKAISQIQESLTTTSTALGKLQDVVNQNAQALNTLVKQLSS

NFGAISSVLNDILSRLDPPEAEVQIDRLITGRLQSLQTYVTQQLIRAAEI

RASANLAATKMSECVLGQSKRVDFCGKGYHLMSFPQAAPHGVVFLHVTYV

PSQERNFTTAPAICHEGKAYFPREGVFVENGTSWFITQRNFFSPQIITTD

NTFVSGNCDVVIGIINNTVYDPLQPELDSFKEELDKYFKNHTSPDVDLGD

ISGINASVVNIQKEIDRLNEVAKNLNESLIDLQELGKYEQ
```

A C-terminal trimerization domain can be added to the protomers of the SARS-CoV S ectodomains trimer to promote trimerization of the ectodomain.

An exemplary sequence of SARS-CoV S ectodomain (TOR2 strain) including a double proline substitution for stabilization in the prefusion conformation, and a T4 fibritin trimerization domain is provided as SEQ ID NO: 30:

```
MFIFLLFLTLTSGSDLDRCTTFDDVQAPNYTQHTSSMRGVYYPDEIFRSD

TLYLTQDLFLPFYSNVTGFHTINHTFGNPVIPFKDGIYFAATEKSNVVRG

WVFGSTMNNKSQSVIIINNSTNVVIRACNFELCDNPFFAVSKPMGTQTHT

MIFDNAFNCTFEYISDAFSLDVSEKSGNFKHLREFVFKNKDGFLYVYKGY

QPIDVVRDLPSGFNTLKPIFKLPLGINIINFRAILTAFSPAQDIWGTSAA

AYFVGYLKPTTFMLKYDENGTITDAVDCSQNPLAELKCSVKSFEIDKGIY

QTSNFRVVPSGDVVRFPNITNLCPFGEVENATKFPSVYAWERKKISNCVA

DYSVLYNSTFFSTFKCYGVSATKLNDLCFSNVYADSFVVKGDDVRQIAPG

QTGVIADYNYKLPDDFMGCVLAWNTRNIDATSTGNYNYKYRYLRHGKLRP

FERDISNVPFSPDGKPCTPPALNCYWPLNDYGFYTTTGIGYQPYRVVVLS

FELLNAPATVCGPKLSTDLIKNQCVNFNFNGLTGTGVLTPSSKRFQPFQQ

FGRDVSDFTDSVRDPKTSEILDISPCAFGGVSVITPGTNASSEVAVLYQD

VNCTDVSTAIHADQLTPAWRIYSTGNNVFQTQAGCLIGAEHVDTSYECDI

PIGAGICASYHTVSLLRSTSQKSIVAYTMSLGADSSIAYSNNTIAIPTNF

SISITTEVMPVSMAKTSVDCNMYICGDSTECANLLLQYGSFCTQLNRALS

GIAAEQDRNTREVFAQVKQMYKTPTLKYFGGFNFSQILPDPLKPTKRSFI

EDLLFNKVTLADAGFMKQYGECLGDINARDLICAQKENGLTVLPPLLTDD

MIAAYTAALVSGTATAGWTFGAGAALQIPFAMQMAYRFNGIGVTQNVLYE

NQKQIANQFNKAISQIQESLTTTSTALGKLQDVVNQNAQALNTLVKQLSS

NFGAISSVLNDILSRLDPPEAEVQIDRLITGRLQSLQTYVTQQLIRAAEI

RASANLAATKMSECVLGQSKRVDFCGKGYHLMSFPQAAPHGVVFLHVTYV

PSQERNFTTAPAICHEGKAYFPREGVFVENGTSWFITQRNFFSPQIITTD

NTFVSGNCDVVIGIINNTVYDPLQPELDSFKEELDKYFKNHTSPDVDLGD

ISGINASVVNIQKEIDRLNEVAKNLNESLIDLQELGKYEQGGYIPEAPRD

GQAYVRKDGEWVLLSTF
```

In some embodiments, the recombinant SARS-CoV S ectodomain trimer comprises protomers comprising the ectodomain sequence of SEQ ID NO: 7. In some embodiments, the recombinant SARS-CoV S ectodomain trimer comprises protomers comprising residues 14-1190 of SEQ ID NO: 7 or residues 14-1217 of SEQ ID NO: 30. In some embodiments, the recombinant SARS-CoV S ectodomain trimer comprises protomers comprising an ectodomain sequence at least 90% identical to the ectodomain sequence of SEQ ID NO: 7, wherein the SARS-CoV S ectodomain trimer is stabilized in the prefusion conformation and comprises the "2P" substitution and/or modifications to remove the S1/S2 cleavage site and the S2' cleavage site of the protomers. In some embodiments, the recombinant SARS-CoV S ectodomain trimer comprises protomers comprising an amino acid sequence at least 90% identical to residues 14-1190 of SEQ ID NO: 7, wherein the SARS-CoV S ectodomain trimer is stabilized in the prefusion conformation and comprises the "2P" substitution and/or modifications to remove the S1/S2 cleavage site and the S2' cleavage site of the protomers.

C. HKU1-CoV

In some embodiments, the immunogen comprises a recombinant HKU1-CoV S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions that stabilize the HKU1-CoV S ectodomain trimer in the prefusion conformation are located between residues 1050 to 1070 (such as between residues 1060 to 1070 or between residues 1065 to 1070) of the S ectodomain protomers in the trimer. In some embodiments, the HKU1-CoV S ectodomain trimer is stabilized in the prefusion conformation by N1067P and L1068P substitutions ("2P") in the S ectodomain protomers in the trimer. The amino acid numbering for HKU1-CoV S proteins is with reference to the HKU1-CoV S sequence provided as SEQ ID NO: 7.

In some embodiments, the recombinant HKU1-CoV S ectodomain trimer stabilized in the prefusion conformation comprises single-chain S ectodomain protomers comprising mutations to the S1/S2 and/or S2' protease cleavage sites to prevent protease cleavage at these sites.

In some embodiments, the protomers of the recombinant HKU1-CoV S ectodomain trimer stabilized in the prefusion conformation by the one or more proline substitutions (such as N1067P and L1068P substitutions) comprise additional modifications for stabilization in the prefusion conformation.

With reference to the HKU1-CoV S protein sequence provided as SEQ ID NO: 8, the ectodomain of the HKU1-CoV S protein includes about residues 14-1290. Residues 1-13 are the signal peptide, which is removed during cellular processing. The S 1/S2 cleavage site is located at about position 756/757. The S2' cleavage site is located at about position 900/901. The HR1 is located at about residues 996-1064. The central helix is located at about residues 1069-1110. The HR2 is located at about 1245-1276. The C-terminal end of the S2 ectodomain is located at about residue 1290. In some embodiments, the protomers of the prefusion-stabilized HKU1-CoV S ectodomain trimer can have a C-terminal residue (which can be linked to a trimerization domain, or a transmembrane domain, for example) of the C-terminal residue of the HR2 (e.g., position 1276), or the ectodomain (e.g., position 1290), or from one of positions 1276-1290. The position numbering of the S protein may vary between HKU1-CoV stains, but the sequences can be aligned to determine relevant structural domains and cleavage sites. It will be appreciated that a few residues (such as up to 10) on the N and C-terminal ends of the ectodomain can be removed or modified in the disclosed immunogens without decreasing the utility of the S ectodomain trimer as an immunogen.

Exemplary HKU1-CoV S protein sequences are provided below. The prefusion stabilizing substitutions disclosed herein (and other modifications, such as substitutions to generate a single chain) can be incorporated into HKU1-CoV S protein sequences.

An exemplary sequence of HKU1-CoV S protein (including the ectodomain and TM and CT domains) is provided as SEQ ID NO: 8 (GenBank GI: 123867264, incorporated by reference herein):

MFLIIFILPTTLAVIGDENCINSFINDYNKTIPRISEDVVDVSLGLGTYY

VLNRVYLNTTLLFTGYFPKSGANFRDLALKGSIYLSTLWYKPPFLSDENN

GIFSKVKNTKLYVNNTLYSEFSTIVIGSVFVNTSYTIVVQPHNGILEITA

CQYTMCEYPHTVCKSKGSIRNESWHIDSSEPLCLFKKNFTYNVSADWLYF

HFYQERGVFYAYYADVGMPTTFLFSLYLGTILSHYYVMPLTCNAISSNTD

NETLEYWVTPLSRRQYLLNFDEHGVITNAVDCSSSFLSEIQCKTQSFAPN

TGVYDLSGFTVKPVATVYRRIPNLPDCDIDNWLNNVSVPSPLNWERRIFS

NCNFNLSTLLRLVHVDSFSCNNLDKSKIFGSCENSITVDKFAIPNRRRDD

LQLGSSGFLQSSNYKIDISSSSCQLYYSLPLVNVTINNENPSSWNRRYGF

GSFNLSSYDVVYSDHCFSVNSDFCPCADPSVVNSCAKSKPPSAICPAGTK

YRHCDLDTTLYVKNWCRCSCLPDPISTYSPNTCPQKKVVVGIGEHCPGLG

INEEKCGTQLNHSSCFCSPDAFLGWSFDSCISNNRCNIFSNFIFNGINSG

TTCSNDLLYSNTEISTGVCVNYDLYGITGQGIFKEVSAAYYNNWQNLLYD

SNGNIIGFKDFLINKTYTILPCYSGRVSAAFYQNSSSPALLYRNLKCSYV

LNNISFISQPFYFDSYLGCVLNAVNLTSYSVSSCDLRMGSGFCIDYALPS

SRRKRRGISSPYRFVTFEPFNVSFVNDSVETVGGLFEIQIPTNFTIAGHE

EFIQTSSPKVTIDCSAFVCSNYAACHDLLSEYGTFCDNINSILNEVNDLL

DITQLQVANALMQGVTLSSNLNTNLHSDVDNIDFKSLLGCLGSQCGSSSR

SLLEDLLENKVKLSDVGFVEAYNNCTGGSEIRDLLCVQSENGIKVLPPIL

SETQISGYTTAATVAAMFPPWSAAAGVPFSLNVQYRINGLGVTMDVLNKN

QKLIANAFNKALLSIQNGFTATNSALAKIQSVVNANAQALNSLLQQLENK

FGAISSSLQEILSRLDNLEAQVQIDRLINGRLTALNAYVSQQLSDITLIK

AGASRAIEKVNECVKSQSPRINFCGNGNHILSLVQNAPYGLLFIHFSYKP

TSFKTVLVSPGLCLSGDRGIAPKQGYFIKQNDSWMFTGSSYYYPEPISDK

NVVFMNSCSVNFTKAPFIYLNNSIPNLSDFEAELSLWFKNHTSIAPNLTE

NSHINATFLDLYYEMNVIQESIKSLNSSFINLKEIGTYEMYVKWPWYIWL

LIVILFIIFLMILFFICCCTGCGSACFSKCHNCCDEYGGHNDFVIKASHD

D

An exemplary sequence of HKU1-CoV S ectodomain including a double proline substitution for stabilization in the prefusion conformation is provided as (SEQ ID NO: 9, which also includes mutations to eliminate the S1/S2 cleavage site:

MFLIIFILPTTLAVIGDENCTNSFINDYNKTIPRISEDVVDVSLGLGTYY
VLNRVYLNTTLLFTGYFPKSGANFRDLALKGSIYLSTLWYKPPFLSDENN
GIFSKVKNTKLYVNNTLYSEFSTIVIGSVFVNTSYTIVVQPHNGILEITA
CQYTMCEYPHTVCKSKGSIRNESWHIDSSEPLCLFKKNFTYNVSADWLYF
HFYQERGVFYAYYADVGMPTTFLFSLYLGTILSHYYVMPLTCNAISSNTD
NETLEYWVTPLSRRQYLLNFDEHGVITNAVDCSSSFLSEIQCKTQSFAPN
TGVYDLSGFTVKPVATVYRRIPNLPDCDIDNWLNNVSVPSPLNWERRIFS
NCNFNLSTLLRLVHVDSFSCNNLDKSKIFGSCENSITVDKFAIPNRRRDD
LQLGSSGFLQSSNYKIDISSSSCQLYYSLPLVNVTINNENPSSWNRRYGF
GSFNLSSYDVVYSDHCFSVNSDFCPCADPSVVNSCAKSKPPSAICPAGTK
YRHCDLDTTLYVKNWCRCSCLPDPISTYSPNTCPQKKVVVGIGEHCPGLG
INEEKCGTQLNHSSCFCSPDAFLGWSFDSCISNNRCNIFSNFIFNGINSG
TTCSNDLLYSNTEISTGVCVNYDLYGITGQGIFKEVSAAYYNNWQNLLYD
SNGNIIGFKDFLINKTYTILPCYSGRVSAAFYQNSSSPALLYRNLKCSYV
LNNISFISQPFYFDSYLGCVLNAVNLTSYSVSSCDLRMGSGFCIDYALPS
SGGSGSGISSPYRFVTFEPFNVSFVNDSVETVGGLFEIQIPTNFTIAGHE
EFIQTSSPKVTIDCSAFVCSNYAACHDLLSEYGTFCDNINSILNEVNDLL
DITQLQVANALMQGVTLSSNLNTNLHSDVDNIDFKSLLGCLGSQCGSSSR
SLLEDLLENKVKLSDVGFVEAYNNCTGGSEIRDLLCVQSENGIKVLPPIL
SETQISGYTTAATVAAMFPPWSAAAGVPFSLNVQYRINGLGVTMDVLNKN
QKLIANAFNKALLSIQNGFTATNSALAKIQSVVNANAQALNSLLQQLFNK
FGAISSSLQEILSRLDPPEAQVQIDRLINGRLTALNAYVSQQLSDITLIK
AGASRAIEKVNECVKSQSPRINFCGNGNHILSLVQNAPYGLLFIHFSYKP
TSFKTVLVSPGLCLSGDRGIAPKQGYFIKQNDSWMFTGSSYYYPEPISDK
NVVFMNSCSVNFTKAPFIYLNNSIPNLSDFEAELSLWFKNHTSIAPNLTE
NSHINATFLDLYYEMNVIQESIKSLN

A C-terminal trimerization domain can be added to the protomers of the HKU1-CoV S ectodomains trimer to promote trimerization of the ectodomain.

An exemplary sequence of HKU1-CoV S ectodomain including a double proline substitution for stabilization in the prefusion conformation, mutations to eliminate the S1/S2 cleavage site, and a T4 fibritin trimerization domain is provided as SEQ ID NO: 31:

MFLIIFILPTTLAVIGDFNCTNSFINDYNKTIPRISEDVVDVSLGLGTYY
VLNRVYLNTTLLFTGYFPKSGANFRDLALKGSIYLSTLWYKPPFLSDENN
GIFSKVKNTKLYVNNTLYSEFSTIVIGSVFVNTSYTIVVQPHNGILEITA
CQYTMCEYPHTVCKSKGSIRNESWHIDSSEPLCLFKKNFTYNVSADWLYF
HFYQERGVFYAYYADVGMPTTFLFSLYLGTILSHYYVMPLTCNAISSNTD

-continued

NETLEYWVTPLSRRQYLLNFDEHGVITNAVDCSSSFLSEIQCKTQSFAPN
TGVYDLSGFTVKPVATVYRRIPNLPDCDIDNWLNNVSVPSPLNWERRIFS
NCNENLSTLLRLVHVDSFSCNNLDKSKIFGSCENSITVDKFAIPNRRRDD
LQLGSSGFLQSSNYKIDISSSSCQLYYSLPLVNVTINNENPSSWNRRYGF
GSFNLSSYDVVYSDHCFSVNSDFCPCADPSVVNSCAKSKPPSAICPAGTK
YRHCDLDTTLYVKNWCRCSCLPDPISTYSPNTCPQKKVVVGIGEHCPGLG
INEEKCGTQLNHSSCFCSPDAFLGWSFDSCISNNRCNIFSNFIFNGINSG
TTCSNDLLYSNTEISTGVCVNYDLYGITGQGIFKEVSAAYYNNWQNLLYD
SNGNIIGFKDFLINKTYTILPCYSGRVSAAFYQNSSSPALLYRNLKCSYV
LNNISFISQPFYFDSYLGCVLNAVNLTSYSVSSCDLRMGSGFCIDYALPS
SGGSGSGISSPYRFVTFEPFNVSFVNDSVETVGGLFEIQIPTNFTIAGHE
EFIQTSSPKVTIDCSAFVCSNYAACHDLLSEYGTFCDNINSILNEVNDLL
DITQLQVANALMQGVTLSSNLNINLHSDVDNIDFKSLLGCLGSQCGSSSR
SLLEDLLENKVKLSDVGFVEAYNNCTGGSEIRDLLCVQSENGIKVLPPIL
SETQISGYTTAATVAAMFPPWSAAAGVPFSLNVQYRINGLGVTMDVLNKN
QKLIANAFNKALLSIQNGFTATNSALAKIQSVVNANAQALNSLLQQLFNK
FGAISSSLQEILSRLDPPEAQVQIDRLINGRLTALNAYVSQQLSDITLIK
AGASRAIEKVNECVKSQSPRINFCGNGNHILSLVQNAPYGLLFIHFSYKP
TSFKTVLVSPGLCLSGDRGIAPKQGYFIKQNDSWMFTGSSYYYPEPISDK
NVVFMNSCSVNFTKAPFIYLNNSIPNLSDFEAELSLWFKNHTSIAPNLTE
NSHINATFLDLYYEMNVIQESIKSLNGGYIPEAPRDGQAYVRKDGEWVLL
STF

In some embodiments, the recombinant HKU1-CoV S ectodomain trimer comprises protomers comprising the ectodomain sequence of SEQ ID NO: 9. In some embodiments, the recombinant HKU1-CoV S ectodomain trimer comprises protomers comprising residues 14-1276 of SEQ ID NO: 9 or residues 14-1303 of SEQ ID NO: 31. In some embodiments, the recombinant HKU1-CoV S ectodomain trimer comprises protomers comprising an ectodomain sequence at least 90% identical to the ectodomain sequence of SEQ ID NO: 9, wherein the HKU1-CoV S ectodomain trimer is stabilized in the prefusion conformation and comprises the "2P" substitution and/or modifications to remove the S1/S2 cleavage site and the S2' cleavage site of the protomers. In some embodiments, the recombinant HKU1-CoV S ectodomain trimer comprises protomers comprising an amino acid sequence at least 90% identical to residues 14-1276 of SEQ ID NO: 9 or residues 14-1303 of SEQ ID NO: 31, wherein the HKU1-CoV S ectodomain trimer is stabilized in the prefusion conformation and comprises the "2P" substitution and/or modifications to remove the S1/S2 cleavage site and the S2' cleavage site of the protomers.

D. HKU9-CoV

In some embodiments, the immunogen comprises a recombinant HKU9-CoV S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions that stabilize the HKU9-CoV S ectodomain trimer in the prefusion conformation are located between residues 966 to 986 (such as between residues 976 to 986 or between residues 981 to 986) of the S ectodomain protomers in the trimer. In some embodiments, the HKU9-CoV S ectodomain trimer is stabilized in the prefusion conformation by G1018P and L1019P substitutions ("2P") in the S ectodomain protomers in the trimer. The amino acid numbering for HKU9-CoV S proteins is with reference to the HKU9-CoV S sequence provided as SEQ ID NO: 12.

In some embodiments, the recombinant HKU9-CoV S ectodomain trimer stabilized in the prefusion conformation comprises single-chain S ectodomain protomers comprising mutations to the S1/S2 and/or S2' protease cleavage sites to prevent protease cleavage at these sites.

In some embodiments, the protomers of the recombinant HKU9-CoV S ectodomain trimer stabilized in the prefusion conformation by the one or more proline substitutions (such as G1018P and L1019P substitutions) comprises additional modifications for stabilization in the prefusion conformation.

With reference to the HKU9-CoV S protein sequence provided as SEQ ID NO: 12, the ectodomain of the HKU9-CoV S protein includes about residues 15-1207. Residues 1-14 are the signal peptide, which is removed during cellular processing. The S 1/S2 cleavage site is located at about position 676/677. The S2' cleavage site is located at about position 809/810. The HR1 is located at about residues 912-980. The central helix is located at about residues 986-1026. The HR2 is located at about 1162-1193. The C-terminal end of the S2 ectodomain is located at about residue 1207. In some embodiments, the protomers of the prefusion-stabilized HKU9-CoV S ectodomain trimer can have a C-terminal residue (which can be linked to a trimerization domain, or a transmembrane domain, for example) of the C-terminal residue of the HR2 (e.g., position 1193), or the ectodomain (e.g., position 1207), or from one of positions 1193-1207. The position numbering of the S protein may vary between HKU9-CoV stains, but the sequences can be aligned to determine relevant structural domains and cleavage sites. It will be appreciated that a few residues (such as up to 10) on the N and C-terminal ends of the ectodomain can be removed or modified in the disclosed immunogens without decreasing the utility of the S ectodomain trimer as an immunogen.

Exemplary HKU9-CoV S protein sequences are provided below. The prefusion stabilizing substitutions disclosed herein (and other modifications, such as substitutions to generate a single chain) can be incorporated into HKU9-CoV S protein sequences.

An exemplary sequence of HKU9-CoV S protein (including the ectodomain and TM and CT domains) is provided as SEQ ID NO: 12 (GenBank GI:148841195, incorporated by reference herein):

MLLILVLGVSLAAASRPECENPRFTLTPLNHTLNYTSIKAKVSNVLLPDP
YIAYSGQTLRQNLFMADMSNTILYPVTPPANGANGGFIYNTSIIPVSAGL
FVNTWMYRQPASSRAYCQEPFGVAFGDTFENDRIAILIMAPDNLGSWSAV
APRNQTNIYLLVCSNATLCINPGFNRWGPAGSFIAPDALVDHSNSCFVNN
TFSVNISTSRISLAFLFKDGDLLIYHSGWLPTSNFEHGFSRGSHPMTYFM
SLPVGGNLPRAQFFQSIVRSNAIDKGDGMCTNFDVNLHVAHLINRDLLVS
YENNGSVANAADCADSAAEELYCVTGSFDPPTGVYPLSRYRAQVAGFVRV
TQRGSYCTPPYSVLQDPPQPVVWRRYMLYDCVFDFTVVVDSLPTHQLQCY
GVSPRRLASMCYGSVTLDVMRINETHLNNLFNRVPDTFSLYNYALPDNFY
GCLHAFYLNSTAPYAVANRFPIKPGGRQSNSAFIDTVINAAHYSPFSYVY
GLAVITLKPAAGSKLVCPVANDTVVITDRCVQYNLYGYTGTGVLSKNTSL
VIPDGKVFTASSTGTIIGVSINSTTYSIMPCVTVPVSVGYHPNFERALLE
NGLSCSQRSRAVTEPVSVLWSASATAQDAFDTPSGCVVNVELRNTTIVNT
CAMPIGNSLCFINGSIATANADSLPRLQLVNYDPLYDNSTATPMTPVYWV
KVPTNFTLSATEEYIQTTAPKITIDCARYLCGDSSRCLNVLLHYGTFCND
INKALSRVSTILDSALLSLVKELSINTRDEVTTFSFDGDYNFTGLMGCLG
PNCGATTYRSAFSDLLYDKVRITDPGFMQSYQKCIDSQWGGSIRDLLCTQ
TYNGIAVLPPIVSPAMQALYTSLLVGAVASSGYTFGITSAGVIPFATQLQ
FRLNGIGVTTQVLVENQKLIASSENNALVNIQKGFTETSIALSKMQDVIN
QHAAQLHTLVVQLGNSFGAISSSINEIFSRLEGLAANAEVDRLINGRMMV
LNTYVTQLLIQASEAKAQNALAAQKISECVKAQSLRNDFCGNGTHVLSIP
QLAPNGVLFIHYAYTPTEYAFVQTSAGLCHNGTGYAPRQGMFVLPNNTNM
WHFTTMQFYNPVNISASNTQVLTSCSVNYTSVNYTVLEPSVPGDYDFQKE
FDKFYKNLSTIFNNTENPNDFNFSTVDVTAQIKSLHDVVNQLNQSFIDLK
KLNVYEKTIKWPWYVWLAMIAGIVGLVLAVIMLMCMTNCCSCFKGMCDCR
RCCGSYDSYDDVYPAVRVNKKRTV

An exemplary sequence of HKU9-CoV S protein including a double proline substitution for stabilization in the prefusion conformation is provided as SEQ ID NO: 13:

MLLILVLGVSLAAASRPECENPRFTLTPLNHTLNYTSIKAKVSNVLLPDP
YIAYSGQTLRQNLFMADMSNTILYPVTPPANGANGGFIYNTSIIPVSAGL
FVNTWMYRQPASSRAYCQEPFGVAFGDTFENDRIAILIMAPDNLGSWSAV
APRNQTNIYLLVCSNATLCINPGFNRWGPAGSFIAPDALVDHSNSCFVNN
TFSVNISTSRISLAFLFKDGDLLIYHSGWLPTSNFEHGFSRGSHPMTYFM
SLPVGGNLPRAQFFQSIVRSNAIDKGDGMCTNFDVNLHVAHLINRDLLVS
YENNGSVANAADCADSAAEELYCVTGSFDPPTGVYPLSRYRAQVAGFVRV
TQRGSYCTPPYSVLQDPPQPVVWRRYMLYDCVFDFTVVVDSLPTHQLQCY
GVSPRRLASMCYGSVTLDVMRINETHLNNLFNRVPDTFSLYNYALPDNFY
GCLHAFYLNSTAPYAVANRFPIKPGGRQSNSAFIDTVINAAHYSPFSYVY
GLAVITLKPAAGSKLVCPVANDTVVITDRCVQYNLYGYTGTGVLSKNTSL
VIPDGKVETASSTGTIIGVSINSTTYSIMPCVTVPVSVGYHPNFERALLE
NGLSCSQRSRAVTEPVSVLWSASATAQDAFDTPSGCVVNVELRNTTIVNT

-continued
CAMPIGNSLCFINGSIATANADSLPRLQLVNYDPLYDNSTATPMTPVYWV

KVPTNFTLSATEEYIQTTAPKITIDCARYLCGDSSRCLNVLLHYGTFCND

INKALSRVSTILDSALLSLVKELSINTRDEVTTFSFDGDYNFTGLMGCLG

PNCGATTYRSAFSDLLYDKVRITDPGFMQSYQKCIDSQWGGSIRDLLCTQ

TYNGIAVLPPIVSPAMQALYTSLLVGAVASSGYTFGITSAGVIPFATQLQ

FRLNGIGVTTQVLVENQKLIASSENNALVNIQKGFTETSIALSKMQDVIN

QHAAQLHTLVVQLGNSFGAISSSINEIFSRLEPPAANAEVDRLINGRMMV

LNTYVTQLLIQASEAKAQNALAAQKISECVKAQSLRNDECGNGTHVLSIP

QLAPNGVLFIHYAYTPTEYAFVQTSAGLCHNGTGYAPRQGMFVLPNNTNM

WHFTTMQFYNPVNISASNTQVLTSCSVNYTSVNYTVLEPSVPGDYDFQKE

FDKFYKNLSTIFNNTFNPNDENFSTVDVTAQIKSLHDVVNQLNQSFIDLK

KLNVYEK

A C-terminal trimerization domain can be added to the protomers of the HKU9-CoV S ectodomains trimer to promote trimerization of the ectodomain.

An exemplary sequence of HKU9-CoV S protein including a double proline substitution for stabilization in the prefusion conformation, and a T4 fibritin trimerization domain is provided as SEQ ID NO: 32:

MLLILVLGVSLAAASRPECENPRFTLTPLNHTLNYTSIKAKVSNVLLPDP

YIAYSGQTLRQNLFMADMSNTILYPVTPPANGANGGFIYNTSIIPVSAGL

FVNTWMYRQPASSRAYCQEPFGVAFGDTFENDRIAILIMAPDNLGSWSAV

APRNQTNIYLLVCSNATLCINPGFNRWGPAGSFIAPDALVDHSNSCFVNN

TFSVNISTSRISLAFLFKDGDLLIYHSGWLPTSNFEHGFSRGSHPMTYFM

SLPVGGNLPRAQFFQSIVRSNAIDKGDGMCTNFDVNLHVAHLINRDLLVS

YENNGSVANAADCADSAAEELYCVTGSFDPPTGVYPLSRYRAQVAGFVRV

TQRGSYCTPPYSVLQDPPQPVVWRRYMLYDCVFDFTVVVDSLPTHQLQCY

GVSPRRLASMCYGSVTLDVMRINETHLNNLFNRVPDTFSLYNYALPDNFY

GCLHAFYLNSTAPYAVANRFPIKPGGRQSNSAFIDTVINAAHYSPFSYVY

GLAVITLKPAAGSKLVCPVANDTVVITDRCVQYNLYGYTGTGVLSKNTSL

VIPDGKVETASSTGTIIGVSINSTTYSIMPCVTVPVSVGYHPNFERALLE

NGLSCSQRSRAVTEPVSVLWSASATAQDAFDTPSGCVVNVELRNTTIVNT

CAMPIGNSLCFINGSIATANADSLPRLQLVNYDPLYDNSTATPMTPVYWV

KVPTNFTLSATEEYIQTTAPKITIDCARYLCGDSSRCLNVLLHYGTFCND

INKALSRVSTILDSALLSLVKELSINTRDEVTTFSEDGDYNFTGLMGCLG

PNCGATTYRSAFSDLLYDKVRITDPGFMQSYQKCIDSQWGGSIRDLLCTQ

TYNGIAVLPPIVSPAMQALYTSLLVGAVASSGYTFGITSAGVIPFATQLQ

FRLNGIGVTTQVLVENQKLIASSENNALVNIQKGFTETSIALSKMQDVIN

QHAAQLHTLVVQLGNSFGAISSSINEIFSRLEPPAANAEVDRLINGRMMV

LNTYVTQLLIQASEAKAQNALAAQKISECVKAQSLRNDFCGNGTHVLSIP

QLAPNGVLFIHYAYTPTEYAFVQTSAGLCHNGTGYAPRQGMFVLPNNTNM

WHFTTMQFYNPVNISASNTQVLTSCSVNYTSVNYTVLEPSVPGDYDFQKE

-continued
FDKFYKNLSTIFNNTFNPNDFNFSTVDVTAQIKSLHDVVNQLNQSFIDLK

KLNVYEKGGYIPEAPRDGQAYVRKDGEWVLLSTF

In some embodiments, the recombinant HKU9-CoV S ectodomain trimer comprises protomers comprising the ectodomain sequence of SEQ ID NO: 13. In some embodiments, the recombinant HKU9-CoV S ectodomain trimer comprises protomers comprising residues 15-1207 of SEQ ID NO: 13 or residues 15-1234 of SEQ ID NO: 32. In some embodiments, the recombinant HKU9-CoV S ectodomain trimer comprises protomers comprising an ectodomain sequence at least 90% identical to the ectodomain sequence of SEQ ID NO: 13, wherein the HKU9-CoV S ectodomain trimer is stabilized in the prefusion conformation and comprises the "2P" substitution and/or modifications to remove the S1/S2 cleavage site and the S2' cleavage site of the protomers. In some embodiments, the recombinant HKU9-CoV S ectodomain trimer comprises protomers comprising an amino acid sequence at least 90% identical to residues 15-1207 of SEQ ID NO: 13 or residues 15-1234 of SEQ ID NO: 32, wherein the HKU9-CoV S ectodomain trimer is stabilized in the prefusion conformation and comprises the "2P" substitution and/or modifications to remove the S1/S2 cleavage site and the S2' cleavage site of the protomers.

E. OC43-CoV

In some embodiments, the immunogen comprises a recombinant OC43-CoV S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions that stabilize the OC43-CoV S ectodomain trimer in the prefusion conformation are located between residues 1062-1082 (such as between residues 1072-1082 or between residues 1077-1082) of the S ectodomain protomers in the trimer. In some embodiments, the OC43-CoV S ectodomain trimer is stabilized in the prefusion conformation by A1079P and L1080P substitutions ("2P") in the S ectodomain protomers in the trimer. The amino acid numbering for OC43-CoV S proteins is with reference to the OC43-CoV S sequence provided as SEQ ID NO: 10.

In some embodiments, the recombinant OC43-CoV S ectodomain trimer stabilized in the prefusion conformation comprises single-chain S ectodomain protomers comprising mutations to the S1/S2 and/or S2' protease cleavage sites to prevent protease cleavage at these sites.

In some embodiments, the protomers of the recombinant OC43-CoV S ectodomain trimer stabilized in the prefusion conformation by the one or more proline substitutions (such as A1079P and L1080P substitutions) comprise additional modifications for stabilization in the prefusion conformation.

With reference to the OC43-CoV S protein sequence provided as SEQ ID NO: 10, the ectodomain of the OC43-CoV S protein includes about residues 15-1301. Residues 1-14 are the signal peptide, which is removed during cellular processing. The S1/S2 cleavage site is located at about position 767/768. The S2' cleavage site is located at about position 912/913. The HR1 is located at about residues 1008-1076. The central helix is located at about residues 1081-1122. The HR2 is located at about 1257-1287. The C-terminal end of the S2 ectodomain is located at about residue 1301. In some embodiments, the protomers of the prefusion-stabilized OC43-CoV S ectodomain trimer can have a C-terminal residue (which can be linked to a trimerization domain, or a transmembrane domain, for example) of the C-terminal residue of the HR2 (e.g., position 1287), or the ectodomain (e.g., position 1301), or from one of positions 1287-1301. The position numbering of the S protein may vary between OC43-CoV stains, but the sequences can be aligned to determine relevant structural domains and cleavage sites. It will be appreciated that a few residues (such as up to 10) on the N and C-terminal ends of the ectodomain can be removed or modified in the disclosed immunogens without decreasing the utility of the S ectodomain trimer as an immunogen.

Exemplary OC43-CoV S protein sequences are provided below. The prefusion stabilizing substitutions disclosed herein (and other modifications, such as substitutions to generate a single chain) can be incorporated into OC43-CoV S protein sequences.

An exemplary sequence of OC43-CoV S protein (including the ectodomain and TM and CT domains) is provided as GenBank GI: 744516696, incorporated by reference herein. Another exemplary sequence of OC43-CoV S protein is provided as GenBank GI:549302, incorporated by reference herein):

```
                                          (SEQ ID NO: 10)
MFLILLISLPTAFAVIGDLKCPLDSRTGSLNNIDTGPPSISTATVDVTNG
LGTYYVLDRVYLNTTLFLNGYYPTSGSTYRNMALKGTDKLSTLWFKPPFL
SDFINGIFAKVKNTKVFKDGVMYSEFPAITIGSTFVNTSYSVVVQPRTIN
STQDGVNKLQGLLEVSVCQYNMCEYPHTICHPKLGNHFKELWHMDTGVVS
CLYKRNFTYDVNATYLYFHFYQEGGTFYAYFTDTGVVTKFLFNVYLGMAL
SHYYVMPLTCISRRDIGFTLEYWVTPLTSRQYLLAFNQDGIIFNAVDCMS
DFMSEIKCKTQSIAPPTGVYELNGYTVQPIADVYRRKPDLPNCNIEAWLN
DKSVPSPLNWERKTFSNCNFNMSSLMSFIQADSFTCNNIDAAKIYGMCFS
SITIDKFAIPNGRKVDLQLGNLGYLQSFNYRIDTTATSCQLYYNLPAANV
SVSRENPSTWNKRFGFIENSVFKPQPAGVLTNHDVVYAQHCFKAPKNFCP
CKLNSSLCVGSGPGKNNGIGTCPAGTNYLTCHNLCNPDPITFTGPYKCPQ
TKSLVGIGEHCSGLAVKSDYCGGNPCTCQPQAFLGWSADSCLQGDKCNIF
ANLILHDVNSGLTCSTDLQKANTDIKLGVCVNYDLYGISGQGIFVEVNAT
YYNSWQNLLYDSNGNLYGERDYITNRTFMIRSCYSGRVSAAFHANSSEPA
LLFRNIKCNYVENNSLIRQLQPINYFDSYLGCVVNAYNSTAISVQTCDLT
VGSGYCVDYSKNRRSRRAITTGYRFTNFEPFTVNSVNDSLEPVGGLYEIQ
IPSEFTIGNMEEFIQTSSPKVTIDCAAFVCGDYAACKSQLVEYGSFCDNI
NAILTEVNELLDTTQLQVANSLMNGVTLSTKLKDGVNFNVDDINFSSVLG
CLGSECSKASSRSAIEDLLEDKVKLSDVGFVAAYNNCTGGAEIRDLICVQ
SYKGIKVLPPLLSENQISGYTLAATSASLFPPWTAAAGVPFYLNVQYRIN
GLGVTMDVLSQNQKLIANAFNNALDAIQEGFDATNSALVKIQAVVNANAE
ALNNLLQQLSNRFGAISSSLQEILSRLDALEAEAQIDRLINGRLTALNAY
VSQQLSDSTLVKFSAAQAMEKVNECVKSQSSRINFCGNGNHIISLVQNAP
YGLYFIHFSYVPTKYVTAKVSPGLCIAGDRGIAPKSGYFVNVNNTWMYTG
SGYYYPEPITENNVVVMSTCAVNYTKAPYVMLNTSTPNLPDFREELDQWF
KNQTSVAPDLSLDYINVTFLDLQVEMNRLQEAIKVLNQSYINLKDIGTYE
YYVKWPWYVWLLIGLAGVAMLVLLFFICCCTGCGTSCFKKCGGCCDDYTG
YQELVIKTSHDD
```

An exemplary sequence of OC43-CoV S ectodomain including a double proline substitution for stabilization in the prefusion conformation is provided as SEQ ID NO: 11, which also includes mutations to eliminate the S1/S2 cleavage site:

```
MFLILLISLPTAFAVIGDLKCPLDSRTGSLNNIDTGPPSISTATVDVTNG
LGTYYVLDRVYLNTTLFLNGYYPTSGSTYRNMALKGTDKLSTLWFKPPFL
SDFINGIFAKVKNTKVFKDGVMYSEFPAITIGSTFVNTSYSVVVQPRTIN
STQDGVNKLQGLLEVSVCQYNMCEYPHTICHPKLGNHFKELWHMDTGVVS
CLYKRNFTYDVNATYLYFHFYQEGGTFYAYFTDTGVVTKFLFNVYLGMAL
SHYYVMPLICISRRDIGFTLEYWVTPLTSRQYLLAFNQDGIIFNAVDCMS
DFMSEIKCKTQSIAPPTGVYELNGYTVQPIADVYRRKPDLPNCNIEAWLN
DKSVPSPLNWERKTFSNCNFNMSSLMSFIQADSFTCNNIDAAKIYGMCFS
SITIDKFAIPNGRKVDLQLGNLGYLQSFNYRIDTTATSCQLYYNLPAANV
SVSRFNPSTWNKRFGFIENSVFKPQPAGVLTNHDVVYAQHCFKAPKNFCP
CKLNSSLCVGSGPGKNNGIGTCPAGTNYLTCHNLCNPDPITFTGPYKCPQ
TKSLVGIGEHCSGLAVKSDYCGGNPCTCQPQAFLGWSADSCLQGDKCNIF
ANLILHDVNSGLTCSTDLQKANTDIKLGVCVNYDLYGISGQGIFVEVNAT
YYNSWQNLLYDSNGNLYGFRDYITNRTFMIRSCYSGRVSAAFHANSSEPA
LLERNIKCNYVENNSLIRQLQPINYFDSYLGCVVNAYNSTAISVQTCDLT
VGSGYCVDYSKNGGSGSAITTGYRFTNFEPFTVNSVNDSLEPVGGLYEIQ
IPSEFTIGNMEEFIQTSSPKVTIDCAAFVCGDYAACKSQLVEYGSFCDNI
NAILTEVNELLDTTQLQVANSLMNGVTLSTKLKDGVNFNVDDINFSSVLG
CLGSECSKASSRSAIEDLLFDKVKLSDVGFVAAYNNCTGGAEIRDLICVQ
SYKGIKVLPPLLSENQISGYTLAATSASLFPPWTAAAGVPFYLNVQYRIN
GLGVTMDVLSQNQKLIANAFNNALDAIQEGFDAINSALVKIQAVVNANAE
ALNNLLQQLSNRFGAISSSLQEILSRLDPPEAEAQIDRLINGRLTALNAY
VSQQLSDSTLVKFSAAQAMEKVNECVKSQSSRINFCGNGNHIISLVQNAP
YGLYFIHFSYVPTKYVTAKVSPGLCIAGDRGIAPKSGYFVNVNNTWMYTG
SGYYYPEPITENNVVVMSTCAVNYTKAPYVMLNTSTPNLPDFREELDQWF
KNQTSVAPDLSLDYINVTFLDLQVEMNRLQEAIKVLN
```

A C-terminal trimerization domain can be added to the protomers of the OC43-CoV S ectodomains trimer to promote trimerization of the ectodomain.

An exemplary sequence of OC43-CoV S ectodomain including a double proline substitution for stabilization in the prefusion conformation, mutations to eliminate the S1/S2 cleavage site, and a T4 fibritin trimerization domain is provided as SEQ ID NO: 33:

MFLILLISLPTAFAVIGDLKCPLDSRTGSLNNIDTGPPSISTATVDVTNG

LGTYYVLDRVYLNTTLFLNGYYPTSGSTYRNMALKGTDKLSTLWFKPPFL

SDFINGIFAKVKNTKVFKDGVMYSEFPAITIGSTFVNTSYSVVVQPRTIN

STQDGVNKLQGLLEVSVCQYNMCEYPHTICHPKLGNHFKELWHMDTGVVS

CLYKRNFTYDVNATYLYFHFYQEGGTFYAYFTDTGVVTKFLFNVYLGMAL

SHYYVMPLTCISRRDIGFTLEYWVTPLTSRQYLLAFNQDGIIFNAVDCMS

DFMSEIKCKTQSIAPPTGVYELNGYTVQPIADVYRRKPDLPNCNIEAWLN

DKSVPSPLNWERKTFSNCNFNMSSLMSFIQADSFTCNNIDAAKIYGMCFS

SITIDKFAIPNGRKVDLQLGNLGYLQSFNYRIDTTATSCQLYYNLPAANV

SVSRENPSTWNKRFGFIENSVFKPQPAGVLTNHDVVYAQHCFKAPKNFCP

CKLNSSLCVGSGPGKNNGIGTCPAGTNYLTCHNLCNPDPITFTGPYKCPQ

TKSLVGIGEHCSGLAVKSDYCGGNPCTCQPQAFLGWSADSCLQGDKCNIF

ANLILHDVNSGLTCSTDLQKANTDIKLGVCVNYDLYGISGQGIFVEVNAT

YYNSWQNLLYDSNGNLYGERDYITNRTFMIRSCYSGRVSAAFHANSSEPA

LLERNIKCNYVENNSLIRQLQPINYFDSYLGCVVNAYNSTAISVQTCDLT

VGSGYCVDYSKNGGSGSAITTGYRFTNFEPFTVNSVNDSLEPVGGLYEIQ

IPSEFTIGNMEEFIQTSSPKVTIDCAAFVCGDYAACKSQLVEYGSFCDNI

NAILTEVNELLDTTQLQVANSLMNGVTLSTKLKDGVNFNVDDINFSSVLG

CLGSECSKASSRSAIEDLLFDKVKLSDVGFVAAYNNCTGGAEIRDLICVQ

SYKGIKVLPPLLSENQISGYTLAATSASLFPPWTAAAGVPFYLNVQYRIN

GLGVTMDVLSQNQKLIANAFNNALDAIQEGFDANSALVKIQAVVNANAEA

LNNLLQQLSNRFGAISSSLQEILSRLDPPEAEAQIDRLINGRLTALNAYV

SQQLSDSTLVKFSAAQAMEKVNECVKSQSSRINFCGNGNHIISLVQNAPY

GLYFIHFSYVPTKYVTAKVSPGLCIAGDRGIAPKSGYFVNVNNTWMYTG

SGYYYPEPITENNVVVMSTCAVNYTKAPYVMLNTSTPNLPDFREELDQW

FKNQTSVAPDLSLDYINVTFLDLQVEMNRLQEAIKVLNGGYIPEAPRDG

QAYVRKDGEWVLLSTF

In some embodiments, the recombinant OC43-CoV S ectodomain trimer comprises protomers comprising the ectodomain sequence of SEQ ID NO: 11. In some embodiments, the recombinant OC43-CoV S ectodomain trimer comprises protomers comprising residues 15-1287 of SEQ ID NO: 11 or residues 15-1314 of SEQ ID NO: 33. In some embodiments, the recombinant OC43-CoV S ectodomain trimer comprises protomers comprising an ectodomain sequence at least 90% identical to the ectodomain sequence of SEQ ID NO: 11 or residues 15-1314 of SEQ ID NO: 33, wherein the OC43-CoV S ectodomain trimer is stabilized in the prefusion conformation and comprises the "2P" substitution and/or modifications to remove the S1/S2 cleavage site and the S2' cleavage site of the protomers. In some embodiments, the recombinant OC43-CoV S ectodomain trimer comprises protomers comprising an amino acid sequence at least 90% identical to residues 15-1287 of SEQ ID NO: 11, wherein the OC43-CoV S ectodomain trimer is stabilized in the prefusion conformation and comprises the "2P" substitution and/or modifications to remove the S1/S2 cleavage site and the S2' cleavage site of the protomers.

F. WIV1-CoV

In some embodiments, the immunogen comprises a recombinant WIV1-CoV S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions that stabilize the WIV1-CoV S ectodomain trimer in the prefusion conformation are located between residues 952 to 972 (such as between residues 962 to 972 or between residues 967 to 972) of the S ectodomain protomers in the trimer. In some embodiments, the WIV1-CoV S ectodomain trimer is stabilized in the prefusion conformation by K969P and V970P substitutions ("2P") in the S ectodomain protomers in the trimer. The amino acid numbering for WIV1-CoV S proteins is with reference to the WIV1-CoV S sequence provided as SEQ ID NO: 14.

In some embodiments, the recombinant WIV1-CoV S ectodomain trimer stabilized in the prefusion conformation comprises single-chain S ectodomain protomers comprising mutations to the S1/S2 and/or S2' protease cleavage sites to prevent protease cleavage at these sites.

In some embodiments, the protomers of the recombinant WIV1-CoV S ectodomain trimer stabilized in the prefusion conformation by the one or more proline substitutions (such as K969P and V970P substitutions) comprises additional modifications for stabilization in the prefusion conformation.

With reference to the WIV1-CoV S protein sequence provided as SEQ ID NO: 14, the ectodomain of the WIV1-CoV S protein includes about residues 16-1191. Residues 1-15 are the signal peptide, which is removed during cellular processing. The S 1/S2 cleavage site is located at about position 668/669. The S2' cleavage site is located at about position 798/799. The HR1 is located at about residues 898-996. The central helix is located at about residues 971-1012. The HR2 is located at about 1146-1177. The C-terminal end of the S2 ectodomain is located at about residue 1191. In some embodiments, the protomers of the prefusion-stabilized WIV1-CoV S ectodomain trimer can have a C-terminal residue (which can be linked to a trimerization domain, or a transmembrane domain, for example) of the C-terminal residue of the HR2 (e.g., position 1177), or the ectodomain (e.g., position 1191), or from one of positions 1177-1191. The position numbering of the S protein may vary between WIV1-CoV stains, but the sequences can be aligned to determine relevant structural domains and cleavage sites. It will be appreciated that a few residues (such as up to 10) on the N and C-terminal ends of the ectodomain can be removed or modified in the disclosed immunogens without decreasing the utility of the S ectodomain trimer as an immunogen.

Exemplary WIV1-CoV S protein sequences are provided below. The prefusion stabilizing substitutions disclosed herein (and other modifications, such as substitutions to generate a single chain) can be incorporated into WIV1-CoV S protein sequences.

An exemplary sequence of WIV1-CoV S protein (including the ectodomain and TM and CT domains) is provided as SEQ ID NO: 14 (GenBank GI: 556015140, incorporated by reference herein):

MKLLVLVFATLVSSYTIEKCLDFDDRTPPANTQFLSSHRGVYYPDDIFRS
NVLHLVQDHELPEDSNVTRFITFGLNEDNPIIPFKDGIYFAATEKSNVIR
GWVFGSTMNNKSQSVIIMNNSTNLVIRACNFELCDNPFFVVLKSNNTQIP
SYIFNNAFNCTFEYVSKDENLDLGEKPGNFKDLREFVFRNKDGFLHVYSG
YQPISAASGLPTGFNALKPIFKLPLGINITNFRTLLTAFPPRPDYWGTSA
AAYFVGYLKPTTEMLKYDENGTITDAVDCSQNPLAELKCSVKSFEIDKGI
YQTSNERVAPSKEVVRFPNITNLCPFGEVFNATTFPSVYAWERKRISNCV
ADYSVLYNSTSFSTFKCYGVSATKLNDLCFSNVYADSFVVKGDDVRQIAP
GQTGVIADYNYKLPDDFTGCVLAWNTRNIDATQTGNYNYKYRSLRHGKLR
PFERDISNVPFSPDGKPCTPPAFNCYWPLNDYGFYITNGIGYQPYRVVVL
SFELLNAPATVCGPKLSTDLIKNQCVNFNENGLTGTGVLTPSSKRFQPFQ
QFGRDVSDETDSVRDPKTSEILDISPCSFGGVSVITPGTNTSSEVAVLYQ
DVNCTDVPVAIHADQLTPSWRVHSTGNNVFQTQAGCLIGAEHVDTSYECD
IPIGAGICASYHTVSSLRSTSQKSIVAYTMSLGADSSIAYSNNTIAIPTN
FSISITTEVMPVSMAKTSVDCNMYICGDSTECANLLLQYGSFCTQLNRAL
SGIAVEQDRNTREVFAQVKQMYKTPTLKDFGGFNFSQILPDPLKPTKRSF
IEDLLFNKVTLADAGFMKQYGECLGDINARDLICAQKENGLTVLPPLLTD
DMIAAYTAALVSGTATAGWTFGAGAALQIPFAMQMAYRENGIGVTQNVLY
ENQKQIANQFNKAISQIQESLITTSTALGKLQDVVNQNAQALNTLVKQLS
SNFGAISSVLNDILSRLDKVEAEVQIDRLITGRLQSLQTYVTQQLIRAAE
IRASANLAATKMSECVLGQSKRVDFCGKGYHLMSFPQAAPHGVVFLHVTY
VPSQERNFTTAPAICHEGKAYFPREGVFVENGTSWFITQRNFFSPQIITT
DNTFVSGSCDVVIGIINNTVYDPLQPELDSFKEELDKYFKNHTSPDVDLG
DISGINASVVNIQKEIDRLNEVAKNLNESLIDLQELGKYEQYIKWPWYVW
LGFIAGLIAIVMVTILLCCMTSCCSCLKGACSCGSCCKFDEDDSEPVLKG
VKLHYT

An exemplary sequence of WIV1-CoV S protein including a double proline substitution for stabilization in the prefusion conformation is provided as SEQ ID NO: 15:

MKLLVLVFATLVSSYTIEKCLDFDDRTPPANTQFLSSHRGVYYPDDIFRS
NVLHLVQDHELPEDSNVTRFITFGLNEDNPIIPFKDGIYFAATEKSNVIR
GWVFGSTMNNKSQSVIIMNNSTNLVIRACNFELCDNPFFVVLKSNNTQIP
SYIFNNAFNCTFEYVSKDENLDLGEKPGNFKDLREFVFRNKDGFLHVYSG
YQPISAASGLPTGFNALKPIFKLPLGINITNFRTLLTAFPPRPDYWGTSA
AAYFVGYLKPTTFMLKYDENGTITDAVDCSQNPLAELKCSVKSFEIDKGI
YQTSNFRVAPSKEVVRFPNITNLCPFGEVENATTFPSVYAWERKRISNCV
ADYSVLYNSTSFSTFKCYGVSATKLNDLCFSNVYADSFVVKGDDVRQIAP
GQTGVIADYNYKLPDDFTGCVLAWNTRNIDATQTGNYNYKYRSLRHGKLR
PFERDISNVPFSPDGKPCTPPAFNCYWPLNDYGFYITNGIGYQPYRVVVL
SFELLNAPATVCGPKLSTDLIKNQCVNFNFNGLTGTGVLTPSSKRFQPFQ
QFGRDVSDETDSVRDPKTSEILDISPCSFGGVSVITPGTNTSSEVAVLYQ
DVNCTDVPVAIHADQLTPSWRVHSTGNNVFQTQAGCLIGAEHVDTSYECD
IPIGAGICASYHTVSSLRSTSQKSIVAYTMSLGADSSIAYSNNTIAIPTN
FSISITTEVMPVSMAKTSVDCNMYICGDSTECANLLLQYGSFCTQLNRAL
SGIAVEQDRNTREVFAQVKQMYKTPTLKDFGGFNFSQILPDPLKPTKRSF
IEDLLENKVTLADAGFMKQYGECLGDINARDLICAQKENGLTVLPPLLTD
DMIAAYTAALVSGTATAGWTFGAGAALQIPFAMQMAYRFNGIGVTQNVLY
ENQKQIANQFNKAISQIQESLTTTSTALGKLQDVVNQNAQALNTLVKQLS
SNFGAISSVLNDILSRLDPPEAEVQIDRLITGRLQSLQTYVTQQLIRAAE
IRASANLAATKMSECVLGQSKRVDFCGKGYHLMSFPQAAPHGVVFLHVTY
VPSQERNFTTAPAICHEGKAYFPREGVFVENGTSWFITQRNFFSPQIITT
DNTFVSGSCDVVIGIINNTVYDPLQPELDSFKEELDKYFKNHTSPDVDLG
DISGINASVVNIQKEIDRLNEVAKNLNESLIDLQELGKYEQ

A C-terminal trimerization domain can be added to the protomers of the WIV1-CoV S ectodomains trimer to promote trimerization of the ectodomain.

An exemplary sequence of WIV1-CoV S protein including a double proline substitution for stabilization in the prefusion conformation, and a T4 fibritin trimerization domain is provided as SEQ ID NO: 34:

MKLLVLVFATLVSSYTIEKCLDEDDRTPPANTQFLSSHRGVYYPDDIFRS
NVLHLVQDHFLPFDSNVTRFITFGLNFDNPIIPFKDGIYFAATEKSNVIR
GWVFGSTMNNKSQSVIIMNNSTNLVIRACNFELCDNPFFVVLKSNNTQIP
SYIFNNAFNCTFEYVSKDENLDLGEKPGNFKDLREFVERNKDGFLHVYSG
YQPISAASGLPTGFNALKPIFKLPLGINITNFRTLLTAFPPRPDYWGTSA
AAYFVGYLKPTTFMLKYDENGTITDAVDCSQNPLAELKCSVKSFEIDKGI
YQTSNFRVAPSKEVVREPNITNLCPFGEVENATTFPSVYAWERKRISNCV
ADYSVLYNSTSFSTFKCYGVSATKLNDLCFSNVYADSFVVKGDDVRQIAP
GQTGVIADYNYKLPDDFTGCVLAWNTRNIDATQTGNYNYKYRSLRHGKLR
PFERDISNVPFSPDGKPCTPPAFNCYWPLNDYGFYITNGIGYQPYRVVVL
SFELLNAPATVCGPKLSTDLIKNQCVNFNFNGLTGTGVLTPSSKRFQPFQ
QFGRDVSDFTDSVRDPKTSEILDISPCSFGGVSVITPGTNTSSEVAVLYQ
DVNCTDVPVAIHADQLTPSWRVHSTGNNVFQTQAGCLIGAEHVDTSYECD
IPIGAGICASYHTVSSLRSTSQKSIVAYTMSLGADSSIAYSNNTIAIPTN
FSISITTEVMPVSMAKTSVDCNMYICGDSTECANLLLQYGSFCTQLNRAL
SGIAVEQDRNTREVFAQVKQMYKTPTLKDFGGFNFSQILPDPLKPTKRSF
IEDLLFNKVTLADAGFMKQYGECLGDINARDLICAQKENGLTVLPPLLTD
DMIAAYTAALVSGTATAGWTFGAGAALQIPFAMQMAYRFNGIGVTQNVLY

-continued

ENQKQIANQFNKAISQIQESLTTTSTALGKLQDVVNQNAQALNTLVKQLS

SNFGAISSVLNDILSRLDPPEAEVQIDRLITGRLQSLQTYVTQQLIRAAE

IRASANLAATKMSECVLGQSKRVDFCGKGYHLMSFPQAAPHGVVFLHVTY

VPSQERNFTTAPAICHEGKAYFPREGVFVENGTSWFITQRNFFSPQIITT

DNTFVSGSCDVVIGIINNTVYDPLQPELDSFKEELDKYFKNHTSPDVDLG

DISGINASVVNIQKEIDRLNEVAKNLNESLIDLQELGKYEQGGYIPEAPR

DGQAYVRKDGEWVLLSTF

In some embodiments, the recombinant WIV1-CoV S ectodomain trimer comprises protomers comprising the ectodomain sequence of SEQ ID NO: 15. In some embodiments, the recombinant WIV1-CoV S ectodomain trimer comprises protomers comprising residues 16-1191 of SEQ ID NO: 15 or residues 16-1218 of SEQ ID NO: 34. In some embodiments, the recombinant WIV1-CoV S ectodomain trimer comprises protomers comprising an ectodomain sequence at least 90% identical to the ectodomain sequence of SEQ ID NO: 15, wherein the WIV1-CoV S ectodomain trimer is stabilized in the prefusion conformation and comprises the "2P" substitution and/or modifications to remove the S1/S2 cleavage site and the S2' cleavage site of the protomers. In some embodiments, the recombinant WIV1-CoV S ectodomain trimer comprises protomers comprising an amino acid sequence at least 90% identical to residues 16-1191 of SEQ ID NO: 15 or residues 16-1218 of SEQ ID NO: 34, wherein the WIV1-CoV S ectodomain trimer is stabilized in the prefusion conformation and comprises the "2P" substitution and/or modifications to remove the S1/S2 cleavage site and the S2' cleavage site of the protomers.

G. MHV-CoV

In some embodiments, the immunogen comprises a recombinant MHV-CoV S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions that stabilize the MHV-CoV S ectodomain trimer in the prefusion conformation are located between residues 852 to 872 (such as between residues 862 to 872 or between residues 867 to 872) of the S ectodomain protomers in the trimer. In some embodiments, the MHV-CoV S ectodomain trimer is stabilized in the prefusion conformation by I869P and I870P substitutions ("2P") in the S ectodomain protomers in the trimer. The amino acid numbering for MHV-CoV S proteins is with reference to the MHV-CoV S sequence provided as SEQ ID NO: 16.

In some embodiments, the recombinant MHV-CoV S ectodomain trimer stabilized in the prefusion conformation comprises single-chain S ectodomain protomers comprising mutations to the S1/S2 and/or S2' protease cleavage sites to prevent protease cleavage at these sites.

In some embodiments, the protomers of the recombinant MHV-CoV S ectodomain trimer stabilized in the prefusion conformation by the one or more proline substitutions (such as I869P and I870P substitutions) comprises additional modifications for stabilization in the prefusion conformation.

With reference to the MHV-CoV S protein sequence provided as SEQ ID NO: 16, the ectodomain of the MHV-CoV S protein includes about residues 15-1297. Residues 1-14 are the signal peptide, which is removed during cellular processing. The S1/S2 cleavage site is located at about position 757/758. The S2' cleavage site is located at about position 906/907. The HR1 is located at about residues 1002-1070. The central helix is located at about residues 1075-1116. The HR2 is located at about 1252-1283. The C-terminal end of the S2 ectodomain is located at about residue 1297. In some embodiments, the protomers of the prefusion-stabilized MHV-CoV S ectodomain trimer can have a C-terminal residue (which can be linked to a trimerization domain, or a transmembrane domain, for example) of the C-terminal residue of the HR2 (e.g., position 1283), or the ectodomain (e.g., position 1297), or from one of positions 1283-1297. The position numbering of the S protein may vary between MHV-CoV stains, but the sequences can be aligned to determine relevant structural domains and cleavage sites. It will be appreciated that a few residues (such as up to 10) on the N and C-terminal ends of the ectodomain can be removed or modified in the disclosed immunogens without decreasing the utility of the S ectodomain trimer as an immunogen.

Exemplary MHV-CoV S protein sequences are provided below. The prefusion stabilizing substitutions disclosed herein (and other modifications, such as substitutions to generate a single chain) can be incorporated into MHV-CoV S protein sequences.

An exemplary sequence of MHV-CoV S protein (including the ectodomain and TM and CT domains) is provided as SEQ ID NO: 16 (GenBank GI:328496819, incorporated by reference herein). Another exemplary MHV-CoV sequence is provided as GenBank GI:81971726, incorporated by reference herein:

MLSVFILFLPSCLGYIGDFRCINLVNTDTSNASAPSVSTEVVDVSKGIGT

YYVLDRVYLNATLLLTGYYPVDGSNYRNLALTGTNTLSLNWYKPPFLSEF

NDGIFAKVKNLKASLPKDSTSYFPTIVIGSNFVTTSYTVVLEPYNGIIMA

SICQYTICLLPYTDCKPNTGGNKLIGFWHIDLKSPVCILKRNFTENVNAD

WLYFHFYQQGGTFYAYYADAGSATTFLESSYIGDVLIQYFVLPFVCTPTT

TGVFSPQYWVTPLVKRQYLFNFNQKGTITSAVDCASSYTSEIKCKTQSMN

PNTGVYDLSGYTVQPVGLVYRRVRNLPDCRIEDWLAAKTVPSPLNWERKT

FQNCNFNLSSLLRLVQAGSLSCSNIDAAKVYGMCFGSMSIDKFAIPNSRR

VDLQLGNSGFLQSFNYKIDTRATSCQLYYSLAQSNVTVNNHNPSSWNRRY

GENDVATFGRGKHDVAYAEACFTVGASYCPCANPSIVSPCTTGKPKFANC

PTGTTNRECNVLALGSNLFKCDCTCNPSPLTTYDLRCLQGRSMLGVGDHC

EGLGVLEDKCGGSNTCNCSADAFVGWAKDSCLSNGRCHIFSNLMLNGINS

GTTCSTDLQLPNTEVVTGICVKYDLYGITGQGVFKEVKADYYNSWQNLLY

DVNGNLNGFRDIVINKTYLTRSCYSGRVSAAYHQDAPEPALLYRNLKCDY

VENNNIFREETPLNYEDSYLGCVVNADNSTEQAVDACDLRMGSGLCVNYS

TAHRARTSVSTGYKLTTFEPFTVSIVNDSVESVGGLYEMQIPTNFTIASH

QEFIQTRAPKVTIDCAAFVCGDYTTCRQQLVEYGSFCDNINAILGEVNNL

IDTMQLQVASALIQGVTLSSRLADGISGQIDDINFSPLLGCLGSQCSEGT

MAAQGRSTVEDLLFDKVKLSDVGFVEAYNNCTGGQEVRDLLCVQSENGIK

VLPPVLSENQVSGYTAGATASSMFPPWSAAAGVPFSLSVQYRINGLGVTM

NVLSENQKMIASAFNNAIGAIQEGFDATNSALAKIQSVVNANAEALNNLL

NQLSNRFGAISASLQEILSRLDALEAQAQIDRLINGRLTALNAYVSKQLS

DMTLIKVSAAQAIEKVNECVKSQSPRINFCGNGNHILSLVQNAPYGLYFL

HFSYVPTSFTTANVSPGLCISGDRGLAPKAGYFVQDDGEWKFTGSNYYYP

EPITDKNSVVMSSCAVNYTKAPEVFLNTSISNLPDFKEELDKWFKNQTSV

APDLSLDFEKLNVTFLDLSDEMNRIQEAIKKLNESYINLKEIGTYEMYVK

WPWYVWLLIGLAGVAVCVLLFFICCCTGCGSCCFKKCGNCCDEYGGHQDS

IVIHNISSHED

An exemplary sequence of MHV-CoV S ectodomain including a double proline substitution for stabilization in the prefusion conformation is provided as SEQ ID NO: 17:

MLSVFILFLPSCLGYIGDFRCINLVNTDTSNASAPSVSTEVVDVSKGIGT

YYVLDRVYLNATLLLTGYYPVDGSNYRNLALIGTNTLSLNWYKPPFLSEF

NDGIFAKVKNLKASLPKDSTSYFPTIVIGSNFVTTSYTVVLEPYNGIIMA

SICQYTICLLPYTDCKPNTGGNKLIGFWHIDLKSPVCILKRNFTENVNAD

WLYFHFYQQGGTFYAYYADAGSATTFLESSYIGDVLTQYFVLPFVCTPTT

TGVFSPQYWVTPLVKRQYLFNFNQKGTITSAVDCASSYTSEIKCKTQSMN

PNTGVYDLSGYTVQPVGLVYRRVRNLPDCRIEDWLAAKTVPSPLNWERKT

FQNCNFNLSSLLRLVQAGSLSCSNIDAAKVYGMCFGSMSIDKFAIPNSRR

VDLQLGNSGFLQSFNYKIDTRATSCQLYYSLAQSNVTVNNHNPSSWNRRY

GENDVATFGRGKHDVAYAEACFTVGASYCPCANPSIVSPCTTGKPKFANC

PTGTTNRECNVLALGSNLFKCDCTCNPSPLITYDLRCLQGRSMLGVGDHC

EGLGVLEDKCGGSNTCNCSADAFVGWAKDSCLSNGRCHIFSNLMLNGINS

GTTCSTDLQLPNTEVVTGICVKYDLYGITGQGVFKEVKADYYNSWQNLLY

DVNGNLNGFRDIVINKTYLTRSCYSGRVSAAYHQDAPEPALLYRNLKCDY

VENNNIFREETPLNYFDSYLGCVVNADNSTEQAVDACDLRMGSGLCVNYS

TAHRARTSVSTGYKLTTFEPFTVSIVNDSVESVGGLYEMQIPTNFTIASH

QEFIQTRAPKVTIDCAAFVCGDYTTCRQQLVEYGSFCDNINAILGEVNNL

IDTMQLQVASALIQGVTLSSRLADGISGQIDDINFSPLLGCLGSQCSEGT

MAAQGRSTVEDLLFDKVKLSDVGFVEAYNNCTGGQEVRDLLCVQSFNGIK

VLPPVLSENQVSGYTAGATASSMFPPWSAAAGVPFSLSVQYRINGLGVTM

NVLSENQKMIASAFNNAIGAIQEGFDATNSALAKIQSVVNANAEALNNLL

NQLSNRFGAISASLQEILSRLDPPEAQAQIDRLINGRLTALNAYVSKQLS

DMTLIKVSAAQAIEKVNECVKSQSPRINFCGNGNHILSLVQNAPYGLYFL

HFSYVPTSFTTANVSPGLCISGDRGLAPKAGYFVQDDGEWKFTGSNYYYP

EPITDKNSVVMSSCAVNYTKAPEVFLNTSISNLPDFKEELDKWFKNQTSV

APDLSLDFEKLNVTFLDLSDEMNRIQEAIKKLNESYINLKEIGTYEM

A C-terminal trimerization domain can be added to the protomers of the MHV-CoV S ectodomains trimer to promote trimerization of the ectodomain.

An exemplary sequence of MHV-CoV S ectodomain including a double proline substitution for stabilization in the prefusion conformation, and a T4 fibritin trimerization domain is provided as SEQ ID NO: 35:

MLSVFILFLPSCLGYIGDFRCINLVNTDTSNASAPSVSTEVVDVSKGIGT

YYVLDRVYLNATLLLTGYYPVDGSNYRNLALTGTNTLSLNWYKPPFLSEF

NDGIFAKVKNLKASLPKDSTSYFPTIVIGSNFVTTSYTVVLEPYNGIIMA

SICQYTICLLPYTDCKPNTGGNKLIGFWHIDLKSPVCILKRNFTENVNAD

WLYFHFYQQGGTFYAYYADAGSATTFLFSSYIGDVLTQYEVLPFVCTPTT

TGVFSPQYWVTPLVKRQYLENFNQKGTITSAVDCASSYTSEIKCKTQSMN

PNTGVYDLSGYTVQPVGLVYRRVRNLPDCRIEDWLAAKTVPSPLNWERKT

FQNCNFNLSSLLRLVQAGSLSCSNIDAAKVYGMCFGSMSIDKFAIPNSRR

VDLQLGNSGFLQSFNYKIDTRATSCQLYYSLAQSNVTVNNHNPSSWNRRY

GENDVATFGRGKHDVAYAEACFTVGASYCPCANPSIVSPCTTGKPKFANC

PTGTTNRECNVLALGSNLFKCDCTCNPSPLTTYDLRCLQGRSMLGVGDHC

EGLGVLEDKCGGSNTCNCSADAFVGWAKDSCLSNGRCHIFSNLMLNGINS

GTTCSTDLQLPNTEVVTGICVKYDLYGITGQGVFKEVKADYYNSWQNLLY

DVNGNLNGFRDIVINKTYLTRSCYSGRVSAAYHQDAPEPALLYRNLKCDY

VENNNIFREETPLNYEDSYLGCVVNADNSTEQAVDACDLRMGSGLCVNYS

TAHRARTSVSTGYKLTTFEPFTVSIVNDSVESVGGLYEMQIPTNFTIASH

QEFIQTRAPKVTIDCAAFVCGDYTTCRQQLVEYGSFCDNINAILGEVNNL

IDTMQLQVASALIQGVTLSSRLADGISGQIDDINFSPLLGCLGSQCSEGT

MAAQGRSTVEDLLFDKVKLSDVGFVEAYNNCTGGQEVRDLLCVQSFNGIK

VLPPVLSENQVSGYTAGATASSMFPPWSAAAGVPFSLSVQYRINGLGVTM

NVLSENQKMIASAFNNAIGAIQEGFDATNSALAKIQSVVNANAEALNNLL

NQLSNRFGAISASLQEILSRLDPPEAQAQIDRLINGRLTALNAYVSKQLS

DMTLIKVSAAQAIEKVNECVKSQSPRINFCGNGNHILSLVQNAPYGLYFL

HFSYVPTSFTTANVSPGLCISGDRGLAPKAGYFVQDDGEWKFTGSNYYYP

EPITDKNSVVMSSCAVNYTKAPEVFLNTSISNLPDFKEELDKWFKNQTSV

APDLSLDFEKLNVTFLDLSDEMNRIQEAIKKLNESYINLKEIGTYEMGGY

IPEAPRDGQAYVRKDGEWVLLSTF

In some embodiments, the recombinant MHV-CoV S ectodomain trimer comprises protomers comprising the ectodomain sequence of SEQ ID NO: 17. In some embodiments, the recombinant MHV-CoV S ectodomain trimer comprises protomers comprising residues 15-1297 of SEQ ID NO: 17 or residues 15-1324 of SEQ ID NO: 35. In some embodiments, the recombinant MHV-CoV S ectodomain trimer comprises protomers comprising an ectodomain sequence at least 90% identical to the ectodomain sequence of SEQ ID NO: 17, wherein the MHV-CoV S ectodomain trimer is stabilized in the prefusion conformation and comprises the "2P" substitution and/or modifications to remove the S1/S2 cleavage site and the S2' cleavage site of the protomers. In some embodiments, the recombinant MHV-CoV S ectodomain trimer comprises protomers comprising an amino acid sequence at least 90% identical to residues 15-1297 of SEQ ID NO: 17 or residues 15-1324 of SEQ ID NO: 35, wherein the MHV-CoV S ectodomain trimer is stabilized in the prefusion conformation and comprises the "2P" substitution and/or modifications to remove the S1/S2 cleavage site and the S2' cleavage site of the protomers.

H. NL63-CoV

In some embodiments, the immunogen comprises a recombinant NL63-CoV S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions that stabilize the NL63-CoV S ectodomain trimer in the prefusion conformation are located between residues 1035 to 1055 (such as between residues 1045 to 1055 or between residues 1050 to 1055) of the S ectodomain protomers in the trimer. In some embodiments, the NL63-CoV S ectodomain trimer is stabilized in the prefusion conformation by S1052P and I1053P substitutions ("2P") in the S ectodomain protomers in the trimer. The amino acid numbering for NL63-CoV S proteins is with reference to the NL63-CoV S sequence provided as SEQ ID NO: 18.

In some embodiments, the recombinant NL63-CoV S ectodomain trimer stabilized in the prefusion conformation comprises single-chain S ectodomain protomers comprising mutations to the S1/S2 and/or S2' protease cleavage sites to prevent protease cleavage at these sites.

In some embodiments, the protomers of the recombinant NL63-CoV S ectodomain trimer stabilized in the prefusion conformation by the one or more proline substitutions (such as S1052P and I1053P substitutions) comprises additional modifications for stabilization in the prefusion conformation.

With reference to the NL63-CoV S protein sequence provided as SEQ ID NO: 18, the ectodomain of the NL63-CoV S protein includes about residues 16-1291. Residues 1-15 are the signal peptide, which is removed during cellular processing. The S 1/S2 cleavage site is located at about position 748/749. The S2' cleavage site is located at about position 870/871. The HR1 is located at about residues 967-1049. The central helix is located at about residues 1054-1095. The HR2 is located at about 1246-1272. The C-terminal end of the S2 ectodomain is located at about residue 1291. In some embodiments, the protomers of the prefusion-stabilized NL63-CoV S ectodomain trimer can have a C-terminal residue (which can be linked to a trimerization domain, or a transmembrane domain, for example) of the C-terminal residue of the HR2 (e.g., position 1277) or the ectodomain (e.g., position 1291), or from one of positions 1277-1291. The position numbering of the S protein may vary between NL63-CoV stains, but the sequences can be aligned to determine relevant structural domains and cleavage sites. It will be appreciated that a few residues (such as up to 10) on the N and C-terminal ends of the ectodomain can be removed or modified in the disclosed immunogens without decreasing the utility of the S ectodomain trimer as an immunogen.

Exemplary NL63-CoV S protein sequences are provided below. The prefusion stabilizing substitutions disclosed herein (and other modifications, such as substitutions to generate a single chain) can be incorporated into NL63-CoV S protein sequences.

An exemplary sequence of NL63-CoV S protein (including the ectodomain and TM and CT domains) is provided as SEQ ID NO: 18 (GenBank GI: 71153773, incorporated by reference herein):

MKLFLILLVLPLASCFFTCNSNANLSMLQLGVPDNSSTIVTGLLPTHWFC

ANQSTSVYSANGFFYIDVGNHRSAFALHTGYYDANQYYIYVTNEIGLNAS

VTLKICKFSRNTTFDFLSNASSSEDCIVNLLFTEQLGAPLGITISGETVR

LHLYNVTRTFYVPAAYKLTKLSVKCYFNYSCVFSVVNATVTVNVTTHNGR

VVNYTVCDDCNGYTDNIFSVQQDGRIPNGFPENNWELLINGSTLVDGVSR

LYQPLRLTCLWPVPGLKSSTGFVYFNATGSDVNCNGYQHNSVVDVMRYNL

NFSANSLDNLKSGVIVEKTLQYDVLFYCSNSSSGVLDTTIPFGPSSQPYY

CFINSTINTTHVSTFVGILPPTVREIVVARTGQFYINGFKYFDLGFIEAV

NFNVTTASATDFWTVAFATFVDVLVNVSATNIQNLLYCDSPFEKLQCEHL

QFGLQDGFYSANFLDDNVLPETYVALPIYYQHTDINFTATASFGGSCYVC

KPHQVNISLNGNTSVCVRTSHESIRYIYNRVKSGSPGDSSWHIYLKSGTC

PFSFSKLNNFQKFKTICFSTVEVPGSCNFPLEATWHYTSYTIVGALYVTW

SEGNSITGVPYPVSGIREFSNLVLNNCTKYNIYDYVGTGIIRSSNQSLAG

GITYVSNSGNLLGFKNVSIGNIFIVTPCNQPDQVAVYQQSIIGAMTAVNE

SRYGLQNLLQLPNFYYVSNGGNNCTTAVMTYSNFGICADGSLIPVRPRNS

SDNGISAIITANLSIPSNWTTSVQVEYLQITSTPIVVDCATYVCNGNPRC

KNLLKQYTSACKTIEDALRLSAHLETNDVSSMLTEDSNAFSLANVTSFGD

YNLSSVLPQRNIRSSRIAGRSALEDLLFSKVVTSGLGTVDVDYKSCTKGL

SIADLACAQYYNGIMVLPGVADAERMAMYTGSLIGGMVLGGLTSAAAIPF

SLALQARLNYVALQTDVLQENQKILAASENKAINNIVASFSSVNDAITQT

AEAIHTVTIALNKIQDVVNQQGSALNHLTSQLRHNFQAISNSIQAIYDRL

DSIQADQQVDRLITGRLAALNAFVSQVLNKYTEVRGSRRLAQQKINECVK

SQSNRYGFCGNGTHIFSIVNSAPDGLLFLHTVLLPTDYKNVKAWSGICVD

GIYGYVLRQPNLVLYSDNGVFRVTSRIMFQPRLPVLSDFVQIYNCNVTFV

NISRVELHTVIPDYVDVNKTLQEFAQNLPKYVKPNFDLTPFNLTYLNLSS

ELKQLEAKTASLFQTTVELQGLIDQINSTYVDLKLLNRFENYIKWPWWVW

LIISVVFVVLLSLLVFCCLSTGCCGCCNCLTSSMRGCCDCGSTKLPYYEF

EKVHVQ

An exemplary sequence of NL63-CoV S ectodomain including a double proline substitution for stabilization in the prefusion conformation is provided as SEQ ID NO: 19:

MKLFLILLVLPLASCFFTCNSNANLSMLQLGVPDNSSTIVTGLLPTHWFC

ANQSTSVYSANGFFYIDVGNHRSAFALHTGYYDANQYYIYVTNEIGLNAS

VTLKICKFSRNTTFDFLSNASSSFDCIVNLLFTEQLGAPLGITISGETVR

LHLYNVTRTFYVPAAYKLTKLSVKCYFNYSCVFSVVNATVTVNVTTHNGR

VVNYTVCDDCNGYTDNIFSVQQDGRIPNGFPENNWELLINGSTLVDGVSR

LYQPLRLTCLWPVPGLKSSTGFVYFNATGSDVNCNGYQHNSVVDVMRYNL

NFSANSLDNLKSGVIVEKTLQYDVLFYCSNSSSGVLDTTIPFGPSSQPYY

CFINSTINTTHVSTFVGILPPTVREIVVARTGQFYINGFKYFDLGFIEAV

NFNVTTASATDFWTVAFATFVDVLVNVSATNIQNLLYCDSPFEKLQCEHL

QFGLQDGFYSANFLDDNVLPETYVALPIYYQHTDINFTATASFGGSCYVC

KPHQVNISLNGNTSVCVRTSHFSIRYIYNRVKSGSPGDSSWHIYLKSGTC

PFSFSKLNNEQKFKTICFSTVEVPGSCNFPLEATWHYTSYTIVGALYVTW

SEGNSITGVPYPVSGIREFSNLVLNNCTKYNIYDYVGTGIIRSSNQSLAG

GITYVSNSGNLLGFKNVSIGNIFIVTPCNQPDQVAVYQQSIIGAMTAVNE

SRYGLQNLLQLPNFYYVSNGGNNCTTAVMTYSNFGICADGSLIPVRPRNS

SDNGISAIITANLSIPSNWTTSVQVEYLQITSTPIVVDCATYVCNGNPRC

KNLLKQYTSACKTIEDALRLSAHLETNDVSSMLTFDSNAFSLANVTSFGD

YNLSSVLPQRNIRSSRIAGRSALEDLLFSKVVTSGLGTVDVDYKSCTKGL

SIADLACAQYYNGIMVLPGVADAERMAMYTGSLIGGMVLGGLTSAAAIPF

SLALQARLNYVALQTDVLQENQKILAASENKAINNIVASFSSVNDAITQT

AEAIHTVTIALNKIQDVVNQQGSALNHLTSQLRHNFQAISNSIQAIYDRL

DPPQADQQVDRLITGRLAALNAFVSQVLNKYTEVRGSRRLAQQKINECVK

SQSNRYGFCGNGTHIFSIVNSAPDGLLFLHTVLLPTDYKNVKAWSGICVD

GIYGYVLRQPNLVLYSDNGVFRVTSRIMFQPRLPVLSDFVQIYNCNVTFV

NISRVELHTVIPDYVDVNKTLQEFAQNLPKYVKPNFDLTPFNLTYLNLSS

ELKQLEAKTASLFQTTVELQGLIDQINSTYVDLKLLNRFEN

A C-terminal trimerization domain can be added to the protomers of the NL63-CoV S ectodomains trimer to promote trimerization of the ectodomain.

An exemplary sequence of NL63-CoV S ectodomain including a double proline substitution for stabilization in the prefusion conformation, and a T4 fibritin trimerization domain is provided as SEQ ID NO: 36:

MKLFLILLVLPLASCFFTCNSNANLSMLQLGVPDNSSTIVTGLLPTHWFC

ANQSTSVYSANGFFYIDVGNHRSAFALHTGYYDANQYYIYVTNEIGLNAS

VTLKICKFSRNTTFDFLSNASSSFDCIVNLLFTEQLGAPLGITISGETVR

LHLYNVTRTFYVPAAYKLTKLSVKCYFNYSCVFSVVNATVTVNVTTHNGR

VVNYTVCDDCNGYTDNIFSVQQDGRIPNGFPFNNWFLLTNGSTLVDGVSR

LYQPLRLTCLWPVPGLKSSTGFVYFNATGSDVNCNGYQHNSVVDVMRYNL

NFSANSLDNLKSGVIVFKTLQYDVLFYCSNSSSGVLDTTIPFGPSSQPYY

CFINSTINTTHVSTFVGILPPTVREIVVARTGQFYINGFKYFDLGFIEAV

NFNVTTASATDFWTVAFATFVDVLVNVSATNIQNLLYCDSPFEKLQCEHL

QFGLQDGFYSANFLDDNVLPETYVALPIYYQHTDINFTATASFGGSCYVC

KPHQVNISLNGNTSVCVRTSHFSIRYIYNRVKSGSPGDSSWHIYLKSGTC

PFSFSKLNNFQKFKTICFSTVEVPGSCNFPLEATWHYTSYTIVGALYVTW

SEGNSITGVPYPVSGIREFSNLVLNNCTKYNIYDYVGTGIIRSSNQSLAG

GITYVSNSGNLLGFKNVSIGNIFIVTPCNQPDQVAVYQQSIIGAMTAVNE

SRYGLQNLLQLPNFYYVSNGGNNCTTAVMTYSNFGICADGSLIPVRPRNS

SDNGISAIITANLSIPSNWTTSVQVEYLQITSTPIVVDCATYVCNGNPRC

KNLLKQYTSACKTIEDALRLSAHLETNDVSSMLTEDSNAFSLANVTSFGD

YNLSSVLPQRNIRSSRIAGRSALEDLLFSKVVTSGLGTVDVDYKSCTKGL

SIADLACAQYYNGIMVLPGVADAERMAMYTGSLIGGMVLGGLTSAAAIPF

SLALQARLNYVALQTDVLQENQKILAASENKAINNIVASFSSVNDAITQT

AEAIHTVTIALNKIQDVVNQQGSALNHLTSQLRHNFQAISNSIQAIYDRL

DPPQADQQVDRLITGRLAALNAFVSQVLNKYTEVRGSRRLAQQKINECVK

SQSNRYGFCGNGTHIFSIVNSAPDGLLFLHTVLLPTDYKNVKAWSGICVD

GIYGYVLRQPNLVLYSDNGVFRVTSRIMFQPRLPVLSDFVQIYNCNVTFV

NISRVELHTVIPDYVDVNKTLQEFAQNLPKYVKPNFDLTPFNLTYLNLSS

ELKQLEAKTASLFQTTVELQGLIDQINSTYVDLKLLNRFENGGYIPEAPR

DGQAYVRKDGEWVLLSTF

In some embodiments, the recombinant NL63-CoV S ectodomain trimer comprises protomers comprising the ectodomain sequence of SEQ ID NO: 19. In some embodiments, the recombinant NL63-CoV S ectodomain trimer comprises protomers comprising residues 16-1291 of SEQ ID NO: 19 or residues 16-1318 of SEQ ID NO: 36. In some embodiments, the recombinant NL63-CoV S ectodomain trimer comprises protomers comprising an ectodomain sequence at least 90% identical to the ectodomain sequence of SEQ ID NO: 19, wherein the NL63-CoV S ectodomain trimer is stabilized in the prefusion conformation and comprises the "2P" substitution and/or modifications to remove the S1/S2 cleavage site and the S2' cleavage site of the protomers. In some embodiments, the recombinant NL63-CoV S ectodomain trimer comprises protomers comprising an amino acid sequence at least 90% identical to residues 16-1291 of SEQ ID NO: 19 or residues 16-1318 of SEQ ID NO: 36, wherein the NL63-CoV S ectodomain trimer is stabilized in the prefusion conformation and comprises the "2P" substitution and/or modifications to remove the S1/S2 cleavage site and the S2' cleavage site of the protomers.

I. 229E-CoV

In some embodiments, the immunogen comprises a recombinant 229E-CoV S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions that stabilize the 229E-CoV S ectodomain trimer in the prefusion conformation are located between residues 852 to 872 (such as between residues 862 to 872 or between residues 867 to 872) of the S ectodomain protomers in the trimer. In some embodiments, the 229E-CoV S ectodomain trimer is stabilized in the prefusion conformation by I869P and I870P substitutions ("2P") in the S ectodomain protomers in the trimer. The amino acid numbering for 229E-CoV S proteins is with reference to the 229E-CoV S sequence provided as SEQ ID NO: 20.

In some embodiments, the recombinant 229E-CoV S ectodomain trimer stabilized in the prefusion conformation comprises single-chain S ectodomain protomers comprising mutations to the S1/S2 and/or S2' protease cleavage sites to prevent protease cleavage at these sites.

In some embodiments, the protomers of the recombinant 229E-CoV S ectodomain trimer stabilized in the prefusion conformation by the one or more proline substitutions (such as I869P and I870P substitutions) comprises additional modifications for stabilization in the prefusion conformation.

With reference to the 229E-CoV S protein sequence provided as SEQ ID NO: 20, the ectodomain of the 229E-CoV S protein includes about residues 17-1108. Residues 1-16 are the signal peptide, which is removed during cellular processing. The S 1/S2 cleavage site is located at about position 565/566. The S2' cleavage site is located at about position 687/688. The HR1 is located at about residues 784-866. The central helix is located at about residues 871-912. The HR2 is located at about 1050-1094. The C-terminal end of the S2 ectodomain is located at about residue 1108. In some embodiments, the protomers of the prefusion-stabilized 229E-CoV S ectodomain trimer can have a C-terminal residue (which can be linked to a trimerization domain, or a transmembrane domain, for example) of the C-terminal residue of the HR2 (e.g., position 1099), or the ectodomain (e.g., position 1108), or from one of positions 1099-1108. The position numbering of the S protein may vary between 229E-CoV stains, but the sequences can be aligned to determine relevant structural domains and cleavage sites. It will be appreciated that a few residues (such as up to 10) on the N and C-terminal ends of the ectodomain can be removed or modified in the disclosed immunogens without decreasing the utility of the S ectodomain trimer as an immunogen.

Exemplary 229E-CoV S protein sequences are provided below. The prefusion stabilizing substitutions disclosed herein (and other modifications, such as substitutions to generate a single chain) can be incorporated into 229E-CoV S protein sequences.

An exemplary sequence of 229E-CoV S protein (including the ectodomain and TM and CT domains) is provided as SEQ ID NO: 20 (GenBank GI: 1060650120, incorporated by reference herein):

MFVLLVAYALLHIAGCQTINGTNTSHSVCNGCVGHSENVFAVESGGYIPS
NFAFNNWFLLTNTSSVVDGVVRSFQPLLLNCLWSVSGSQFTTGFVYFNGT
GRGACKGFYSNASSDVIRYNINFEENLRRGTILFKTSYGAVVFYCTNNTL
VSGDAHIPSGTVLGNFYCFVNTTIGNETTSAFVGALPKTVREFVISRTGH
FYINGYRYFSLGDVEAVNFNVTNAATTVCTVALASYADVLVNVSQTAIAN
IIYCNSVINRLRCDQLSFDVPDGFYSTSPIQPVELPVSIVSLPVYHKHTF
IVLYVNFEHRRGPGKCYNCRPAVINITLANFNETKGPLCVDTSHFTTQFV
DNVKLARWSASINTGNCPFSFGKVNNFVKFGSVCFSLKDIPGGCAMPIMA
NLVNSKSHNIGSLYVSWSDGDVITGVPKPVEGVSSFMNVTLNKCTKYNIY
DVSGVGVIRISNDTFLNGITYTSTSGNLLGFKDVTNGTIYSITPCNPPDQ
LVVYQQAVVGAMLSENFTSYGFSNVVEMPKFFYASNGTYNCTDAVLTYSS
FGVCADGSIIAVQPRNVSYDSVSAIVTANLSIPFNWTTSVQVEYLQITST
PIVVDCSTYVCNGNVRCVELLKQYTSACKTIEDALRNSAMLESADVSEML
TFDKKAFTLANVSSFGDYNLSSVIPSLPRSGSRVAGRSAIEDILFSKLVT
SGLGTVDADYKKCTKGLSIADLACAQYYNGIMVLPGVADAERMAMYTGSL
IGGIALGGLTSAASIPFSLAIQSRLNYVALQTDVLQENQRILAASENKAM
TNIVDAFTGVNDAITQTSQALQTVATALNKIQDVVNQQGNSLNHLTSQLR
QNFQAISSSIQAIYDRLDIIQADQQVDRLITGRLAALNVFVSHTLTKYTE
VRASRQLAQQKVNECVKSQSKRYGFCGNGTHIFSLVNAAPEGLVFLHTVL
LPTQYKDVEAWSGLCVDGINGYVLRQPNLALYKEGNYYRITSRIMFEPRI
PTIADFVQIENCNVTFVNISRSELQTIVPEYIDVNKTLQELSYKLPNYTV
PDLVVEQYNQTILNLTSEISTLENKSAELNYTVQKLQTLIDNINSTLVDL
KWLNRVETYIKWPWWVWLCISVVLIFVVSMLLLCCCSTGCCGFFSCFASS
IRGCCESTKLPYYDVEKIHIQ

An exemplary sequence of 229E-CoV S ectodomain including a double proline substitution for stabilization in the prefusion conformation is provided as SEQ ID NO: 21:

MFVLLVAYALLHIAGCQTTNGTNTSHSVCNGCVGHSENVFAVESGGYIPS
NFAFNNWFLLTNTSSVVDGVVRSFQPLLLNCLWSVSGSQFTTGFVYFNGT
GRGACKGFYSNASSDVIRYNINFEENLRRGTILFKTSYGAVVFYCTNNTL
VSGDAHIPSGTVLGNFYCFVNTTIGNETTSAFVGALPKTVREFVISRTGH
FYINGYRYFSLGDVEAVNFNVTNAATTVCTVALASYADVLVNVSQTAIAN
IIYCNSVINRLRCDQLSFDVPDGFYSTSPIQPVELPVSIVSLPVYHKHTF
IVLYVNFEHRRGPGKCYNCRPAVINITLANFNETKGPLCVDTSHFTTQFV
DNVKLARWSASINTGNCPFSFGKVNNFVKFGSVCFSLKDIPGGCAMPIMA
NLVNSKSHNIGSLYVSWSDGDVITGVPKPVEGVSSEMNVTLNKCTKYNIY
DVSGVGVIRISNDTFLNGITYTSTSGNLLGFKDVTNGTIYSITPCNPPDQ
LVVYQQAVVGAMLSENFTSYGFSNVVEMPKFFYASNGTYNCTDAVLTYSS
FGVCADGSIIAVQPRNVSYDSVSAIVTANLSIPFNWTTSVQVEYLQITST
PIVVDCSTYVCNGNVRCVELLKQYTSACKTIEDALRNSAMLESADVSEML
TFDKKAFTLANVSSFGDYNLSSVIPSLPRSGSRVAGRSAIEDILFSKLVT
SGLGTVDADYKKCTKGLSIADLACAQYYNGIMVLPGVADAERMAMYTGSL
IGGIALGGLISAASIPFSLAIQSRLNYVALQTDVLQENQRILAASENKAM
TNIVDAFTGVNDAITQTSQALQTVATALNKIQDVVNQQGNSLNHLTSQLR
QNFQAISSSIQAIYDRLDPPQADQQVDRLITGRLAALNVFVSHTLTKYTE
VRASRQLAQQKVNECVKSQSKRYGFCGNGTHIFSLVNAAPEGLVFLHTVL
LPTQYKDVEAWSGLCVDGINGYVLRQPNLALYKEGNYYRITSRIMFEPRI

-continued

```
PTIADFVQIENCNVTFVNISRSELQTIVPEYIDVNKTLQELSYKLPNYTV

PDLVVEQYNQTILNLTSEISTLENKSAELNYTVQKLQTLIDNINSTLVDL

KWLNRVET
```

A C-terminal trimerization domain can be added to the protomers of the 229E-CoV S ectodomains trimer to promote trimerization of the ectodomain.

An exemplary sequence of 229E-CoV S ectodomain including a double proline substitution for stabilization in the prefusion conformation, and a T4 fibritin trimerization domain is provided as SEQ ID NO: 37:

```
MFVLLVAYALLHIAGCQTTNGTNTSHSVCNGCVGHSENVFAVESGGYIPS

NFAFNNWFLLTNTSSVVDGVVRSFQPLLLNCLWSVSGSQFTTGFVYFNGT

GRGACKGFYSNASSDVIRYNINFEENLRRGTILFKTSYGAVVFYCINNTL

VSGDAHIPSGTVLGNFYCFVNTTIGNETTSAFVGALPKTVREFVISRTGH

FYINGYRYFSLGDVEAVNFNVTNAATTVCTVALASYADVLVNVSQTAIAN

IIYCNSVINRLRCDQLSFDVPDGFYSTSPIQPVELPVSIVSLPVYHKHTF

IVLYVNFEHRRGPGKCYNCRPAVINITLANFNETKGPLCVDTSHFTTQFV

DNVKLARWSASINTGNCPFSFGKVNNFVKFGSVCFSLKDIPGGCAMPIMA

NLVNSKSHNIGSLYVSWSDGDVITGVPKPVEGVSSFMNVTLNKCTKYNIY

DVSGVGVIRISNDTFLNGITYTSTSGNLLGFKDVTNGTIYSITPCNPPDQ

LVVYQQAVVGAMLSENFTSYGFSNVVEMPKFFYASNGTYNCTDAVLTYSS

FGVCADGSIIAVQPRNVSYDSVSAIVTANLSIPFNWTTSVQVEYLQITST

PIVVDCSTYVCNGNVRCVELLKQYTSACKTIEDALRNSAMLESADVSEML

TFDKKAFTLANVSSFGDYNLSSVIPSLPRSGSRVAGRSAIEDILFSKLVT

SGLGTVDADYKKCTKGLSIADLACAQYYNGIMVLPGVADAERMAMYTGSL

IGGIALGGLISAASIPFSLAIQSRLNYVALQTDVLQENQRILAASENKAM

TNIVDAFTGVNDAITQTSQALQTVATALNKIQDVVNQQGNSLNHLTSQLR

QNFQAISSSIQAIYDRLDPPQADQQVDRLITGRLAALNVFVSHTLTKYTE

VRASRQLAQQKVNECVKSQSKRYGFCGNGTHIFSLVNNAAPEGLVFLHTVL

LPTQYKDVEAWSGLCVDGINGYVLRQPNLALYKEGNYYRITSRIMFEPRI

PTIADFVQIENCNVTFVNISRSELQTIVPEYIDVNKTLQELSYKLPNYTV

PDLVVEQYNQTILNLTSEISTLENKSAELNYTVQKLQTLIDNINSTLVDL

KWLNRVETGGYIPEAPRDGQAYVRKDGEWVLLSTF
```

In some embodiments, the recombinant 229E-CoV S ectodomain trimer comprises protomers comprising the ectodomain sequence of SEQ ID NO: 21. In some embodiments, the recombinant 229E-CoV S ectodomain trimer comprises protomers comprising residues 17-1108 of SEQ ID NO: 21 or residues 17-1135 of SEQ ID NO: 37. In some embodiments, the recombinant 229E-CoV S ectodomain trimer comprises protomers comprising an ectodomain sequence at least 90% identical to the ectodomain sequence of SEQ ID NO: 21, wherein the 229E-CoV S ectodomain trimer is stabilized in the prefusion conformation and comprises the "2P" substitution and/or modifications to remove the S1/S2 cleavage site and the S2' cleavage site of the protomers. In some embodiments, the recombinant 229E-CoV S ectodomain trimer comprises protomers comprising an amino acid sequence at least 90% identical to residues 17-1108 of SEQ ID NO: 21 or residues 17-1135 of SEQ ID NO: 37, wherein the 229E-CoV S ectodomain trimer is stabilized in the prefusion conformation and comprises the "2P" substitution and/or modifications to remove the S 1/S2 cleavage site and the S2' cleavage site of the protomers.

I. PEDV-CoV

In some embodiments, the immunogen comprises a recombinant PEDV-CoV S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions that stabilize the PEDV-CoV S ectodomain trimer in the prefusion conformation are located between residues 1059 to 1079 (such as between residues 1069 to 1079 or between residues 1073 to 1079) of the S ectodomain protomers in the trimer. In some embodiments, the PEDV-CoV S ectodomain trimer is stabilized in the prefusion conformation by I1076P and L1077P substitutions ("2P") in the S ectodomain protomers in the trimer. The amino acid numbering for PEDV-CoV S proteins is with reference to the PEDV-CoV S sequence provided as SEQ ID NO: 38.

In some embodiments, the recombinant PEDV-CoV S ectodomain trimer stabilized in the prefusion conformation comprises single-chain S ectodomain protomers comprising mutations to the S1/S2 and/or S2' protease cleavage sites to prevent protease cleavage at these sites.

In some embodiments, the protomers of the recombinant PEDV-CoV S ectodomain trimer stabilized in the prefusion conformation by the one or more proline substitutions (such as I1076P and L1077P substitutions) comprises additional modifications for stabilization in the prefusion conformation.

With reference to the PEDV-CoV S protein sequence provided as SEQ ID NO: 38, the ectodomain of the PEDV-CoV S protein includes about residues 21-1322. Residues 1-20 are the signal peptide, which is removed during cellular processing. The S 1/S2 cleavage site is located at about position 736/737. The S2' cleavage site is located at about position 743/744. The HR1 is located at about residues 991-1073. The central helix is located at about residues 1078-1119. The HR2 is located at about 1277-1308. The C-terminal end of the S2 ectodomain is located at about residue 1322. In some embodiments, the protomers of the prefusion-stabilized PEDV-CoV S ectodomain trimer can have a C-terminal residue (which can be linked to a trimerization domain, or a transmembrane domain, for example) of the C-terminal residue of the HR2 (e.g., position 1308), or the ectodomain (e.g., position 1322), or from one of positions 1308-1322. The position numbering of the S protein may vary between PEDV-CoV stains, but the sequences can be aligned to determine relevant structural domains and cleavage sites. It will be appreciated that a few residues (such as up to 10) on the N and C-terminal ends of the ectodomain can be removed or modified in the disclosed immunogens without decreasing the utility of the S ectodomain trimer as an immunogen.

Exemplary PEDV-CoV S protein sequences are provided below. The prefusion stabilizing substitutions disclosed herein (and other modifications, such as substitutions to generate a single chain) can be incorporated into PEDV-CoV S protein sequences.

An exemplary sequence of PEDV-CoV S protein (including the ectodomain and TM and CT domains) is provided as SEQ ID NO: 38 (GenBank GI: AHZ94887.1, incorporated by reference herein):

MKSLTYFWLFLPVLSTLSLPQDVTRCSANTNFRRFFSKFNVQAPAVVVLG
GYLPIGENQGVNSTWYCAGQHPTASGVHGIFVSHIRGGHGFEIGISQEPF
DPSGYQLYLHKATNGNTNATARLRICQFPSIKTLGPTANNDVTTGRNCLE
NKAIPAHMSEHSVVGITWDNDRVTVFSDKIYYFYFKNDWSRVATKCYNSG
GCAMQYVYEPTYYMLNVISAGEDGISYQPCTANCIGYAANVFATEPNGHI
PEGFSENNWELLSNDSTLVHGKVVSNQPLLVNCLLAIPKIYGLGQFFSFN
QTIDGVCNGAAVQRAPEALRFNINDISVILAEGSIVLHTALGTNFSFVCS
NSSNPHLATFAIPLGATQVPYYCFFKVDTYNSTVYKFLAVLPPTVREIVI
TKYGDVYVNGFGYLHLGLLDAVTINFTGHGTDDDVSGEWTIASTNFVDAL
IEVQGTAIQRILYCDDPVSQLKCSQVAFDLDDGFYTISSRNLLSHEQPIS
FVTLPSENDHSFVNITVSASFGGHSGANLIASDTTINGFSSFCVDTRQFT
ISLFYNVINSYGYVSKSQDSNCPFTLQSVNDYLSFSKFCVSTSLLASACT
IDLFGYPEFGSGVKFTSLYFQFTKGELITGTPKPLEGVTDVSFMTLDVCT
KYTIYGFKGEGIITLINSSFLAGVYYTSDSGQLLAFKNVTSGAVYSVTPC
SFSEQAAYVDDDIVGVISSLSSSTFNSTRELPGFFYHSNDGSNCTEPVLV
YSNIGVCKSGSIGYVPSQSGQVKIAPTVTGNISIPTNFSMSIRTEYLQLY
NTPVSVDCATYVCNGNSRCKQLLTQYTAACKTIESALQLSARLESVEVNS
MLTISDEALQLATISSENGDGYNFTNVLGVSVYDPASRRVVQKRSFIEDL
LFNKVVINGLGTVDEDYKRCSNGRSVADLVCAQYYSGVMVLPGVVDAEKL
HMYSASLIGGMVLGGFTSAAALPFSYAVQARLNYLALQTDVLQRNQQLLA
ESENSAIGNITSAFESVKEAISQTSKGLNTVAHALTKVQEVVNSQGAALT
QLTVQLQHNFQAISSSIDDIYSRLDILSADAQVDRLITGRLSALNAFVAQ
TLTKYTEVQASRKLAQQKVNECVKSQSQRYGFCGGDGEHIFSLVQAAPQG
LLFLHTVLVPSDFVDVIAIAGLCVNDEIALTLREPGLVLFTHELQNHTAT
EYFVSSRRMFEPRKPTVSDFVQIESCVVTYVNLTRDQLPDVIPDYIDVNK
TLYEILASLPNRTGPSLPLDVFNATYLNLTGEIADLEQRSESLRNTTEEL
QSLIYNINNTLVDLEWLNRVETYIKWPWWVWLIIFIVLIFVVSLLVFCCI
STGCCGCCGCCCACFSGCCRGPRLQPYEVFEKVHVQ

An exemplary sequence of PEDV-CoV S ectodomain including a double proline substitution for stabilization in the prefusion conformation is provided as SEQ ID NO: 39:

MKSLTYFWLFLPVLSTLSLPQDVTRCSANTNFRRFFSKFNVQAPAVVVLG
GYLPIGENQGVNSTWYCAGQHPTASGVHGIFVSHIRGGHGFEIGISQEPF
DPSGYQLYLHKATNGNTNATARLRICQFPSIKTLGPTANNDVTTGRNCLE
NKAIPAHMSEHSVVGITWDNDRVTVFSDKIYYFYFKNDWSRVATKCYNSG
GCAMQYVYEPTYYMLNVTSAGEDGISYQPCTANCIGYAANVFATEPNGHI
PEGFSFNNWELLSNDSTLVHGKVVSNQPLLVNCLLAIPKIYGLGQFFSFN
QTIDGVCNGAAVQRAPEALRFNINDISVILAEGSIVLHTALGTNFSFVCS
NSSNPHLATFAIPLGATQVPYYCFFKVDTYNSTVYKFLAVLPPTVREIVI
TKYGDVYVNGFGYLHLGLLDAVTINFTGHGTDDDVSGFWTIASTNFVDAL
IEVQGTAIQRILYCDDPVSQLKCSQVAFDLDDGFYTISSRNLLSHEQPIS
FVTLPSENDHSFVNITVSASFGGHSGANLIASDTTINGFSSFCVDTRQFT
ISLFYNVINSYGYVSKSQDSNCPFTLQSVNDYLSFSKFCVSTSLLASACT
IDLFGYPEFGSGVKFTSLYFQFTKGELITGTPKPLEGVTDVSFMTLDVCT
KYTIYGFKGEGIITLTNSSFLAGVYYTSDSGQLLAFKNVTSGAVYSVTPC
SFSEQAAYVDDDIVGVISSLSSSTFNSTRELPGFFYHSNDGSNCTEPVLV
YSNIGVCKSGSIGYVPSQSGQVKIAPTVTGNISIPTNFSMSIRTEYLQLY
NTPVSVDCATYVCNGNSRCKQLLTQYTAACKTIESALQLSARLESVEVNS
MLTISDEALQLATISSENGDGYNFTNVLGVSVYDPASRRVVQKRSFIEDL
LFNKVVINGLGTVDEDYKRCSNGRSVADLVCAQYYSGVMVLPGVVDAEKL
HMYSASLIGGMVLGGFTSAAALPFSYAVQARLNYLALQTDVLQRNQQLLA
ESENSAIGNITSAFESVKEAISQTSKGLNTVAHALTKVQEVVNSQGAALT
QLTVQLQHNFQAISSSIDDIYSRLDPPSADAQVDRLITGRLSALNAFVAQ
TLTKYTEVQASRKLAQQKVNECVKSQSQRYGFCGGDGEHIFSLVQAAPQG
LLFLHTVLVPSDFVDVIAIAGLCVNDEIALTLREPGLVLFTHELQNHTAT
EYFVSSRRMFEPRKPTVSDFVQIESCVVTYVNLTRDQLPDVIPDYIDVNK
TLYEILASLPNRTGPSLPLDVENATYLNLTGEIADLEQRSESLRNTTEEL
QSLIYNINNTLVDLEWLNRVET

A C-terminal trimerization domain can be added to the protomers of the PEDV-CoV S ectodomains trimer to promote trimerization of the ectodomain.

An exemplary sequence of PEDV-CoV S ectodomain including a double proline substitution for stabilization in the prefusion conformation, and a T4 fibritin trimerization domain is provided as SEQ ID NO: 40:

MKSLTYFWLFLPVLSTLSLPQDVTRCSANTNFRRFFSKFNVQAPAVVVLG
GYLPIGENQGVNSTWYCAGQHPTASGVHGIFVSHIRGGHGFEIGISQEPF
DPSGYQLYLHKATNGNTNATARLRICQFPSIKTLGPTANNDVTTGRNCLE
NKAIPAHMSEHSVVGITWDNDRVTVFSDKIYYFYFKNDWSRVATKCYNSG
GCAMQYVYEPTYYMLNVISAGEDGISYQPCTANCIGYAANVFATEPNGHI
PEGFSNNWELLSNDSTLVHGKVVSNQPLLVNCLLAIPKIYGLGQFFSFN
QTIDGVCNGAAVQRAPEALRFNINDISVILAEGSIVLHTALGTNFSFVCS
NSSNPHLATFAIPLGATQVPYYCFFKVDTYNSTVYKFLAVLPPTVREIVI
TKYGDVYVNGFGYLHLGLLDAVTINFTGHGTDDDVSGFWTIASTNFVDAL
IEVQGTAIQRILYCDDPVSQLKCSQVAFDLDDGFYTISSRNLLSHEQPIS

-continued

```
FVTLPSFNDHSFVNITVSASFGGHSGANLIASDTTINGFSSFCVDTRQFT

ISLFYNVINSYGYVSKSQDSNCPFTLQSVNDYLSFSKFCVSTSLLASACT

IDLFGYPEFGSGVKFTSLYFQFTKGELITGTPKPLEGVTDVSFMTLDVCT

KYTIYGFKGEGIITLTNSSFLAGVYYTSDSGQLLAFKNVTSGAVYSVTPC

SFSEQAAYVDDDIVGVISSLSSSTFNSTRELPGFFYHSNDGSNCTEPVLV

YSNIGVCKSGSIGYVPSQSGQVKIAPTVTGNISIPTNFSMSIRTEYLQLY

NTPVSVDCATYVCNGNSRCKQLLTQYTAACKTIESALQLSARLESVEVNS

MLTISDEALQLATISSENGDGYNFTNVLGVSVYDPASRRVVQKRSFIEDL

LFNKVVINGLGTVDEDYKRCSNGRSVADLVCAQYYSGVMVLPGVVDAEKL

HMYSASLIGGMVLGGFTSAAALPESYAVQARLNYLALQTDVLQRNQQLLA

ESENSAIGNITSAFESVKEAISQTSKGLNTVAHALTKVQEVVNSQGAALT

QLTVQLQHNFQAISSSIDDIYSRLDPPSADAQVDRLITGRLSALNAFVAQ

TLTKYTEVQASRKLAQQKVNECVKSQSQRYGFCGGDGEHIFSLVQAAPQG

LLFLHTVLVPSDFVDVIAIAGLCVNDEIALTLREPGLVLFTHELQNHTAT

EYFVSSRRMFEPRKPTVSDFVQIESCVVTYVNLTRDQLPDVIPDYIDVNK

TLYEILASLPNRTGPSLPLDVENATYLNLTGEIADLEQRSESLRNTTEEL

QSLIYNINNTLVDLEWLNRVETGGYIPEAPRDGQAYVRKDGEWVLLSTF
```

In some embodiments, the recombinant PEDV-CoV S ectodomain trimer comprises protomers comprising the ectodomain sequence of SEQ ID NO: 39. In some embodiments, the recombinant PEDV-CoV S ectodomain trimer comprises protomers comprising residues 21-1322 of SEQ ID NO: 39 or residues 21-1349 of SEQ ID NO: 40. In some embodiments, the recombinant PEDV-CoV S ectodomain trimer comprises protomers comprising an ectodomain sequence at least 90% identical to the ectodomain sequence of SEQ ID NO: 39, wherein the PEDV-CoV S ectodomain trimer is stabilized in the prefusion conformation and comprises the "2P" substitution and/or modifications to remove the S1/S2 cleavage site and the S2' cleavage site of the protomers. In some embodiments, the recombinant PEDV-CoV S ectodomain trimer comprises protomers comprising an amino acid sequence at least 90% identical to residues 21-1322 of SEQ ID NO: 39 or residues 21-1349 of SEQ ID NO: 40, wherein the PEDV-CoV S ectodomain trimer is stabilized in the prefusion conformation and comprises the "2P" substitution and/or modifications to remove the S1/S2 cleavage site and the S2' cleavage site of the protomers.

I. SDCV

In some embodiments, the immunogen comprises a recombinant swine delta coronavirus (SDCV) S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions that stabilize the SDCV S ectodomain trimer in the prefusion conformation are located between residues 838 to 858 (such as between residues 848 to 858 or between residues 854 to 858) of the S ectodomain protomers in the trimer. In some embodiments, the SDCV S ectodomain trimer is stabilized in the prefusion conformation by E855P and V856P substitutions ("2P") in the S ectodomain protomers in the trimer. The amino acid numbering for SDCV S proteins is with reference to the SDCV S sequence provided as SEQ ID NO: 41.

In some embodiments, the recombinant SDCV S ectodomain trimer stabilized in the prefusion conformation comprises single-chain S ectodomain protomers comprising mutations to the S1/S2 and/or S2' protease cleavage sites to prevent protease cleavage at these sites.

In some embodiments, the protomers of the recombinant SDCV S ectodomain trimer stabilized in the prefusion conformation by the one or more proline substitutions (such as E855P and V856P substitutions) comprises additional modifications for stabilization in the prefusion conformation.

With reference to the SDCV S protein sequence provided as SEQ ID NO: 41, the ectodomain of the SDCV S protein includes about residues 20-1093. Residues 1-19 are the signal peptide, which is removed during cellular processing. The HR1 is located at about residues 770-854. The central helix is located at about residues 857-898. The HR2 is located at about 1034-1079. The C-terminal end of the S2 ectodomain is located at about residue 1093. In some embodiments, the protomers of the prefusion-stabilized SDCV S ectodomain trimer can have a C-terminal residue (which can be linked to a trimerization domain, or a transmembrane domain, for example) of the C-terminal residue of the HR2 (e.g., position 1079), or the ectodomain (e.g., position 1093), or from one of positions 1079-1093. The position numbering of the S protein may vary between SDCV stains, but the sequences can be aligned to determine relevant structural domains and cleavage sites. It will be appreciated that a few residues (such as up to 10) on the N and C-terminal ends of the ectodomain can be removed or modified in the disclosed immunogens without decreasing the utility of the S ectodomain trimer as an immunogen.

Exemplary SDCV S protein sequences are provided below. The prefusion stabilizing substitutions disclosed herein (and other modifications, such as substitutions to generate a single chain) can be incorporated into SDCV S protein sequences.

An exemplary sequence of SDCV S protein (including the ectodomain and TM and CT domains) is provided as SEQ ID NO: 41 (GenBank GI: AMN91621.1, incorporated by reference herein):

```
MQRALLIMTLLCLARAKFADDLLDLLTFPGAHRFLHKPTRNDSILYSRAN

NNFDVGVLPGYPTKNVNLFSPLINSTLPINGLHRSYQPLMLNCLTKITNQ

TLSMYLQPSEIQTYSCGGAMVKYQTHDAVRIILDLIATDRISVEVVGQAG

ENYVFVCSDQFNYTTALHNSTFFSLNSQLYCFTNNTYLGILPPDLTDFTV

YRTGQFYANGYLLGTLPITVNYVRLYRGQLSANSAHFALANLTDTLITLT

NTTISQITYCDKSVVDSIACQRSSHQVEDGFYSDPKSAVRARQRTIVTLP

KLPELEVVQLNISAHMDFGEARLDSVTINGNTSYCVTKPYFRLETNFLCR

GCTMNLRTDTCSFDLSAVNNGMSFSQFCLSTESGACEMKIIVTYVWNYLL

RQRLYVTAVEGQTHTGTTSVHATDTSSVITDVCTDYTIYGVSGTGIIKPS
```

-continued

DLLLHNGIAFTSPTGELYAFKNITTGKTLQVLPCETPSQLIVINNTVVGA

ITSSNSTENNRFTTTIVTPTFFYSTNATTLNCTKPVLSYGPISVCSDGAI

AGTSTLQNTRPSIVSLYDGEIEIPSAFSLSVQTEYLQVQAEQVIVDCPQY

VCNGNSRCLQLLAQYTSACSNIEVALHSSAQLDSREIISMFKTSTQSLQL

ANITNEKGDYNFSSILTSRVGGRSAIEDLLFNKVVTSGLGTVDQDYKSCS

RNMAIADLVCSQYYNGIMVLPGVVDAEKMAMYTGSLTGAMVFGGLTAAAA

IPFATAVQARLNYVALQTNVLQENQKILAESENQAVGNISLALSSVNDAI

QQTSEALNTVAIAIKKIQTVVNQQGEALSHLTAQLSNNFQAISTSIQDIY

NRLEEVEANQQVDRLINGRLAALNAYVTQLLNQMSQIRQSRLLAQQKINE

CVKSQSPRYGFCGNGTHIFSLTQTAPNGIFFMHAVLVPNKFTRVNASAGI

CVDNTRGYSLQPQLILYQFNNSWRVTPRNMYEPRLPRQADFIQLTDCSVT

FYNTTAANLPNIIPDVIDVNQTVSDIIDNLPTATPPQWDVGIYNNTILNL

TVEINDLQERSKNLSQIADRLQNYIDNLNNTLVDLEWLNRVETYLKWPWY

IWLAIALALIAFVTILITIFLCTGCCGGCFGCCGGCFGLFSKKKRYTDDQ

PTPSFKFKEW

An exemplary sequence of SDCV S ectodomain including a double proline substitution for stabilization in the prefusion conformation is provided as SEQ ID NO: 42:

MQRALLIMTLLCLARAKFADDLLDLLTFPGAHRFLHKPTRNDSILYSRAN

NNFDVGVLPGYPTKNVNLFSPLINSTLPINGLHRSYQPLMLNCLTKITNQ

TLSMYLQPSEIQTYSCGGAMVKYQTHDAVRIILDLIATDRISVEVVGQAG

ENYVFVCSDQFNYTTALHNSTFFSLNSQLYCFINNTYLGILPPDLTDFTV

YRTGQFYANGYLLGTLPITVNYVRLYRGQLSANSAHFALANLTDTLITLT

NTTISQITYCDKSVVDSIACQRSSHQVEDGFYSDPKSAVRARQRTIVTLP

KLPELEVVQLNISAHMDFGEARLDSVTINGNTSYCVTKPYFRLETNFLCR

GCTMNLRTDTCSFDLSAVNNGMSFSQFCLSTESGACEMKIIVTYVWNYLL

RQRLYVTAVEGQTHTGTTSVHATDTSSVITDVCTDYTIYGVSGIGIIKPS

DLLLHNGIAFTSPTGELYAFKNITTGKTLQVLPCETPSQLIVINNTVVGA

ITSSNSTENNRFTTTIVTPTFFYSTNATTLNCTKPVLSYGPISVCSDGAI

AGTSTLQNTRPSIVSLYDGEIEIPSAFSLSVQTEYLQVQAEQVIVDCPQY

VCNGNSRCLQLLAQYTSACSNIEVALHSSAQLDSREIISMFKTSTQSLQL

ANITNFKGDYNFSSILTSRVGGRSAIEDLLENKVVTSGLGTVDQDYKSCS

RNMAIADLVCSQYYNGIMVLPGVVDAEKMAMYTGSLTGAMVFGGLTAAAA

IPFATAVQARLNYVALQTNVLQENQKILAESFNQAVGNISLALSSVNDAI

QQTSEALNTVAIAIKKIQTVVNQQGEALSHLTAQLSNNFQAISTSIQDIY

NRLEPPEANQQVDRLINGRLAALNAYVTQLLNQMSQIRQSRLLAQQKINE

CVKSQSPRYGFCGNGTHIFSLTQTAPNGIFFMHAVLVPNKFTRVNASAGI

CVDNTRGYSLQPQLILYQFNNSWRVTPRNMYEPRLPRQADFIQLTDCSVT

FYNTTAANLPNIIPDVIDVNQTVSDIIDNLPTATPPQWDVGIYNNTILNL

TVEINDLQERSKNLSQIADRLQNYIDNLNNTLVDLEWLNRVET

A C-terminal trimerization domain can be added to the protomers of the SDCV S ectodomains trimer to promote trimerization of the ectodomain.

An exemplary sequence of SDCV S ectodomain including a double proline substitution for stabilization in the prefusion conformation, and a T4 fibritin trimerization domain is provided as SEQ ID NO: 43:

MQRALLIMTLLCLARAKFADDLLDLLTFPGAHRFLHKPTRNDSILYSRAN

NNFDVGVLPGYPTKNVNLFSPLINSTLPINGLHRSYQPLMLNCLTKITNQ

TLSMYLQPSEIQTYSCGGAMVKYQTHDAVRIILDLIATDRISVEVVGQAG

ENYVFVCSDQFNYTTALHNSTFFSLNSQLYCFTNNTYLGILPPDLTDFTV

YRTGQFYANGYLLGTLPITVNYVRLYRGQLSANSAHFALANLTDTLITLI

NTTISQITYCDKSVVDSIACQRSSHQVEDGFYSDPKSAVRARQRTIVTLP

KLPELEVVQLNISAHMDFGEARLDSVTINGNTSYCVTKPYFRLETNFLCR

GCTMNLRTDTCSFDLSAVNNGMSFSQFCLSTESGACEMKIIVTYVWNYLL

RQRLYVTAVEGQTHTGTTSVHATDTSSVITDVCTDYTIYGVSGTGIIKPS

DLLLHNGIAFTSPTGELYAFKNITTGKTLQVLPCETPSQLIVINNTVVGA

ITSSNSTENNRFTTTIVTPTFFYSTNATTLNCTKPVLSYGPISVCSDGAI

AGTSTLQNTRPSIVSLYDGEIEIPSAFSLSVQTEYLQVQAEQVIVDCPQY

VCNGNSRCLQLLAQYTSACSNIEVALHSSAQLDSREIISMFKTSTQSLQL

ANITNFKGDYNFSSILTSRVGGRSAIEDLLFNKVVTSGLGTVDQDYKSCS

RNMAIADLVCSQYYNGIMVLPGVVDAEKMAMYTGSLTGAMVFGGLTAAAA

IPFATAVQARLNYVALQTNVLQENQKILAESFNQAVGNISLALSSVNDAI

QQTSEALNTVAIAIKKIQTVVNQQGEALSHLTAQLSNNFQAISTSIQDIY

NRLEPPEANQQVDRLINGRLAALNAYVTQLLNQMSQIRQSRLLAQQKINE

CVKSQSPRYGFCGNGTHIFSLTQTAPNGIFFMHAVLVPNKFTRVNASAGI

CVDNTRGYSLQPQLILYQFNNSWRVTPRNMYEPRLPRQADFIQLTDCSVT

FYNTTAANLPNIIPDVIDVNQTVSDIIDNLPTATPPQWDVGIYNNTILNL

TVEINDLQERSKNLSQIADRLQNYIDNLNNTLVDLEWLNRVETGGYIPEA

PRDGQAYVRKDGEWVLLSTF

In some embodiments, the recombinant SDCV S ectodomain trimer comprises protomers comprising the ectodomain sequence of SEQ ID NO: 42. In some embodiments, the recombinant SDCV S ectodomain trimer comprises protomers comprising residues 20-1093 of SEQ ID NO: 42 or residues 20-1120 of SEQ ID NO: 43. In some embodiments, the recombinant SDCV S ectodomain trimer comprises protomers comprising an ectodomain sequence at least 90% identical to the ectodomain sequence of SEQ ID NO: 39, wherein the SDCV S ectodomain trimer is stabilized in the prefusion conformation and comprises the "2P" substitution and/or modifications to remove the S1/S2 cleavage site and the S2' cleavage site of the protomers. In some embodiments, the recombinant SDCV S ectodomain trimer comprises protomers comprising an amino acid sequence at least 90% identical to residues 20-1093 of SEQ ID NO: 39 or residues 20-1120 of SEQ ID NO: 43, wherein the SDCV S ectodomain trimer is stabilized in the prefusion conformation and comprises the "2P" substitution and/or modifications to remove the S1/S2 cleavage site and the S2' cleavage site of the protomers.

J. Single Chain S proteins

In some embodiments, the CoV S ectodomain trimer can be composed of three single-chain CoV S ectodomain protomers, each including a single polypeptide chain including the S1 protein and S2 ectodomain Single chain CoV S ectodomain protomers can be generated by mutating the S1/S2 and S2' protease cleavage sites to prevent cleavage and formation of distinct S1 and S2 polypeptide chains. In some embodiments, the S1 and S2 polypeptides in the single chain CoV S ectodomain protomers are joined by a linker, such as a peptide linker. Examples of peptide linkers that can be used include glycine, serine, and glycine-serine linkers. Any of the stabilizing mutations (or combinations thereof) disclosed herein can be included in the single chain coronavirus S ectodomain protomers as long as the coronavirus S ectodomain trimer composed of such protomers retains the desired properties (e.g., the prefusion conformation).

K. Linkage to a Trimerization Domain

In several embodiments, the S ectodomain protomers in the disclosed coronavirus S ectodomain trimers can be linked at their C-terminus (C-terminal linkage) to a trimerization domain to promote trimerization of the S ectodomain protomers, and to stabilize the membrane proximal aspect of the recombinant S ectodomains in a trimeric configuration.

Non-limiting examples of exogenous multimerization domains that promote stable trimers of soluble recombinant proteins include: the GCN4 leucine zipper (Harbury et al. 1993 *Science* 262:1401-1407), the trimerization motif from the lung surfactant protein (Hoppe et al. 1994 *FEBS Lett* 344:191-195), collagen (McAlinden et al. 2003 *J Biol Chem* 278:42200-42207), and the phage T4 fibritin Foldon (Miroshnikov et al. 1998 *Protein Eng* 11:329-414), any of which can be linked to a recombinant coronavirus S ectodomain described herein (e.g., by linkage to the C-terminus of S2) to promote trimerization of the recombinant coronavirus S ectodomain.

In some examples, the C-terminus of the S2 subunit of the S ectodomain can be linked to a T4 fibritin Foldon domain. In specific examples, the T4 fibritin Foldon domain can include the amino acid sequence GYIPEAPRDGQAYVRKDGEWVLLSTF (SEQ ID NO: 27), which adopts a β-propeller conformation, and can fold and trimerize in an autonomous way (Tao et al. 1997 Structure 5:789-798).

Optionally, the heterologous trimerization is connected to the recombinant coronavirus S ectodomain via a peptide linker, such as an amino acid linker. Non-limiting examples of peptide linkers that can be used include glycine, serine, and glycine-serine linkers.

L. Membrane Anchored Embodiments

In some embodiments, the coronavirus S ectodomain trimer can be membrane anchored, for example, for embodiments where the coronavirus S ectodomain trimer is expressed on an attenuated viral vaccine, or a virus like particle. In such embodiments, the protomers in the trimer typically each comprise a C-terminal linkage to a transmembrane domain, such as the transmembrane domain (and optionally the cytosolic tail) of corresponding coronavirus. For example, the protomers of a disclosed SARS-CoV S ectodomain trimer can be linked to a SARS-CoV S transmembrane and cytosolic tail. In some embodiments, one or more peptide linkers (such as a gly-ser linker, for example, a 10 amino acid glycine-serine peptide linker can be used to link the recombinant S ectodomain protomer to the transmembrane domain. The protomers linked to the transmembrane domain can include any of the stabilizing mutations provided herein (or combinations thereof) as long as the recombinant coronavirus S ectodomain trimer formed from the protomers linked to the transmembrane domain retains the desired properties (e.g., the coronavirus S prefusion conformation).

M. Additional Description

The coronavirus S protein or fragments thereof can be produced using recombinant techniques, or chemically or enzymatically synthesized.

Analogs and variants of the coronavirus S protein or fragments thereof may be used in the methods and systems of the present invention. Through the use of recombinant DNA technology, variants of the coronavirus S protein or fragments thereof may be prepared by altering the underlying DNA. All such variations or alterations in the structure of the coronavirus S ectodomain or fragments thereof resulting in variants are included within the scope of this invention. Such variants include insertions, substitutions, or deletions of one or more amino acid residues, glycosylation variants, unglycosylated coronavirus S ectodomain or fragments thereof, organic and inorganic salts, covalently modified derivatives of the coronavirus S protein or fragments thereof, or a precursor thereof. Such variants may maintain one or more of the functional, biological activities of the coronavirus S protein or fragment thereof, such as binding to cell surface receptor. The coronavirus S protein or a fragment thereof can be modified, for example, by PEGylation, to increase the half-life of the protein in the recipient, to retard clearance from the pericardial space, and/or to make the protein more stable for delivery to a subject.

In some embodiments, a coronavirus S protein or fragment thereof useful within the disclosure is modified to produce peptide mimetics by replacement of one or more naturally occurring side chains of the 20 genetically encoded amino acids (or D-amino acids) with other side chains, for example with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from a 5-membered ring to a 4-, 6-, or 7-membered ring. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl. Peptides, as well as peptide analogs and mimetics, can also be covalently bound to one or more of a variety of nonproteinaceous polymers, for example, polyethylene glycol, polypropylene glycol, or polyoxyalkenes, as described in U.S. Pat. Nos. 4,640,835; 4,496,668; 4,301,144; 4,668,417; 4,791,192; and 4,179,337.

N. Protein Nanoparticles

In some embodiments a protein nanoparticle is provided that includes one or more of the disclosed recombinant coronavirus S ectodomain trimers (e.g., a MERS-CoV S ectodomain trimer or a SARS-CoV S ectodomain trimer).

Non-limiting example of nanoparticles include ferritin nanoparticles, encapsulin nanoparticles, Sulfur Oxygenase Reductase (SOR) nanoparticles, and lumazine synthase nanoparticles, which are comprised of an assembly of monomeric subunits including ferritin proteins, encapsulin proteins, SOR proteins, and lumazine synthase, respectively. Additional protein nanoparticle structures are described by Heinze et al., J Phys Chem B., 120(26):5945-52, 2016; Hsia et al., Nature, 535(7610):136-9, 2016; and King et al., Nature, 510(7503):103-8, 2014; each of which is incorporated by reference herein. To construct such protein nanoparticles a protomer of the coronavirus S ectodomain trimer can be linked to a subunit of the protein nanoparticle (such as a ferritin protein, an encapsulin protein, a SOR protein, or a lumazine synthase protein) and expressed in cells under appropriate conditions. The fusion protein self-assembles into a nanoparticle any can be purified.

In some embodiments, a protomer of a disclosed recombinant coronavirus S ectodomain trimer (e.g., a MERS-CoV S ectodomain trimer or a SARS-CoV S ectodomain trimer) can be linked to a ferritin subunit to construct a ferritin nanoparticle. Ferritin nanoparticles and their use for immunization purposes (e.g., for immunization against influenza antigens) have been disclosed in the art (see, e.g., Kanekiyo et al., Nature, 499:102-106, 2013, incorporated by reference herein in its entirety). Ferritin is a globular protein that is found in all animals, bacteria, and plants, and which acts primarily to control the rate and location of polynuclear $Fe(III)_2O_3$ formation through the transportation of hydrated iron ions and protons to and from a mineralized core. The globular form of the ferritin nanoparticle is made up of monomeric subunits, which are polypeptides having a molecule weight of approximately 17-20 kDa. An example of the amino acid sequence of one such monomeric ferritin subunit is represented by:

(SEQ ID NO: 23)
ESQVRQQFSKDIEKLLNEQVNKEMQSSNLYMSMSSWCYTHSLDGAGLFLF

DHAAEEYEHAKKLIIFLNENNVPVQLTSISAPEHKFEGLTQIFQKAYEHE

QHISESINNIVDHAIKSKDHATFNFLQWYVAEQHEEEVLEKDILDKIELI

GNENHGLYLADQYVKGIAKSRKS

Each monomeric subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, D & E' from the N-terminus respectively. The N-terminal sequence lies adjacent to the capsid three-fold axis and extends to the surface, while the E helices pack together at the four-fold axis with the C-terminus extending into the capsid core. The consequence of this packing creates two pores on the capsid surface. It is expected that one or both of these pores represent the point by which the hydrated iron diffuses into and out of the capsid. Following production, these monomeric subunit proteins self-assemble into the globular ferritin protein. Thus, the globular form of ferritin comprises 24 monomeric, subunit proteins, and has a capsid-like structure having 432 symmetry. Methods of constructing ferritin nanoparticles are known to the person of ordinary skill in the art and are further described herein (see, e.g., Zhang, Int. J. Mol. Sci., 12:5406-5421, 2011, which is incorporated herein by reference in its entirety).

In specific examples, the ferritin polypeptide is E. coli ferritin, Helicobacter pylori ferritin, human light chain ferritin, bullfrog ferritin or a hybrid thereof, such as E. coli-human hybrid ferritin, E. coli-bullfrog hybrid ferritin, or human-bullfrog hybrid ferritin. Exemplary amino acid sequences of ferritin polypeptides and nucleic acid sequences encoding ferritin polypeptides for use to make a ferritin nanoparticle including a recombinant coronavirus S ectodomain can be found in GENBANK®, for example at accession numbers ZP_03085328, ZP_06990637, EJB64322.1, AAA35832, NP_000137 AAA49532, AAA49525, AAA49524 and AAA49523, which are specifically incorporated by reference herein in their entirety as available Apr. 10, 2015. In some embodiments, a recombinant coronavirus S ectodomain can be linked to a ferritin subunit including an amino acid sequence at least 80% (such as at least 85%, at least 90%, at least 95%, or at least 97%) identical to amino acid sequence set forth as SEQ ID NO: 122.

In some embodiments, a protomer of a disclosed recombinant coronavirus S ectodomain trimer (e.g., a MERS-CoV S ectodomain trimer or a SARS-CoV S ectodomain trimer) can be linked to a lumazine synthase subunit to construct a lumazine synthase nanoparticle. The globular form of lumazine synthase nanoparticle is made up of monomeric subunits; an example of the sequence of one such lumazine synthase subunit is provides as the amino acid sequence set forth as:

(SEQ ID NO: 24)
MQIYEGKLTAEGLRFGIVASRFNHALVDRLVEGAIDAIVRHGGREEDITL

VRVPGSWEIPVAAGELARKEDIDAVIAIGVLIRGATPHFDYIASEVSKGL

ADLSLELRKPITFGVITADTLEQAIERAGTKHGNKGWEAALSAIEMANLE

KSLR.

In some embodiments, a protomer of a disclosed recombinant coronavirus S ectodomain trimer can be linked to a lumazine synthase subunit including an amino acid sequence at least 80% (such as at least 85%, at least 90%, at least 95%, or at least 97%) identical to amino acid sequence set forth as SEQ ID NO: 24.

In some embodiments, a protomer of a disclosed recombinant coronavirus S ectodomain trimer (e.g., a MERS-CoV S ectodomain trimer or a SARS-CoV S ectodomain trimer) can be linked to an encapsulin nanoparticle subunit to construct an encapsulin nanoparticle. The globular form of the encapsulin nanoparticle is made up of monomeric subunits; an example of the sequence of one such encapsulin subunit is provides as the amino acid sequence set forth as (SEQ ID NO: 25)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF

In some embodiments, a protomer of a disclosed recombinant coronavirus S ectodomain trimer can be linked to an encapsulin subunit including an amino acid sequence at least 80% (such as at least 85%, at least 90%, at least 95%, or at least 97%) identical to amino acid sequence set forth as SEQ ID NO: 25.

Encapsulin proteins are a conserved family of bacterial proteins also known as linocin-like proteins that form large protein assemblies that function as a minimal compartment to package enzymes. The encapsulin assembly is made up of monomeric subunits, which are polypeptides having a molecule weight of approximately 30 kDa. Following production, the monomeric subunits self-assemble into the globular encapsulin assembly including 60, or in some cases, 180 monomeric subunits. Methods of constructing encapsulin nanoparticles are known to the person of ordinary skill in the art, and further described herein (see, for example, Sutter et al., Nature Struct. and Mol. Biol., 15:939-947, 2008, which is incorporated by reference herein in its entirety). In specific examples, the encapsulin polypeptide is bacterial encapsulin, such as *Thermotoga maritime* or *Pyrococcus furiosus* or *Rhodococcus erythropolis* or *Myxococcus xanthus* encapsulin.

In some embodiments, a protomer of a disclosed recombinant coronavirus S ectodomain trimer (e.g., a MERS-CoV S ectodomain trimer or a SARS-CoV S ectodomain trimer) can be linked to a Sulfur Oxygenase Reductase (SOR) subunit to construct a recombinant SOR nanoparticle. In some embodiments, the SOR subunit can include the amino acid sequence set forth as

```
                                         (SEQ ID NQ: 26)
MEFLKRSFAPLTEKQWQEIDNRAREIFKTQLYGRKFVDVEG-
PYGWEYAAHPL

GEVEVLSDENEVVKWGLRKSLPLIELRATFTLDLWELDNLERGKPNVDLS

SLEETVRKVAEFEDEVIFRGCEKSGVKGLLSFEERKIECGSTPKDLLEAI

VRALSIFSKDGIEGPYTLVINTDRWINFLKEEAGHYPLEKRVEECLRGGK

IITTPRIEDALVVSERGGDFKLILGQDLSIGYEDREKDAVRLFITETFTF

QVVNPEALILLKF
```

In some embodiments, a protomer of a disclosed recombinant coronavirus S ectodomain trimer can be linked to a SOR subunit including an amino acid sequence at least 80% (such as at least 85%, at least 90%, at least 95%, or at least 97%) identical to amino acid sequence set forth as SEQ ID NO: 26.

SOR proteins are microbial proteins (for example from the thermoacidophilic archaeon *Acidianus ambivalens* that form 24 subunit protein assemblies. Methods of constructing SOR nanoparticles are known to the person of ordinary skill in the art (see, e.g., Urich et al., Science, 311:996-1000, 2006, which is incorporated by reference herein in its entirety). An example of an amino acid sequence of a SOR protein for use to make SOR nanoparticles is set forth in Urich et al., Science, 311:996-1000, 2006, which is incorporated by reference herein in its entirety.

For production purposes, the recombinant coronavirus S ectodomain linked to the nanoparticle subunit can include an N-terminal signal peptide that is cleaved during cellular processing. For example, the recombinant coronavirus S ectodomain protomer linked to the protein nanoparticle subunit can include a signal peptide at its N-terminus including, for example, a native coronavirus S signal peptide.

The protein nanoparticles can be expressed in appropriate cells (e.g., HEK 293 Freestyle cells) and fusion proteins are secreted from the cells self-assembled into nanoparticles. The nanoparticles can be purified using known techniques, for example by a few different chromatography procedures, e.g. Mono Q (anion exchange) followed by size exclusion (SUPEROSE® 6) chromatography.

Several embodiments include a monomeric subunit of a ferritin, encapsulin, SOR, or lumazine synthase protein, or any portion thereof which is capable of directing self-assembly of monomeric subunits into the globular form of the protein Amino acid sequences from monomeric subunits of any known ferritin, encapsulin, SOR, or lumazine synthase protein can be used to produce fusion proteins with the recombinant coronavirus S ectodomain or immunogenic fragment thereof, so long as the monomeric subunit is capable of self-assembling into a nanoparticle displaying the recombinant coronavirus S ectodomain or immunogenic fragment thereof on its surface.

The fusion proteins need not comprise the full-length sequence of a monomeric subunit polypeptide of a ferritin, encapsulin, SOR, or lumazine synthase protein. Portions, or regions, of the monomeric subunit polypeptide can be utilized so long as the portion comprises amino acid sequences that direct self-assembly of monomeric subunits into the globular form of the protein.

III. Polynucleotides and Expression

Polynucleotides encoding a protomer of any of the disclosed recombinant S ectodomain trimers are also provided. These polynucleotides include DNA, cDNA and RNA sequences which encode the protomer, as well as vectors including the DNA, cDNA and RNA sequences, such as a DNA or RNA vector used for immunization. The genetic code to construct a variety of functionally equivalent nucleic acids, such as nucleic acids which differ in sequence but which encode the same protein sequence, or encode a conjugate or fusion protein including the nucleic acid sequence.

An exemplary nucleic acid sequence encoding MERS-CoV S protein is provided as SEQ ID NO: 5:

```
atgattcactccgtgttcctgctgatgttcctgctgactcctacagagag ctatgtggatgtgggacctgattccgtcaagagcgcctgcatcgaagtgg acattcagcagaccttctttgataagacatggccaagacccatcgacgtg agcaaagccgatggcatcatctaccctcaggggaggacctattccaatat cacaattacttaccagggcctgttccatatcagggagaccacggcgata tgtacgtgtattctgctggccatgcaacagggaccacacctcagaagctg tttgtggctaactacagccaggacgtcaaacagttcgcaaatggatttgt ggtccgcatcggcgccgctgcaaactctaccggcacagtgatcatttcac ctagcacttccgcaaccatccgaaaaatctacccagccttcatgctggga agctccgtgggcaatttagcgacgggaaaatgggacggttctttaacca caccctggtgctgctgcctgatggatgcggcacactgctgagggctttct actgtatcctggagccacgcagcggaaaccactgcccgcaggaaatagc tacacctcctttgccacatatcatactccagctaccgactgttccgatgg caactacaatcgaaacgcctctctgaatagtttcaaggaatacttcaacc tgcggaattgcacattcatgtacacttataacatcaccgaggacgaaatt ctggagtggttcggaatcactcagaccgcacagggcgtgcacctgttttc tagtcgctacgtcgacctgtatggcgggaacatgttccagtttgccactc tgcccgtgtacgataccatcaagtactattccatcattcctcattcaatc
```

```
cgcagcattcagtccgatcgaaaggcttgggccgctttctacgtgtataa
actgcagccactgaccttcctgctggactttagcgtcgatggctacatcc
ggagagccattgactgcgggtttaatgatctgtcccagctgcactgttct
tacgaaagtttcgacgtggagtccggcgtgtattctgtctcaagctttga
ggccaagccctctgggagtgtggtcgagcaggctgaaggagtggagtgcg
atttcagtcctctgctgtcagggacccccctcaggtgtacaacttcaag
cggctggtctttactaactgtaactacaatctgaccaagctgctgtcact
gttcagcgtgaatgactttacatgctcccagatcagcccgcagccattg
ctagtaactgttactcctctctgatcctggactacttctcatatccactg
agtatgaagagcgacctgagcgtgagttcagccggccccatcagccagtt
caactataaacagagcttcagcaatcctacatgcctgattctggctactg
tgccacataatctgactaccatcactaagcccctgaaatactcctatatt
aacaagtgcagccggttcctgtccgacgatagaaccgaagtgccacagct
ggtcaacgccaatcagtactctccctgtgtgagtatcgtcccttcaaccg
tgtgggaagacggggattactatagaaaacagctgagcccctggaggga
ggaggatggctggtggcatccggatctacagtcgccatgactgagcagct
gcagatgggttcggaatcacagtgcagtacggcacagacactaactctg
tctgtcccaagctggaattcgctaacgatactaagatcgcaagtcagctg
ggaaactgcgtggagtactctctgtatggcgtgagtggcagaggggtctt
ccagaattgtaccgcagtgggcgtccgacagcagcggtttgtgtacgacg
cctatcagaatctggtcggctactatagcgacgatgggaactactattgc
ctgagggctgtgtgagcgtccctgtgtccgtcatctacgataaggaaac
caaaacacacgccacactgttcgggtccgtggcttgcgagcatattagct
ccacaatgtctcagtacagtagatcaactaggtcaatgctgaagaggcgc
gatagcacctatggacctctgcagacaccagtggggtgtgtcctgggact
ggtgaactctagtctgtttgtcgaggactgcaagctgcccctgggccaga
gcctgtgcgccctgccgacaccccagcaccctgaccccccggagcgtg
cggagcgtgcccggcgagatgcggctggccagcatcgccttcaaccacc
catccaggtggaccagctgaacagcagctacttcaagctgagcatcccca
ccaacttcagcttcggcgtgacccaggagtacatccagaccaccatccag
aaggtgaccgtggactgcaagcagtacgtgtgcaacggcttccagaagtg
cgagcagctgctgcgggagtacggccagttctgcagcaagatcaaccagg
ccctgcacggcgccaacctgcggcaggacgacagcgtgcggaacctgttc
gccagcgtgaagagcagccagagcagcccatcatccccggcttcggcgg
cgacttcaacctgacccctgctggagcccgtgagcatcagccaccggcagcc
ggagcgcccggagcgccatcgaggacctgctgttcgacaaggtgaccatc
gccgaccccggctacatgcagggctacgacgactgcatgcagcagggccc
cgccagcgcccgggacctgatctgcgcccagtacgtggccggctacaagg
tgctgccccctgatggacgtgaacatggaggccgcctacaccagcagc
ctgctgggcagcatcgccggcgtgggctggaccgccggcctgagcagctt
cgccgccatcccttcgcccagagcatcttctaccggctgaacggcgtgg
```

```
gcatcacccagcaggtgctgagcgagaaccagaagctgatcgccaacaag
ttcaaccaggccctgggcgccatgcagaccggcttcaccaccaccaacga
ggccttccacaaggtgcaggacgccgtgaacaacaacgcccaggccctga
gcaagctggccagcgagctgagcaacaccttcggcgccatcagcgccagc
atcggcgacatcatccagcggctggacgtgctggagcaggacgcccagat
cgaccggctgatcaacggccggctgaccaccctgaacgccttcgtggccc
agcagctggtgcgggagcgagagcgccgccctgagcgcccagctggccaag
gacaaggtgaacgagtgcgtgaaggcccagagcaagcggagcggcttctg
cggccagggcacccacatcgtgagcttcgtggtgaacgcccccaacggcc
tgtacttcatgcacgtgggctactacccagcaaccacatcgaggtggtg
agcgcctacggcctgtgcgacgccgccaaccccaccaactgcatcgcccc
cgtgaacggctacttcatcaagaccaacaacacccggatcgtggacgagt
ggagctacaccggcagcagcttctacgccccgagcccatcaccagcctg
aacaccaagtacgtggccccccaggtgacctaccagaacatcagcaccaa
cctgccccccccctgctgggcaacagcaccggcatcgacttccaggacg
agctggacgagttcttcaagaacgtgagcaccagcatccccaacttcggc
agcctgacccagatcaacaccaccctgctggacctgacctacgagatgct
gagcctgcagcaggtggtgaaggccctgaacgagagctacatcgacctga
aggagctgggcaactacacctactacaacaagtggccctggtacatctgg
ctgggcttcatcgccggcctggtggccctggccctgtgcgtgttcttcat
cctgtgctgcaccggctgcggcaccaactgcatgggcaagctgaagtgca
accggtgctgcgaccggtacgaggagtacgacctggagccccacaaggtg
cacgtgcactga
```

The DNA sequence of the MERS-CoV S protomer provided above can be modified to introduce the amino acid substitutions and deletions disclosed herein for prefusion stabilization, such as the "2P" substitutions.

In several embodiments, the nucleic acid molecule encodes a precursor of the protomer, that, when expressed in an appropriate cell, is processed into a disclosed coronavirus S ectodomain protomer that can self-assemble into the corresponding recombinant coronavirus S ectodomain trimer. For example, the nucleic acid molecule can encode a recombinant coronavirus S ectodomain including a N-terminal signal sequence for entry into the cellular secretory system that is proteolytically cleaved in the during processing of the recombinant coronavirus S ectodomain in the cell.

In several embodiments, the nucleic acid molecule encodes a precursor S polypeptide that, when expressed in an appropriate cell, is processed into a disclosed recombinant coronavirus S ectodomain protomer including S1 and S2 polypeptides, wherein the recombinant S ectodomain protomer includes any of the appropriate stabilizing modifications described herein, and optionally can be linked to a trimerization domain, such as a T4 Fibritin trimerization domain.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, 4th ed, Cold Spring Harbor, N.Y., 2012) and Ausubel et al. (In Current Protocols in Molecular Biology, John Wiley & Sons, New York, through supplement 104, 2013).

Nucleic acids can also be prepared by amplification methods Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a disclosed recombinant coronavirus S ectodomain protomer can include a recombinant DNA which is incorporated into a vector (such as an expression vector) into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a disclosed recombinant coronavirus S ectodomain protomer can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the disclosed recombinant S ectodomain protomer can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli*, *Bacillus subtilis*, *Saccharomyces cerevisiae*, *Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), 4th Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as GnTI$^{-/-}$ cells (ATCC® No. CRL-3022), or HEK-293F cells.

Transformation of a host cell with recombinant DNA can be carried out by conventional techniques. Where the host is prokaryotic, such as, but not limited to, *E. coli*, competent cells which are capable of DNA uptake can be prepared from cells harvested after exponential growth phase and subsequently treated by the CaCl$_2$ method using standard procedures. Alternatively, MgCl$_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). Appropriate expression systems such as plasmids and vectors of use in producing proteins in cells including higher eukaryotic cells such as the COS, CHO, HeLa and myeloma cell lines.

In one non-limiting example, a disclosed immunogen is expressed using the pVRC8400 vector (described in Barouch et al., *J. Virol.*, 79, 8828-8834, 2005, which is incorporated by reference herein).

Modifications can be made to a nucleic acid encoding a disclosed recombinant coronavirus S ectodomain protomer without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In some embodiments, the disclosed recombinant coronavirus S ectodomain protomer can be expressed in cells under conditions where the recombinant coronavirus S ectodomain protomer can self-assemble into trimers which are secreted from the cells into the cell media. In such embodiments, each recombinant coronavirus S ectodomain protomer contains a leader sequence (signal peptide) that causes the protein to enter the secretory system, where the signal peptide is cleaved and the protomers form a trimer, before being secreted in the cell media. The medium can be centrifuged and recombinant coronavirus S ectodomain trimer purified from the supernatant.

IV. Viral Vectors

A nucleic acid molecule encoding a protomer of a disclosed recombinant coronavirus S ectodomain trimer can be included in a viral vector, for example, for expression of the immunogen in a host cell, or for immunization of a subject as disclosed herein. In some embodiments, the viral vectors are administered to a subject as part of a prime-boost vaccination. In several embodiments, the viral vectors are included in a vaccine, such as a primer vaccine or a booster vaccine for use in a prime-boost vaccination.

In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

A number of viral vectors have been constructed, that can be used to express the disclosed antigens, including polyoma, i.e., SV40 (Madzak et al., 1992, *J. Gen. Virol.*, 73:15331536), adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV (Margolskee, 1992, *Curr. Top. Microbiol. Immunol.*, 158: 67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In several embodiments, the viral vector can include an adenoviral vector that expresses a protomer of a disclosed recombinant coronavirus S ectodomain trimer. Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) can be used to generate the adenoviral vector. For example, a simian adenovirus can be used as the source of the viral genome of the adenoviral vector. A simian adenovirus can be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. In one example, a chimpanzee serotype C Ad3 vector is used (see, e.g., Peruzzi et al., Vaccine, 27:1293-1300, 2009). Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. The person of ordinary skill in the art is familiar with replication competent and deficient adenoviral vectors (including singly and multiply replication deficient adenoviral vectors). Examples of replication-deficient adenoviral vectors, including multiply replication-deficient adenoviral vectors, are disclosed in U.S. Pat. Nos. 5,837,511; 5,851,806; 5,994,106; 6,127,175; 6,482,616; and 7,195,896, and International Patent Application Nos. WO 94/28152, WO 95/02697, WO 95/16772, WO 95/34671, WO 96/22378, WO 97/12986, WO 97/21826, and WO 03/02231 1.

V. Virus-Like Particles

In some embodiments, a virus-like particle (VLP) is provided that includes a disclosed recombinant coronavirus S ectodomain trimer. Typically such VLPs include a recombinant coronavirus S ectodomain trimer that is membrane anchored by a C-terminal transmembrane domain, for example the recombinant coronavirus S ectodomain protomers in the trimer each can be linked to a transmembrane domain and cytosolic tail from the corresponding coronavirus. VLPs lack the viral components that are required for virus replication and thus represent a highly attenuated, replication-incompetent form of a virus. However, the VLP can display a polypeptide (e.g., a recombinant coronavirus S ectodomain trimer) that is analogous to that expressed on infectious virus particles and can eliciting an immune response to the corresponding coronavirus when administered to a subject. Virus like particles and methods of their production are known and familiar to the person of ordinary skill in the art, and viral proteins from several viruses are known to form VLPs, including human papillomavirus, HIV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rotavirus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Virol. 70: 5422-9 (1996)), hepatitis E virus (Li et al., J. Virol. 71: 7207-13 (1997)), and Newcastle disease virus. The formation of such VLPs can be detected by any suitable technique. Examples of suitable techniques known in the art for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

VI. Immunogenic Compositions

Immunogenic compositions comprising a disclosed immunogen (e.g., a disclosed recombinant coronavirus S ectodomain trimer or nucleic acid molecule encoding a protomer of disclosed recombinant coronavirus S ectodomain trimer) and a pharmaceutically acceptable carrier are also provided. Such pharmaceutical compositions can be administered to subjects by a variety of administration modes known to the person of ordinary skill in the art, for example, intramuscular, intradermal, subcutaneous, intravenous, intra-arterial, intra-articular, intraperitoneal, intranasal, sublingual, tonsillar, oropharyngeal, or other parenteral and mucosal routes. In several embodiments, pharmaceutical compositions including one or more of the disclosed immunogens are immunogenic compositions. Actual methods for preparing administrable compositions will be known or apparent to those skilled in the art and are described in more detail in such publications as *Remingtons Pharmaceutical Sciences*, 19th Ed., Mack Publishing Company, Easton, Pa., 1995.

Thus, an immunogen described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. The immunogenic composition may optionally include an adjuvant to enhance an immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, Ind.) and IL-12 (Genetics Institute, Cambridge, Mass.), among many other suitable adjuvants well known in the art, may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some instances it may be desirable to combine a disclosed immunogen, with other pharmaceutical products (e.g., vaccines) which induce protective responses to other agents. For example, a composition including a recombinant paramyxovirus as described herein can be can be administered simultaneously (typically separately) or sequentially with other vaccines recommended by the Advisory Committee on Immunization Practices (ACIP; cdc.gov/vaccines/acip/index.html) for the targeted age group (e.g., infants from approximately one to six months of age), such as an influenza vaccine or a varicella zoster vaccine. As such, a disclosed immunogen including a recombinant coronavirus S ectodomain trimer described herein may be administered simultaneously or sequentially with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

In some embodiments, the composition can be provided as a sterile composition. The pharmaceutical composition typically contains an effective amount of a disclosed immunogen and can be prepared by conventional techniques. Typically, the amount of immunogen in each dose of the immunogenic composition is selected as an amount which induces an immune response without significant, adverse side effects. In some embodiments, the composition can be provided in unit dosage form for use to induce an immune response in a subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

VII. Methods of Inducing an Immune Response

The disclosed immunogens (e.g., recombinant coronavirus S ectodomain trimer, a nucleic acid molecule (such as an RNA molecule) or vector encoding a protomer of a disclosed recombinant coronavirus S ectodomain trimer, or a protein nanoparticle or virus like particle comprising a disclosed recombinant coronavirus S ectodomain trimer) can be administered to a subject to induce an immune response to the corresponding coronavirus S ectodomain in the subject. In a particular example, the subject is a human. The immune response can be a protective immune response, for example a response that inhibits subsequent infection with the corresponding coronavirus. Elicitation of the immune response can also be used to treat or inhibit infection and illnesses associated with the corresponding coronavirus.

A subject can be selected for treatment that has, or is at risk for developing infection with the coronavirus corresponding to the S protein in the immunogen, for example because of exposure or the possibility of exposure to the coronavirus. Following administration of a disclosed immunogen, the subject can be monitored for infection or symptoms associated with the coronavirus, or both.

Typical subjects intended for treatment with the therapeutics and methods of the present disclosure include humans, as well as non-human primates and other animals. To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize coronavirus infection. These and other routine methods allow the clinician to select patients in need of therapy using the methods and pharmaceutical compositions of the disclosure. In accordance with these methods and principles, a composition can be administered according to the teachings herein, or other conventional methods, as an independent prophylaxis or treatment program, or as a follow-up, adjunct or coordinate treatment regimen to other treatments.

The administration of a disclosed immunogen can be for prophylactic or therapeutic purpose. When provided prophylactically, the disclosed therapeutic agents are provided in advance of any symptom, for example, in advance of infection. The prophylactic administration of the disclosed therapeutic agents serves to prevent or ameliorate any subsequent infection. When provided therapeutically, the disclosed therapeutic agents are provided at or after the onset of a symptom of disease or infection, for example, after development of a symptom of infection with the coronavirus corresponding to the S protein in the immunogen, or after diagnosis with the coronavirus infection. The therapeutic agents can thus be provided prior to the anticipated exposure to the coronavirus so as to attenuate the anticipated severity, duration or extent of an infection and/or associated disease symptoms, after exposure or suspected exposure to the virus, or after the actual initiation of an infection.

The immunogens described herein, and immunogenic compositions thereof, are provided to a subject in an amount effective to induce or enhance an immune response against the coronavirus S protein in the immunogen in the subject, preferably a human. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to coronavirus S proteins. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be a different disclosed immunogen. In some examples that the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example a relatively large dose in a primary immunization and then a boost with relatively smaller doses.

In some embodiments, the boost can be administered about two, about three to eight, or about four, weeks following the prime, or about several months after the prime. In some embodiments, the boost can be administered about 5, about 6, about 7, about 8, about 10, about 12, about 18, about 24, months after the prime, or more or less time after the prime. Periodic additional boosts can also be used at appropriate time points to enhance the subject's "immune memory." The adequacy of the vaccination parameters chosen, e.g., formulation, dose, regimen and the like, can be determined by taking aliquots of serum from the subject and assaying antibody titers during the course of the immunization program. In addition, the clinical condition of the subject can be monitored for the desired effect, e.g., prevention of infection or improvement in disease state (e.g., reduction in viral load). If such monitoring indicates that vaccination is sub-optimal, the subject can be boosted with an additional dose of immunogenic composition, and the vaccination parameters can be modified in a fashion expected to potentiate the immune response.

In some embodiments, the prime-boost method can include DNA-primer and protein-boost vaccination protocol to a subject. The method can include two or more administrations of the nucleic acid molecule or the protein.

For protein therapeutics, typically, each human dose will comprise 1-1000 µg of protein, such as from about 1 µg to about 100 µg, for example, from about 1 µg to about 50 µg, such as about 1 µg, about 2 µg, about 5 µg, about 10 µg, about 15 µg, about 20 µg, about 25 µg, about 30 µg, about 40 µg, or about 50 µg.

The amount utilized in an immunogenic composition is selected based on the subject population (e.g., infant or elderly). An optimal amount for a particular composition can be ascertained by standard studies involving observation of antibody titers and other responses in subjects. It is understood that a therapeutically effective amount of a disclosed immunogen, such as a disclosed recombinant coronavirus S ectodomain trimer, viral vector, or nucleic acid molecule in a immunogenic composition, can include an amount that is ineffective at eliciting an immune response by administration of a single dose, but that is effective upon administration of multiple dosages, for example in a prime-boost administration protocol.

Upon administration of a disclosed immunogen of this disclosure, the immune system of the subject typically responds to the immunogenic composition by producing antibodies specific for the coronavirus S ectodomain trimer included in the immunogen. Such a response signifies that an immunologically effective dose was delivered to the subject.

In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, the recombinant coronavirus S ectodomain trimer included in the immunogen.

Coronavirus infection does not need to be completely eliminated or reduced or prevented for the methods to be effective. For example, elicitation of an immune response to a coronavirus with one or more of the disclosed immunogens can reduce or inhibit infection with the coronavirus by a desired amount, for example, by at least 10%, at least 20%, at least 50%, at least 60%, at least 70%, at least 80%, at least 90%, at least 95%, at least 98%, or even at least 100% (elimination or prevention of detectable infected cells), as compared to infection with the coronavirus in the absence of the immunogen. In additional examples, coronavirus replication can be reduced or inhibited by the disclosed methods. Coronavirus replication does not need to be completely eliminated for the method to be effective. For example, the immune response elicited using one or more of the disclosed immunogens can reduce replication of the corresponding coronavirus by a desired amount, for example, by at least 10%, at least 20%, at least 50%, at least 60%, at least 70%, at least 80%, at least 90%, at least 95%, at least 98%, or even at least 100% (elimination or prevention of detectable replication of the coronavirus), as compared to replication of the coronavirus in the absence of the immune response.

In some embodiments, the disclosed immunogen is administered to the subject simultaneously with the administration of the adjuvant. In other embodiments, the disclosed immunogen is administered to the subject after the administration of the adjuvant and within a sufficient amount of time to induce the immune response.

One approach to administration of nucleic acids is direct immunization with plasmid DNA, such as with a mammalian expression plasmid Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In some embodiments, a plasmid DNA vaccine is used to express a disclosed immunogen in a subject. For example, a nucleic acid molecule encoding a disclosed immunogen can be administered to a subject to induce an immune response to the coronavirus S protein included in the immunogen. In some embodiments, the nucleic acid molecule can be included on a plasmid vector for DNA immunization, such as the pVRC8400 vector (described in Barouch et al., J. Virol, 79, 8828-8834, 2005, which is incorporated by reference herein).

In another approach to using nucleic acids for immunization, a disclosed recombinant coronavirus S ectodomain or recombinant coronavirus S ectodomain trimer can be expressed by attenuated viral hosts or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (*Bacillus Calmette Guerin*) provides another vector for expression of the peptides (see Stover, Nature 351:456-460, 1991).

In one embodiment, a nucleic acid encoding a disclosed recombinant coronavirus S ectodomain or coronavirus S ectodomain trimer is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

In another embodiment, an mRNA-based immunization protocol can be used to deliver a nucleic acid encoding a disclosed recombinant coronavirus S ectodomain or coronavirus S ectodomain trimer directly into cells. In some embodiments, nucleic acid-based vaccines based on mRNA may provide a potent alternative to the previously mentioned approaches. mRNA vaccines preclude safety concerns about DNA integration into the host genome and can be directly translated in the host cell cytoplasm. Moreover, the simple cell-free, in vitro synthesis of RNA avoids the manufacturing complications associated with viral vectors. Two exemplary forms of RNA-based vaccination that can be used to deliver a nucleic acid encoding a disclosed recombinant coronavirus S ectodomain or coronavirus S ectodomain trimer include conventional non-amplifying mRNA immunization (see, e.g., Petsch et al., "Protective efficacy of in vitro synthesized, specific mRNA vaccines against influenza A virus infection," Nature biotechnology, 30(12):1210-6, 2012) and self-amplifying mRNA immunization (see, e.g., Geall et al., "Nonviral delivery of self-amplifying RNA vaccines," PNAS, 109(36): 14604-14609, 2012; Magini et al., "Self-Amplifying mRNA Vaccines Expressing Multiple Conserved Influenza Antigens Confer Protection against Homologous and Heterosubtypic Viral Challenge," PLoS One, 11(8):e0161193, 2016; and Brito et al., "Self-amplifying mRNA vaccines," Adv Genet., 89:179-233, 2015).

In some embodiments, administration of a therapeutically effective amount of one or more of the disclosed immunogens to a subject induces a neutralizing immune response in the subject. To assess neutralization activity, following immunization of a subject, serum can be collected from the subject at appropriate time points, frozen, and stored for neutralization testing. Methods to assay for neutralization activity are known to the person of ordinary skill in the art and are further described herein, and include, but are not limited to, plaque reduction neutralization (PRNT) assays, microneutralization assays, flow cytometry based assays, single-cycle infection assays. In some embodiments, the serum neutralization activity can be assayed using a panel of coronavirus pseudoviruses. For example, to test the immunogenicity of the vaccine candidates against multiple MERS-CoV strains—without the requirement of a biosafety level 3 facility—a pseudotyped reporter virus neutralization assay was previously developed (Wand et al., Nat Commun, 6:7712, 2015), similar to that previously developed for SARS-CoV (Martin et al., *Vaccine* 26, 6338, 2008; Yang et al., *Nature* 428, 561, 2004; Naldini et al., *PNAS* 93, 11382, 1996; Yang et al., *PNAS* 102, 797, 2005).

In some embodiments, administration of a therapeutically effective amount of one or more of the disclosed immunogens to a subject induces a neutralizing immune response in the subject. To assess neutralization activity, following immunization of a subject, serum can be collected from the subject at appropriate time points, frozen, and stored for neutralization testing. Methods to assay for neutralization activity are known to the person of ordinary skill in the art and are further described herein, and include, but are not limited to, plaque reduction neutralization (PRNT) assays, microneutralization assays, flow cytometry based assays, single-cycle infection assays. In some embodiments, the serum neutralization activity can be assayed using a panel of coronavirus pseudoviruses.

EXAMPLES

The following examples are provided to illustrate particular features of certain embodiments, but the scope of the claims should not be limited to those features exemplified.

Example 1

Prefusion Stabilized MERS-CoV S Protein

This example describes development of a recombinant MERS-CoV S ectodomain trimer that is stabilized in a prefusion conformation.

The structure of the prefusion S ectodomain trimer of a human betacoronavirus was recently elucidated (Kirchdoerfer et al., "Prefusion structure of a human coronavirus spike protein," Nature, 351:118-121, 2016). This structure was further investigated to reveal several key details about human coronavirus spike architecture. First, receptor-binding elements within S1 cap the fusion-mediating elements in S2, likely preventing their conformational rearrangement (FIG. 1) until triggering occurs.

The S1 C-terminal domains appear interdigitated and form extensive quaternary interactions (FIG. 2A), suggesting conformational flexibility or "breathing" would be required for the HKU1-CoV Spike to make receptor interactions similar to those made between the SARS-CoV receptor binding domain (RBD) and ACE2 receptors (FIG. 2A). In addition, the structure revealed two sub-domains, SD-1 and SD-2, in HKU1-CoV S1 (FIGS. 2C, 2D), The SD-2 loop contains the site dedicated to HKU1-CoV S furin cleavage; and furin cleavage at the S1/S2 junction is a process necessary for infection (FIG. 2D). S2 contains four classical components of a Class 1 fusion machine: a fusion peptide (FIG. 3A), two heptad repeats, HR1 (FIG. 3B) and HR2, and a transmembrane domain.

Figures 4A, 4B, 4C:
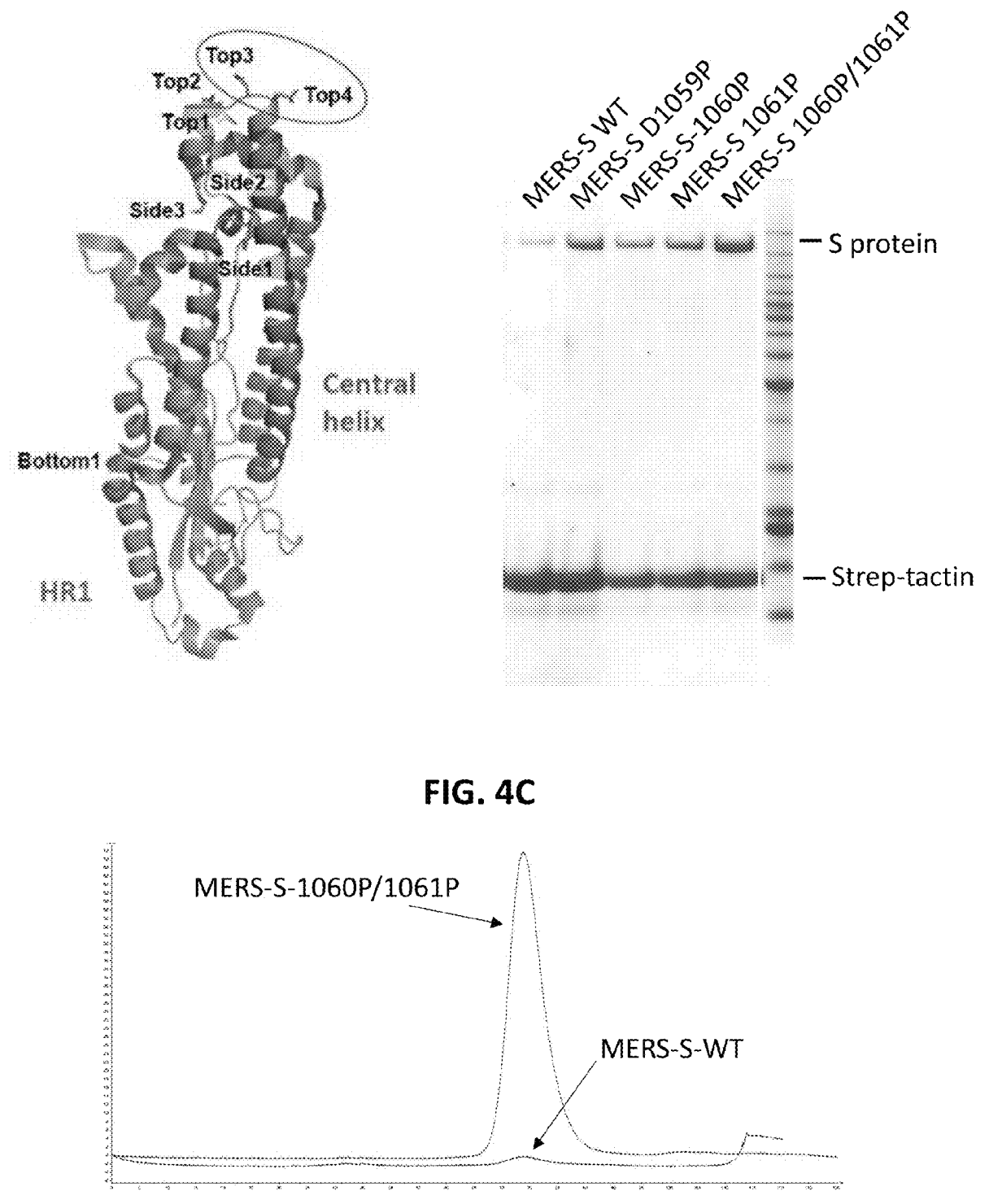

Structure-based stabilization of betacoronavirus prefusion trimers. The HKU1-CoV prefusion S structure was used as a starting point to design mutations that would stabilize betacoronavirus S trimers in the prefusion conformation. Dozens of possible stabilizing mutations were designed and tested in the context of the MERS-CoV S protein. Two mutations were identified to be particularly effective for stabilizing the MERS-CoV S protein in its prefusion conformation: V1060P and L1061P (or their combination) (FIG. 4). MERS-CoV S proteins including these mutations also had >50 fold increased expression (FIG. 4). These two proline substitutions are located at the top portion (membrane distal) of the MERS-CoV S2 central helix and HR1 to prevent pre-to-postfusion conformational changes. Prefusion stabilization of the MERS-CoV S protein is preliminarily indicated by increased expression levels when these mutations are combined compared to an S2 truncated, but otherwise wild-type (WT) MERS-CoV S (C6) (FIGS. 4B, 4C). WT MERS-CoV S likely spontaneously flips from pre-to-postfusion conformation. Corresponding double proline mutations in SARS-CoV and HKU1-CoV S also increased expression above WT S.

S protein immunogens were expressed from codon-optimized genes encoding the S ectodomain (without TM and CT) with a C-terminal T4 fibritin trimerization domain, an HRV3C cleavage site, a 6xHis-tag and a Twin-Strep-tag that were cloned into the eukaryotic-expression vector pαH. Following sequence verification, expression plasmids were transiently transfected into FreeStyle293 cells. Three hours after transfection, kifunensine was added to a final concentration of 5 μM. Cultures were harvested six days later, and secreted protein was purified from the supernatant and soluble protein w purified from the supernatant by passage over $Ni^{2+}$-NTA and StrepTactin resin using affinity tags on the C-terminus of the proteins. The purified proteins were then be passed over a size-exclusion column to assess their oligomeric state and to isolate monodisperse fractions corresponding to trimeric ectodomains. Protein expression levels were then assessed by SDS-PAGE (10 μL of protein-bound resin was boiled and loaded per lane). This expression strategy was used to generated generate and test proline-substituted variants of MERS-CoV S (Eng1 strain, residues 1-1291), SARS-CoV S (Tort strain, residues 1-1190) and HCoV-HKU1 S (N5 strain, residues 1-1276). The MERS-CoV S ectodomain trimers included a 748-RSVR-751 (residues 748-751 of SEQ ID NO: 1) to 748-ASVG-751 (residues 748-751 of SEQ ID NO: 3) substitutions to remove the S1/S2 cleavage site.

Mice (N=5/group) were vaccinated with 0.1 rig, 1 μg, or 10 μg of the MERS-CoV S trimer stabilized in the prefusion conformation by V1060P and L1061P substitutions to evaluate the effectiveness of the resulting immune response (FIG. 5). As a comparison, mice were also vaccinated with the MERS-CoV S1 protein, which was previously found to induce robust neutralizing antibody responses associated with protection, and MERS-CoV S ectodomain trimers with WT sequence. Control mice were given PBS. The immunogens were based on the England1 ("Eng") MERS-CoV strain.

Immunizations were performed as weeks 0 and 3. Two weeks following the last immunization, serum was collected and tested for neutralization against various MERS pseudovirus strains: England1, Florida USA2, Bisha1, Korea002, JordanN3, Buraidah1, and Indiana USA1 Serum was diluted, in triplicate, and incubated with MERS-CoV pseudovirus prior to inoculation of Huh7.5 cells. Dilution curves were fitted to mock cells and cells exposed to un-neutralized virus as 100% and 0% neutralization, respectively. IC90 titers were calculated as the dilution of serum needed to neutralize 90% of MERS-CoV pseudovirus.

Vaccination with the MERS-CoV S1, wild-type MERS-CoV S ectodomain, or the prefusion stabilized MERS-CoV S ectodomain induced similar robust levels of neutralizing antibodies against homologous MERS-CoV England1 reporter pseudovirus at dosages of 10 μg, but the prefusion-stabilized spike was superior at lower dosages (FIG. 5A). Further, when tested against homologous virus strains, the prefusion stabilized MERS-CoV ectodomain trimer produced a superior immune response (FIG. 5B).

Additional assays were performed to show that vaccination with MERS S-2P ectodomain trimer elicited more non-RBD binding antibodies than MERS S1 ectodomain trimer (FIG. 6A), and higher levels of neutralizing activity targeting a greater diversity of epitopes than antigens based on RBD or S1 monomer (FIG. 6B).

Figure 7:
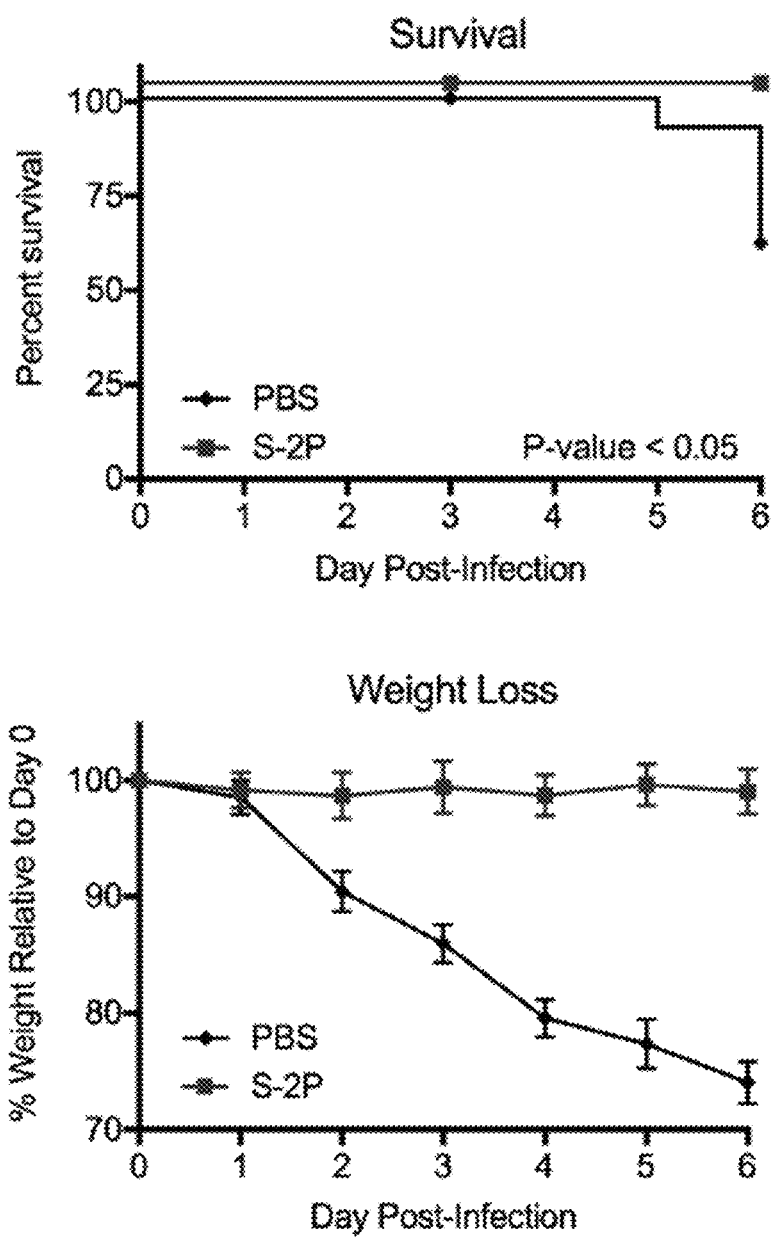
FIG. 7 is a set of graphs showing that MERS-CoV S-2P immunization protects against lethal MERS challenge in mice. C57BL/6J mice were genetically engineered using CRISPR-Cas9 genomic editing to encode human DPP4 mutations (288L and 330R; "288/330$^{+/+}$") as previously described (see, Cockrell et al., "A mouse model for MERS coronavirus-induced acute respiratory distress syndrome." *Nature Microbiology*. 2:16226, 2016, which is incorporated by reference herein). 288/330+/+ mice were vaccinated with 0.1 µg MERS-CoV S-2P or PBS, with Sigma Adjuvant System at weeks 0 and 3. Four weeks following final vaccination, mice were challenged with a lethal dose of mouse-adapted MERS virus and monitored for survival and weight loss.

Additionally, challenge studies were performed to determine if the prefusion-stabilized MERS-CoV S ectodomain trimer could prevent MERS-CoV infection in an animal model (FIG. 7). The challenge studies were performed using C57BL/6J mice that were genetically engineered using CRISPR-Cas9 genomic editing to encode human DPP4 mutations (288L and 330R; "288/330$^{+/+}$") as previously described (see, Cockrell et al., "A mouse model for MERS coronavirus-induced acute respiratory distress syndrome." Nature Microbiology. 2:16226, 2016, which is incorporated by reference herein). These mice are known to be susceptible to invention with MERS-CoV. The 288/330' mice were vaccinated with 0.1 μg MERS CoV-S ectodomain timer with the double proline mutation using the Sigma Adjuvant System at weeks 0 and 3. Four weeks following final vaccination, the mice were challenged with a lethal dose of mouse-adapted MERS virus and monitored for survival and weight loss. As shown in FIG. 7, prior immunization with the prefusion stabilized MERS-CoV S ectodomain trimer protected against lethal MERS challenge in mice.

Example 2

Prefusion Stabilized Coronavirus Spike Proteins

HKU1-CoV is closely related to other betacoronaviruses, such as the zoonotic viruses SARS-CoV and MERS-CoV, both of which are associated with high mortality. Accordingly, additional coronavirus S ectodomain trimers stabilized in the prefusion conformation by double proline mutations at the HR1/central helix junction were evaluated as vaccine candidates.

Figure 8:
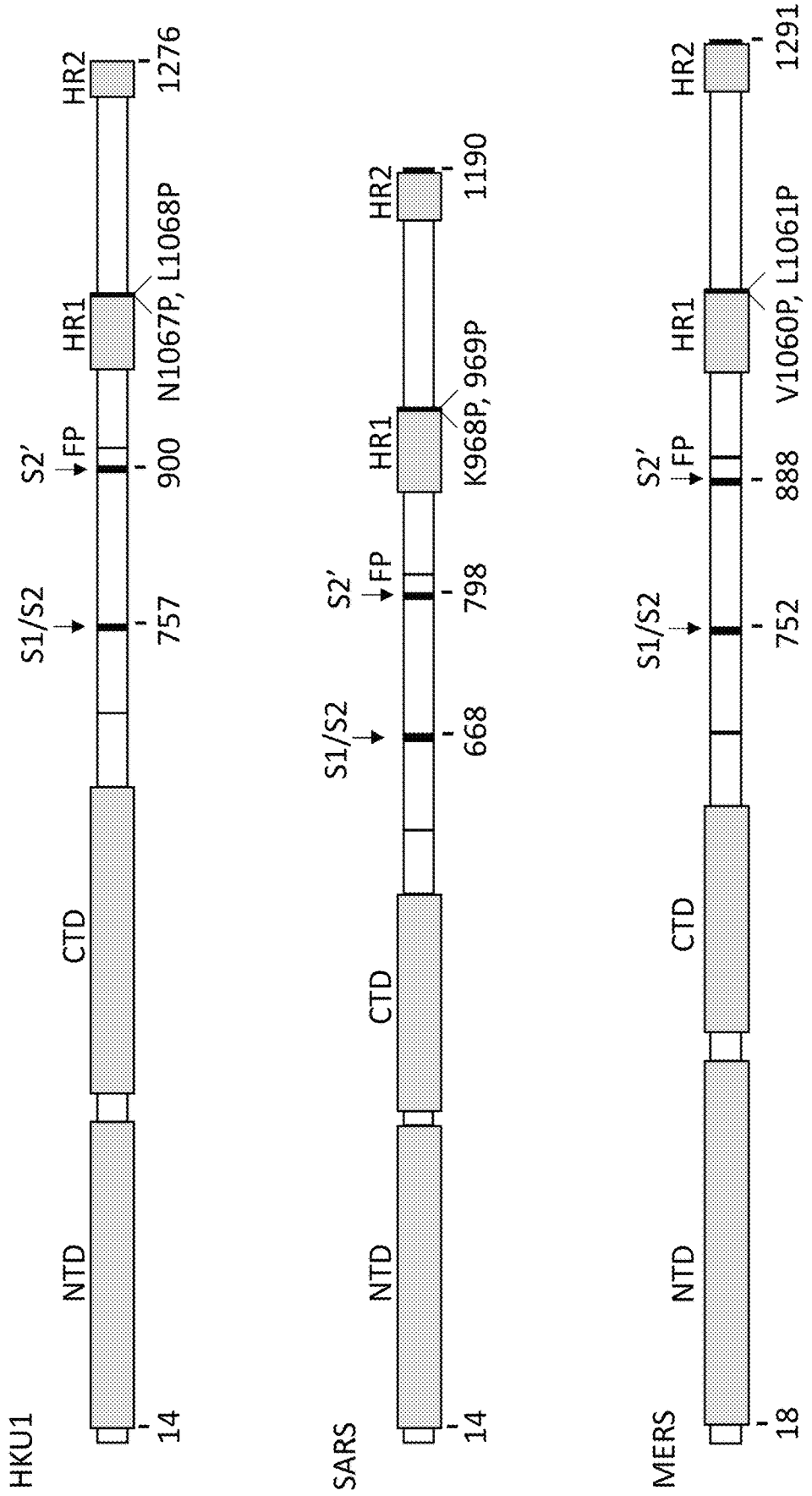
FIG. 8 illustrates the structural domains of the HKU1-CoV, SARS-CoV, and MERS-CoV S proteins, as well as positioning of double proline substitutions to stabilize these proteins in the prefusion conformation.
Figure 9A:
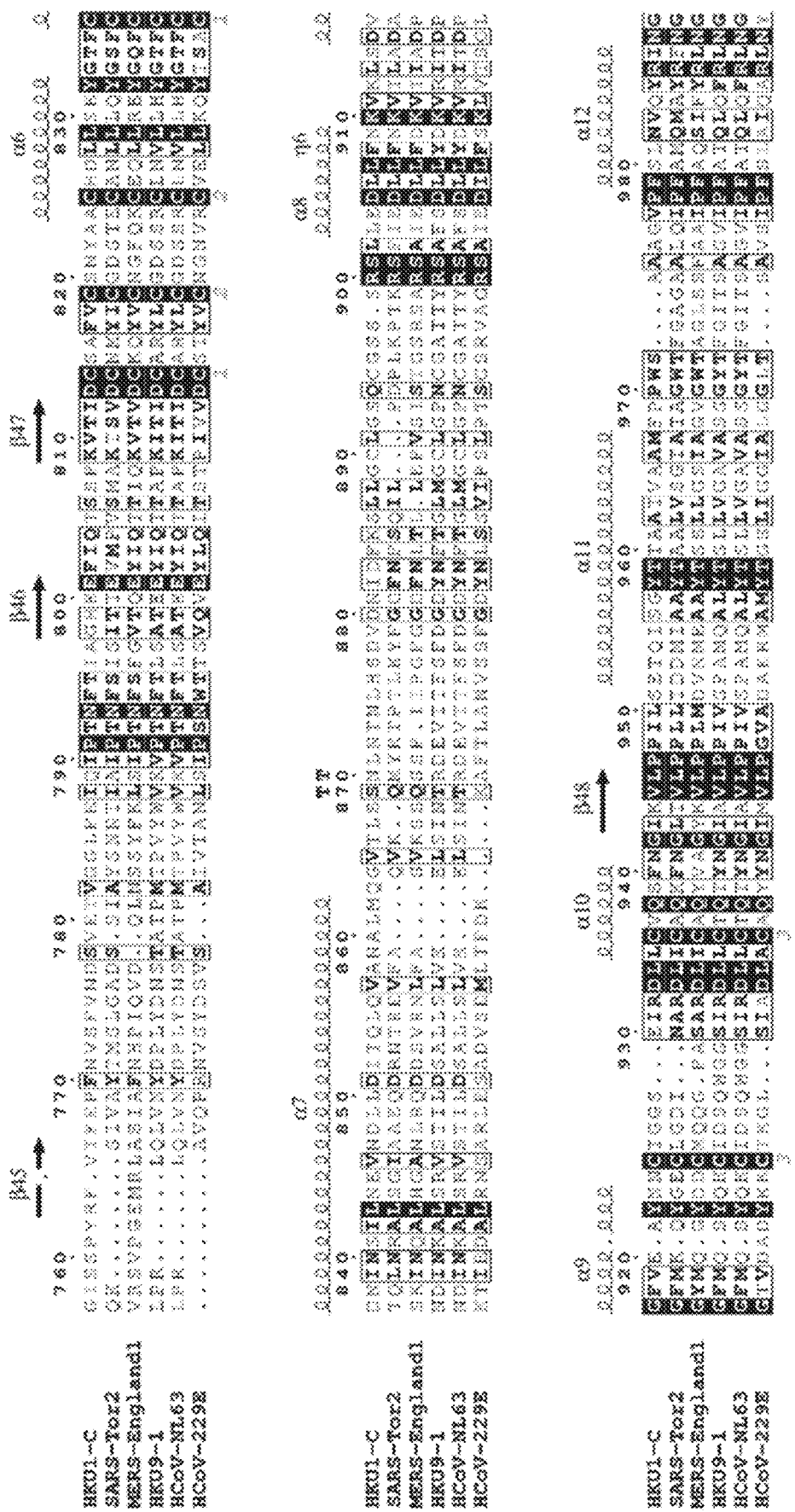
Figure 9B:
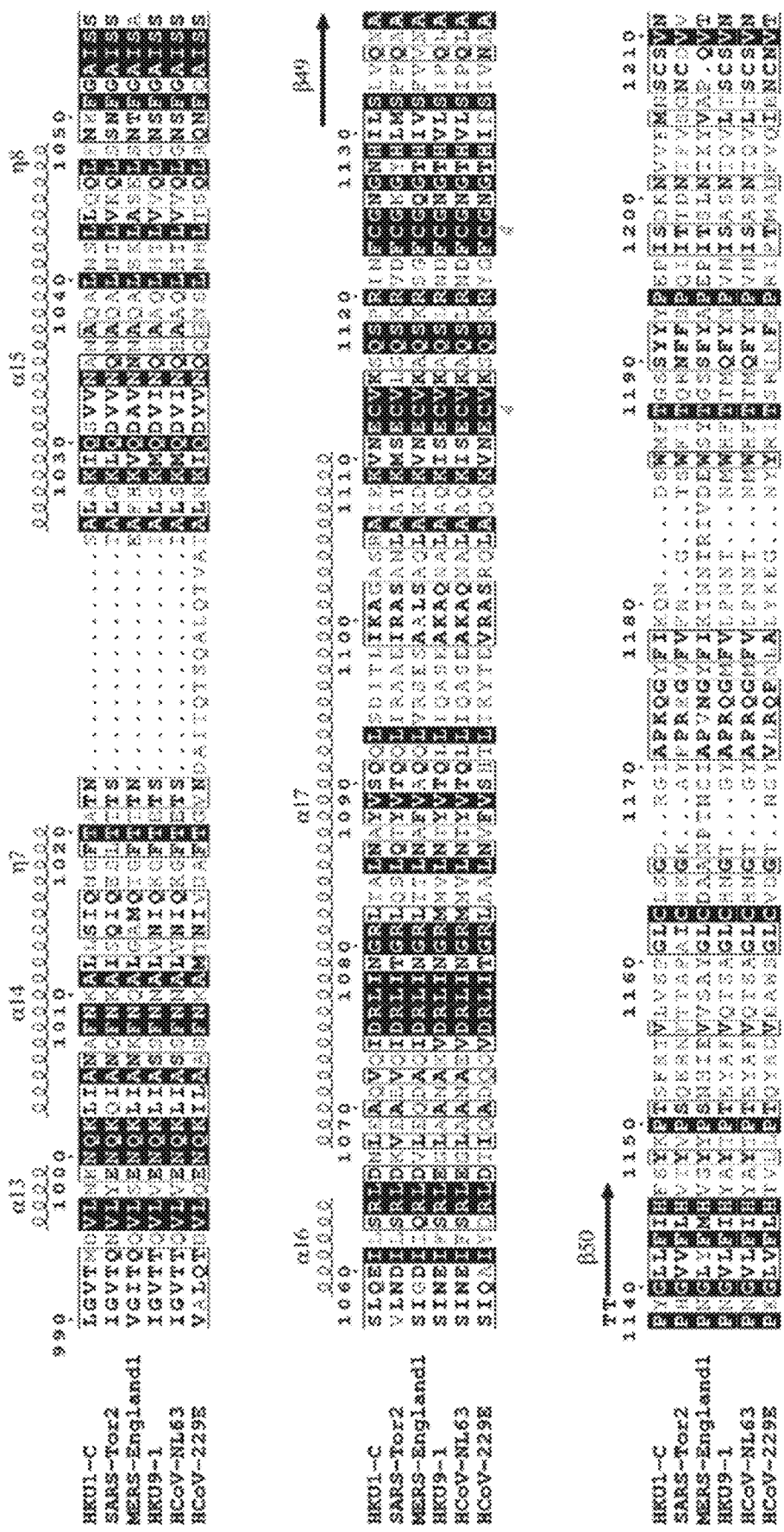

Due to the structural similarity of coronavirus S proteins, the sequences of these proteins can be readily aligned to identify structural domains, such as the HR1 and central helix. FIG. 8 illustrates the structural domains of the HKU1, SARS, and MERS-CoV S proteins, as well as positioning of double proline substitutions to stabilize these proteins in the prefusion conformation. FIG. 8 shows a sequence alignment of the S2 subunit of the HKU1-CoV, SARS-CoV, MERS-CoV, HKU9-CoV, NL63-CoV, and 229E-CoV S proteins, showing relevant sequence homology. The HR1 spans the α13, α14, α17, and α16 helices, including approximately residues 996-1064 (relative to HKU1-CoV numbering shown in the figure). The central helix is the α17 helix, including approximately residues 1068-1110. The HR2 includes approximates residues 1245-1276 (relative to HKU1-CoV numbering shown in the figure). The transmembrane domain begins at approximately residue 1292 (relative to HKU1-CoV numbering shown in the figure).

Proline substitutions were introduced into the SARS-CoV, HKU1-CoV, OC43-CoV, HKU9-CoV, WIV1-CoV, MHV-CoV, NL63-CoV and 229E-CoV. The SARS-CoV substitutions were K968P, V969P, or K968P and V969P. The HKU1-CoV substitutions are N1067P, L1068P, or N1067P and L1068P. The OC43-CoV substitutions are A1079P, L1080P, or A1079P and L1080P. The HKU9-CoV substitutions are G983P, L984P, or G983P and L984P. The WIV1-CoV substitutions are K969P, V970P, or K969P and V970P. The MHV-CoV substitutions are A1073P, L1074P, or A1073P and L1074P. The NL63-CoV substitutions are S1052P, I1053P, or S1052P and I1053P. The 229E-CoV substitutions are I869P, I870P, or I869P and I870P. Soluble SARS-CoV, HKU1-CoV, OC43-CoV, HKU9-CoV, WIV1-CoV, MHV-CoV, NL63-CoV and 229E-CoV S ectodomain trimers containing the indicated mutations, a signal peptide, and a C-terminal linkage to a T4 Fibritin trimerization domain and streptavidin tag were expressed in cells and purified as described in Example 1. Including the signal peptide and T4 Fibritin trimerization domain, protomer sequences of the referenced ectodomain trimers including the double proline substitutions are as follows:

SARS-CoV S 2P (K968P and V969P, SEQ ID NO: 30)
HKU1-CoV S 2P (N1067P and L1068P, SEQ ID NO: 31)
HKU9-CoV S 2P (G983P and L984P, SEQ ID NO: 32)
OC43-CoV S 2P (A1079P and L1080P, SEQ ID NO: 33)
WIV1-CoV S 2P (K969P and V970P, SEQ ID NO: 34)
MHV-CoV S 2P (A1073P and L1074P, SEQ ID NO: 35)
NL63-CoV S 2P (S1052P and I1053P, SEQ ID NO: 36)
229E-CoV S 2P (I869P and I870P, SEQ ID NO: 37)
PEDV-CoV S 2P (I1076P and L1077P, SEQ ID NO: 40)

Figure 10:
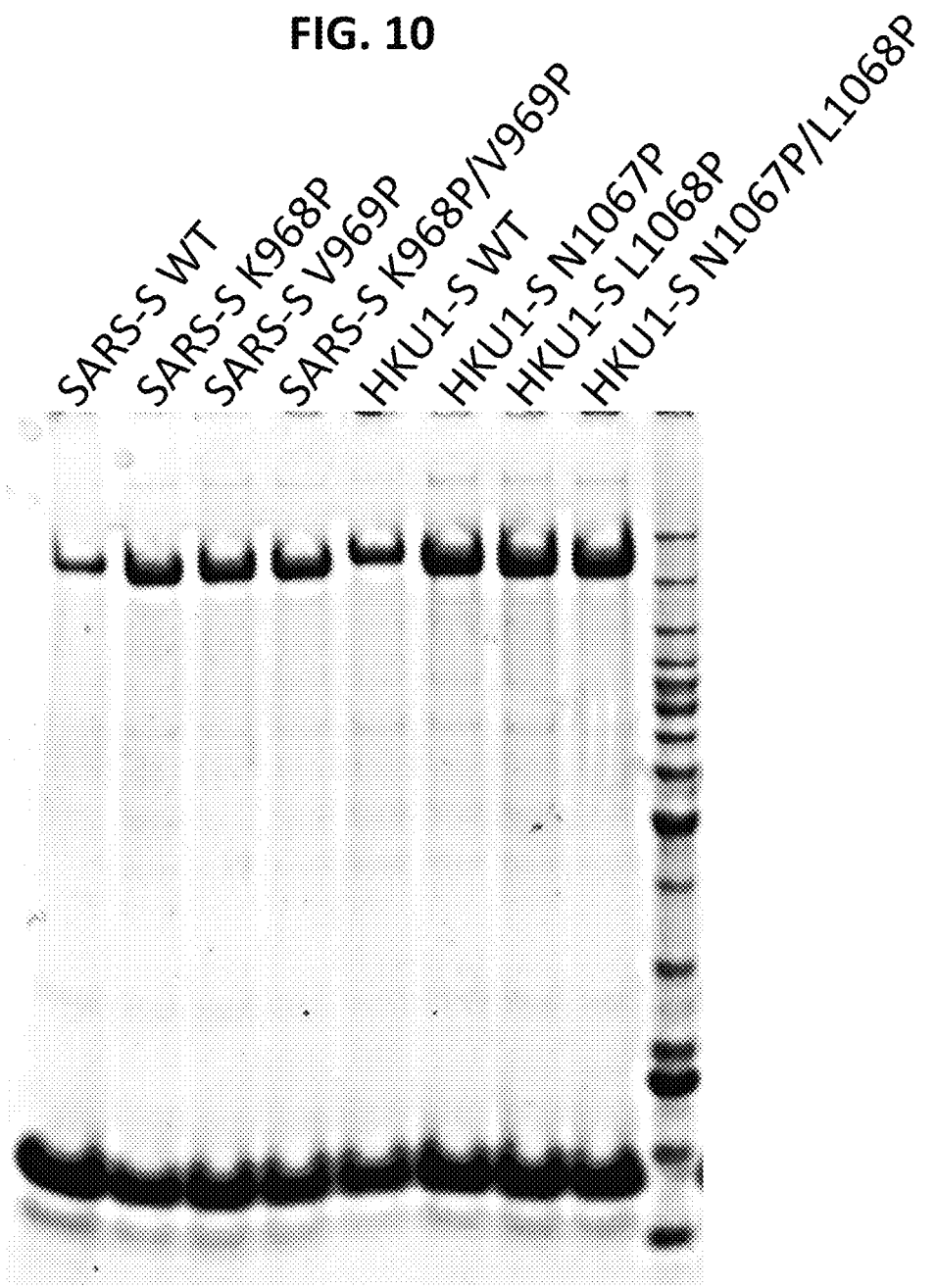
FIG. 10 shows a Coomassie-stained polyacrylamide gel illustrating that introduction of proline substitutions in the SARS-CoV (K968P and V969P substitutions, SARS-S-2P) and HKU1-CoV (N1067P and L1068P substitutions, HKU1-S-2P) S ectodomains at the locations corresponding to the MERS-CoV S V1060P and L1061P substitutions boosts the expression of the SARS-CoV and HKU1-CoV S ectodomains.

As shown in FIG. 10, the proline substitutions boosted the expression of the SARS-CoV and HKU1-CoV S ectodomains.

Figure 11:
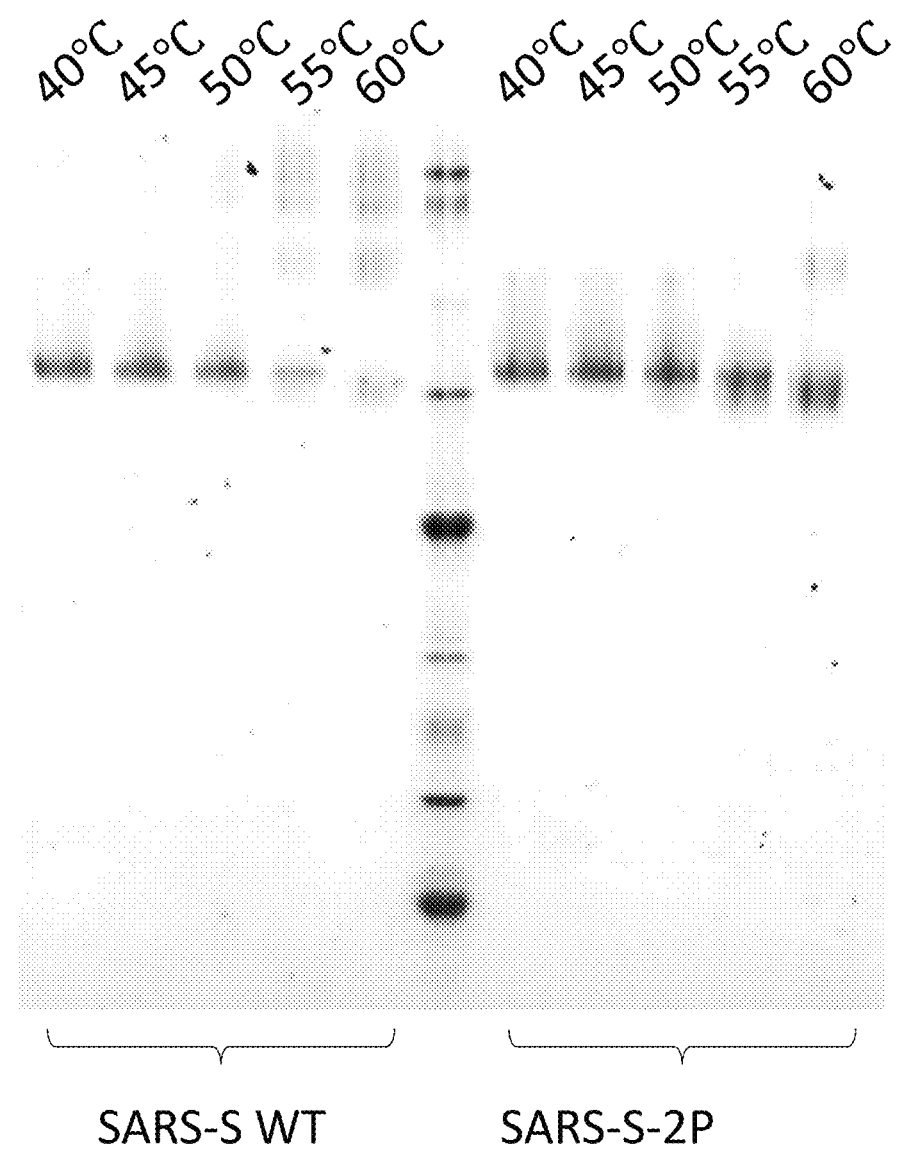

The thermal stability of the wild-type SARS-CoV S ectodomain (SARS-S-WT) and SARS-CoV S ectodomain with K968P and V969P (SARS-S-2P) was assessed (FIG. 11). About 3 µg SARS-S-WT or SARS-S-2P samples in TBS buffer (2 mM Tris pH8.0, 200 mM NaCl) were incubated at different temperature for 1 hour. The samples were then analyzed on the NativePAGE Novex Bis-Tris gels (Invitrogen) using procedures suggested by the manufacturer. As shown in FIG. 11, the SARS-S-2P has higher thermal stability than SARS-S-WT.

The expressed protein trimers were further analyzed by gel chromatography. FIG. 12 illustrates results from chromatography experiments concerning wild-type SARS-CoV S ectodomain (SARS-S-WT), SARS-CoV S ectodomain with K968P and V969P (SARS-S-2P), wild-type MERS-CoV S ectodomain (MERS-S-WT), MERS-CoV S ectodomain with V1060P and L1061P (MERS-S-2P), wild-type HKU1-CoV S ectodomain (HKU1-S-WT), HKU1-CoV S ectodomain with N1067P and L1068P (HKU1-S-2P). In all three cases, a larger peak was observed for the double proline mutant, show a many-fold increase in expression of the double proline mutant relative to the WT ectodomain trimer.

Figure 13A:
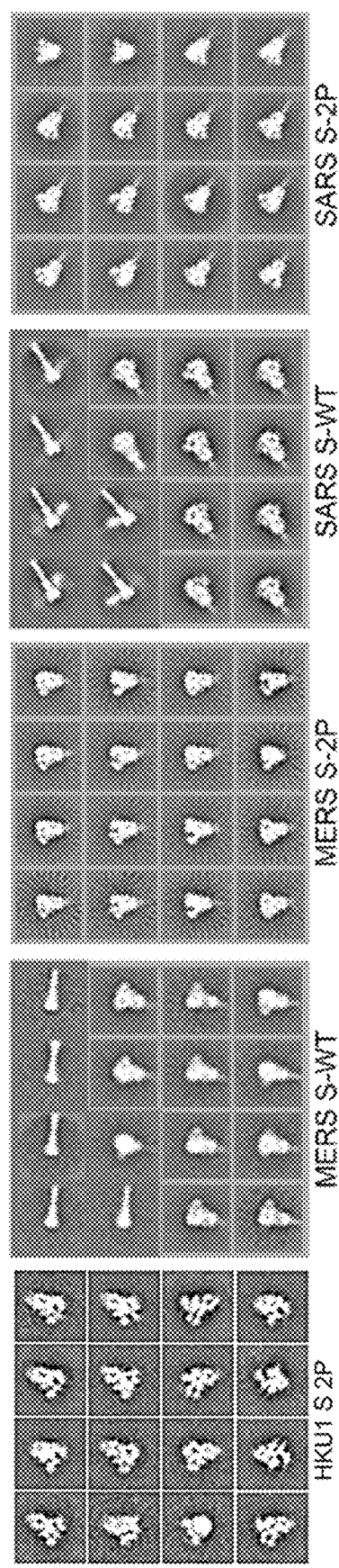
FIGS. 13A-13C show images of negative-stain electron microscopy of purified ectodomain trimers of MERS-CoV S 2P (V1060P and L1061P, SEQ ID NO: 28), SARS-CoV S 2P (K968P and V969P, SEQ ID NO: 30), HKU1-CoV S 2P (N1067P and L1068P, SEQ ID NO: 31), OC43-CoV S 2P (A1079P and L1080P, SEQ ID NO: 33), WIV1-CoV S 2P (K969P and V970P, SEQ ID NO: 34), PEDV-CoV S 2P (I1076P and L1077P, SEQ ID NO: 40), 229E S-2P (I869P and I870P, SEQ ID NO: 37), and SDCV 2-2P. Each of these ectodomain trimers was purified as a single peak and formed trimers in the typical prefusion conformation.

The conformation of the double proline mutant SARS-CoV, HKU1-CoV, and MERS-CoV S variants was assessed by negative stain electron microscopy (FIG. 13A). In each case the S variants with the double proline mutant were homogeneous and form trimers in the expected prefusion shape. Each of these ectodomain trimers was purified as a single peak and formed trimers in the typical prefusion conformation. In contrast, corresponding S proteins with native sequences formed trimers of mixed conformation, with some trimers in the typical prefusion conformation and others in the typical elongated post-fusion conformation.

Figure 13B:
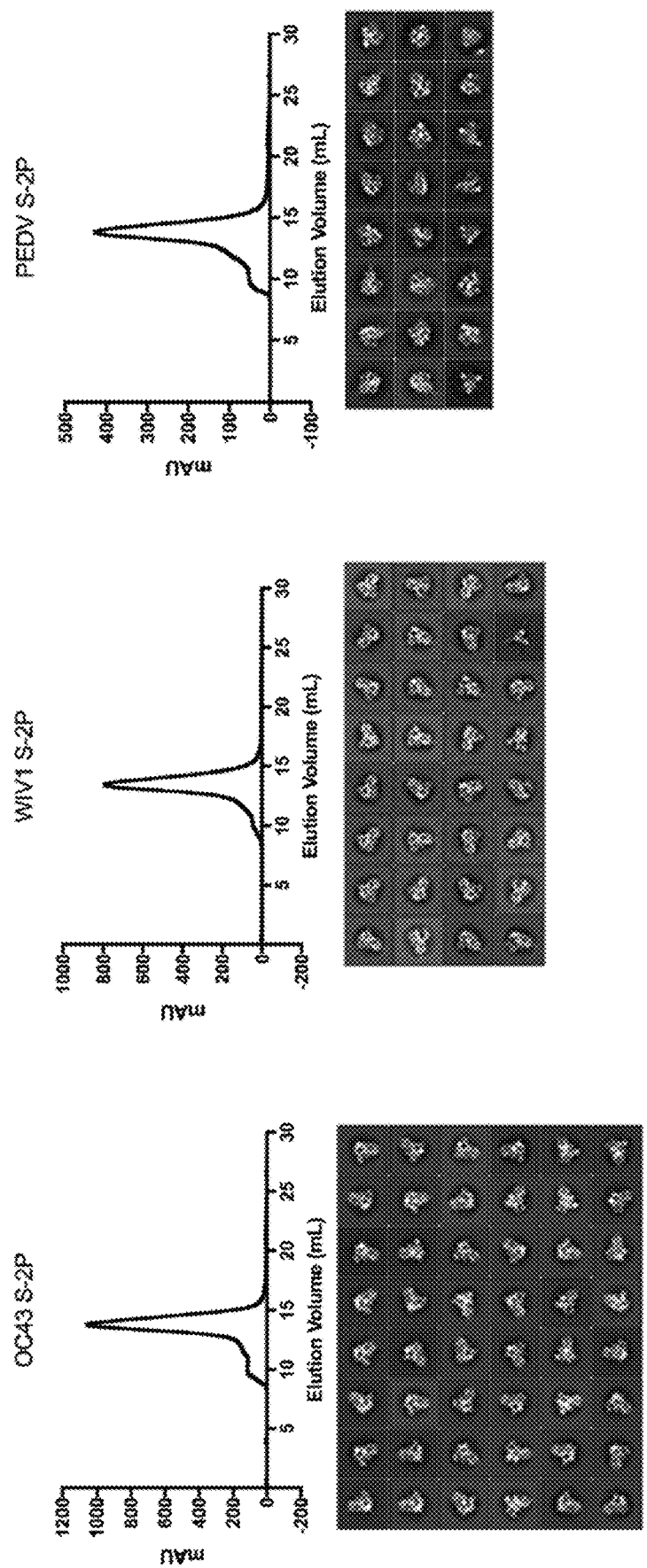
Figure 13C:
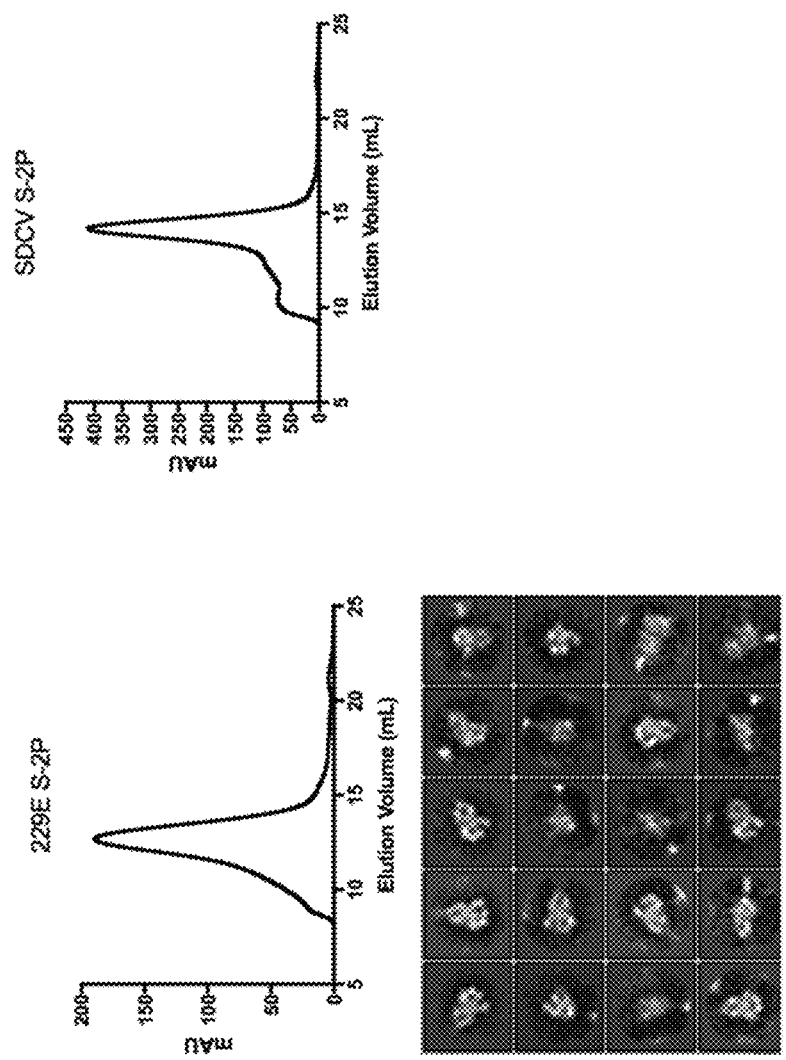

Additionally, the conformation of the double proline mutant OC43-CoV, WIV1-CoV, and PEDV-CoV, and 229E-CoV S variants was also assessed by negative stain electron microscopy (FIGS. 13B-13C). In each case the S variants with the double proline mutant were homogeneous and form trimers in the expected prefusion shape. Each of these ectodomain trimers was purified as a single peak and formed trimers in the typical prefusion conformation.

Figure 14A:
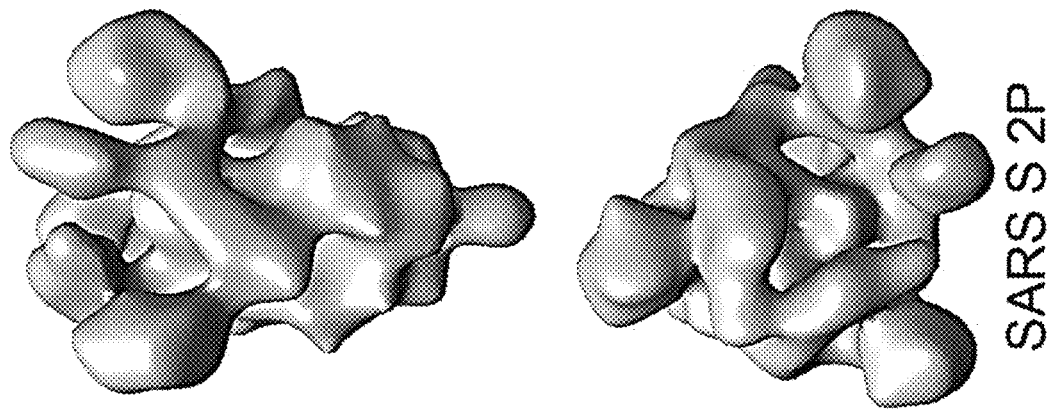
Figure 14B:
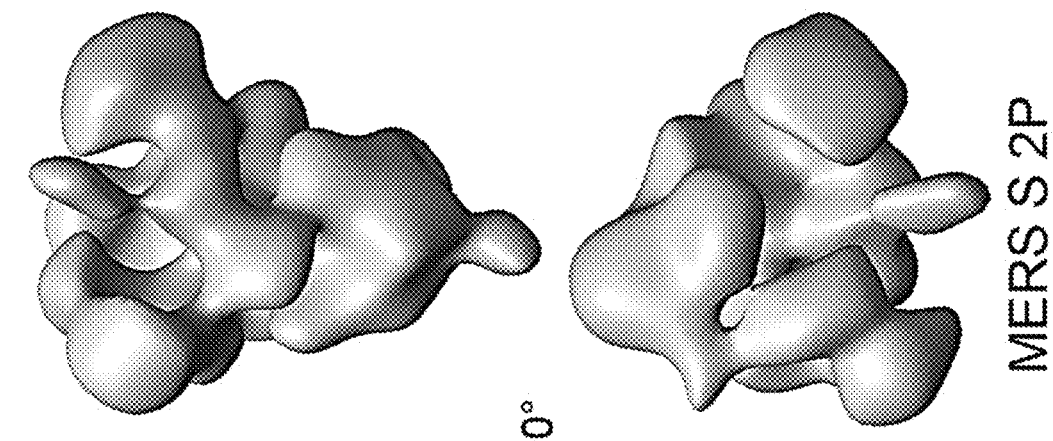
Figure 14C:
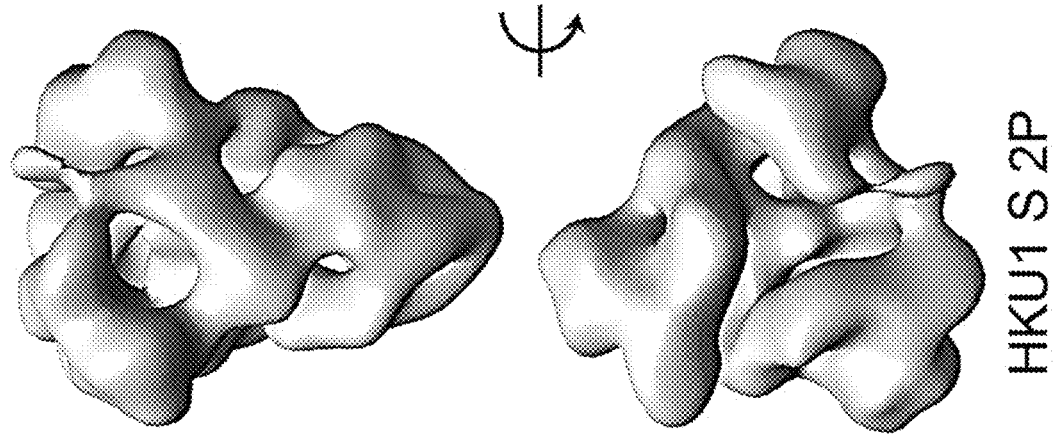

When low resolution negative stain reconstructions of S trimer constructs from HKU1-CoV (FIG. 14A), MERS-CoV (FIG. 14B), SARS-CoV (FIG. 14C), OC43-CoV S 2P (FIG. 14D), WIV1-CoV S 2P (FIG. 14E), PEDV-CoV S 2P (FIG. 14F), and 229E S-2P (FIG. 14G) were reconstructed from the EM data, the articles all formed homogeneous trimeric spike protein structures.

To assess the immunogenicity of the SARS-CoV S 2P ectodomain trimer, mice (N=5/group) were vaccinated with 0.1 rig or 1 µg of the SARS-CoV S trimer stabilized in the prefusion conformation by K968P and V969P substitutions (SEQ ID NO: 30) to evaluate the effectiveness of the resulting immune response (FIG. 15). As a comparison, mice were also vaccinated with the SARS-CoV S ectodomain trimers with WT sequence. The immunogens were based on the TOR2 SARS-CoV strain Immunizations were performed as weeks 0 and 3. Two weeks following the last immunization, serum was collected and tested for neutralization against autologous SARS pseudovirus. Serum was diluted, in triplicate, and incubated with SARS-CoV pseudovirus prior to inoculation of Huh7.5 cells. Dilution curves were fitted to mock cells and cells exposed to un-neutralized virus as 100% and 0% neutralization, respectively. IC90 titers were calculated as the dilution of serum needed to neutralize 90% of SARS-CoV pseudovirus. As shown in FIG. 15, vaccination with the prefusion stabilized SARS-CoV S ectodomain induced a superior immune response relative to the wild-type SARS-CoV S ectodomain, particularly at the 0.1 µg dose.

Additionally, mice (N=5/group) were vaccinated with 0.1 rig, 1 µg, or 10 µg of the HKU1-CoV S trimer stabilized in the prefusion conformation by N1067P and L1068P substitutions (SEQ ID NO: 31) to evaluate the effectiveness of the resulting immune response (FIG. 15). As a comparison, mice were also vaccinated with the HKU1-CoV S ectodomain trimers with WT sequence Immunizations were performed as weeks 0 and 3. Two weeks following the last immunization, serum was collected and tested for neutralization against autologous HKU1-CoV pseudovirus. Serum was diluted, in triplicate, and incubated with HKU1-CoV pseudovirus prior to inoculation of Huh7.5 cells. Dilution curves were fitted to mock cells and cells exposed to un-neutralized virus as 100% and 0% neutralization, respectively. IC90 titers were calculated as the dilution of serum needed to neutralize 90% of HKU1-CoV pseudovirus. As shown in FIG. 15, vaccination with the prefusion stabilized HKU1-CoV S ectodomain induced a superior immune response relative to the wild-type HKU1-CoV S ectodomain, particularly at the 0.1 µg dose.

Figure 16:
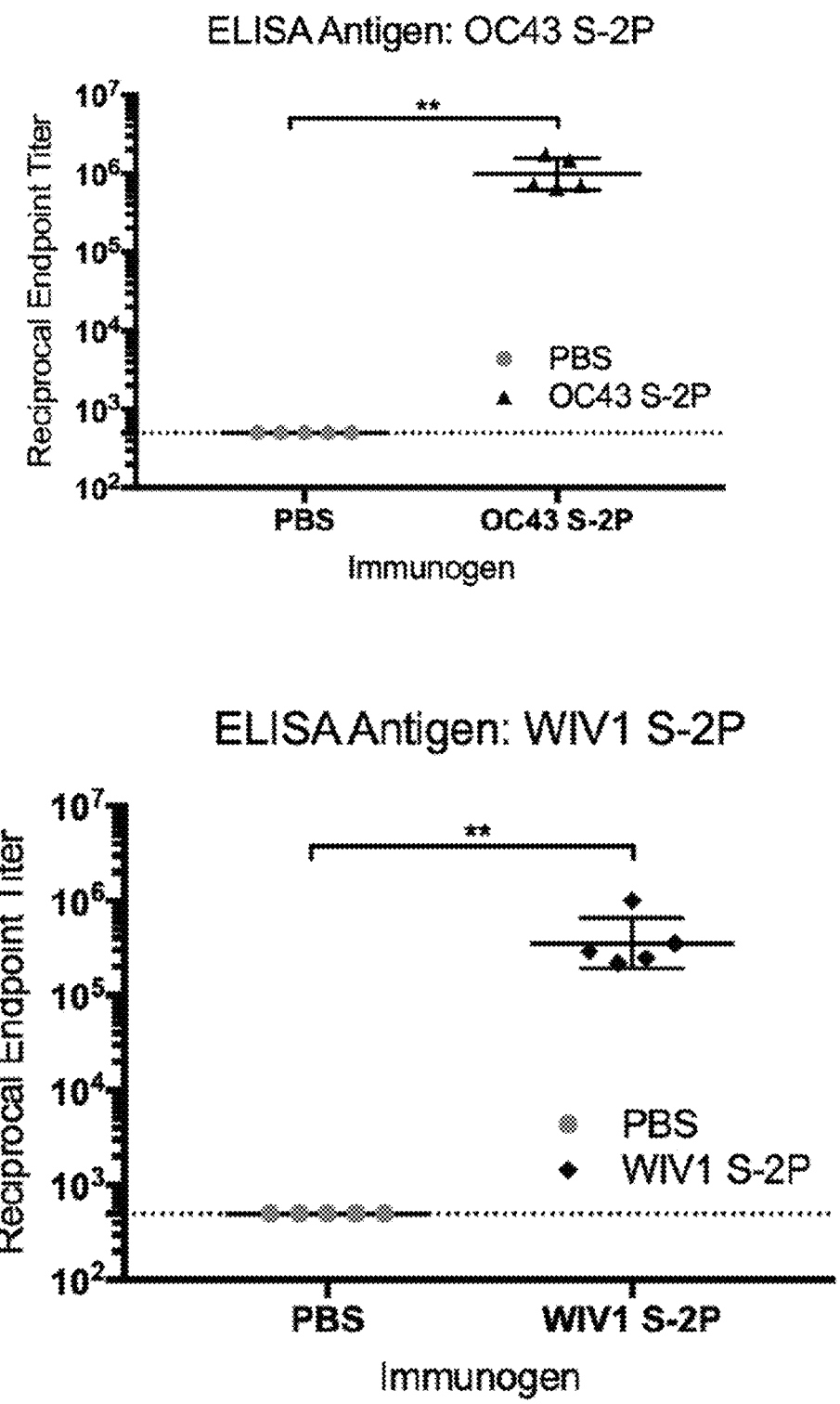
FIG. 16 shows results from immunogenicity assays in mice using the OC43-CoV S-2P and WIV1-CoV S-2P ectodomain trimer immunogens. BALB/c mice were vaccinated with 1 µg of OC43 S-2P ectodomain trimer or WIV1-CoV S-2P ectodomain trimer, with Sigma Adjuvant System at weeks 0 and 3. Two weeks following final vaccination, mice were bled for antibody analysis. Binding antibody titers to OC43 S-2P ectodomain trimer or WIV1-CoV S-2P ectodomain trimer were measured by ELISA. The geometric mean titer (GMT) and geometric SDs of each group are represented. The dotted line represents the assay limit of detection. \*\*denotes p-value<0.01, determined by Mann-Whitney t-test.

In additional assays, mice (N=5/group) were vaccinated with 1 µg of the OC43-CoV S ectodomain trimer stabilized in the prefusion conformation by A1079P and L1080P substitutions (SEQ ID NO: 33) or with 1 µg of the WIV1-CoV S ectodomain trimer stabilized in the prefusion conformation by K969P and V970P substitutions (SEQ ID NO: 34) to evaluate the effectiveness of the resulting immune response (FIG. 16). PBS was used as a control. Immunizations were performed as weeks 0 and 3. Two weeks following the last immunization, serum was collected and tested for binding to the corresponding immunogen by ELISA. As shown in FIG. 16, vaccination with the prefusion stabilized OC43-CoV S ectodomain trimer or the prefusion stabilized WIV1-CoV S ectodomain trimer elicited antibodies that target the corresponding ectodomain trimers.

It will be apparent that the precise details of the methods or compositions described may be varied or modified without departing from the spirit of the described embodiments. We claim all such modifications and variations that fall within the scope and spirit of the claims below.

It is claimed:

1. A nucleic acid molecule encoding a recombinant coronavirus S protein comprising two proline substitutions between the heptad repeat 1 (HR1) and the central helix of the S protein.

2. The nucleic acid molecule of claim 1, wherein the coronavirus is a betacoronavirus.

3. The nucleic acid molecule of claim 1, wherein the coronavirus is one of MERS-CoV, SARS-CoV, NL63-CoV, 229E-CoV, OC43-CoV, HKU1-CoV, WIV1-CoV, MHV, HKU9-CoV, PEDV-CoV, or SDCV.

4. The nucleic acid molecule of claim 1, wherein the recombinant coronavirus S protein further comprises a mutation to inhibit cleavage of a S1/S2 protease cleavage site.

5. The nucleic acid molecule of claim 1, operably linked to a promoter.

6. An immunogenic composition comprising the nucleic acid molecule of claim 1, and a pharmaceutically acceptable carrier.

7. A method for generating an immune response to a coronavirus S protein in a subject, comprising administering to the subject an effective amount of the nucleic acid molecule of claim 1 to generate the immune response.

8. The method of claim 7, wherein the immune response inhibits infection with the coronavirus.

9. The nucleic acid molecule of claim 1, wherein the nucleic acid molecule is an mRNA molecule.

10. The nucleic acid molecule of claim 9, wherein the coronavirus is a betacoronavirus.

11. The nucleic acid molecule of claim 9, wherein the coronavirus is one of MERS-CoV, SARS-CoV, NL63-CoV, 229E-CoV, OC43-CoV, HKU1-CoV, WIV1-CoV, MHV, HKU9-CoV, PEDV-CoV, or SDCV.

12. The nucleic acid molecule of claim 9, wherein the recombinant coronavirus S protein further comprises a mutation to inhibit cleavage of a S1/S2 protease cleavage site.

13. An immunogenic composition comprising the nucleic acid molecule of claim 9, and a pharmaceutically acceptable carrier.

14. A method for generating an immune response to a coronavirus S protein in a subject, comprising administering to the subject an effective amount of the nucleic acid molecule of claim 9 to generate the immune response.

15. The method of claim 14, wherein the immune response inhibits infection with the coronavirus.

* * * * *